US006777406B2

(12) United States Patent
Fevig et al.

(10) Patent No.: US 6,777,406 B2
(45) Date of Patent: Aug. 17, 2004

(54) SUBSTITUTED PYRROLOQUINOLINES AND PYRIDOQUINOLINES AS SEROTININ AGONISTS AND ANTAGONISTS

(75) Inventors: John M. Fevig, Lincoln University, PA (US); Ian S. Mitchell, Wilmington, DE (US); Taekyu Lee, Wilmington, DE (US); Wenting Chen, Exton, PA (US); Joseph Cacciola, Newark, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 10/026,993

(22) Filed: Dec. 19, 2001

(65) Prior Publication Data

US 2004/0092502 A1 May 13, 2004

Related U.S. Application Data

(60) Provisional application No. 60/256,745, filed on Dec. 20, 2000.

(51) Int. Cl.$^7$ ................. C07D 471/106; A61K 31/437; A61K 31/4375; A61P 25/24; A61P 25/18

(52) U.S. Cl. ........................ 514/215; 546/66; 546/68; 540/580; 540/544; 540/494; 540/556; 540/579; 514/288; 544/343; 544/99; 544/14

(58) Field of Search ..................... 546/66, 68; 540/580; 514/288, 215

(56) References Cited

U.S. PATENT DOCUMENTS

| 3,914,421 A | 10/1975 | Rajagopalan | ............... 424/248 |
| 4,013,652 A | 3/1977 | Rajagopalan | ............... 260/244 |
| 4,115,577 A | 9/1978 | Rajagopalan | ............... 424/256 |
| 4,183,936 A | 1/1980 | Rajagopalan | ............... 424/256 |
| 4,219,550 A | 8/1980 | Rajagopalan | ............... 424/246 |
| 4,238,607 A | 12/1980 | Rajagopalan | ............... 544/14 |

FOREIGN PATENT DOCUMENTS

EP         0473550         8/1991

OTHER PUBLICATIONS

Arnt, J., "Pharmacological Specificity of Conditioned Avoidance Response Inhibition in Rats: Inhibition by Neuroleptics and Correlation to Dopamine Receptor Blockade", Acta pharmacol. et toxicol., vol. 51, pp. 321–329 (1982).
Aubé, et al., "Application of the Intramolecular Schmidt Reaction to the Asymmetric Synthesis of (–)-Indolizidine 209B from Pulegone", Heterocycles, vol. 35, No. 2, pp. 1141–1147 (1993).
Batchelor, M.J. et al., "Total Synthesis of Close Analogues of the Immunosuppressant FK506", Tetrahedon, vol. 50, No. 3, pp. 809–826 (1994).

Beak, P. et al., "α–Lithioamine Synthetic Equivalents from Dipole–Stabilized Carbanions: The t–Boc Group as an Activator for α'–Lithiantion of Carbamates", Tetrahedron Letters, vol. 30, No. 10, pp. 1197–1200 (1989).
Berendsen, H.H.G. et al., "Involvement of 5–HT$_{1C}$–receptors in drug–induced penile erections in rats", Psychopharmacology, vol. 101, pp. 57–61 (1990).
Berridge, M.J. et al., "Lithium amplifies agonist–dependent phosphatidylinositol responses in brain and salivary glands", Biochem. J., vol. 206, pp. 587–595 (1982).
Costall, B. et al., "Detection of the Neuroleptic Properties of Clozapine, Sulpiride and Thioridazine", Psychopharmacologia (Berl.), vol. 43, pp. 69–74 (1975).
Crisp, G.T. et al., "Palladium–Catalyzed Carbonylative Coupling of Vinyl Triflates with Organostannanes. A Total Synthesis of ()Δ$^{9(12)}$–Capnellene", J. Am. Chem. Soc., vol. 106, pp. 7500–7506 (1984).
Curzon, G. et al., "$m$ –CPP: a tool for studying behavioral responses associated with 5HT$_{1C}$ receptors", TiPS, vol. 11, pp. 181–182 (1990).
Dike, S.Y. et al., "A New Enantioselective Chemoenzymatic Synthesis of R–(–)Thiazesim Hydrochloride", Bioorganic & Medicinal Chemistry Letters, vol. 1, No. 8, pp. 383–386 (1991).

(List continued on next page.)

Primary Examiner—Mark L. Berch
Assistant Examiner—Kahsay Habte
(74) Attorney, Agent, or Firm—Sammy G. Duncan, Jr.; Maureen P. O'Brien

(57) ABSTRACT

The present invention is directed to certain novel compounds represented by structural Formula (I)

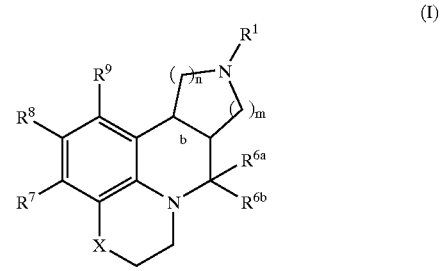

or pharmaceutically acceptable salt forms thereof, wherein is $R^1$, $R^{6a}$, $R^{6b}$, $R^7$, $R^8$, $R^9$, X, b, m, and n are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

18 Claims, No Drawings

OTHER PUBLICATIONS

Egan, C.T. et al., "Agonist activity of LSD and lisuride at cloned 5HT$_{2A}$ and 5HT$_{2C}$ receptors", Psychopharmacology, vol. 136, pp. 409–414 (1998).

Fitzgerald, L.W. et al., "High–Affinity Agonist Binding Correlates with Efficacy (Intrinsic Activity) at the Human Serotonin 5–HT$_{2A}$ and 5–HT$_{2C}$ Receptors . . . ", Journal of Neurochemistry, vol. 72, No. 5, pp. 2127–2134 (1999).

Frost, J.J. et al., "In Vivo Binding of $^3$H–N–Methylspiperone to Dopamine and Serotonin Receptors", Life Sciences, vol. 40, pp. 987–995 (1987).

Glennon, R.A. et al., "[$^{125}$I]–1–(2, 5–Dimethoxy–4–iodophenyl)–2–amino–propane: An Iodinated Radioligand That Specifically Labels the Agonist High–Affinity State of 5–HT$_2$ Serotonin Receptors", J. Med. Chem., vol. 31, pp. 5–7 (1988).

Gore, P.H., "The Friedel–Crafts Acylation Reaction and Its Application to Polycyclic Aromatic Hydrocarbons", Chem. Rev., pp. 229–281 (1955).

Horlick, R.A. et al., "Rapid Generation of Stable Cell Lines Expressing Corticotropin–Releasing Hormone Receptors to Drug Discovery", Protein Expression and Purification, vol. 9, pp. 301–308 (1997).

House, H.O., Modern Synthetic Reactions, 2nd ed., W.A. Benjamin, Inc. (table of contents) (1972).

Ismaiel, A.M. et al., "Blinding of N$_2$–Substituted Pyridol[4, 3–b]Indole Analogs of Spiperone at Human 5–HT2A, 5–HT2B, and 5HT2C Serotonin Receptors", Med. Chem. Res., pp. 197–211 (1996).

Iwao, M. et al., "Directed Lithiation of 1–(tert–Butoxycarbonyl)Indolines. A Convenient Route to 7–Substituted Indolines", Heterocycles, vol. 34, No. 5, pp. 1031–1038 (1992).

Knochel, P. et al., "Preparation and Reactions of Polyfunctional Organozinc Reagents in Organic Synthesis", Chem. Rev., vol. 93, pp. 2117–2188 (1993).

Koek, W. et al., "Behavioral Pharmacology of Antagonists at 5–HT$_2$/5–HT$_{1C}$ Receptors", Neuroscience & Biobehavioral Reviews, vol. 16, pp. 95–105 (1992).

Leonard, B.E., "The Comparative Pharmacology of New Antidepressants", J. Clin. Psychiatry, vol. 54, No. 8 (suppl.), pp. 3–15 (1993), and vol. 54, No. 12, p. 491 (1993) (correction).

Leonhardt, S. et al., "Molecular Pharmacological Differences in the Interaction of Serotonin with 5–Hydroxytryptamine$_{1C}$ and 5–Hydroxytryptamine$_2$ Receptors", Molecular Pharmacology, vol. 42, pp. 328–335 (1992).

Lucaites, V.L. et al., "Receptor Subtype and Density Determine the Coupling Repertoire of the 5–HT$_2$ Receptor Subfamily", Life Sciences, vol. 59, No. 13, pp. 1081–1095 (1996).

Lucki, I. et al., "Differential Actions of Serotonin Antagonists on Two Behavioral Models of Serotonin Receptor Activation in the Rat", The Journal of Pharmocology and Experimental Therapeutics, vol. 228, No. 1, pp. 133–139 (1984).

Miyaura, N. et al., "Palladium–Catalyzed Cross–Coupling Reactions of Organoboron Compounds", Chem. Rev., vol. 95, pp. 2457–2483 (1995).

Motoyoshiya, J., "Recent development of Z–selective Horner–Wadsworth–Emmons reaction", Trends in Organic Chemistry, vol. 7, pp. 63–73 (1998).

Neumann, W.P., "Tri–n–butyltin Hydride as Reagent in Organic Synthesis", Synthesis, pp. 665–683 (1987).

Nozulak, J. et al., "(+)=cis–4,5,7a,8,9,10,11, 11a–Octahydro–7H–10–methylindolo[1,7–bc][2,6]–naphthyridine: A 5–HT$_{2C/2B}$ Receptor Antagonist with Low 5–HT$_{2A}$ Receptor Affinity", J. Med. Chem., vol. 38, pp. 28–33 (1995).

Nukui, S. et al., "Regio–and Stereoselective Functionalization of an Optically Active Tetrahydroindolizine Derivative. Catalytic Asymmetric Syntheses of Lentiginosine, 1,2–Diepilentiginosine, and Gephyrotoxin 209D", J. Org. Chem, vol. 60, pp. 398–404 (1995).

Olah, G.A., Friedel–Crafts and Related Reactions, Interscience Publishers, a division of John Wiley & Sons Inc., vol. III, Part 1, pp. xi–xxvi (1964).

Olah, G.A., Friedel–Crafts and Related Reactions, Interscience Publishers, a division of John Wiley & Sons Inc., vol. III, Part 2, pp. vii–xxii (1964).

Olah, G.A., Friedel–Crafts Chemistry, John Wiley & Sons, Inc. (table of contents) (1973).

Old, D.W. et al., "A Highly Active Catalyst for Palladium–Catalyzed Cross–Coupling Reactions: Room–Temperature Suzuki Couplings and Amination of Unactivated Aryl Chlorides", J. Am. Chem. Soc., vol. 120, pp. 9722–9723 (1998).

Padwa, A., 1–3 Dipolar Cycloaddition Chemistry, John Wiley & Sons, Inc., vol. 1, p. xi (1984).

Padwa, A., 1–3 Dipolar Cycloaddition Chemistry, John Wiley & Sons, Inc., vol. 2, p. xi (1984).

Petasis, N.A. et al., "Methylenations of Heteroatom–Substituted Carbonyls with Dimethyl Titanocene", Tetrahedron Letters, vol. 36, No. 14, pp. 2393–2396 (1995).

Remington, J.P., Remington's Pharaceutical Sciences, 17th ed., Mack Publishing Company, p. 1418 (1985).

Sawyer, J.S., "Recent Advances in Diaryl Ether Synthesis", Tetrahedron, vol. 56, pp. 5045–5065 (2000).

Sibi, M.P. et al., "N,N'–Dimethoxy-N,N'–Dimethylethanediamide: A Useful αOxo–N–Methoxy–N–Methylamide and 1,2–Diketone Synthon", Tetrahedron Letters, vol. 33, No. 15, pp. 1941–1944 (1992).

Smith, P.A.S., "The Schmidt Reaction: Experimental Conditions and Mechanism", J. Am. Chem. Soc., vol. 70, pp. 320–323 (1948).

Stanforth, S.P., "Catalytic Cross–coupling Reactions in Biaryl Synthesis", Tetrahedron, vol. 54, pp. 263–303 (1998).

Still, W.C. et al., "Direct Synthesis of Z–Unsaturated Esters. A useful Modification of the Horner–Emmons Olefination", Tetrahedron Letters, vol. 24, No. 41, pp. 4405–4408 (1983).

Trost, B.M. et al., "Palladium–Mediated Cycloaddition Approach to Cyclopentanoids. Introduction and Initial Studies", J. Am. Chem. Soc., vol. 105, pp. 2315–2325 (1983).

Tsuji, J., Palladium Reagents and Catalysts, Innovations in Organic Synthesis, John Wiley & Sons Ltd., pp. v–ix (1995).

Ugedo, L. et al., "Ritanserin, a 5–HT$_2$ receptor antagonist, activates midbrain dopamine neurons by blocking serotonergic inhibition", Psychopharmacology, vol. 98, pp. 45–50 (1989).

Weichert, A. et al., "Palladium(0) Catalized Cross Coupling Reactions of Hindered, Double Activated Aryl Halides with Organozinc Reagents—The Effect of Copper(1) Cocatalysis", Synlett, pp. 473–476 (1996).

SUBSTITUTED PYRROLOQUINOLINES AND PYRIDOQUINOLINES AS SEROTININ AGONISTS AND ANTAGONISTS

This application claims the benefit of Ser. No. 60/256,745, filed Dec. 20, 2000.

FIELD OF THE INVENTION

The present invention is directed to certain novel compounds represented by structural Formula (I)

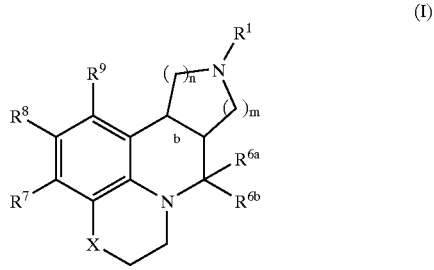

(I)

or pharmaceutically acceptable salt forms thereof, wherein $R^1$, $R^{6a}$, $R^{6b}$, $R^7$, $R^8$, $R^9$, X, b, m, and n are described herein. The invention is also concerned with pharmaceutical formulations comprising these novel compounds as active ingredients and the use of the novel compounds and their formulations in the treatment of certain disorders. The compounds of this invention are serotonin agonists and antagonists and are useful in the control or prevention of central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility.

BACKGROUND OF THE INVENTION

There exists a substantial correlation for the relationship between 5-HT2 receptor modulation and a variety of diseases and therapies. To date, three subtypes of the 5-HT2 receptor class have been identified, 5-HT2A, 5-HT2B, and 5-HT2C. Prior to the early 1990's the 5-HT2C and 5-HT2A receptors were referred to as 5-HT1C and 5-HT2, respectively.

The agonism or antagonism of 5-HT2 receptors, either selectively or nonselectively, has been associated with the treatment of various central nervous system (CNS) disorders Ligands possessing affinity for the 5-HT2 receptors have been shown to have numerous physiological and behavioral effects (Trends in Pharmacological Sciences, 11, 181, 1990). In the recent past the contribution of serotonergic activity to the mode of action of antidepressant drugs has been well documented. Compounds that increase the overall basal tone of serotonin in the CNS have been successfully developed as antidepressants. The serotonin selective reuptake inhibitors (SSRI) function by increasing the amount of serotonin present in the nerve synapse. These breakthrough treatments, however, are not without side effects and suffer from delayed onset of action (Leonard, J. Clin. Psychiatry, 54(suppl), 3, 1993). Due to the mechanism of action of the SSRIs, they effect the activity of a number of serotonin receptor subtypes. This non-specific modulation of the serotonin family of receptors most likely plays a significant role in the side effect profile. In addition, these compounds often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

There is ample evidence to support the role of selective 5-HT2 receptor ligands in a number of disease therapies. Modulation of 5-HT2 receptors has been associated with the treatment of schizophrenia and psychoses (Ugedo, L., et. al., Psychopharmacology, 98, 45, 1989). Mood, behavior and hallucinogenesis can be affected by 5-HT2 receptors in the limbic system and cerebral cortex. 5-HT2 receptor modulation in the hypothalamus can influence appetite, thermoregulation, sleep, sexual behavior, motor activity, and neuroendocrine function (Hartig, P., et. al., Annals New York Academy of Science, 149, 159). There is also evidence indicating that 5-HT2 receptors mediate hypoactivity, effect feeding in rats, and mediate penile erections (Pyschopharmacology, 101, 57, 1990).

Compounds exhibiting selectivity for the 5-HT2B receptor are useful in treating conditions such as tachygastria, hypermotility associated with irritable bowel disorder, constipation, dyspepsia, and other peripherally mediated conditions.

5-HT2A antagonists have been shown to be effective in the treatment of schizophrenia, anxiety, depression, and migraines (Koek, W., Neuroscience and Behavioral reviews, 16, 95, 1996). Aside from the beneficial antipsychotic effects, classical neuroleptic are frequently responsible for eliciting acute extrapyramidal side effects and neuroendocrine disturbances. These compounds generally possess signifcant dopamine D2 receptor affinity (as well as other nuisance receptor affinity) which frequently is associated with extra pyramidal symptoms and tardive dyskinesia, thus detracting from their efficacy as front line treatments in schizophrenia and related disorders. Compounds possessing a more favorable selectivity profile would represent a possible improvement for the treatment of CNS disorders.

U.S. Pat. Nos. 3,914,421; 4,013,652; 4,115,577; 4,183,936; and 4,238,607 disclose pyridopyrrolobenzheterocycles of formula:

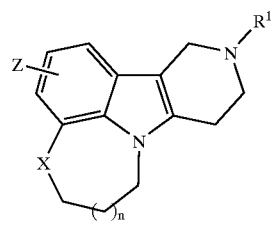

where X is O, S, S(=O), or $SO_2$; n is 0 or 1; $R^1$ is various carbon substituents, and Z is a monosubstituent of H, methyl, or chloro.

U.S. Pat. No. 4,219,550 discloses pyridopyrrolo-benzheterocycles of formula:

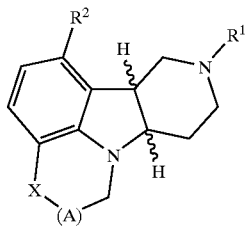

where X is O or S; $R^1$ is $C_{1-4}$ alkyl or cyclopropyl; $R^2$ is H, $CH_3$, $OCH_3$, Cl, Br, F, or $CF_3$; and (A) is $-CH_2-$, $-CH(CH_3)-$, or $-CH_2CH_2-$.

European Patent Application EP 473,550 A1 discloses indolonaphthyridines of formula:

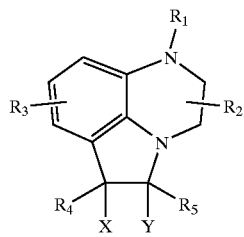

wherein X and Y are H or a simple ring, $R^1$, is H, alkyl, alkylcarbonylalkyl, arylcarbonylalkyl, aralkyl, or a mono or disubstituted carbamoylalkyl; and $R^3$, $R^4$, and $R^5$ are H, halogen, alkyl, alkoxy, alkylthio or trifluoromethyl.

None of the above references suggest or disclose the compounds of the present invention.

There remains a need to discover new compounds useful as serotonin agonists and antagonists which are useful in the control or prevention of central nervous system disorders. As such, the present invention discloses novel compounds which are of low molecular weight, useful as serotonin agonists and antagonists, and provide good in vitro potency.

SUMMARY OF THE INVENTION

One object of the present invention is to provide novel compounds which are useful as agonists or antagonists of 5-HT2 receptors, more specifically 5-HT2A and 5-HT2C receptors, or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility comprising administering to a host in need of such treatment a therapeutically effective amount of at least one of the compounds of the present invention or a pharmaceutically acceptable salt or prodrug form thereof. More specifically, the present invention provides a method for treating obesity anxiety, depression, or schizophrenia.

These and other objects, which will become apparent during the following detailed description, have been achieved by the inventors, discovery that compounds of Formula (I):

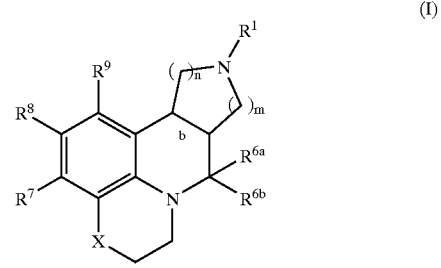

or pharmaceutically acceptable salt or prodrug forms thereof, wherein $R^1$, $R^{6a}$, $R^{6b}$, $R^7$, $R^8$, $R^9$, X, b, m, and n are defined below, are effective agonists or antagonists of 5-HT2 receptors.

DETAILED DESCRIPTION OF THE EMBODIMENTS

Thus, in a first embodiment, the present invention provides a novel compound of Formula (I):

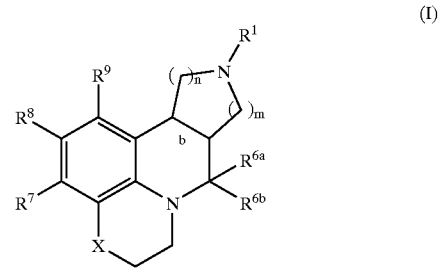

or a stereoisomer or a pharmaceutically acceptable salt form thereof, wherein:

b is a single bond wherein the bridging hydrogens are either cis or trans;

X is a bond, $-CH_2-$, $-O-$, $-S-$, $-S(=O)-$, $-S(=O)_2-$, $NR^{10}-$, $-CH_2CH_2-$, $-OCH_2-$, $-SCH_2-$, $-S(=O)CH_2-$, $-S(=O)_2CH_2-$, $-CH_2O-$, $-CH_2S-$, $-CH_2S(=O)-$, $-CH_2S(=O)_2-$, $-NR^{10}CH_2-$, $-CH_2NR^{10}-$, $-NHC(=O)-$, or $-C(=O)NH-$;

$R^1$ is selected from
H,
$C(=O)R^2$,
$C(=O)OR^2$,
$C_{1-8}$ alkyl,
$C_{2-8}$ alkenyl,
$C_{2-8}$ alkynyl,
$C_{3-7}$ cycloalkyl,
$C_{1-6}$ alkyl substituted with Z,
$C_{2-6}$ alkenyl substituted with Z,
$C_{2-6}$ alkynyl substituted with Z,
$C_{3-6}$ cycloalkyl substituted with Z,
aryl substituted with Z,
5-6 membered heterocyclic ring system containing at least one heteroatom selected from the group consisting of N, O, and S, said heterocyclic ring system substituted with Z;
$C_{1-3}$ alkyl substituted with Y,
$C_{2-3}$ alkenyl substituted with Y,
$C_{2-3}$ alkynyl substituted with Y, C$_{1-6}$ alkyl substituted with 0–2 R$^2$,
C$_{2-6}$ alkenyl substituted with 0–2 R$^2$,
C$_{2-6}$ alkynyl substituted with 0–2 R$^2$,
aryl substituted with 0–2 R$^2$, and
5–6 membered heterocyclic ring system containing at least one heteroatom selected from the group consisting of N, O, and S, said heterocyclic ring system substituted with 0–2 R$^2$;

Y is selected from
C$_{3-6}$ cycloalkyl substituted with Z, aryl substituted with Z,
5–6 membered heterocyclic ring system containing at least one heteroatom selected from the group consisting of N, O, and S, said heterocyclicring system substituted with Z;
C$_{3-6}$ cycloalkyl substituted with —(C$_{1-3}$ alkyl)—Z,
aryl substituted with —(C$_{1-3}$ alkyl)—Z, and
5–6 membered heterocyclic ring system containing at least one heteroatom selected from the group consisting of N, O, and S, said heterocyclic ring system substituted with —(C$_{1-3}$ alkyl)—Z;

Z is selected from H,
—CH(OH)R$^2$,
—C(ethylenedioxy)R$^2$,
—OR$^2$,
SR$^2$,
—NR$^2$R$^3$,
—C(O)R$^2$,
—C(O)NR$^2$R$^3$,
—NR$^3$C(O)R$^2$,
—C(O) OR$^2$,
—OC(O)R$^2$,
—CH(=NR$^4$)NR$^2$R$^3$,
—NHC(=NR$^4$)NR$^2$R$^3$,
—S(O)R$^2$,
—S(O)$_2$R$^2$,
S(O)$_2$NR$^2$R$^3$, and —NR$^3$S(O)$_2$R$^2$;

R$^2$, at each occurrence, is independently selected from halo,
C$_{1-3}$ haloalkyl,
C$_{1-4}$ alkyl,
C$_{2-4}$ alkenyl,
C$_{2-4}$ alkynyl,
C$_{3-6}$ cycloalkyl,
aryl substituted with 0–5 R$^{42}$;
C$_{3-10}$ carbocyclic residue substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from H, C$_{1-4}$ alkyl, C$_{2-4}$ alkenyl, C$_{2-4}$ alkynyl, and C$_{1-4}$ alkoxy;
alternatively, R$^2$ and R$^3$ join to form a 5- or 6-membered ring optionally substituted with —O—or —N(R$^4$)—;

R$^4$, at each occurrence, is independently selected from H and C$_{1-4}$ alkyl;

R$^{6a}$ is H or C$_{1-4}$ alkyl;
R$^{6b}$ is H;
alternatively, R$^{6a}$ and R$^{6b}$ are taken together to form =O or =S;

R$^7$ and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{3-10}$ cycloalkyl substituted with 0–2 R$^{33}$,
C$_{1-4}$ alkyl substituted with 0–2 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$,
NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$,
S(O)NR$^{12}$R$^{13}$, S(O)$_2$NR$^{12}$R$^{13}$, NR$^{14}$S(O)R$^{12}$, NR$^{14}$S(O)$_2$R$^{12}$,
NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^8$ is selected from
H, halo, —CF$_3$, —OCF$_3$, —OH, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{3-10}$ cycloalkyl substituted with 0–2 R$^{33}$,
C$_{1-4}$ alkyl substituted with 0–2 R$^{11}$,
C$_{2-4}$ alkenyl substituted with 0–2 R$^{11}$,
C$_{2-4}$ alkynyl substituted with 0–1 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$,
NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$,
S(O)NR$^{12}$R$^{13}$, S(O)$_2$, NR$^{12}$R$^{13}$, NR$^{14}$S(O)R$^{12}$, NR$^{14}$S(O)$_2$R$^{12}$,
NR$^{12}$C(O)R$^{15}$, NR$^{12}$C(O)OR$^{15}$, NR$^{12}$S(O)$_2$R$^{15}$, and NR$^{12}$C(O) NHR$^{15}$;

R$^{10}$ is selected from H,
C$_{1-4}$ alkyl substituted with 0–2 R$^{10A}$,
C$_{2-4}$ alkenyl substituted with 0–2 R$^{10A}$,
C$_{2-4}$ alkynyl substituted with 0–1 R$^{10A}$, and
C$_{1-4}$ alkoxy;

R$^{10A}$ is selected from
C$_{1-4}$ alkoxy,
C$_{3-6}$ carbocyclic residue substituted with 0–3 R$^{33}$,
phenyl substituted with 0–3 R$^{33}$, and
5–6 membered heterocyclic ring system containing 1, 2, or 3 heteroatoms selected from the group consisting of N, O, and S; substituted with 0–2 R$^{44}$;

R$^{11}$ is selected from
H, halo, —CF$_3$, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$,
NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$,
S(O)NR$^{12}$R$^{13}$, S(O)$_2$NR$^{12}$R$^{13}$, NR$^{14}$S(O)R$^{12}$, NR$^{14}$S(O)$_2$R$^{12}$,
NR$^{12}$C(O)R$^{15}$, NR$^{12}$C(O)OR$^{15}$, NR$^{12}$S(O)$_2$R$^{15}$, and NR$^{12}$C(O)NHR$^{15}$;

$R^{12}$, at each occurrence, is independently selected from
  $C_{1-4}$ alkyl substituted with 0–1 $R^{12a}$,
  $C_{2-4}$ alkenyl substituted with 0–1 $R^{12a}$,
  $C_{2-4}$ alkynyl substituted with 0–1 $R^{12a}$,
  $C_{3-6}$ cycloalkyl substituted with 0–3 $R^{33}$,
  aryl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{31}$;

$R^{12a}$, at each occurrence, is independently selected from
  phenyl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, $C_{1-3}$ alkyloxy-, and =O;

$R^{31}$, at each occurrence, is independently selected from H, OH, halo, $CF_3$, $SO_2R^{45}$, $NR^{46}R^{47}$, $C_{1-4}$ alkyl, and =O;

$R^{33}$, at each occurrence, is independently selected from H, OH, halo, CN, $NO_2$, $CF_3$, $SO_2R^{45}$, $NR^{46}R^{47}$, —C(=O)H, =O, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;
  $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and
  $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN, =O;
  $C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$,
  aryl substituted with 0–3 $R^{42}$, and
  5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, CH(=NH)$NH_2$, NHC(=NH) $NH_2$,
  $C_{2-6}$ alkenyl, $C_{2-6}$ alkynyl, $C_{1-4}$ alkoxy, $C_{1-4}$ haloalkyl, $C_{3-6}$ cycloalkyl,
  $C_{1-4}$ alkyl substituted with 0–1 $R^{43}$,
  aryl substituted with 0–3 $R^{44}$, and
  5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —C(=O)NH($C_{1-4}$ alkyl), —$SO_2$($C_{1-4}$ alkyl), —C(=O)O($C_{1-4}$ alkyl), —C(=O)($C_{1-4}$ alkyl), and —C(=O)H;

n is 1 or 2;

m is 1 or 2; and n plus m is 2, 3, or 4;

provided when n is 1, m is 2, and $R^7$, $R^8$, and $R^9$ are independently selected from H, halogen, $C_{1-4}$ alkyl, $C_{1-4}$ alkoxy, $C_{1-4}$ alkylthio or trifluoromethyl; then X is not a bond.

[2] In an another embodiment, the present invention provides a novel compound of Formula (I) wherein:

X is a bond, —$CH_2$—, —O—, —S—, —S(=O)—, —S(=O)$_2$—, —$NR^{10}$—, —$CH_2CH_2$—, —$OCH_2$—, —$SCH_2$—, —$CH_2O$—, —$CH_2S$—, —$NR^{10}CH_2$—, or —$CH_2NR^{10}$—;

$R^1$ is selected from
  H,
  C(=O)$R^2$,
  C(=O)O$R^2$,
  $C_{1-8}$ alkyl,
  $C_{2-8}$ alkenyl,
  $C_{2-8}$ alkynyl,
  $C_{3-7}$ cycloalkyl,
  $C_{1-6}$ alkyl substituted with 0–2 $R^2$,
  $C_{2-6}$ alkenyl substituted with 0–2 $R^2$,
  $C_{2-6}$ alkynyl substituted with 0–2 $R^2$,
  aryl substituted with 0–2 $R^2$, and
  5–6 membered heterocyclic ring system containing at least one heteroatom selected from the group consisting of N, O, and S, said heterocyclic ring system substituted with 0–2 $R^2$;

$R^2$, at each occurrence, is independently selected from F, Cl, $CH_2F$, $CHF_2$, $CF_3$,
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{42}$;
  $C_{3-10}$ carbocyclic residue substituted with 0–3 $R^{41}$, and
  5–10 membered heterocyclic ring system containing from 1–4 heteroatoms selected from the group consisting of N, O, and S substituted with 0–3 $R^{41}$;

$R^{6a}$ is H or $C_{1-4}$ alkyl;

$R^{6b}$ is H;

alternatively, $R^{6a}$ and $R^{6b}$ are taken together to form =O or =S;

$R^7$ and $R^9$, at each occurrence, are independently selected from

H, halo, —$CF_3$, —$OCF_3$, —OH, —CN, —$NO_2$, —$NR^{46}R^{47}$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O))$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, $NR^{14}$S(O)$_2R^{12}$, $NR^{12}$C(O)$R^{15}$, $NR^{12}$C(O)$OR^{15}$, $NR^{12}$S(O)$_2R^{15}$, and $NR^{12}$C(O) $NHR^{15}$;

$R^8$ is selected from

H, halo, —$CF_3$, —$OCF_3$, —OH, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O) $NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$) $NR^{12}R^{13}$, S(O)$R^{12}$, S(O)$_2R^{12}$, S(O)$NR^{12}R^{13}$, S(O)$_2$ $NR^{12}R^{13}$, $NR^{14}$S(O)$R^{12}$, $NR^{14}$S(O), $_2R^{12}$, $NR^{12}$C (O)$R^{15}$, $NR^{12}$C(O)$OR^{15}$, $NR^{12}$S(O)$_2R^{15}$, and $NR^{12}$C (O) $NHR^{15}$;

$R^{10}$ is selected from H, $C_{1-4}$ alkyl, $C_{2-4}$ alkenyl, $C_{2-4}$ alkynyl, and $C_{1-4}$ alkoxy;

$R^{11}$ is selected from

H, halo, —$CF_3$, —CN, —$NO_2$, $C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, C(O)H, C(O)$R^{12}$, C(O) $NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$) $NR^{12}R^{13}$, S(O)$R^{12}$, S(O)$_2R^{12}$, S(O)$NR^{12}R^{13}$, S(O)$_2$ $NR^{12}R^{13}$, $NR^{14}$S(O)$R^{12}$, $NR^{14}$S(O)$_2R^{12}$, $NR^{12}$C(O) $R^{15}$, $NR^{12}$C(O)$OR^{15}$, $NR^{12}$S(O)$_2R^{15}$, and $NR^{12}$C(O) $NHR^{15}$;

$R^{12}$, at each occurrence, is independently selected from $C_{1-4}$ alkyl substituted with 0–1 $R^{12a}$, $C_2C_4$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, aryl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O—or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$, —C(=O)H, $C_{1-4}$ alkyl, $C_{2-4}$ alkenyl, $C_{2-4}$ alkynyl, $C_{1-4}$ haloalkyl, $C_{1-3}$ haloalkyl-oxy-, $C_{1-3}$ alkyloxy-, and =O;

$R^{31}$, at each occurrence, is independently selected from H, OH, halo, $CF_3$, $SO_2R^{45}$, $NR^{46}R^{47}$, $C_{1-4}$ alkyl, and =O;

$R^{33}$, at each occurrence, is independently selected from H, OH, halo, CN, $NO_2$, $CF_3$, $SO_2R^{45}$, $NR^{46}R^{47}$, —C(=O)H, =O, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;

$C_{1-6}$ alkyl substituted with OH, methoxy, ethoxy, propoxy, butoxy, —$SO_2R^{45}$, —$NR^{46}R^{47}$, $NR^{46}R^{47}$C (=O)—, or ($C_{1-4}$ alkyl)$CO_2$—; and $C_{2-6}$ alkenyl substituted with OH, methoxy, ethoxy, propoxy, butoxy, —$SO_2R^{45}$, —$NR^{46}R^{47}$, $NR^{46}R^{47}$C (=O)—, or ($C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN;

$C_{2-8}$ alkenyl, $C_{2-8}$ alkynyl, $C_{1-4}$ alkoxy, $C_{1-4}$ haloalkyl $C_{1-4}$ alkyl substituted with 0–1 $R^{43}$, aryl substituted with 0–3 $R^{42}$, and 5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(=NH)$NH_2$, $C_{2-6}$ alkenyl, $C_{2-6}$ alkynyl, $C_{1-4}$ alkoxy, $C_{1-4}$ haloalkyl, $C_{3-6}$ cycloalkyl, $C_{1-4}$ alkyl substituted with 0–1 $R^{43}$, aryl substituted with 0–3 $R^{44}$, and 5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

n is 1 or 2;

m is 1 or 2; and n plus m is 2, 3, or 4;

provided when n is 1, m is 2, and $R^7$, $R^8$, and $R^9$ are independently selected from H, halogen, $C_{1-4}$ alkyl, $C_{1-4}$ alkoxy, $C_{1-4}$ alkylthio or trifluoromethyl; then X is not a bond.

[3] In an another embodiment, the present invention provides a novel compound of Formula (I) wherein:

X is a bond, —$CH_2$—, —O—, —S—, —$CH_2CH_2$—, —$OCH_2$—, —$SCH_2$—, —$CH_2O$—, or —$CH_2S$—;

$R^1$ is selected from

H, $C(=O)R^2$, $C(=O)$ $OR^2$, $C_{1-6}$ alkyl, $C_{2-6}$ alkenyl, $C_{2-6}$ alkynyl, $C_{3-6}$ cycloalkyl, $C_{1-4}$ alkyl substituted with 0–2 $R^2$, $C_{2-4}$ alkenyl substituted with 0–2 $R^2$, and $C_{2-4}$ alkynyl substituted with 0–2 $R^2$;

$R^2$, at each occurrence, is independently selected from $C_{1-4}$ alkyl, $C_{2-4}$ alkenyl, $C_{2-4}$ alkynyl, $C_{3-6}$ cycloalkyl, phenyl substituted with 0–5 $R^{42}$;

$C_{3-10}$ carbocyclic residue substituted with 0–3 $R^{41}$, and

5–10 membered heterocyclic ring system containing from 1–4 heteroatoms selected from the group consisting of N, O, and S substituted with 0–3 $R^{41}$;

$R^{6a}$ is H or $C_{1-4}$ alkyl;

$R^{6b}$ is H;

alternatively, $R^{6a}$ and $R^{6b}$ are taken together to form =O or =S;

$R^7$ and $R^9$, at each occurrence, are independently selected from

H, halo, —$CF_3$, —$OCF_3$, —OH, —CN, —$NO_2$, —$NR^{46}R^{47}$, $C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^8$ is selected from

H, halo, —$CF_3$, —$OCF_3$, —OH, —CN, —$NO_2$, $C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy, $C_{3-10}$ cycloalkyl substituted with 0–2 $R^{33}$, $C_{1-4}$ alkyl substituted with 0–2 $R^{11}$, $C_{2-4}$ alkenyl substituted with 0–2 $R^{11}$, $C_{2-4}$ alkynyl substituted with 0–1 $R^{11}$, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from

H, halo, —$CF_3$, —CN, —$NO_2$, $C_{1-6}$ alkyl, $C_{2-6}$ alkenyl, $C_{2-6}$ alkynyl, $C_{1-4}$ haloalkyl, $C_{1-6}$ alkoxy, $C_{3-10}$ cycloalkyl, $C_{3-10}$ carbocyclic residue substituted with 0–3 $R^{33}$, aryl substituted with 0–5 $R^{33}$, 5–10 membered heterocyclic ring system containing from 1–4 heteroatoms selected from the group consisting of N, O, and S substituted with 0–3 $R^{31}$;

$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, and $NR^{14}S(O)_2R^{12}$;

$R^{12}$, at each occurrence, is independently selected from $C_{1-4}$ alkyl substituted with 0–1 $R^{12a}$, $C_{2-4}$ alkenyl substituted with 0–1 $R^{12a}$, $C_{2-4}$ alkynyl substituted with 0–1 $R^{12a}$, $C_{3-6}$ cycloalkyl substituted with 0–3 $R^{33}$, aryl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;

$C_{3-10}$ carbocyclic residue substituted with 0–3 $R^{33}$, and

5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, F, Cl, CN, $NO_2$, $CF_3$, $SO_2R^{45}$, $NR^{46}R^{47}$, —C(=O)H, methyl, ethyl, methoxy, ethoxy, trifluoromethyl, trifluoromethoxy, and =O;

$R^{31}$, at each occurrence, is independently selected from H, OH, halo, $CF_3$, $SO_2R^{45}$, $NR^{46}R^{47}$, $C_{1-4}$ alkyl, and =O;

$R^{33}$, at each occurrence, is independently selected from
H, OH, halo, CN, $NO_2$, $CF_3$, $SO_2R^{45}$, $NR^{46}R^{47}$, —C(=O)H,
=O, phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and
$C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;

$R^{41}$, at each occurrence, is independently selected from
H, $CF_3$, halo, OH, $CO_2H$, $SO_2R^{45}$, $NR^{46}R^{47}$, $NO_2$, CN, $C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $NR^{46}R^{47}$, $NO_2$, CN, CH(=NH)$NH_2$, NHC(=NH) $NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

n is 1 or 2;

m is 1 or 2; and n plus m is 2, 3, or 4;

provided when n is 1, m is 2, and $R^7$, $R^8$, and $R^9$ are independently selected from H, halogen, $C_{1-4}$ alkyl, $C_{1-4}$ alkoxy, $C_{1-4}$ alkylthio or trifluoromethyl; then X is not a bond.

[4] In an another embodiment, the present invention provides a novel compound of Formula (I) wherein:

X is a bond, —$CH_2$—, —O—, —S—, —$OCH_2$—, or —$SCH_2$—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2, or 3 heteroatoms selected from the group consisting of N, O, and S substituted with 0–3 $R^{41}$;

$R^{6a}$ is H, methyl, ethyl, propyl, or butyl;

$R^{6b}$ is H;

alternatively, $R^{6a}$ and $R^{6b}$ are taken together to form =O or =S;

$R^7$ and $R^9$, at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^8$ is selected from
H, halo, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, $NR^{12}C(O)NHR^{15}$, $NR^{14}C(O)R^{12}$, $NR^{14}C(O)$ $OR^{12}$, and $NR^{14}S(O)_2R^{12}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from H, OH, halo, CN, $NO_2$, $CF_3$, $SO_2R^{45}$, $NR^{46}R^{47}$, —C(=O)H,
phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or $(C_{1-4}$ alkyl)$CO_2$—; and
$C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or $(C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(=NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

n is 1 or 2;

m is 1 or 2; and n plus m is 2 or 3;

provided when n is 1, m is 2, and $R^7$, $R^8$, and $R^9$ are independently selected from H, halogen, $C_{1-4}$ alkyl, $C_{1-4}$ alkoxy, $C_{1-4}$ alkylthio or trifluoromethyl; then X is not a bond.

[5] In an another embodiment, the present invention provides a novel compound of Formula (I) wherein:

X is a bond, —$CH_2$—, —O—, —S—, —$OCH_2$—, or —$SCH_2$—;

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2, or 3 heteroatoms selected from the group consisting of N, O, and S substituted with 0–3 $R^{41}$;

$R^{6a}$ is H;

$R^{6b}$ is H;

alternatively, $R^{6a}$ and $R^{6b}$ are taken together to form =O;

$R^7$ and $R^9$, at each occurrence, are independently selected from
H, F, Cl, —$CH_3$, —$OCH_3$, —$CF_3$, —$OCF_3$, —CN, and —$NO_2$, $R^8$ is selected from
H, F, Cl, Br, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O) OR^{15}$, $NR^{12}S(O)_2R^{15}$, $NR^{12}C(O)NHR^{15}$, $NR^{14}C(O)R^{12}$, $NR^{14}C(O)OR^{12}$, and $NR^{14}S(O)_2R^{12}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, ($C_{1-4}$ haloalkyl)oxy,
$C_{3-10}$ cycloalkyl substituted with 0–2 $R^{33}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$,
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from phenyl substituted with 0–5 $R^{33}$;
$C_{3-10}$ carbocyclic residue substituted with 0–3 $R^{33}$, and 5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, is quinolinyl, tetrahydroquinolinyl, isoquinolinyl, and tetrahydroisoquinolinyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from H, OH, halo, CN, $NO_2$, $CF_3$, $SO_2R^{45}$, $NR^{46}R^{47}$, —C(=O)H,
phenyl, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—; and
$C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(=NH)$NH_2$, $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

n is 1; and
m is 1.

[6] In an another embodiment, the present invention provides a novel compound of Formula (I) wherein:

X is a bond, —$CH_2$—, —O—, —S—, —$OCH_2$—, or —$SCH_2$—;

$R^1$ is selected from H,
$C_{1-5}$ alkyl substituted with 0–1 $R^2$,
$C_{2-5}$ alkenyl substituted with 0–1 $R^2$, and
$C_{2-3}$ alkynyl substituted with 0–1 $R^2$;

$R^2$ is cyclopropyl, cyclobutyl, cyclopentyl, cyclohexyl, or phenyl;

$R^{6a}$ is H;

$R^{6b}$ is H;

$R^7$ and $R^9$, at each occurrence, are independently selected from H, F, Cl, —$CH_3$, —$OCH_3$, —$CF_3$, —$OCF_3$, —CN, and —$NO_2$;

$R^8$ is selected from $R^{11}$;
methyl substituted with $R^{11}$;
phenyl substituted with 0–3 $R^{33}$;
pyridyl substituted with 0–2 $R^{33}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, $NR^{12}C(O)NHR^{15}$, $NR^{14}C(O)R^{12}$, $NR^{14}C(O)oRL^2$, and $NR^{14}S(O)_2R^{12}$;

$R^{11}$ is selected from
phenyl-substituted with 0–5 fluoro;
pyridyl substituted with 0–2 $R^{33}$;
naphthyl-substituted with 0–2 $R^{33}$;
2-($H_3CCH_2C$(=O))-phenyl-substituted with $R^{33}$;
2-($H_3CC$(=O))-phenyl-substituted with $R^{33}$;
2-(HC(=O))-phenyl-substituted with $R^{33}$;
2-($H_3CCH$(OH))-phenyl-substituted with $R^{33}$;
2-($H_3CCH_2CH$(OH))-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH$(OMe))-phenyl-substituted with $R^{33}$;
2-($H_3COC$(=O))-phenyl-substituted with $R^{33}$;
2-($HOCH_2CH$=CH)-phenyl-substituted with $R^{33}$;
2-((MeOC=O)CH=CH)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
3-($H_3C$)-phenyl-substituted with $R^{33}$;
3-($F_3C$)-phenyl-substituted with $R^{33}$;
3-($H_3CS$)-phenyl-substituted with $R^{33}$;
4-(NC)-phenyl-substituted with $R^{33}$;
4-(fluoro)-phenyl-substituted with $R^{33}$;
4-(chloro)-phenyl-substituted with $R^{33}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C$(=O))-phenyl-substituted with $R^{33}$;
4-(($H_3C$)$_2CHC$(=O))-phenyl-substituted with $R^{33}$;

19

4-(H₃CCH₂C(=O))-phenyl-substituted with R³³;
4-(H₃CC(=O))-phenyl-substituted with R³³;
4-(H₃CCH₂CH₂CH(OH))-phenyl-substituted with R³³;
4-((H₃C)₂CHCH(OH))-phenyl-substituted with R³³;
4-(H₃CCH₂CH(OH))-phenyl-substituted with R³³;
4-(H₃CCH(OH))-phenyl-substituted with R³³;
4-(cyclopropyloxy)-phenyl-substituted with R³³;
4-(cyclobutyloxy)-phenyl-substituted with R³³; and
4-(cyclopentyloxy)-phenyl-substituted with R³³;

R¹² is selected from
  methyl substituted with R¹¹;
  phenyl substituted with 0–5 fluoro;
  pyridyl substituted with 0–2 R³³;
  naphthyl substituted with 0–2 R³³;
  2-(H₃CCH₂C(=O))-phenyl-substituted with R³³;
  2-(H₃CC(=O))-phenyl-substituted with R³³;
  2-(HC(=O))-phenyl-substituted with R³³;
  2-(H₃CCH(OH))-phenyl-substituted with R³³;
  2-(H₃CCH₂CH(OH))-phenyl-substituted with R³³;
  2-(HOCH₂)-phenyl-substituted with R³³;
  2-(HOCH₂CH₂)-phenyl-substituted with R³³;
  2-(H₃OCCH₂)-phenyl-substituted with R³³;
  2-(H₃COCH₂CH₂)-phenyl-substituted with R³³;
  2-(H₃CCH(OMe))-phenyl-substituted with R³³;
  2-(H₃COC(=O))-phenyl-substituted with R³³;
  2-(HOCH₂CH=CH)-phenyl-substituted with R³³;
  2-((MeOC=O)CH=CH)-phenyl-substituted with R³³;
  2-(methyl)-phenyl-substituted with R³³;
  2-(ethyl)-phenyl-substituted with R³³;
  2-(i-propyl)-phenyl-substituted with R³³;
  2-(F₃C)-phenyl-substituted with R³³;
  2-(NC)-phenyl-substituted with R³³;
  2-(H₃CO)-phenyl-substituted with R³³;
  2-(fluoro)-phenyl-substituted with R³³;
  2-(chloro)-phenyl-substituted with R³³;
  3-(NC)-phenyl-substituted with R³³;
  3-(H₃CO)-phenyl-substituted with R³³;
  3-(fluoro)-phenyl-substituted with R³³;
  3-(chloro)-phenyl-substituted with R³³;
  3-(H₃C)-phenyl-substituted with R³³;
  3-(F₃C)-phenyl-substituted with R³³;
  3-(H₃CS)-phenyl-substituted with R³³;
  4-(fluoro)-phenyl-substituted with R³³;
  4-(chloro)-phenyl-substituted with R³³;
  4-(H₃CS)-phenyl-substituted with R³³;
  4-(H₃CO)-phenyl-substituted with R³³;
  4-(ethoxy)-phenyl-substituted with R³³;
  4-(i-propoxy)-phenyl-substituted with R³³;
  4-(i-butoxy)-phenyl-substituted with R³³;
  4-(H₃CCH₂CH₂C(=O))-phenyl-substituted with R³³;
  4-((H₃C)₂CHC(=O))-phenyl-substituted with R³³;
  4-((H₃CCH₂C(=O))-phenyl-substituted with R³³;
  4-(H₃CC(=O))-phenyl-substituted with R³³;
  4-(H₃CCH₂CH₂CH(OH))-phenyl-substituted with R³³;
  4-((H₃C)₂CHCH(OH))-phenyl-substituted with R³³;
  4-(H₃CCH₂CH(OH))-phenyl-substituted with R³³;
  4-(H₃CCH(OH))-phenyl-substituted with R³³;
  4-(cyclopropyloxy)-phenyl-substituted with R³³;
  4-(cyclobutyloxy)-phenyl-substituted with R³³; and
  4-(cyclopentyloxy)-phenyl-substituted with R³³;

R¹³ is H, methyl, or ethyl;
alternatively, R¹² and R¹³ join to form a 5- or 6-membered ring selected from pyrrolyl, pyrrolidinyl, imidazolyl, piperidinyl, piperizinyl, methylpiperizinyl, and morpholinyl;
alternatively, R¹² and R¹³ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, quinolinyl, tetrahydroquinolinyl, isoquinolinyl, and tetrahydroisoquinolinyl; wherein said bicyclic heterocyclic ring system is substituted with 0–1 R¹⁶;

R¹⁵ is H, methyl, ethyl, propyl, or butyl;

R¹⁶, at each occurrence, is independently selected from H, OH, F, Cl, CN, NO₂, methyl, ethyl, methoxy, ethoxy, trifluoromethyl, and trifluoromethoxy;

R³³, at each occurrence, is independently selected from H, F, Cl, —CH₃, —OCH₃, —SCH₃, —CF₃, —OCF₃, —CN, and —NO₂;

n is 1; and m is 1.

[7] In an another embodiment, the present invention provides a novel compound of Formula (I-a):

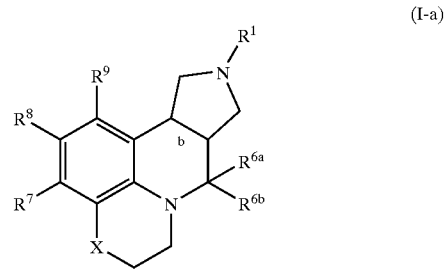

(I-a)

wherein:
  b is a single bond wherein the bridging hydrogens are either cis or trans;
  X is a bond, —CH₂—, —O—, —S—, —OCH₂—, or —SCH₂—;
  R¹ is selected from
    hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl,
    4-methylpentyl, 2-fluoroethyl, 2,2-difluoroethyl, 2,2,2-trifluoroethyl,
    2-propenyl, 2-methyl-2-propenyl, trans-2-butenyl, 3-methyl-2-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl,
    cyclopropyl, cyclobutyl, cyclopentyl, cyclohexyl, cyclopropylmethyl, cyclobutylmethyl, cyclopentylmethyl, cyclohexylmethyl,
    benzyl, 2-methylbenzyl, 3-methylbenzyl, 4-methylbenzyl, 2,5-dimethylbenzyl, 2,4-dimethylbenzyl, 3,5-dimethylbenzyl, 2,4,6-trimethyl-benzyl, 3-methoxy-benzyl, 3,5-dimethoxy-benzyl, pentafluorobenzyl, 2-phenylethyl, 1-phenyl-2-propyl, 4-phenylbutyl, 4-phenylbenzyl, 2-phenylbenzyl,
    (2,3-dimethoxy-phenyl)C(=O)—, (2,5-dimethoxy-phenyl)C(=O)—, (3,4-dimethoxy-phenyl)C(=O)—, (3,5-dimethoxy-phenyl)C(=O)—, cyclopropyl-C(=O)—, isopropyl-C(=O)—, ethyl-CO₂—, propyl-CO₂—, t-butyl-CO₂—, 2,6-dimethoxy-benzyl, 2,4-dimethoxy-benzyl, 2,4,6-trimethoxy-benzyl, 2,3-dimethoxy-benzyl, 2,4,5- trimethoxy-benzyl, 2,3,4-trimethoxy-benzyl, 3,4-dimethoxy-benzyl, 3,4,5-trimethoxy-benzyl, (4-fluoro-phenyl)ethyl,
—CH=CH$_2$, —CH$_2$—CH=CH$_2$, —CH=CH—CH$_3$, —C≡CH, —C—C≡CH$_3$, and —CH$_2$—C≡CH; and $R^{6a}$ is H;

$R^{6b}$ is H;

alternatively, $R^{6a}$ and $R^{6b}$ are taken together to form =O;

$R^7$, $R^8$, and $R^9$, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl;

2-Cl-phenyl; 2-F-phenyl; 2-Br-phenyl; 2-CN-phenyl; 2-Me-phenyl; 2-CF$_3$-phenyl; 2-MeO-phenyl; 2-CF$_3$O-phenyl; 2-NO$_2$-phenyl; 2-MeS-phenyl; 2-CHO-phenyl; 2-HOCH$_2$-phenyl;

3-Cl-phenyl; 3-F-phenyl; 3-Br-phenyl; 3-CN-phenyl; 3-Me-phenyl; 3-Et-phenyl; 3-n-Pr-phenyl; 3-isoPr-phenyl; 3-n-Bu-phenyl; 3-CF$_3$-phenyl; 3-MeO-phenyl; 3-MeS-phenyl; 3-isopropoxyphenyl; 3-CF$_3$O-phenyl; 3-NO$_2$-phenyl; 3-CHO-phenyl; 3-HOCH$_2$-phenyl; 3-MeOCH$_2$-phenyl; 3-Me2NCH$_2$-phenyl;

4-Cl-phenyl; 4-F-phenyl; 4-Br-phenyl; 4-CN-phenyl; 4-Me-phenyl; 4-Et-phenyl; 4-n-Pr-phenyl; 4-iso-Pr-phenyl; 4-n-Bu-phenyl; 4-CF$_3$-phenyl; 4-MeO-phenyl; 4-isopropoxyphenyl; 4-CF$_3$O-phenyl; 4-MeS-phenyl;

4-acetylphenyl; 3-acetamidophenyl; 4-pyridyl; 2-furanyl; 2-thiophenyl; 2-naphtyl; 1-pyrrolidinyl, 2,3-diCl-phenyl; 2,3-diF-phenyl; 2,3-diMe-phenyl; 2,3-diCF$_3$-phenyl; 2,3-diMeo-phenyl; 2,3-diCF$_3$O-phenyl;

2,4-diCl-phenyl; 2,4-diF-phenyl; 2,4-diMe-phenyl; 2,4-diCF$_3$-phenyl; 2,4-diMeo-phenyl; 2,4-diCF$_3$O-phenyl;

2,5-diCl-phenyl; 2,5-diF-phenyl; 2,5-diMe-phenyl; 2,5-diCF$_3$-phenyl; 2,5-diMeO-phenyl; 2,5-diCF$_3$O-phenyl;

2,6-diCl-phenyl; 2,6-diF-phenyl; 2,6-diMe-phenyl; 2,6-diCF$_3$-phenyl; 2,6-diMeO-phenyl; 2,6-diCF$_3$O-phenyl;

3,4-diCl-phenyl; 3,4-diF-phenyl; 3,4-diMe-phenyl; 3,4-diCF$_3$-phenyl; 3,4-diMeO-phenyl; 3,4-diCF$_3$O-phenyl;

2,4,6-triCl-phenyl; 2,4,6-triF-phenyl; 2,4,6-triMe-phenyl; 2,4,6-triCF$_3$-phenyl; 2,4,6-triMeO-phenyl; 2,4,6-triCF$_3$O-phenyl; 2,4,5-triMe-phenyl; 2,3,4-triF-phenyl; 2-Me-4-MeO-5-F-phenyl; 2,6-diCl-4-MeO-phenyl; 2,4-diMeO-6-F-phenyl; 2,6-diF-4-Cl-phenyl; 2,3,4,6-tetraF-phenyl; 2,3,4,5,6-pentaF-phenyl;

2-Cl-4-F-phenyl; 2-Cl-6-F-phenyl; 2-Cl-3-Me-phenyl; 2-Cl-4-MeO-phenyl; 2-Cl-4-EtO-phenyl; 2-Cl-4-iPrO-phenyl; 2-Cl-4-CF$_3$-phenyl; 2-Cl-4-CF$_3$O-phenyl; 2-Cl-4-(CHF2)O-phenyl; 2-F-3-Cl-phenyl; 2-F-4-MeO-phenyl; 2-F-5-Me-phenyl;

2-Me-3-Cl-phenyl; 2-Me-3-CN-phenyl; 2-Me-4-Cl-phenyl; 2-Me-4-F-phenyl; 2-Me-4-CN-phenyl; 2-Me-4-MeO-phenyl; 2-Me-4-EtO-phenyl; 2-Me-4-MeS-phenyl; 2-Me-4-H$_2$NCO-phenyl; 2-Me-4-MeOC(=O)-phenyl; 2-Me-4-CH$_3$C(=O)-phenyl; 2-Me-5-F-phenyl; 2-Et-4-MeO-phenyl; 2-MeO-S-F-phenyl; 2-Meo-4-isopropyl-phenyl; 2-CF$_3$-4-Cl-phenyl; 2-CF$_3$-4-F-phenyl; 2-CF$_3$-4-MeO-phenyl; 2-CF$_3$-4-EtO-phenyl; 2-CF$_3$-4-iPrO-phenyl; 2-CF$_3$-4-CN-phenyl; 2-CF$_3$-6-F-phenyl; 2-CHO-4-MeO-phenyl; 2-MeOC(=O)-3-MeO-phenyl; 2-CH$_3$CH(OH)-4-MeO-phenyl; 2-CH$_3$CH(OH)-4-F-phenyl; 2-CH$_3$CH(OH)-4-Cl-phenyl; 2-CH$_3$CH(OH)-4-Me-phenyl; 2-CH$_3$CH(OMe)-4-MeO-phenyl; 2-CH$_3$C(=O)-4-MeO-phenyl; 2-CH$_3$C(=O)-4-F-phenyl; 2-CH$_3$C(=O)-4-Cl-phenyl; 2-CH$_3$C(=O)-4-Me-phenyl; 2-H$_2$C(OH)-4-MeO-phenyl;

2-H$_2$C(OMe)-4-MeO-phenyl; 2-H$_3$CCH$_2$CH(OH)-4-MeO-phenyl; 2-H$_3$CCH$_2$C(=O)-4-MeO-phenyl; 2-CH$_3$CO$_2$CH$_2$CH$_2$-4-MeO-phenyl; (Z)-2-HOCH$_2$CH=CH-4-MeO-phenyl; (E)-2-HOCH$_2$CH=CH-4-MeO-phenyl; (Z)-2-CH$_3$CO$_2$CH=CH-4-MeO-phenyl; (E)-2-CH$_3$CO$_2$CH=CH-4-MeO-phenyl; 2-CH$_3$OCH$_2$CH$_2$-4-MeO-phenyl;

3-CN-4-F-phenyl; 3-H$_2$NCO-4-F-phenyl; (2-Cl-phenyl)-CH=CH—; (3-Cl-phenyl)-CH=CH—; (2,6-diF-phenyl)-CH=CH—; phenyl-CH=CH—; (2-Me-4-MeO-phenyl)-CH=CH—;

cyclohexyl; cyclopentyl; cyclohexylmethyl; benzyl; 2-F-benzyl; 3-F-benzyl; 4-F-benzyl; 3-MeO-benzyl; 3-OH-benzyl; 2-MeO-benzyl; 2-OH-benzyl; tetrahydroquinolin-1-yl; tetrahydroindolin-1-yl; tetrahydroisoindolin-1-yl;

phenyl-S—; phenyl-NH—; pyrid-3-yl-NH—; (4-Me-pyrid-3-yl)-NH—; (4-Cl-pyrid-3-yl)-NH—; (1-naphthyl)-NH—; (2-naphthyl)-NH—; (2-Me-naphth-1-yl)-NH—; (4-Me-naphth-1-yl)-NH—; (3-quinolinyl)-NH—;

(2-[1,1'-biphenyl])-NH—; (3-[1,1'-biphenyl])-NH—; (4-[1,1'-biphenyl])-NH—; (2-F-phenyl)-NH—; (2-Cl-phenyl)-NH—; (2-CF$_3$-phenyl)-NH—; (2-CH$_3$-phenyl)-NH—; (2-OMe-phenyl)-NH—; (2-CN-phenyl)-NH—; (2-OCF$_3$-phenyl)-NH—; (2-SMe-phenyl)-NH—; (3-F-phenyl)-NH—; (3-Cl-phenyl)-NH—; (3-CF$_3$-phenyl)-NH—; (3-CH$_3$-phenyl)-NH—; (3-OMe-phenyl)-NH—; (3-CN-phenyl)-NH—; (3-OCF$_3$-phenyl)-NH—; (3-SMe-phenyl)-NH—; (4-F-phenyl)-NH—; (4-Cl-phenyl)-NH—; (4-CF$_3$-phenyl)-NH—; (4-CH$_3$-phenyl)-NH—; (4-OMe-phenyl)-NH—; (4-CN-phenyl)-NH—; (4-OCF$_3$-phenyl)-NH—; (4-SMe-phenyl)-NH—; (2,3-diCl-phenyl)-NH—; (2,4-diCl-phenyl)-NH—; (2,5-diCl-phenyl)-NH—; (2,6-diCl-phenyl)-NH—; (3,4-diCl-phenyl)-NH—; (3,5-diCl-phenyl)-NH—; (2,3-diF-phenyl)-NH—; (2,4-diF-phenyl)-NH—; (2,5-diF-phenyl)-NH—; (2,6-diF-phenyl)-NH—; (3,4-diF-phenyl)-NH—; (3,5-diF-phenyl)-NH—; (2,3-diCH$_3$-phenyl)-NH—; (2,4-diCH$_3$-phenyl)-NH—; (2,5-diCH$_3$-phenyl)-NH—; (2,6-diCH$_3$-phenyl)-NH—; (3,4-diCH$_3$-phenyl)-NH—; (3,5-diCH$_3$-phenyl)-NH—; (2,3-diCF$_3$-phenyl)-NH—; (2,4-diCF$_3$-phenyl)-NH—; (2,5-diCF$_3$-phenyl)-NH—; (2,6-diCF$_3$-phenyl)-NH—; (3,4-diCF$_3$-phenyl)-NH—; (3,5-diCF$_3$-phenyl)-NH—; (2,3-diOMe-phenyl)-NH—; (2,4-diOMe-phenyl)-NH—; (2,5-diOMe-phenyl)-NH—; (2,6-diOMe-phenyl)-NH—; (3,4-diOMe-phenyl)-NH—; (3,5-diOMe-phenyl)-NH—; (2-F-3-Cl-phenyl)-NH—; (2-F-4-Cl-phenyl)-NH—; (2-F-5-Cl-phenyl)-NH—; (2-F-6-Cl-phenyl)-NH—; (2-F-3-CH$_3$-phenyl)-NH—; (2-F-4-CH$_3$-phenyl)-NH—; (2-F-5-CH$_3$-phenyl)-NH—; (2-F-6-CH$_3$-phenyl)-NH—; (2-F-3-CF$_3$-phenyl)-NH—; (2-F-4-CF$_3$-phenyl)-NH—;

(2-F-5-CF$_3$-phenyl)-NH—; (2-F-6-CF$_3$-phenyl)-NH—; (2-F-3-OMe-phenyl)-NH—; (2-F-4-OMe-phenyl)-NH—; (2-F-5-OMe-phenyl)-NH—; (2-F-6-OMe-phenyl)-NH—; (2-CF-3-F-phenyl)-NH—; (2-Cl-4-F-phenyl)-NH—; (2-CF-5-F-phenyl)-NH—; (2-CF-6-F-phenyl)-NH—; (2-Cl-3-CH$_3$-phenyl)-NH—; (2-Cl-4-CH$_3$-phenyl)-NH—; (2-F-5-CH$_3$-phenyl )-NH—; (2-Cl-6-CH$_3$-phenyl)-NH—; (2-Cl-3-CF$_3$-phenyl)-NH—; (2-Cl-4-CF$_3$-phenyl)-NH—; (2-F-5-CF$_3$-phenyl)-NH—; (2-Cl-6-CF$_3$-phenyl)-NH—; (2-Cl-3-OMe-phenyl)-NH—; (2-Cl-4-OMe-phenyl)-NH—; (2-Cl-5-OMe-phenyl)-NH—; (2-Cl-6-OMe-phenyl)-NH—; (2-CH$_3$-3-F-phenyl)-NH—; (2-CH$_3$-4-F-phenyl)-NH—; (2-CH$_3$-5-F-phenyl)-NH—; (2-CH$_3$-6-F-phenyl)-NH—; (2-CH$_3$-3-Cl-phenyl)-NH—; (2-CH$_3$-4-Cl-phenyl)-NH—; (2-CH$_3$-5-Cl-phenyl)-NH—; (2-CH$_3$-6-Cl-phenyl)-NH—; (2-CH$_3$-3-CF$_3$-phenyl)-NH—; (2-CH$_3$-4-CF$_3$-phenyl)-NH—; (2-CH$_3$-5-CF$_3$-phenyl)-NH—; (2-CH$_3$-6-CF$_3$-phenyl)-NH—; (2-CH$_3$-3-OMe-phenyl)-NH—; (2-CH$_3$-4-OMe-phenyl)-NH—; (2-CH$_3$-5-OMe-phenyl)-NH—; (2-CH$_3$-6-OMe-phenyl)-NH—; (2-CF$_3$-3-F-phenyl)-NH—; (2-CF$_3$-4-F-phenyl)-NH—; (2-CF$_3$-5-F-phenyl)-NH—; (2-CF$_3$-6-F-phenyl)-NH—; (2-CF$_3$-3-Cl-phenyl)-NH—; (2-CF$_3$-4-Cl-phenyl)-NH—; (2-CF$_3$-5-Cl-phenyl)-NH—; (2-CF$_3$-6-Cl-phenyl)-NH—; (2-CF$_3$-3-CH$_3$-phenyl)-NH—; (2-CF$_3$-4-CH$_3$-phenyl)-NH—; (2-CH$_3$-5-C,F3-phenyl)-NH—; (2-CF$_3$-6-CH$_3$-phenyl)-NH—; (2-CF$_3$-3-OMe-phenyl)-NH—; (2-CF$_3$-4-OMe-phenyl)-NH—; (2-CF$_3$-5-OMe-phenyl)-NH—; (2-CF$_3$-6-OMe-phenyl)-NH—; (2-OMe-3-F-phenyl)-NH—; (2-OMe-4-F-phenyl)-NH—; (2-OMe-5-F-phenyl)-NH—; (2-OMe-6-F-phenyl)-NH—; (2-OMe-3-Cl-phenyl)-NH—; (2-OMe-4-Cl-phenyl)-NH—; (2-OMe-5-Cl-phenyl)-NH—; (2-OMe-6-Cl-phenyl)-NH—; (2-OMe-4-CN-phenyl)-NH—; (2-OMe-4-CHO-phenyl)-NH—; (2-OMe-3-CH$_3$-phenyl)-NH—; (2-OMe-4-CH$_3$-phenyl)-NH—; (2-OMe-5-CH$_3$-phenyl)-NH—; (2-OMe-6-CH$_3$-phenyl)-NH—; (2-OMe-3-CF$_3$-phenyl)-NH—; (2-OMe-4-CF$_3$-phenyl)-NH—; (2-OMe-5-CF$_3$-phenyl)-NH—; (2-OMe-6-CF$_3$-phenyl)-NH—; (2-acetyl-4-Cl-phenyl)-NH—; (2-acetyl-4-Me-phenyl)-NH—; (2-acetyl-4-MeO-phenyl)-NH—; (2-CH$_3$CH(OH)-4-Cl-phenyl)-NH—; (2-CH$_3$CH(OH)-4-Me-phenyl)-NH—; (2-CH$_3$CH(OH)-4-MeO-phenyl)-NH—;
(3-CF$_3$-4-Cl-phenyl)-NH—; (3-F-4-CHO-phenyl)-NH—; (3-CH$_3$-4-CN-phenyl)-NH—; (3-CH$_3$-4-MeO-phenyl)-NH—; (3-CH$_3$-4-Cl-phenyl)-NH—; (3-CH$_3$-4-F-phenyl)-NH—; (3-F-5-CF$_3$-phenyl)-NH—;
(3-CH$_3$-4-CO$_2$Me-phenyl)NH—; (3-CF$_3$-4-C(O)CH$_3$-phenyl)NH—; (3-CHO-4-OMe-phenyl)-NH—; (4-F-3-CF$_3$-phenyl)-NH—;
(2,3,5-triCl-phenyl)-NH—; (2,4,5-triF-phenyl)-NH—; (2,6-diCl-3-Me-phenyl)-NH—; (3,5-diMe-4-MeO-phenyl)-NH—; (2-F-3-Cl-6-CF$_3$-phenyl)-NH—; bynzyl-NH—; (3-quinolinyl)CH$_2$NH—; (2-F-phenyl)CH$_2$NH—; (2-Cl-phenyl)CH$_2$NH—; (2-CF$_3$-phenyl)CH$_2$NH—; (2-CH$_3$-phenyl)CH$_2$NH—; (2-OMe-phenyl)CH$_2$NH—; (2-CN-phenyl)CH$_2$NH—; (2-OCF$_3$-phenyl)CH$_2$NH—; (2-SMe-phenyl)CH$_2$NH—; (3-F-phenyl)CH$_2$NH—; (3-Cl-phenyl)CH$_2$NH—; (3-CF$_3$-phenyl)CH$_2$NH—; (3-CH$_3$-phenyl)CH$_2$NH—; (3-OMe-phenyl)CH$_2$NH—; (3-CN-phenyl)CH$_2$NH—; (3-OCF$_3$-phenyl)CH$_2$NH—; (3-SMe-phenyl)CH$_2$NH—; (4-F-phenyl)CH$_2$NH—; (4-Cl-phenyl)CH$_2$NH—; (4-CF$_3$-phenyl)CH$_2$NH—; (4-CH$_3$-phenyl)CH$_2$NH—; (4OMe-phenyl)CH$_2$NH—; (4-CN-phenyl)CH$_2$NH—; (4-OCF$_3$-phenyl)CH$_2$NH—; (4-SMe-phenyl)CH$_2$NH—; (2,3-diClphenyl)CH$_2$NH—; (2,4-diCl-phenyl)CH$_2$NH—; (2,5-diCl-phenyl)CH$_2$NH—; (2,6-diCl-phenyl)CH$_2$NH—; (3,4-diCl-phenyl)CH$_2$NH—; (3,5-diCl-phenyl)CH$_2$NH—; (2,3-diF-phenyl)CH$_2$NH—; (2,4-diF-phenyl)CH$_2$NH—; (2,5-diF-phenyl)CH$_2$NH—; (2,6-diF-phenyl)CH$_2$NH—; (3,4-diF-phenyl)CH$_2$NH—; (3,5-diF-phenyl)CH$_2$NH—; (2,3-diCH$_3$-phenyl)CH$_2$NH—; (2,4-diCH$_3$-phenyl)CH$_2$NH—; (2,5-diCH$_3$-phenyl)CH$_2$NH—; (2,6-diCH$_3$-phenyl)CH$_2$NH—; (3,4-diCH$_3$-phenyl)CH$_2$NH—; (3,5-diCH$_3$-phenyl)CH$_2$NH—; (2,3-diCF$_3$-phenyl)CH$_2$NH—; (2,4-diCF$_3$-phenyl)CH$_2$NH—; (2,5-diCF$_3$-phenyl)CH$_2$NH—; (2,6-diCF$_3$-phenyl)CH$_2$NH—; (3,4-diCF$_3$-phenyl)CH$_2$NH—; (3,5-diCF$_3$-phenyl)CH$_2$NH—; (2,3-diOMe-phenyl)CH$_2$NH—; (2,4-diOMe-phenyl)CH$_2$NH—; (2,5-diOMe-phenyl)CH$_2$NH—; (2,6-diOMe-phenyl)CH$_2$NH—; (3,4-diOMe-phenyl)CH$_2$NH—; (3,5-diOMe-phenyl)CH$_2$NH—; (2-F-3-Cl-phenyl)CH$_2$NH—; (2-F-4-Cl-phenyl)CH$_2$NH—; (2-F-5-Cl-phenyl)CH$_2$NH—; (2-F-6-Cl-phenyl)CH$_2$NH—; (2-F-3-CH$_3$-phenyl)CH$_2$NH—; (2-F-4-CH$_3$-phenyl)CH$_2$NH—; (2-F-5-CH$_3$-phenyl)CH$_2$NH—; (2-F-6-CH$_3$-phenyl)CH$_2$NH—; (2-F-3-CF$_3$-phenyl)CH$_2$NH—; (2-F-4-CF$_3$-phenyl)CH$_2$NH—; (2-F-5-CF$_3$-phenyl)CH$_2$NH—; (2-F-6-CF$_3$-phenyl)CH$_2$NH—; (2-F-3-OMe-phenyl)CH$_2$NH—; (2-F-4-OMe-phenyl)CH$_2$NH—; (2-F-5-OMe-phenyl)CH$_2$NH—; (2-F-6-OMe-phenyl)CH$_2$NH—; (2-Cl-3-F-phenyl)CH$_2$NH—; (2-Cl-4-F-phenyl)CH$_2$NH—; (2-Cl-5-F-phenyl)CH$_2$NH—; (2-Cl-6-F-phenyl)CH$_2$NH—; (2-Cl-3-CH$_3$-phenyl)CH$_2$NH—; (2-Cl-4-CH$_3$-phenyl)CH$_2$NH—; (2-Cl-5-CH$_3$-phenyl)CH$_2$NH—; (2-Cl-6-CH$_3$-phenyl)CH$_2$NH—; (2-Cl-3-CF$_3$-phenyl)CH$_2$NH—; (2-Cl-4-CF$_3$-phenyl)CH$_2$NH—; (2-F-5-CF$_3$-phenyl)CH$_2$NH—; (2-Cl-6-CF$_3$-phenyl)CH$_2$NH—; (2-Cl-3-OMe-phenyl)CH$_2$NH—; (2-Cl-4-OMe-phenyl)CH$_2$NH—; (2-Cl-5-OMe-phenyl)CH$_2$NH—; (2-Cl-6-OMe-phenyl)CH$_2$NH—; (2-CH$_3$-3-F-phenyl)CH$_2$NH—; (2-CH$_3$-4-F-phenyl)CH$_2$NH—; (2-CH$_3$-5-F-phenyl)CH$_2$NH—; (2-CH$_3$-6-F-phenyl)CH$_2$NH—; (2-CH$_3$-3-Cl-phenyl)CH$_2$NH—; (2-CH$_3$-4-Cl-phenyl)CH$_2$NH—; (2-CH$_3$-5-Cl-phenyl)CH$_2$NH—; (2-CH$_3$-6-Cl-phenyl)CH$_2$NH—; (2-CH$_3$-3-CF$_3$-phenyl)CH$_2$NH—; (2-CH$_3$-4-CF$_3$-phenyl)CH$_2$NH—; (2-CH$_3$-5-CF$_3$-phenyl)CH$_2$NH—; (2-CH$_3$-6-CF$_3$-phenyl)CH$_2$NH—; (2-CH$_3$-3-OMe-phenyl)CH$_2$NH—; (2-CH$_3$-4-OMe-phenyl)CH$_2$NH—; (2-CH$_3$-5-OMe-phenyl)CH$_2$NH—; (2-CH$_3$-6-OMe-phenyl)CH$_2$NH—; (2-CF$_3$-3-F-phenyl)CH$_2$NH—; (2-CF$_3$-4-F-phenyl)CH$_2$NH—; (2-CF$_3$-5-F-phenyl)CH$_2$NH—; (2-CF$_3$-6-F-phenyl)CH$_2$NH—; (2-CF$_3$-3-Cl-phenyl)CH$_2$NH—; (2-CF$_3$-4-Cl-phenyl)CH$_2$NH—; (2-CF$_3$-5-Cl-phenyl)CH$_2$NH—; (2-CF$_3$-6-Cl-phenyl)CH$_2$NH—; (2-CF$_3$-3-CH$_3$-phenyl)CH$_2$NH—; (2-CF$_3$-4-CH$_3$-phenyl)CH$_2$NH—; (2-CH$_3$-5-CF$_3$-phenyl)CH$_2$NH—; (2-CF$_3$-6-CH$_3$-phenyl)CH$_2$NH—; (2-CF$_3$-3-OMephenyl)CH₂NH—; (2-CF₃-4-OMe-phenyl) CH₂NH—; (2-CF₃-5-OMe-phenyl)CH₂NH—; (2.-CF₃-6-OMe-phenyl)CH₂NH—; (2-OMe-3-F-phenyl)CH₂NH—; (2-OMe-4-F-phenyl)CH₂NH—; (2-OMe- 5-F-phenyl)CH₂NH—; (2-OMe-6-F-phenyl)CH₂NH—; (2-OMe-3-Cl-phenyl)CH₂NH—; (2-OMe-4-Cl-phenyl)CH₂NH—; (2-OMe-5-Cl-phenyl)CH₂NH—; (2-OMe-6-Cl-phenyl)CH₂NH—; (2-OMe-4-CN-phenyl)CH₂NH—; (2-OMe-4-CHO-phenyl)CH₂NH—; (2-OMe-3-CH₃-phenyl) CH₂NH—; (2-OMe-4-CH₃-phenyl)CH₂NH—; (2-OMe-5-CH₃-phenyl)CH₂NH—; (2-OMe-6-CH₃-phenyl)CH₂NH—; (2-OMe-3-CF₃-phenyl) CH₂NH—; (2-OMe-4-CF₃-phenyl)CH₂NH—; (2-OMe-5-CF₃-phenyl)CH₂NH—; (2-OMe-6-CF₃-phenyl)CH₂NH—; (2-acetyl-4-Cl-phenyl) CH₂NH—; (2-acetyl-4-Me-phenyl)CH₂NH—; (2-acetyl-4-MeO-phenyl)CH₂NH—; (2-CH₃CH(OH)-4-Cl-phenyl)CH₂NH—; (2-CH₃CH(OH)-4-Me-phenyl)CH₂NH—; (2-CH₃CH(OH)-4-MeO-phenyl)CH₂NH—;

(3-CF₃-4-Cl-phenyl)CH₂NH—; (3-F-4-CHO-phenyl) CH₂NH—; (3-CH₃-4-CN-phenyl)CH₂NH—; (3-CH₃-4-MeO-phenyl)CH₂NH—; (3-CH₃-4-Cl-phenyl)CH₂NH—; (3-CH₃-4-F-phenyl)CH₂NH—; (4-F-3-CF₃-phenyl)CH₂NH—; (3-CH₃-4-CO₂Me-phenyl)CH₂NH—; (3-CF₃-4-C(O)CH₃-phenyl) CH₂NH—; (3-CHO-4-OMe-phenyl)CH₂NH—;

(2,3,5-triCl-phenyl)CH₂NH—; (2,4,5-triF-phenyl) CH₂NH—; (2,6-diCl-3-Me-phenyl)CH₂NH—; (3,5-diMe-4-MeO-phenyl)CH₂NH—; and (2-F-3-Cl-6-CF₃-phenyl)CH₂NH—;

provided that two of R⁷, R⁸, and R⁹, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy.

[8] In an another embodiment, the present invention provides a novel compound of Formula (II):

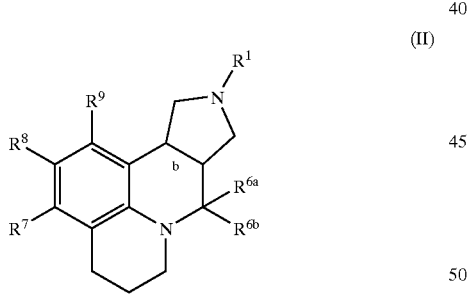

(II)

wherein:
b is a single bond, wherein the bridge hydrogens are in a cis or trans position;
R¹ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-2-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, —CH=CH₂, —CH₂—CH=CH₂, —CH=CH—CH₃, —C≡CH, —C≡—C—CH₃, and —CH₂—C≡CH;

R⁶ᵃ is H;

R⁶ᵇ is H;

alternatively, R⁶ᵃ and R⁶ᵇ are taken together to form =O;

R⁷ and R⁹, at each occurrence, are independently selected from hydrogen, fluoro, methyl, trifluoromethyl, and methoxy;

R⁸ is selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl;

2-Cl-phenyl; 2-F-phenyl; 2-Br-phenyl; 2-CN-phenyl; 2-Me-phenyl; 2-CF₃-phenyl; 2-MeO-phenyl; 2-CF₃O-phenyl; 2-NO₂-phenyl; 2-MeS-phenyl; 2-CHO-phenyl; 2-HOCH₂-phenyl;

3-Cl-phenyl; 3-F-phenyl; 3-Br-phenyl; 3-CN-phenyl; 3-Me-phenyl; 3-Et-phenyl; 3-n-Pr-phenyl; 3-isoPr-phenyl; 3-n-Bu-phenyl; 3-CF₃-phenyl; 3-MeO-phenyl; 3-MeS-phenyl; 3-isopropoxyphenyl; 3-CF₃O-phenyl; 3-NO₂-phenyl; 3-CHO-phenyl; 3-HOCH₂-phenyl; 3-MeOCH₂-phenyl; 3-Me₂NCH₂-phenyl;

4-Cl-phenyl; 4-F-phenyl; 4-Br-phenyl; 4-CN-phenyl; 4-Me-phenyl; 4-Et-phenyl; 4-n-Pr-phenyl; 4-iso-Pr-phenyl; 4-n-Bu-phenyl; 4-CF₃-phenyl; 4-MeO-phenyl; 4-isopropoxyphenyl; 4-CF₃O-phenyl; 4-MeS-phenyl;

4-acetylphenyl; 3-acetamidophenyl; 4-pyridyl; 2-furanyl; 2-thiophenyl; 2-naphthyl; 1-pyrrolidinyl, 2,3-diCl-phenyl; 2,3-diF-phenyl; 2,3-diMe-phenyl; 2,3-diCF₃-phenyl; 2,3-diMeo-phenyl; 2,3-diCF₃O-phenyl;

2,4-diCl-phenyl; 2,4-diF-phenyl; 2,4-diMe-phenyl; 2,4-diCF₃-phenyl; 2,4-diMeo-phenyl; 2,4-diCF₃O-phenyl;

2,5-diCl-phenyl; 2,5-dir-phenyl; 2,5-diMe-phenyl; 2,5-diCF₃-phenyl; 2, 5-diMeo-phenyl; 2, 5-diCF₃O-phenyl;

2,6-diCl-phenyl; 2,6-diF-phenyl; 2,6-diMe-phenyl; 2,6-diCF₃-phenyl; 2,6-diMeo-phenyl; 2,6-diCF₃O-phenyl;

3,4-diCl-phenyl; 3,4-diF-phenyl; 3,4-diMe-phenyl; 3,4-diCF₃-phenyl; 3,4-diMeO-phenyl; 3,4-diCF₃O-phenyl;

2,4,6-triCl-phenyl; 2,4,6-triF -phenyl; 2,4,6-triMe-phenyl; 2,4,6-triCF₃-phenyl; 2,4,6-triMeo-phenyl; 2,4,6-triCF₃O-phenyl; 2,4,5-triMe-phenyl; 2,3,4-triF-phenyl; 2-Me-4-Meo-F-phenyl; 2,6-diCl-4-Meo- phenyl; 2,4-diMeo-6-F-phenyl; 2,6-diF-4-Cl-phenyl; 2,3,4,6-tetraF-phenyl; 2,3,4,5,6-pentaF-phenyl; 2-Cl-4-F-phenyl; 2-Cl-6-F-phenyl; 2-Cl-3-Me-phenyl; 2-Cl-4-MeO-phenyl; 2-Cl-4-EtO-phenyl; 2-Cl-4-iPrO-phenyl; 2-Cl-4-CF₃-phenyl; 2-Cl-4-CF₃O-phenyl; 2-Cl-4-(CHF₂)O-phenyl; 2-F-3-Cl-phenyl; 2-F-4-MeO-phenyl; 2-F-5-Me-phenyl;

2-Me-3-Cl-phenyl; 2-Me-3-CN-phenyl; 2-Me-4-Cl-phenyl; 2-Me-4-F-phenyl; 2-Me-4-CN-phenyl; 2-Me-4-MeO-phenyl; 2-Me-4-EtO-phenyl; 2-Me-4-MeS-phenyl; 2-Me-4-H₂NCO-phenyl; 2-Me-4-MeOC(=O)-phenyl; 2-Me-4-CH₃C(=O)-phenyl; 2-Me-5-F-phenyl; 2-Et-4-MeO-phenyl; 2-MeO-5-F-phenyl; 2-MeO-4-isopropyl-phenyl; 2-CF₃-4-Clphenyl; 2-CF₃-4-F-phenyl; 2-CF₃-4-MeO-phenyl; 2-CF₃-4-EtO-phenyl; 2-CF₃-4-iPrO-phenyl; 2-CF₃-4-CN-phenyl; 2-CF₃-6-F-phenyl; 2-CHO-4-MeO-phenyl; 2-MeOC(=O)-3-MeO-phenyl; 2-CH₃CH(OH)-4-MeO-phenyl; 2-CH₃CH(OH)-4-F-phenyl; 2-CH₃CH(OH)-4-Cl-phenyl; 2-CH₃CH(OH)-4-Me-phenyl; 2-CH₃CH(OMe)-4-MeO-phenyl; 2-CH₃C(=O)-4-MeO-phenyl; 2-CH₃C(=O)-4-F-phenyl; 2-CH₃C(=O)-4-Cl-phenyl; 2-CH₃C(=O)-4-Me-phenyl; 2-H₂C(OH)-4-MeO-phenyl; 2-H₂C(OMe)-4-MeO-phenyl; 2-H₃CCH₂CH(OH)-4-MeO-phenyl; 2-H₃CCH₂C(=O)-4-MeO-phenyl; 2-CH₃CO₂CH₂CH₂-4-MeO-phenyl; (Z)-2-HOCH₂CH=CH-4-MeO-phenyl; (E)-2-HOCH₂CH=CH-4-MeO-phenyl; (Z)-2-CH₃CO₂CH=CH-4-MeO-phenyl; (E)-2-CH₃CO₂CH=CH-4-MeO-phenyl; 2-CH₃OCH₂CH₂-4-MeO-phenyl;

3-CN-4-F-phenyl; 3-H₂NCO-4-F-phenyl; (2-Cl-phenyl)-CH=CH—; (3-Cl-phenyl)-CH=CH—; (2,6-diF-phenyl)-CH=CH—; phenyl-CH=CH—; (2-Me-4-MeO-phenyl)-CH=CH—;

cyclohexyl; cyclopentyl; cyclohexylmethyl; benzyl; 2-F-benzyl; 3-F-benzyl; 4-F-benzyl; 3-MeO-benzyl; 3-OH-benzyl; 2-MeO-benzyl; 2-OH-benzyl; tetrahydroquinolin-1-yl; tetrahydroindolin-1-yl; tetrahydroisoindolin-1-yl;

phenyl-S—; phenyl-NH—; pyrid-3-yl-NH—; (4-Me-pyrid-3-yl)-NH—; (4-Cl-pyrid-3-yl)-NH—; (1-naphthyl)-NH—; (2-naphthyl)-NH—; (2-Me-naphth-1-yl)-NH—; (4-Me-naphth-1-yl)-NH—; (3-quinolinyl)-NH—;

(2-[1,1'-biphenyl])-NH—; (3-[1,1'-biphenyl])-NH—; (4-[1,1'-biphenyl])-NH—; (2-F-phenyl)-NH—; (2-Cl-phenyl)-NH—; (2-CF₃-phenyl)-NH—; (2-CH₃-phenyl)-NH—; (2-OMe-phenyl)-NH—; (2-CN-phenyl)-NH—; (2-OCF₃-phenyl)-NH—; (2-SMe-phenyl)-NH—; (3-F-phenyl)-NH—; (3-Cl-phenyl)-NH—; (3-CF₃-phenyl)-NH—; (3-CH₃-phenyl)-NH—; (3-OMe-phenyl)-NH—; (3-CN-phenyl)-NH—; (3-OCF₃-phenyl)-NH—; (3-SMe-phenyl)-NH—; (4-F-phenyl)-NH—; (4-Cl-phenyl)-NH—; (4-CF₃-phenyl)-NH—; (4-CH₃-phenyl)-NH—; (4-OMe-phenyl)-NH—; (4-CN-phenyl)-NH—; (4-OCF₃-phenyl)-NH—; (4-SMe-phenyl)-NH—; (2,3-diCl-phenyl)-NH—; (2,4-diCl-phenyl)-NH—; (2,5-diCl-phenyl)-NH—; (2,6-diCl-phenyl)-NH—; (3,4-diCl-phenyl)-NH—; (3,5-diCl-phenyl)-NH—; (2,3-diF-phenyl)-NH—; (2,4-diF-phenyl)-NH—; (2,5-diF-phenyl)-NH—; (2,6-diF-phenyl)-NH—; (3,4-diF-phenyl)-NH—; (3,5-diF-phenyl)-NH—; (2,3-diCH₃-phenyl)-NH—; (2,4-diCH₃-phenyl)-NH—; (2,5-diCH₃-phenyl)-NH—; (2,6-diCH₃-phenyl)-NH—; (3,4-diCH₃-phenyl)-NH—; (3,5-diCH₃-phenyl)-NH—; (2,3-diCF₃-phenyl)-NH—; (2,4-diCF₃-phenyl)-NH—; (2,5-diCF₃-phenyl)-NH—; (2,6-diCF₃-phenyl)-NH—; (3,4-diCF₃-phenyl)-NH—; (3,5-diCF₃-phenyl)-NH—; (2,3-diOMe-phenyl)-NH—; (2,4-diOMe-phenyl)-NH—; (2,5-diOMe-phenyl)-NH—; (2,6-diOMe-phenyl)-NH—; (3,4-diOMe-phenyl)-NH—; (3,5-diOMe-phenyl)-NH—; (2-F-3-Cl-phenyl)-NH—; (2-F-4-Cl-phenyl)-NH—; (2-F-5-Cl-phenyl)-NH—; (2-F-6-Cl-phenyl)-NH—; (2-F-3-CH₃-phenyl)-NH—; (2-F-4-CH₃-phenyl)-NH—; (2-F-5-CH₃-phenyl)-NH—; (2-F-6-CH₃-phenyl)-NH—; (2-F-3-CF₃-phenyl)-NH—; (2-F-4-CF₃-phenyl)-NH—; (2-F-5-CF₃-phenyl)-NH—; (2-F-6-CF₃-phenyl)-NH—; (2-F-3-OMe-phenyl)-NH—; (2-F-4-OMe-phenyl)-NH—; (2-F-5-OMe-phenyl)-NH—; (2-F-6-OMe-phenyl)-NH—; (2-Cl-3-F-phenyl)-NH—; (2-Cl-4-F-phenyl)-NH—; (2-Cl-5-F-phenyl)-NH—; (2-Cl-6-F-phenyl)-NH—; (2-Cl-3-CH₃-phenyl)-NH—; (2-Cl-4-CH₃-phenyl)-NH—; (2-Cl-5-CH₃-phenyl)-NH—; (2-Cl-6-CH₃-phenyl)-NH—; (2-Cl-3-CF₃-phenyl)-NH—; (2-Cl-4-CF₃-phenyl)-NH—; (2-F-5-CF₃-phenyl)-NH—; (2-Cl-6-CF₃-phenyl)-NH—; (2-Cl-3-OMe-phenyl)-NH—; (2-Cl-4-OMe-phenyl)-NH—; (2-Cl-5-OMe-phenyl)-NH—; (2-Cl-6-OMe-phenyl)-NH—; (2-CH₃-3-F-phenyl)-NH—; (2-CH₃-4-F-phenyl)-NH—; (2-CH₃-5-F-phenyl)-NH—; (2-CH₃-6-F-phenyl)-NH—; (2-CH₃-3-Cl-phenyl)-NH—; (2-CH₃-4-Cl-phenyl)-NH—; (2-CH₃-5-Cl-phenyl)-NH—; (2-CH₃-6-Cl-phenyl)-NH—; (2-CH₃-3-CF₃-phenyl)-NH—; (2-CH₃-4-CF₃-phenyl)-NH—; (2-CH₃-5-CF₃-phenyl)-NH—; (2-CH₃-6-CF₃-phenyl)-NH—; (2-CH₃-3-OMe-phenyl)-NH—; (2-CH₃-4-OMe-phenyl)-NH—; (2-CH₃-5-OMe-phenyl)-NH—; (2-CH₃-6-OMe-phenyl)-NH—; (2-CF₃-3-F-phenyl)-NH—; (2-CF₃-4-F-phenyl)-NH—; (2-CF₃-5-F-phenyl)-NH—; (2-CF₃-6-F-phenyl)-NH—; (2-CF₃-3-Cl-phenyl)-NH—; (2-CF₃-4-Cl-phenyl)-NH—; (2-CF₃-5-Cl-phenyl)-NH—; (2-CF₃-6-Cl-phenyl)-NH—; (2-CF₃-3-CH₃-phenyl)-NH—; (2-CF₃-4-CH₃-phenyl)-NH—; (2-CF₃-5-CH₃-phenyl)-NH—; (2-CF₃-6-CH₃-phenyl)-NH—; (2-CF₃-3-OMe-phenyl)-NH—; (2-CF₃-4-OMe-phenyl)-NH—; (2-CF₃-5-OMe-phenyl)-NH—; (2-CF₃-6-OMe-phenyl)-NH—; (2-OMe-3-F-phenyl)-NH—; (2-OMe-4-F-phenyl)-NH—; (2-OMe-5-F-phenyl)-NH—; (2-OMe-6-F-phenyl)-NH—; (2-OMe-3-Cl-phenyl)-NH—; (2-OMe-4-Cl-phenyl)-NH—; (2-OMe-5-Cl-phenyl)-NH—; (2-OMe-6-Cl-phenyl)-NH—; (2-OMe-4-CN-phenyl)-NH—; (2-OMe-4-CHO-phenyl)-NH—; (2-OMe-3-CH₃-phenyl)-NH—; (2-OMe-4-CH₃-phenyl)-NH—; (2-OMe-5-CH₃-phenyl)-NH—; (2-OMe-6-CH₃-phenyl)-NH—; (2-OMe-3-CF₃-phenyl)-NH—; (2-OMe-4-CF₃-phenyl)-NH—; (2-OMe-5-CF₃-phenyl)-NH—; (2-OMe-6-CF₃-phenyl)-NH—; (2-acetyl-4-C₁-phenyl)-NH—; (2-acetyl-4-Me-phenyl)-NH—; (2-acetyl-4-MeO-phenyl)-NH—; (2-CCH₃CH(OH)-4-Cl-phenyl)-NH—; (2-CH₃CH(OH)-4-Me-phenyl)-NH—; (2-CH₃CH(OH)-4-MeO-phenyl)-NH—;

(3-CF₃-4-Cl-phenyl)-NH—; (3-F-4-CHO-phenyl)-NH—; (3-CH₃-4-CN-phenyl)-NH—; (3-CH₃-4-MeO-phenyl)-NH—; (3-CH₃-4-Cl-phenyl)-NH—; (3-CH₃-4-F-phenyl)-NH—; (3-F-5-CF₃-phenyl)-NH—;

(3-CH₃-4-CO₂Me-phenyl)NH—; (3-CF₃-4-C(O)CH₃-phenyl)NH—; (3-CHO-4-OMe-phenyl)-NH—; (4-F-3-CF₃-phenyl)-NH—;

(2,3,5-triCl-phenyl)-NH—; (2,4,5-triF-phenyl)-NH—; (2,6-diCl-3-Me-phenyl)-NH—; (3,5-diMe-4-MeO-phenyl)-NH—; (2-F-3-Cl-6-CF₃-phenyl)-NH—;

benzyl-NH—; (3-quinolinyl)CH₂NH—; (2-F-phenyl)CH₂NH—; (2-Cl-phenyl)CH₂NH—; (2-CF₃-phenyl)CH₂NH—; (2-CH₃-phenyl)CH₂NH—; (2-OMe-phenyl)CH₂NH—; (2-CN-phenyl)CH₂NH—; (2-OCF₃-phenyl)CH₂NH—; (2-SMe-phenyl)CH₂NH—; (3-F-phenyl)CH₂NH—; (3-Cl-phenyl)CH₂NH—; (3-CF₃-phenyl)CH₂NH—;

(3-CH₃-phenyl)CH₂NH—; (3-OMe-phenyl)CH₂NH—; (3-CN-phenyl)CH₂NH—; (3-OCF₃-phenyl)CH₂NH—; (3-SMe-phenyl)CH₂NH—; (4-F-phenyl)CH₂NH—; (4-Cl-phenyl)CH₂NH—; (4-CF₃-phenyl)CH₂NH—; (4-CH₃-phenyl)CH₂NH—; (4-OMe-phenyl)CH₂NH—; (4-CN-phenyl)CH₂NH—; (4-OCF₃-phenyl)CH₂NH—; (4-SMe-phenyl)CH₂NH—; (2,3-diCl-phenyl)CH₂NH—; (2,4-diCl-phenyl)CH₂NH—; (2,5-diCl-phenyl)CH₂NH—; (2,6-diCl-phenyl)CH₂NH—; (3,4-diCl-phenyl)CH₂NH—; (3,5-diCl-phenyl)CH₂NH—; (2,3-diF-phenyl)CH₂NH—; (2,4-diF-phenyl)CH₂NH—; (2,5-diF-phenyl)CH₂NH—; (2,6-diF-phenyl)CH₂NH—; (3,4-diF-phenyl)CH₂NH—; (3,5-diF-phenyl)CH₂NH—; (2,3-diCH₃-phenyl)CH₂NH—; (2,4-diCH₃-phenyl)CH₂NH—; (2,5-diCH₃-phenyl)CH₂NH—; (2,6-diCH₃-phenyl)CH₂NH—; (3,4-diCH₃-phenyl)CH₂NH—; (3,5-diCH₃-phenyl)CH₂NH—; (2,3-diCF₃-phenyl)CH₂NH—; (2,4-diCF₃-phenyl)CH₂NH—; (2,5-diCF₃-phenyl)CH₂NH—; (2,6-diCF₃-phenyl)CH₂NH—; (3,4-diCF₃-phenyl)CH₂NH—; (3,5-diCF₃-phenyl)CH₂NH—; (2,3-diOMe-phenyl)CH₂NH—; (2,4-diOMe-phenyl)CH₂NH—; (2,5-diOMe-phenyl)CH₂NH—; (2,6-diOMe-phenyl)CH₂NH—; (3,4-diOMe-phenyl)CH₂NH—; (3,5-diOMe-phenyl)CH₂NH—; (2-F-3-Cl-phenyl)CH₂NH—; (2-F-4-Cl-phenyl)CH₂NH—; (2-F-5-Cl-phenyl)CH₂NH—; (2-F-6-Cl-phenyl)CH₂NH—; (2-F-3-CH₃-phenyl)CH₂NH—; (2-F-4-CH₃-phenyl)CH₂NH—; (2-F-5-CH₃-phenyl)CH₂NH—; (2-F-6-CH₃-phenyl)CH₂NH—; (2-F-3-CF₃-phenyl)CH₂NH—; (2-F-4-CF₃-phenyl)CH₂NH—; (2-F-5-CF₃-phenyl)CH₂NH—; (2-F-6-CF₃-phenyl)CH₂NH—; (2-F-3-OMe-phenyl)CH₂NH—; (2-F-4-OMe-phenyl)CH₂NH—; (2-F-5-OMe-phenyl)CH₂NH—; (2-F-6-OMe-phenyl)CH₂NH—; (2-Cl-3-F-phenyl)CH₂NH—; (2-Cl-4-F-phenyl)CH₂NH—; (2-Cl-5-F-phenyl)CH₂NH—; (2-Cl-6-F-phenyl)CH₂NH—; (2-Cl-3-CH₃-phenyl)CH₂NH—; (2-Cl-4-CH₃-phenyl)CH₂NH—; (2-Cl-5-CH₃-phenyl)CH₂NH—; (2-Cl-6-CH₃-phenyl)CH₂NH—; (2-Cl-3-CF₃-phenyl)CH₂NH—; (2-Cl-4-CF₃-phenyl)CH₂NH—; (2-Cl-5-CF₃-phenyl)CH₂NH—; (2-Cl-6-CF₃-phenyl)CH₂NH—; (2-Cl-3-OMe-phenyl)CH₂NH—; (2-Cl-4-OMe-phenyl)CH₂NH—; (2-Cl-5-OMe-phenyl)CH₂NH—; (2-Cl-6-OMe-phenyl)CH₂NH—; (2-CH₃-3-F-phenyl)CH₂NH—; (2-CH₃-4-F-phenyl)CH₂NH—; (2-CH₃-5-F-phenyl)CH₂NH—; (2-CH₃-6-F-phenyl)CH₂NH—; (2-CH₃-3-Cl-phenyl)CH₂NH—; (2-CH₃-4-Cl-phenyl)CH₂NH—; (2-CH₃-5-Cl-phenyl)CH₂NH—; (2-CH₃-6-Cl-phenyl)CH₂NH—; (2-CH₃-3-CF₃-phenyl)CH₂NH—; (2-CH₃-4-CF₃-phenyl)CH₂NH—; (2-CH₃-5-CF₃-phenyl)CH₂NH—; (2-CH₃-6-CF₃-phenyl)CH₂NH—; (2-CH₃-3-OMe-phenyl)CH₂NH—; (2-CH₃-4-OMe-phenyl)CH₂NH—; (2-CH₃-5-OMe-phenyl)CH₂NH—; (2-CH₃-6-OMe-phenyl)CH₂NH—; (2-CF₃-3-F-phenyl)CH₂NH—; (2-CF₃-4-F-phenyl)CH₂NH—; (2-CF₃-5-F-phenyl)CH₂NH—; (2-CF₃-6-F-phenyl)CH₂NH—; (2-CF₃-3-Cl-phenyl)CH₂NH—; (2-CF₃-4-Cl-phenyl)CH₂NH—; (2-CF₃-5-Cl-phenyl)CH₂NH—; (2-CF₃-6-Cl-phenyl)CH₂NH—; (2-CF₃-3-CH₃-phenyl)CH₂NH—; (2-CF₃-4-CH₃-phenyl)CH₂NH—; (2-CF₃-5-CH₃-phenyl)CH₂NH—; (2-CF₃-6-CH₃-phenyl)CH₂NH—; (2-CF₃-3-OMe-phenyl)CH₂NH—; (2-CF₃-4-OMe-phenyl)CH₂NH—; (2-CF₃-5-OMe-phenyl)CH₂NH—; (2-CF₃-6-OMe-phenyl)CH₂NH—; (2-OMe-3-F-phenyl)CH₂NH—; (2-OMe-4-F-phenyl)CH₂NH—; (2-OMe-5-F-phenyl)CH₂NH—; (2-OMe-6-F-phenyl)CH₂NH—; (2-OMe-3-Cl-phenyl)CH₂NH—; (2-OMe-4-Cl-phenyl)CH₂NH—; (2-OMe-5-Cl-phenyl)CH₂NH—; (2-OMe-6-Cl-phenyl)CH₂NH—; (2-OMe-4-CN-phenyl)CH₂NH—; (2-OMe-4-CHO-phenyl)CH₂NH—; (2-OMe-3-CH₃-phenyl)CH₂NH—; (2-OMe-4-CH₃-phenyl)CH₂NH—; (2-OMe-5-CH₃-phenyl)CH₂NH—; (2-OMe-6-CH₃-phenyl)CH₂NH—; (2-Oe-3-CF₃-phenyl)CH₂NH—; (2-OMe-4-CH₃-phenyl)CH₂NH—; (2-OMe-3-CF₃-phenyl)CH₂NH—; (2-OMe-6-CF₃-phenyl)CH₂NH—; (2-OMe-5-CF₃-phenyl)CH₂NH—; (2-acetyl-4-Me-phenyl)CH₂NH—; (2-acetyl-4-MeO-phenyl)CH₂NH—; (2-CH₃CH(OH)-4-Cl-phenyl)CH₂NH—; (2-CH₃CH(OH)-4-Me-phenyl)CH₂NH—; (2-CH₃CH(OH)-4-MeO-phenyl)CH₂NH—;

(3-CF₃-4-Cl-phenyl)CH₂NH—; (3-F-4-CHO-phenyl)CH₂NH—; (3-CH₃-4-CN-phenyl)CH₂NH—; (3-CH₃-4-MeO-phenyl)CH₂NH—; (3-CH₃-4-Cl-phenyl)CH₂NH—; (3-CH₃-4-F-phenyl)CH₂NH—; (4F-3-CF₃-phenyl)CH₂NH—; (3-CH₃-4-CO₂Me-phenyl)CH₂NH—; (3-CF₃-4-C(O)CH₃-phenyl)CH₂NH—; (3-CHO-4-OMe-phenyl)CH₂NH—;

(2,3,5-triCl-phenyl)CH₂NH—; (2,4,5-triF-phenyl)CH₂NH—; (2,6-diCl-3-Me-phenyl)CH₂NH—; (3,5-diMe-4-MeO-phenyl)CH₂NH—; and (2-F-3-Cl-6-CF₃-phenyl)CH₂NH—.

[9] In an another genus of each of the above embodiments, the present invention provides a novel compound of Formula (I) wherein X is a bond.

[10] In an another genus of each of the above embodiments, the present invention provides a novel compound of Formula (I) wherein X is —O— or —S—.

[11] In an another genus of each of the above embodiments, the present invention provides a novel compound of Formula (I) wherein X is —OCH₂— or —SCH₂—.

[12] In an another genus of each of the above embodiments, the present invention provides a novel compound of Formula (I) wherein X is —CH₂—.

[13] In an another embodiment, the present invention provides a novel compound of Formula (I) wherein:

X is a bond, —CH₂—, —O—, —S—, —S(=O)—, —S(=O)₂—, —NR¹⁰—, —CH₂CH₂—, —OCH₂—, —SCH₂—, —CH₂O—, —CH₂S—, or —CH₂NR¹⁰—;

R¹ is selected from
  C$_{1-6}$ alkyl substituted with Z,
  C$_{2-6}$ alkenyl substituted with Z,
  C$_{2-6}$ alkynyl substituted with Z,
  C$_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  C$_{1-6}$ alkyl substituted with 0–2 R²,
  C$_{2-6}$ alkenyl substituted with 0–2 R²,
  C$_{2-6}$ alkynyl substituted with 0–2 R²,
  aryl substituted with 0–2 R², and
  5–6 membered heterocyclic ring system containing at least one heteroatom selected from the group consisting of N, O. and S, said heterocyclic ring system substituted with 0–2 R²;

Z is selected from H,
—CH(OH)R$^2$,
—C(ethylenedioxy)R$^2$,
—OR$^2$,
—SR$^2$,
—NR$^2$R$^3$
—C(O)R$_2$,
—C(O)NR$^2$R$^3$,
—NR$^3$C(O)R$^2$,
—C(O)OR$^2$,
—OC(O)R$^2$,
—CH(=NR$^4$)NR$^2$R$^3$,
—NHC(=NR$^4$)NR$^2$R$^3$,
—S(O)R$^2$,
—S(O)$_2$R$^2$,
—S(O)$_2$NR$^2$R$^3$, and —NR$^3$S(O)$_2$R$^2$;

R$^2$, at each occurrence, is independently selected from
C$_{1-4}$ alkyl,
C$_{2-4}$ alkenyl,
C$_{2-4}$ alkynyl,
C$_{3-6}$ cycloalkyl,
aryl substituted with 0–5 R$^{42}$;
C$_{3-10}$ carbocyclic residue substituted with 0–3 R$^{41}$, and
5–10 membered heterocyclic ring system containing from 1–4 heteroatoms selected from the group consisting of N, O, and S substituted with 0–3 R$^{41}$;

R$^3$, at each occurrence, is independently selected from H, C$_{1-4}$ alkyl, C$_{2-4}$ alkenyl, C$_{2-4}$ alkynyl, and C$_{1-4}$ alkoxy;

alternatively, R$^2$ and R$^3$ join to form a 5- or 6-membered ring optionally substituted with —O— or —N(R$^4$)—;

R$^4$, at each occurrence, is independently selected from H, methyl, ethyl, propyl, and butyl;

R$^{6a}$ is H or C$_{1-4}$ alkyl;

R$_{6b}$ is H;

alternatively, R$^{6a}$ and R$^{6b}$ are taken together to form =O or =S;

R$^7$, R$^8$, and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{1-4}$ alkyl substituted with 0–2 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^3$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

R$^{10}$ is selected from H, C$_{1-4}$ alkyl, C$_{2-4}$ alkenyl, C$_{2-4}$ alkynyl, and C$_{1-4}$ alkoxy;

R$^{11}$ is selected from
H, halo, —CF$_3$, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$;

R$^{12}$, at each occurrence, is independently selected from
C$_{1-4}$ alkyl,
C$_{2-4}$ alkenyl,
C$_{2-4}$ alkynyl,
C$_{3-6}$ cycloalkyl,
phenyl substituted with 0–5 R$^{33}$;
C$_{3-10}$ carbocyclic residue substituted with 0–3 R$^{33}$, and
5–10 membered heterocyclic ring system containing from 1–4 heteroatoms selected from the group consisting of N, O, and S substituted with 0–3 R$^{31}$;

R$^{13}$, at each occurrence, is independently selected from H, C$_{1-4}$ alkyl, C$_{2-4}$ alkenyl, and C$_{2-4}$ alkynyl;

alternatively, R$^{12}$ and R$^{13}$ join to form a 5- or 6-membered ring optionally substituted with —O— or —N(R$^{14}$)—;

R$^{14}$, at each occurrence, is independently selected from H and C$_{1-4}$ alkyl;

R$^{31}$, at each occurrence, is independently selected from H, OH, halo, CF$_3$, SO$_2$R$^{45}$, NR$^{46}$R$^{47}$, methyl, ethyl, and propyl;

R$^{33}$, at each occurrence, is independently selected from
H, OH, halo, CN, NO$_2$, CF$_3$, SO$_2$R$^{45}$, NR$^{46}$R$^{47}$,
C$_{1-3}$ alkyl, C$_{2-3}$ alkenyl, C$_{2-3}$ alkynyl, C$_{3-5}$ cycloalkyl, C$_{1-3}$ haloalkyl, C$_{1-3}$ haloalkyl-oxy-, C$_{1-3}$ alkyloxy-, C$_{1-3}$ alkylthio-, C$_{1-3}$ alkyl—C(=O)—, and C$_{1-3}$ alkyl-C(=O)NH—;

R$^{41}$, at each occurrence, is independently selected from
H, CF$_3$, halo, OH, CO$_2$H, SO$_2$R$^{45}$, NR$^{46}$R$^{47}$, NO$_2$, CN, =O,
C$_{2-8}$ alkenyl, C$_{2-8}$ alkynyl, C$_{1-4}$ alkoxy, C$_{1-4}$ haloalkyl
C$_{1-4}$ alkyl substituted with 0–1 R$^{43}$,
aryl substituted with 0–3 R$^{42}$, and
5–10 membered heterocyclic ring system containing from 1–4 heteroatoms selected from the group consisting of N, O, and S substituted with 0–3 R$^{44}$;

R$^{42}$, at each occurrence, is independently selected from
H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$,
C$_{2-6}$ alkenyl, C$_{2-6}$ alkynyl, C$_{1-4}$ alkoxy, C$_{1-4}$ haloalkyl, C$_{3-6}$ cycloalkyl,
C$_{1-4}$ alkyl substituted with 0–1 R$^{43}$,
aryl substituted with 0–3 R$^{44}$, and
5–10 membered heterocyclic ring system containing from 1–4 heteroatoms selected from the group consisting of N, O, and S substituted with 0–3 R$^{44}$;

R$^{43}$ is C$_{3-6}$ cycloalkyl or aryl substituted with 0–3 R$^{44}$;

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, C$_{1-4}$ alkyl, and C$_{1-4}$ alkoxy;

R$^{45}$ is C$_{1-4}$ alkyl;

R$^{46}$, at each occurrence, is independently selected from H and C$_{1-4}$ alkyl;

R$^{47}$, at each occurrence, is independently selected from H, C$_{1-4}$ alkyl, —C(=O)NH(C$_{1-4}$ alkyl), —SO$_2$(C$_{1-4}$ alkyl), —SO$_2$(phenyl), —C(=O)O(C$_{1-4}$ alkyl), —C(=O)(C$_{1-4}$ alkyl) and —C(=O)H;

R$^{48}$, at each occurrence, is independently selected from H, C$_{1-4}$ alkyl, —C(=O)NH(C$_{1-4}$ alkyl), —C(=O)O(C$_{1-4}$ alkyl), —C(=O)(C$_{1-4}$ alkyl), and —C(=O)H;

n is 1 or 2;

m is 1 or 2; and n plus m is 2, 3, or 4;

provided when n is 1, m is 2, and $R^7$, $R^8$, and $R^9$ are independently selected from H, halogen, $C_{1-4}$ alkyl, $C_{1-4}$ alkoxy, $C_{1-4}$ alkylthio or trifluoromethyl; then X is not a bond.

[14] In an another embodiment, the present invention provides a novel compound of Formula (I) wherein:

X is —$CH_2$—, —O—, —S—, —$CH_2CH_2$—, —$OCH_2$—, —$SCH_2$—, —$CH_2O$—, or —$CH_2S$—;

$R^1$ is selected from
- $C_{2-5}$ alkyl substituted with Z,
- $C_{2-5}$ alkenyl substituted with Z,
- $C_{2-5}$ alkynyl substituted with Z,
- $C_{3-6}$ cycloalkyl substituted with Z,
- aryl substituted with Z,
- 5–6 membered heterocyclic ring system containing at least one heteroatom selected from the group consisting of N, O, and S, said heterocyclic ring system substituted with Z;
- $C_{1-5}$ alkyl substituted with 0–2 $R^2$,
- $C_{2-5}$ alkenyl substituted with 0–2 $R^2$, and
- $C_{2-5}$ alkynyl substituted with 0–2 $R^2$;

Z is selected from H,
- —$CH(OH)R^2$,
- —$C$(ethylenedioxy)$R^2$,
- —$OR^2$,
- —$SR^2$,
- —$NR^2R^3$,
- —$C(O)R^2$,
- —$C(O)NR^2R^3$,
- —$NR^3C(O)R^2$,
- —$C(O)OR^2$,
- —$OC(O)R^2$,
- —$CH(=NR^4)NR^2R^3$,
- —$NHC(=NR^4)NR^2R^3$,
- —$S(O)R^2$,
- —$S(O)_2R^2$,
- —$S(O)_2NR^2R^3$, and —$NR^3S(O)_2R^2$;

$R^2$, at each occurrence, is independently selected from
- $C_{1-4}$ alkyl,
- $C_{2-4}$ alkenyl,
- $C_{2-4}$ alkynyl,
- $C_{3-6}$ cycloalkyl,
- aryl substituted with 0–5 $R^{42}$;
- $C_{3-10}$ carbocyclic residue substituted with 0–3 $R^{41}$, and
- 5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H, methyl, ethyl, propyl, and butyl;

$R^{6a}$ is H or $C_{1-4}$ alkyl;

$R^{6b}$ is H;

alternatively, $R^{6a}$ and $R^{6b}$ are taken together to form =O or =S;

$R^7$, $R^8$, and $R^9$, at each occurrence, are independently selected from
H, halo, —$CF_3$, —$OCF_3$, —OH, —$OCH_3$, —CN, —$NO_2$, —$NR^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $CH(=NR^{14})NR^{12}R^{13}$, $NHC(=NR^{14})NR^{12}R^{13}$, $S(O)R^{12}$, $S(O)_2R^{12}$, $S(O)_2NR^{12}R^{13}$, $NR^{14}S(O)_2R^{12}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —$OCF_3$, —OH, —$OCH_3$, —CN, —$NO_2$, —$NR^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $CH(=NR^{14})NR^{12}R^{13}$, $NHC(=NR^{14})NR^{12}R^{13}$, $S(O)R^{12}$, $S(O)_2R^{12}$, $S(O)_2NR^{12}R^{13}$, and $NR^{14}S(O)_2R^{12}$;

$R^{12}$, at each occurrence, is independently selected from
- $C_{1-4}$ alkyl,
- $C_{2-4}$ alkenyl,
- $C_{2-4}$ alkynyl,
- $C_{3-6}$ cycloalkyl,
- phenyl substituted with 0–5 $R^{33}$;
- $C_{3-10}$ carbocyclic residue substituted with 0–3 $R^{33}$, and
- 5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ join to form a 5- or 6-membered ring optionally substituted with —O— or —N($R^{14}$)—;

$R^{14}$, at each occurrence, is independently selected from H and $C_{1-4}$ alkyl;

$R^{31}$, at each occurrence, is independently selected from H, OH, halo, $CF_3$, methyl, and ethyl;

$R^{33}$, at each occurrence, is independently selected from H, OH, halo, CN, $NO_2$, $CF_3$, methyl, and ethyl;

$R^{41}$, at each occurrence, is independently selected from
H, $CF_3$, halo, OH, $CO_2H$, $SO_2R^{45}$, $NR^{46}R^{47}$, $NO_2$, CN, =O,
$C_{2-8}$ alkenyl, $C_{2-8}$ alkynyl, $C_{1-4}$ alkoxy, $C_{1-4}$ haloalkyl,
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SR^{45}$, $NR^{46}R^{47}$, $OR^{48}$, $NO_2$, CN, $CH(=NH)NH_2$, $NHC(=NH)NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-3}$ alkyl;

$R^{47}$, at each occurrence, is independently selected from H, $C_{1-4}$ alkyl, —C(=O)NH($C_{1-4}$ alkyl), —$SO_2$($C_{1-4}$ alkyl), —$SO_2$(phenyl), —C(=O)O($C_{1-4}$ alkyl), —C(=O)($C_{1-4}$ alkyl), and —C(=O)H;

$R^{48}$, at each occurrence, is independently selected from H, $C_{1-4}$ alkyl, —C(=O)NH($C_{1-4}$ alkyl), —C(=O)O($C_{1-4}$ alkyl), —C(=O)($C_{1-4}$ alkyl), and —C(=O)H;

n is 1 or 2;

m is 1 or 2; and n plus m is 2, 3, or 4.

[15] In an another embodiment, the present invention provides a novel compound of Formula (I) wherein:

X is —$CH_2$—, —O— or —S—;

$R^1$ is selected from
  $C_{2-4}$ alkyl substituted with Z,
  $C_{2-4}$ alkenyl substituted with Z,
  $C_{2-4}$ alkynyl substituted with Z,
  $C_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  $C_{2-4}$ alkyl substituted with 0–2 $R^2$, and
  $C_{2-4}$ alkenyl substituted with 0–2 $R^2$;

Z is selected from H,
  —CH (OH) $R^2$,
  —C(ethylenedioxy)$R^2$,
  —$OR^2$,
  —$SR^2$,
  —$NR^2R^3$,
  —C(O)$R^2$,
  —C(O)$NR^2R^3$,
  —$NR^3$C(O)$R^2$,
  —C(O)$OR^2$,
  —S(O)$R^2$,
  —S(O)$_2R^2$,
  —S(O)$_2NR^2R^3$, and —$NR^3$S(O)$_2R^2$;

$R^2$, at each occurrence, is independently selected from phenyl substituted with 0–5 $R^{42}$;
  $C_{3-10}$ carbocyclic residue substituted with 0–3 $R^{41}$, and
  5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

alternatively, $R^2$ and $R^3$ join to form a 5- or 6-membered ring optionally substituted with —O— or —N($R^4$)—;

$R^4$, at each occurrence, is independently selected from H, methyl, ethyl, propyl, and butyl;

$R^{6a}$ is H or $C_{1-4}$ alkyl;

$R^{6b}$ is H;

alternatively, $R^{6a}$ and $R^{6b}$ are taken together to form =O or =S;

$R^7$, $R^8$, and $R^9$, at each occurrence, are independently selected from

H, halo, —$CF_3$, —$OCF_3$, —OH, —$OCH_3$, —CN, —$NO_2$,
  $C_{1-4}$ alkyl, $C_{1-4}$ haloalkyl, $C_{1-4}$ alkoxy, ($C_{1-3}$ haloalkyl)oxy, and
  $C_{1-4}$ alkyl substituted with 0–2 $R^{11}$;

$R^{11}$ is selected from
  H, halo, —$CF_3$, —$OCF_3$, —OH, —$OCH_3$, —CN, —$NO_2$,
  $C_{1-4}$ alkyl, $C_{1-4}$ haloalkyl, $C_{1-4}$ alkoxy, and ($C_{1-3}$ haloalkyl)oxy;

$R^{33}$, at each occurrence, is independently selected from H, OH, halo, $CF_3$, and methyl;

$R^{41}$, at each occurrence, is independently selected from H, $CF_3$, halo, OH, $CO_2H$, $SO_2R^{45}$, $NR^{46}R^{47}$, $NO_2$, CN, =O,
  $C_{2-8}$ alkenyl, $C_{2-8}$ alkynyl, $C_{1-4}$ alkoxy, $C_{1-4}$ haloalkyl,
  $C_{1-4}$ alkyl substituted with 0–1 $R^{43}$,
  aryl substituted with 0–3 $R^{42}$, and
  5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$,
  $C_{2-6}$ alkenyl, $C_{2-6}$ alkynyl, $C_{1-4}$ alkoxy, $C_{1-4}$ haloalkyl,
  $C_{3-6}$ cycloalkyl,
  $C_{1-4}$ alkyl substituted with 0–1 $R^{43}$,
  aryl substituted with 0–3 $R^{44}$, and
  5–10 membered heterocyclic ring system containing from 1–4 heteroatoms selected from the group consisting of N, O, and S substituted with 0–3 $R^{44}$;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from
  H, methyl, ethyl, n-propyl, i-propyl, n-butyl, i-butyl,
  —C(=O)NH(methyl), —C(=O)NH(ethyl), —$SO_2$(methyl), —$SO_2$(ethyl), —$SO_2$(phenyl), —C(=O)O(methyl), —C(=O)O(ethyl), —C(=O)(methyl), —C(=O)(ethyl), and —C(=O)H;

$R_{48}$, at each occurrence, is independently selected from
  H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O) H;

n is 1 or 2;

m is 1 or 2; and n plus m is 2 or 3.

[16] In an another embodiment, the present invention provides a novel compound of Formula (I) wherein:

X is —$CH_2$—, —O— or —S—;

$R^1$ is selected from
  ethyl substituted with Z,
  propyl substituted with Z,
  butyl substituted with Z,
  propenyl substituted with Z,
  butenyl substituted with Z,
  ethyl substituted with $R^2$, propyl substituted with R², 
butyl substituted with R², 
propenyl substituted with R², and 
butenyl substituted with R²; 
Z is selected from H, 
—CH(OH)R², 
—OR², 
—NR²R³, 
—C(O)R², 
—C(O)NR²R³, 
—NR³C(O)R², 
—C(O)OR², 
—S(O)R², 
—S(O)₂R², 
—S(O)₂NR²R³, and —NR³S(O)₂R²; 
R², at each occurrence, is independently selected from 
phenyl substituted with 0–3 R⁴²; 
naphthyl substituted with 0–3 R⁴²; 
cyclopropyl substituted with 0–3 R⁴¹; 
cyclobutyl substituted with 0–3 R⁴¹; 
cyclopentyl substituted with 0–3 R⁴¹; 
cyclohexyl substituted with 0–3 R⁴¹; 
pyridyl substituted with 0–3 R⁴¹; 
indolyl substituted with 0–3 R⁴¹; 
indolinyl substituted with 0–3 R⁴¹; 
benzimidazolyl substituted with 0–3 R⁴¹; 
benzotriazolyl substituted with 0–3 R⁴¹; 
benzothienyl substituted with 0–3 R⁴¹; 
benzofuranyl substituted with 0–3 R⁴¹; 
phthalimid-1-yl substituted with 0–3 R⁴¹; 
inden-2-yl substituted with 0–3 R⁴¹; 
2,3-dihydro-1H-inden-2-yl substituted with 0–3 R⁴¹; 
indazolyl substituted with 0–3 R⁴¹; 
tetrahydroquinolinyl substituted with 0–3 R⁴¹; and 
tetrahydro-isoquinolinyl substituted with 0–3 R⁴¹; 
R³, at each occurrence, is independently selected from 
H, methyl, and ethyl; 
R⁶ᵃ is H or C₁₋₄ alkyl; 
R⁶ᵇ is H; 
alternatively, R⁶ᵃ and R⁶ᵇ are taken together to form =O or =S; 
R⁷, R⁸, and R⁹, at each occurrence, are independently selected from H, F, Cl, methyl, ethyl, methoxy, —CF₃, and —OCF₃; 
R⁴¹, at each occurrence, is independently selected from H, F, Cl, Br, OH, CF₃, NO₂, CN, =O, methyl, ethyl, propyl, butyl, methoxy, and ethoxy; 
R⁴², at each occurrence, is independently selected from H, F, Cl, Br, OH, CF₃, SO₂R⁴⁵, SR⁴⁵, NR⁴⁶R⁴⁷, OR⁴⁸ NO₂, CN, =O, methyl, ethyl, propyl, butyl, methoxy, and ethoxy; 
R⁴⁵ is methyl, ethyl, propyl, or butyl; 
R⁴⁶, at each occurrence, is independently selected from H, methyl, ethyl, propyl, and butyl; 
R⁴⁷, at each occurrence, is independently selected from H, methyl, ethyl, n-propyl, i-propyl, n-butyl, i-butyl, —C(=O)NH(methyl), —C(=O)NH(ethyl), —SO₂(methyl), —SO₂(ethyl), —SO₂(phenyl), —C(=O)O(methyl), —C(=O)O(ethyl), —C(=O)(methyl), —C(=O)(ethyl), and —C(=O)H; 
R⁴⁸, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

n is 1; and 
m is 1.

[17] In an another embodiment, the present invention provides a novel compound of Formula (II):

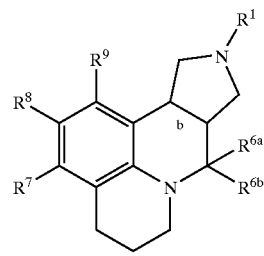

(II)

wherein: 
b is a single bond wherein the bridging hydrogens are either cis or trans; 
R¹ is selected from 
—(CH₂)₃C(=O)(4-fluoro-phenyl), 
—(CH₂)₃C(=O)(4-bromo-phenyl), 
—(CH₂)₃C(=O)(4-methyl-phenyl), 
—(CH₂)₃C(=O)(4-methoxy-phenyl), 
—(CH₂)₃C(=O)(4-(3,4-dichloro-phenyl)phenyl), 
—(CH₂)₃C(=O)(3-methyl-4-fluoro-phenyl), 
—(CH₂)₃C(=O)(2,3-dimethoxy-phenyl), 
—(CH₂)₃C(=O)(phenyl), 
—(CH₂)₃C(=O)(4-chloro-phenyl), 
—(CH₂)₃C(=O)(3-methyl-phenyl), 
—(CH₂)₃C(=O)(4-t-butyl-phenyl), 
—(CH₂)₃C(=O)(3,4-difluoro-phenyl), 
—(CH₂)₃C(=O)(2-methoxy-5-fluoro-phenyl), 
—(CH₂)₃C(=O)(4-fluoro-1-naphthyl), 
—(CH₂)₃C(=O)(benzyl), 
—(CH₂)₃C(=O)(4-pyridyl), 
—(CH₂)₃C(=O)(3-pyridyl), 
—(CH₂)₃CH(OH)(4-fluoro-phenyl), 
—(CH₂)₃CH(OH)(4-pyridyl), 
—(CH₂)₃CH(OH)(2,3-dimethoxy-phenyl), 
—(CH₂)₃S(3-fluoro-phenyl), 
—(CH₂)₃S(4-fluoro-phenyl), 
—(CH₂)₃S(=O)(4-fluoro-phenyl), 
—(CH₂)₃SO₂(3-fluoro-phenyl), 
—(CH₂)₃SO₂(4-fluoro-phenyl), 
—(CH₂)₃O(4-fluoro-phenyl), 
—(CH₂)₃O(phenyl), 
—(CH₂)₃O(3-pyridyl), 
—(CH₂)₃O(4-pyridyl), 
—(CH₂)₃O(2-NH₂-phenyl), 
—(CH₂)₃O(2-NH₂-5-F-phenyl), 
—(CH₂)₃O(2-NH₂-3-F-phenyl), 
—(CH₂)₃O(2-NH₂-4-F-phenyl), 
—(CH₂)₃O(2-NH₂-4-Cl-phenyl), 
—(CH₂)₃O(2-NH₂-4-OH-phenyl), 
—(CH₂)₃O(2-NH₂-4-Br-phenyl), 
—(CH₂)₃O(2-NHC(=O)Me-4-F-phenyl), 
—(CH₂)₃O(2-NHC(=O)Me-phenyl), 
—(CH₂)₃NH(4-fluoro-phenyl), 
—(CH₂)₃N(methyl)(4-fluoro-phenyl), 
—(CH₂)₃CO₂(ethyl), 
—(CH₂)₃C(=O)N(methyl)(methoxy), 
—(CH₂)₃C(=O)NH(4-fluoro-phenyl), 
—(CH₂)₂NHC(=O)(phenyl), 
—(CH₂)₂NMeC(=O)(phenyl), 
—(CH₂)₂NHC(=O)(2-fluoro-phenyl), —(CH₂)₂NMeC(=O)(2-fluoro-phenyl),
—(CH₂)₂NHC(=O)(4-fluoro-phenyl),
—(CH₂)₂NMeC(=O)(4-fluoro-phenyl),
—(CH₂)₂NHC(=O)(2,4-difluoro-phenyl),
—(CH₂)₂NMeC(=O)(2,4-difluoro-phenyl),
—(CH₂)₃(3-indolyl),
—(CH₂)₃(1-methyl-3-indolyl),
—(CH₂)₃(1-indolyl),
—(CH₂)₃(1-indolinyl),
—(CH₂)₃(1-benzimidazolyl),
—(CH₂)₃(1H-1,2,3-benzotriazol-1-yl),
—(CH₂)₃(1H-1,2,3-benzotriazol-2-yl),
—(CH₂)₂(H-1,2,3-benzotriazol-1-yl),
—(CH₂)₂(1H-1,2,3-benzotriazol-2-yl),
—(CH₂)₃(3,4 dihydro-1(2H)-quinolinyl),
—(CH₂)₂C(=O)(4-fluoro-phenyl),
—(CH₂)₂C(=O)NH(4-fluoro-phenyl),
—CH₂CH₂(3-indolyl),
—CH₂CH₂(1-phthalimidyl),
—(CH₂)₄C(=O)N(methyl)(methoxy),
—(CH₂)₄CO₂(ethyl),
—(CH₂)₄C(=O)(phenyl),
—(CH₂)₄(cyclohexyl),
—(CH₂)₃CH(phenyl)₂,
—CH₂CH₂CH=C(phenyl)₂,
—CH₂CH₂CH=CMe(4-F-phenyl),
—(CH₂)₃CH(4-fluoro-phenyl)₂,
—CH₂CH₂CH=C(4-fluoro-phenyl)₂,
—(CH₂)₂(2,3-dihydro-1H-inden-2-yl),
—(CH₂)₃C(=O)(2-NH₂-phenyl),
—(CH₂)₃C(=O)(2-NH₂-5-F-phenyl),
—(CH₂)₃C(=O)(2-NH₂-4-F-phenyl),
—(CH₂)₃C(=O)(2-NH₂-3-F-phenyl),
—(CH₂)₃C(=O)(2-NH₂-4-Cl-phenyl),
—(CH₂)₃C(=O)(2-NH₂-4-OH-phenyl),
—(CH₂)₃C(=O)(2-NH₂-4-Br-phenyl),
—(CH₂)₃(1H-indazol-3-yl),
—(CH₂)₃(5-F-1H-indazol-3-yl),
—(CH₂)₃(7-F-1H-indazol-3-yl),
—(CH₂)₃(6—Cl-1H-indazol-3-yl),
—(CH₂)₃(6-Br-1H-indazol-3-yl),
—(CH₂)₃C(=O)(2-NHMe-phenyl),
—(CH₂)₃(1-benzothien-3-yl),
—(CH₂)₃(6-F-1H-indol-1-yl),
—(CH₂)₃(5-F-1H-indol-1-yl),
—(CH₂)₃(6-F-2,3-dihydro-1H-indol-1-yl),
—(CH₂)₃(5-F-2,3-dihydro-1H-indol-1-yl),
—(CH₂)₃(6-F-1H-indol-3-yl),
—(CH₂)₃(5-F-1H-indol-3-yl),
—(CH₂)₃(5-F-1H-indol-3-yl),
—(CH₂)₃(9H-purin-9-yl),
—(CH₂)₃(7H-purin-7-yl),
—(CH₂)₃(6-F-1H-indazol-3-yl),
—(CH₂)₃C(=O)(2-NHSO₂Me-4-F-phenyl),
—(CH₂)₃C(=O)(2-NHC(=O)Me-4-F-phenyl),
—(CH₂)₃C(=O)(2-NHC(=O)Me-phenyl),
—(CH₂)₃C(=O)(2-NHCO₂Et-4-F-phenyl),
—(CH₂)₃C(=O)(2-NHC(=O)NHEt-4-F-phenyl),
—(CH₂)₃C(=O)(2-NHCHO-4-F-phenyl),
—(CH₂)₃C(=O)(2—OH-4-F-phenyl),
—(CH₂)₃C(=O)(2-MeS-4-F-phenyl),
—(CH₂)₃C(=O)(2-NHSO₂Me-4-F-phenyl),
—(CH₂)₂C(Me)CO₂Me,
—(CH₂)₂C(Me)CH(OH)(4-F-phenyl)₂,
—(CH₂)₂C(Me)CH(OH)(4-Cl-phenyl)₂,
—(CH₂)₂C(Me)C(=O)(4-F-phenyl),
—(CH₂)₂C(Me)C(=O)(2-MeO-4-F-phenyl),
—(CH₂)₂C (Me)C(=O)(3-Me-4-F-phenyl),
—(CH₂)₂C(Me)C(=O)(2-Me-phenyl),
—(CH₂)₂C(Me)C(=O)phenyl,

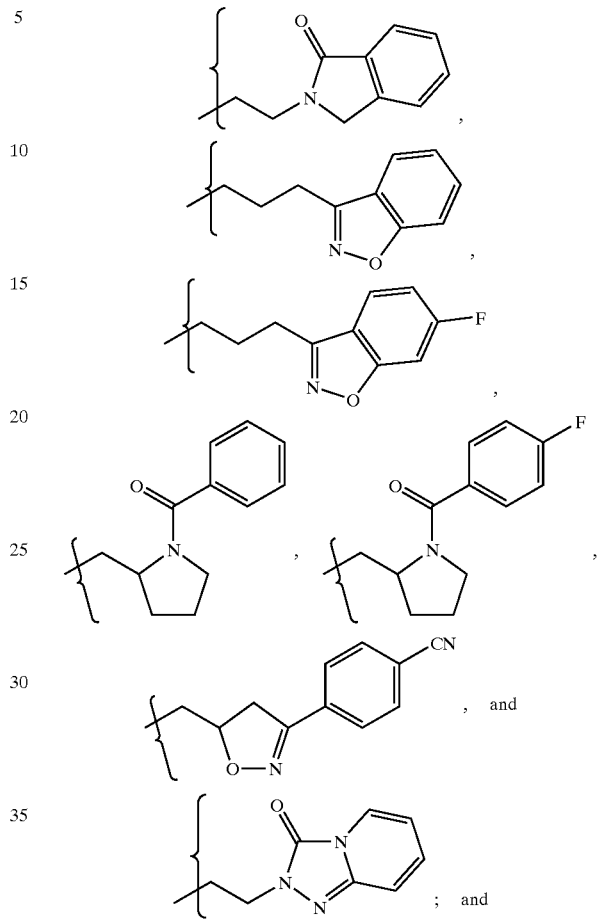

$R^7$, $R^8$, and $R^9$, at each occurrence, are independently selected from
  hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, benzyl,
  HC(=O)—, methylC(=O)—, ethylC(=O)—, propylC(=O)—, isopropylC(=O)—, n-butylC(=O)—, isobutylC(=O)—, secbutylC(=O)—, tertbutylC(=O)—, phenylC(=O)—,
  methylC(=O)NH—, ethylC(=O)NH—, propylC(=O)NH—, isopropylC(=O)NH—, n-butylC(=O)NH—, isobutylC(=O)NH—, secbutylC(=O)NH—, tertbutylC(=O)NH—, phenylC(=O)NH—,
  methylamino-, ethylamino-, propylamino-, isopropylamino-, n-butylamino-, isobutylamino-, secbutylamino-, tertbutylamino-, phenylamino-,
  provided that two of substituents $R^7$, $R^8$, and $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy.

In another subgenus of the above embodiments are compounds wherein b is a single bond wherein the bridge hydrogens are in a cis position; alternatively, are compounds wherein b is a single bond and the bridge hydrogens are in a trans position.

In another subgenus of the above embodiments are compounds wherein X is a bond, —O—, —S—, —OCH$_2$—, —SCH$_2$—, or —CH$_2$—.

In another subgenus of the above embodiments are compounds wherein X is —O—.

In another subgenus of the above embodiments are compounds wherein X is —OCH$_2$—.

In another subgenus of the above embodiments are compounds wherein X is —S—.

In another subgenus of the above embodiments are compounds wherein X is a bond.

In another subgenus of the above embodiments are compounds wherein X is —CH$_2$—.

In another subgenus of the above embodiments are compounds wherein R$^6$ and R$^6$a is each H.

In another subgenus of the above embodiments are compounds wherein R$^7$ and R$^9$, at each occurrence, are independently selected from H, halo, —CF$_3$, —OCF$_3$, —OH, —CN, —NO$_2$, C$_{1-4}$ alkyl, C$_{2-4}$ alkenyl, C$_{2-4}$ alkynyl, C$_{1-4}$ haloalkyl, C$_{1-4}$ alkoxy, and (C$_{1-4}$ haloalkyl)oxy; alternatively R$^7$ and R$^9$, at each occurrence, are independently selected from H, F, Cl, —CF$_3$, —OCF$_3$, —OH, —CN, —NO$_2$, methyl, ethyl, vinyl, allyl, methoxy, and ethoxy; or, alternatively R$^7$ and R$^9$, at each occurrence, are independently selected from H, F, Cl, —CF$_3$, —OCF$_3$, —OH, —CN, —NO$_2$, methyl, and methoxy; or, alternatively R$^7$ and R$^9$, at each occurrence, are H.

In another subgenus of the above embodiments are compounds wherein R$^8$ is methyl substituted by R$^{11}$; phenyl substituted by 0–5 R$^{33}$; —OR$^{12}$; —SR$^{12}$; or —NR$^{12}$R$^{13}$.

In another subgenus of the above embodiments are compounds wherein R$^8$ is methyl substituted by R$^{11}$.

In another subgenus of the above embodiments are compounds wherein R$^8$ is phenyl substituted by 0–5 R$^{33}$.

In another subgenus of the above embodiments are compounds wherein R$^8$ is —NR$^{12}$R$^{13}$.

In another subgenus of the above embodiments are compounds wherein R$^8$ is —OR$^{12}$.

In another subgenus of the above embodiments are compounds wherein R$^8$ is —SR$^{12}$.

In another subgenus of the above embodiments are compounds wherein R$^1$ is selected from H, C$_{1-5}$ alkyl, C$_{2-5}$ alkenyl, C$_{2-5}$ alkynyl, C$_{3-6}$ cycloalkyl, —(C$_{1-3}$ alkyl)C$_{3-6}$ cycloalkyl), —(C$_{2-3}$ alkenyl)C$_{3-6}$ cycloalkyl), and —(C$_{2-3}$ alkynyl)C$_{3-6}$ cycloalkyl.

In another subgenus of the above embodiments are compounds wherein R$^1$ is selected from hydrogen, methyl, ethyl, n-propyl, n-butyl, s-butyl, t-butyl, n-pentyl, n-hexyl, 2-propyl, 2-butyl, 2-pentyl, 2-hexyl, 2-ethylpropyl, 2-methylbutyl, 2-methylpentyl, 2-ethylbutyl, 3-ethylpentyl, 3-methylbutyl, cyclopropyl, cyclobutyl, cyclopentyl, cyclohexyl, cyclopropylmethyl, cyclobutylmethyl, cyclopentylmethyl, and cyclohexylmethyl; alternatively R$^1$ is hydrogen, methyl, ethyl, n-propyl, n-butyl, s-butyl, t-butyl, 2-propyl, 2-butyl, cyclopropylmethyl, cyclobutylmethyl, cyclopentylmethyl, or cyclohexylmethyl; or alternatively R$^1$ is hydrogen, methyl, or ethyl.

In another subgenus of the above embodiments are compounds wherein m is 1 and n is 1 or 2; alternatively, are compounds wherein m is 1 and n is 1.

In an even further more preferred embodiment of the present invention, are compounds of Formula (I) selected from Table 1, Table 2, and Table 3.

In a second embodiment, the present invention provides a pharmaceutical composition comprising a compound of Formula (I) and a pharmaceutically acceptable carrier.

In a third embodiment, the present invention provides a method for the treatment a central nervous system disorder comprising administering to a host in need of such treatment a therapeutically effective amount of a compound of Formula (I), or a pharmaceutically acceptable salt thereof, wherein the compound is a 5HT2a antagonist or a 5HT2c agonist.

In a preferred embodiment the compound is a 5HT2a antagonist.

In another preferred embodiment the compound is a 5HT2c agonist.

In a more preferred embodiment the present invention provides a method for the treatment central nervous system disorders including obesity, anxiety, depression, psychosis, schizophrenia, sleep disorders, sexual disorders, migraine, conditions associated with cephalic pain, social phobias, and gastrointestinal disorders such as dysfunction of the gastrointestinal tract motility comprising administering to a host in need of such treatment a therapeutically effective amount of a compound of Formula (I).

In a further preferred embodiment the central nervous system disorder comprises obesity.

In another further preferred embodiment the central nervous system disorder comprises schizophrenia.

In another further preferred embodiment the central nervous system disorder comprises depression.

In another further preferred embodiment the central nervous system disorder comprises anxiety.

In a fourth embodiment the present invention provides novel compounds of Formula (I) or pharmaceutically acceptable salt forms thereof for use in therapy.

In a fifth embodiment the present invention provides the use of novel compounds of Formula (I) or pharmaceutically acceptable salt forms thereof for the manufacture of a medicament for the treatment of central nervous system disorders including obesity, anxiety, depression, psychosis, schizophrenia, sleep.disorders, sexual disorders, migraine, conditions associated with cephalic pain, social phobias, and gastrointestinal disorders.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The numbering of the tetracyclic ring-system present in the compounds of Formula (I), as defined by nomenclature known to one skilled in the art, is shown for two examples in Formula (I'), when k is 1 and n is 1; and in Formula (I"), when k is 1 and n is 2:

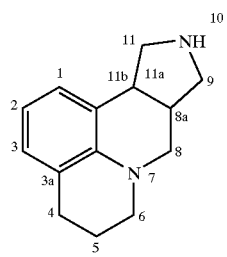

(I')

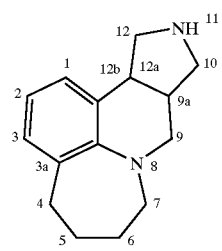

(I")

The tetracyclic ring-system present in compounds of Formula (I) occur as "cis" or "trans" isomers when the carbon-carbon bond b in Formula (I) is a single bond. As such, the terms "cis" and "trans", in conjunction with the tetracyclic ring structure, refer to the configuration of hydrogen atoms on carbon atoms 8a and 11a in Formula (I') or, for example, on carbon atoms 9a and 12a in Formula (I"), above. When both hydrogens are on the same side of the mean plane determined by the octahydro tetracyclic moiety then the configuration is designated "cis", if not, the configuration is designated "trans". It is understood that the above example is for demonstrative purposes only and not intended to limit the scope of the tetracyclic ring-system present in compounds of Formula (I). As such, it is understood that one skilled in the art of organic chemistry can apply the above numbering system to other values of m and n in the scope of compounds of Formula (I) to deterine the appropriate numbering. Additional Examples of the numbering of the tetracyclic ring-system are further provided below in the synthetic EXAMPLES. Lastly, it is understood that the use of "cis" or "trans" in the identification of the tetracyclic ring-system is not meant to construe the configuration of any other cis or trans geometric isomer in the molecule, for example, cis or trans butene.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g. $R^2$, $R^{11}$, $R^{33}$, $R^{41}$, $R^{42}$ etc.) occurs more than one time in any constituent or formula for a compound, its definition at each occurrence is independent of its definition at every other occurrence. Thus, for example, if a group is shown to be substituted with 0–2 $R^2$, then said group may optionally be substituted with up to two $R^2$ groups and $R^2$ at each occurrence is selected independently from the definition of $R^2$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl", or "alkylene" is intended to include both branched and straight-chain saturated aliphatic hydrocarbon groups having the specified number of carbon atoms; for example, "$C_1$–$C_6$ alkyl" or "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms, for example "$C_{2-6}$ alkenyl", and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration, having the specified number of carbon atoms, for example "$C_{2-6}$ alkynyl", and one or more carbon-carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

"Alkoxyl" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" is represents an alkyl group as defined above with the indicated number of carbon atoms attached through a sulpher bridge.

"Halo" or "halogen" as used herein refers to fluororo, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic ring" or "heterocyclic ring system" is intended to mean a stable 5- to 7- membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrazinyl, piperazinyl, imidazolyl, indolyl, benzimidazolyl, IH-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

As used herein, the term "bicyclic heterocyclic ring system" is intended to mean a stable 9- to 10-membered bicyclic heterocyclic ring formed from the substituent $NR^{12}R^{13}$, which is partially unsaturated or unsaturated (aromatic), and which consists of carbon atoms, a nitrogen atom, and 1 or 2 additional heteroatoms independently selected from the group consisting of N, O and S. The additional nitrogen or sulfur heteroatoms may optionally be oxidized. The heterocyclic ring is attached to its pendant group by the nitrogen atom of the group $NR^{12}R^{13}$ and for which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. The term "bicyclic heterocyclic ring system" is intended to be a subset of the term. "heterocyclic ring system". Preferred examples of a 9- to 10- membered bicyclic heterocyclic ring system are benzimidazolyl, benzimidazolinyl, benzoxazolinyl, dihydrobenzthiazolyl, dihydrodioxobenzthiazolyl, benzisoxazolinyl, 1H-indazolyl, indolyl, indolinyl, isoindolinyl, tetrahydro-isoquinolinyl, tetrahydro-quinolinyl, and benzotriazolyl.

Additionally, a subclass of preferred heterocycles are heterocycles which function as an isostere of a cyclic but non-heterocyclic substitutent such as —$CH_2$—$C(=O)$-phenyl. Preferred examples of such heterocycles include, but are not limited to, benzimidazolyl, benzofuranyl, benzothiophenyli benzoxazolyl, benzthiazolyl, benzisoxazolyl, furanyl, imidazolinyl, 1H-indazolyl, indolinyl, isoindolinyl, isoquinolinyl, oxazolyl, piperidinyl, pyrazinyl, pyridinyl, pyrimidinyl, quinolinyl, thiazolyl, thiophenyl, and 1,2,3-triazolyl.

As used herein, the term "aryl", or aromatic residue, is intended to mean an aromatic moiety containing six to ten carbon atoms, such as phenyl, pyridinyl and naphthyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can beprepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like. "Stable compound" and "stable structure" are meant to indicate a compound that is sufficiently robust to survive isolation to a useful degree of purity from a reaction mixture, and formulation into an efficacious therapeutic agent.

SYNTHESIS

Throughout the details of the invention, the following abbreviations are used with the following meanings:

| Reagents: | |
|---|---|
| MCPBA | m-chloroperoxybenzoic acid |
| DIBAL | diisobutyl aluminum hydride |
| Et$_3$N | triethylamine |
| TFA | trifluoroacetic acid |
| LAH | lithium aluminum hydride |
| NBS | N-bromo succinimide |
| Red-Al | Sodium bis(2-methoxyethoxy)aluminum hydride |
| Pd$_2$dba$_3$ | Tris (dibenzylideneacetone) dipalladium(0) |
| ACE-Cl | 2-chloroethylchloroformate |
| Solvents: | |
| THF | tetrahydrofuran |
| MeOH | methanol |
| EtOH | ethanol |
| EtOAc | ethyl acetate |
| HOAc | acetic acid |
| DMF | dimethyl formamide |
| DMSO | dimethyl sulfoxide |
| DME | dimethoxyethane |
| Et$_2$O | diethylether |
| iPrOH | isopropanol |
| MEK | methyl ethyl ketone |
| Others: | |
| Ar | aryl |
| Ph | phenyl |
| Me | methyl |
| Et | ethyl |
| NMR | nuclear magnetic resonance |
| MHz | megahertz |
| BOC | tert-butoxycarbonyl |
| CBZ | benzyloxycarbonyl |

-continued

| | |
|---|---|
| Bn | benzyl |
| Bu | butyl |
| Pr | propyl |
| cat. | catalytic |
| mL | milliliter |
| nM | nanometer |
| ppm | part per million |
| mmol | millimole |
| mg | milligram |
| g | gram |
| kg | kilogram |
| TLC | thin layer chromatography |
| HPLC | high pressure liquid chromatography |
| RPM | revolutions per minute |
| rt | room temperature |
| aq. | aqueous |
| sat. | saturated |

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction iconditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The preparation of compounds of Formula (I) of the present invention may be carried out in a convergent or sequential synthetic manner. Detailed synthetic preparations of the compounds of Formula (I) are shown in the following reaction schemes. The skills required in preparation and purification of the compounds of Formula (I) and the intermediates leading to these compounds are known to those in the art. Purification procedures include, but are not limited to, normal or reverse phase chromatography, crystallization, and distillation.

Several methods for the preparation of the compounds of the present invention are illustrated in the schemes and examples shown below. The substitutions are as described and defined above.

The compounds of Formula (I) where n=1 and m=1 can be prepared as described in Scheme 1. Protection of the anilines (II) with BOC$_2$O and a base such as triethylamine affords a carbamate intermediate which serves to direct subsequent deprotonation with sec-BuLi (TMEDA, −78° C., ether) to occur at the adjacent aryl-H bond (see Beak, P., et. al., *Tetrahedron Lett.* 1989, 30, 1197; and Iwao, M., et. al., *Heterocycles*, 1992, 34, 1031). Quenching with an appropriate electrophile, such as N,N-dimethylformamide, affords the aldehydes (III). Horner-Emmons reaction of aldehydes (III) with an appropriate phosphonate (IV) in the presence of a base affords the α, β-unsaturated esters (V), where the olefin geometry can be controlled by the nature of the phosphonate (IV) and the conditions of the reaction. For example, under standard conditions, using a phosphonate (IV) where R' is Me or Et and using sodium hydride as a base leads to (V) with the E-olefin geometry as the nearly exclusive product. Alternatively, using a phosphonate (IV) where R' is 2,2,2-trifluoroethyl or Ar, generating its potassium enolate with potassium hexamethyldisilazide or potassium carbonate and 18-crown-6, and allowing it to react with aldehyde (III) leads to (V) with Z-olefin geometry as the nearly exclusive product (see Still, W. C., et. al., *Tetrahedron Lett.* 1983, 24, 4405; for a review of Z-selective Horner-Emmons reactions, see Jiro, M. *Trends Org. Chem.* 1998, 7, 63). Olefins (V) can serve as dipolarophiles in 1,3-dipolar cycloadditions with appropriate azomethine ylides to afford the pyrrolidines (VII) (for reviews of 1,3-dipolar cycloaddition chemistry of azomethine ylides, see 1,3-*Dipolar Cycloaddition Chemistry*, A. Padwa, Ed., Wiley-Interscience, New York, 1984). The required azomethine ylide can be generated in several ways, two preferred methods of which are described. The commercially available tertiary amine (VI) can be treated with 5–25 mol % TFA in methylene chloride to generate the required azomethine ylide and 1,3-dipolar cycloaddition then occurs at room temperature or reflux temperature to afford (VII). Alternatively, N-benzylglycine can be refluxed with paraformaldehyde in a suitable solvent such as toluene or benzene to generate the azomethine ylide. These methods produce (VII) where the pyrrolidine nitrogen is protected with a benzyl group. The 1,3-dipolar cycloaddition is stereospecific in that the stereochemistry of the olefin is retained and translated into the relative stereochemistry of the pyrrolidine II products. Thus, E-olefins undergo cyclization to produce pyrrolidines (VII) with a trans configuration of the 3,4-substituents on the pyrrolidine ring and Z-olefins undergo cyclization to produce pyrrolidines (VII) with a cis configuration of the 3,4-substituents on the pyrrolidine ring. Removal of the BOC group under acidic conditions, for example with TFA, affords an aniline which can undergo ring-closing condensation on the ester group, either with heating or with heating in the presence of an acid such as p-toluenesulfonic acid, to afford the tetracyclic compounds (VIII).

Compounds of Formula (I) where n=1 and m=1, and where $R^{6a}$ and $R^{6b}$ taken together are carbonyl, i.e. compounds (IX), are prepared by removal of the N-benzyl group of (VIII) either by catalytic hydrogenation over Pd/C or Pd(OH)$_2$/C catalyst, or by reaction with α-chloroethyl chloroformate (ACE-Cl) and subsequent refluxing in methanol, followed by N-alkylation of the secondary amine with an appropriate $R^1$I and an appropriate base, such as potassium carbonate. Compounds of Formula (I) where n=1 and m=1, and where $R^{6a}$ and $R^{6b}$ are hydrogen, i.e. compounds (XI), can also be prepared from (VIII). Removal of the N-benzyl group as just described can be followed by protecting the secondary amine as a BOC carbamate by reaction with BOC$_2$O to afford (X). Alternatively, (X) can be prepared directly from (VIII) by performing the catalytic hydrogenation using Pd(OH)$_2$/C catalyst in the presence of BOC$_2$O. Reduction of the lactam carbonyl with a reducing agent such as borane-tetrahydrofuran complex or DIBAL, followed by acidic BOC deprotection and subsequent N-alkylation as described above affords tetracyclic compounds (XI).

Alternatively, the compounds of Formula (I) where n 1 and m=1 and where the ring fusion is cis can be prepared as described in Scheme 2. The aldehydes (III), prepared as described in Scheme 1, can be condensed with dimethyl or diethyl malonate in the presence of catalytic piperidine or piperidine benzoate with removal of water to afford an α,β-unsaturated diester. Removal of the BOC group under acidic conditions and subsequent ring-closing condensation, which occurs spontaneously or with heating, affords the tricyclic compounds (XII). The 1,3-dipolar cycloaddition of this substrate with an appropriately generated azomethine ylide as described in Scheme 1 then affords the tetracyclic compounds (XIII) with a cis ring fusion. Decarboxylation can be accomplished by basic hydrolysis followed by heating the resulting acid, such as by refluxing in dioxane, or by heating the ester (XIII) under acidic conditions, to afford (XIV) which has retained the cis ring fusion. Tetracyclic compounds (XIV) can be converted to the compounds of Formula (I) where n=1 and m=1, where the ring fusion is cis, and where $R^6$ and $R^{6a}$ taken together are carbonyl, i.e. compounds (XV), by the procedures described in Scheme 1. Likewise, compounds (XIV) can be converted to the compounds of Formula (I) where n=1 and m=1, where the ring fusion is cis, and where $R^{6a}$ and $R^{6b}$ are hydrogen, i.e. compounds (XVII), by the procedures described in Scheme 1.

Scheme 1.

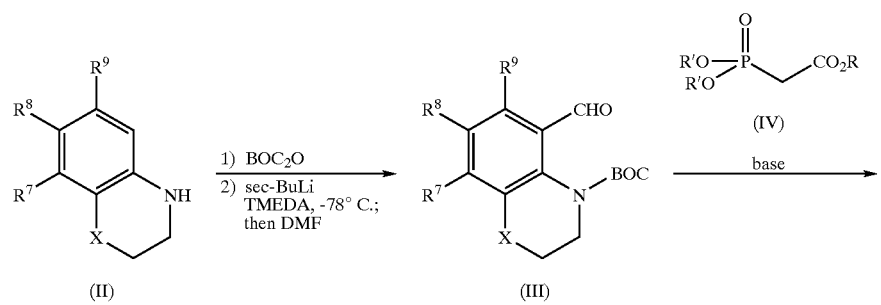

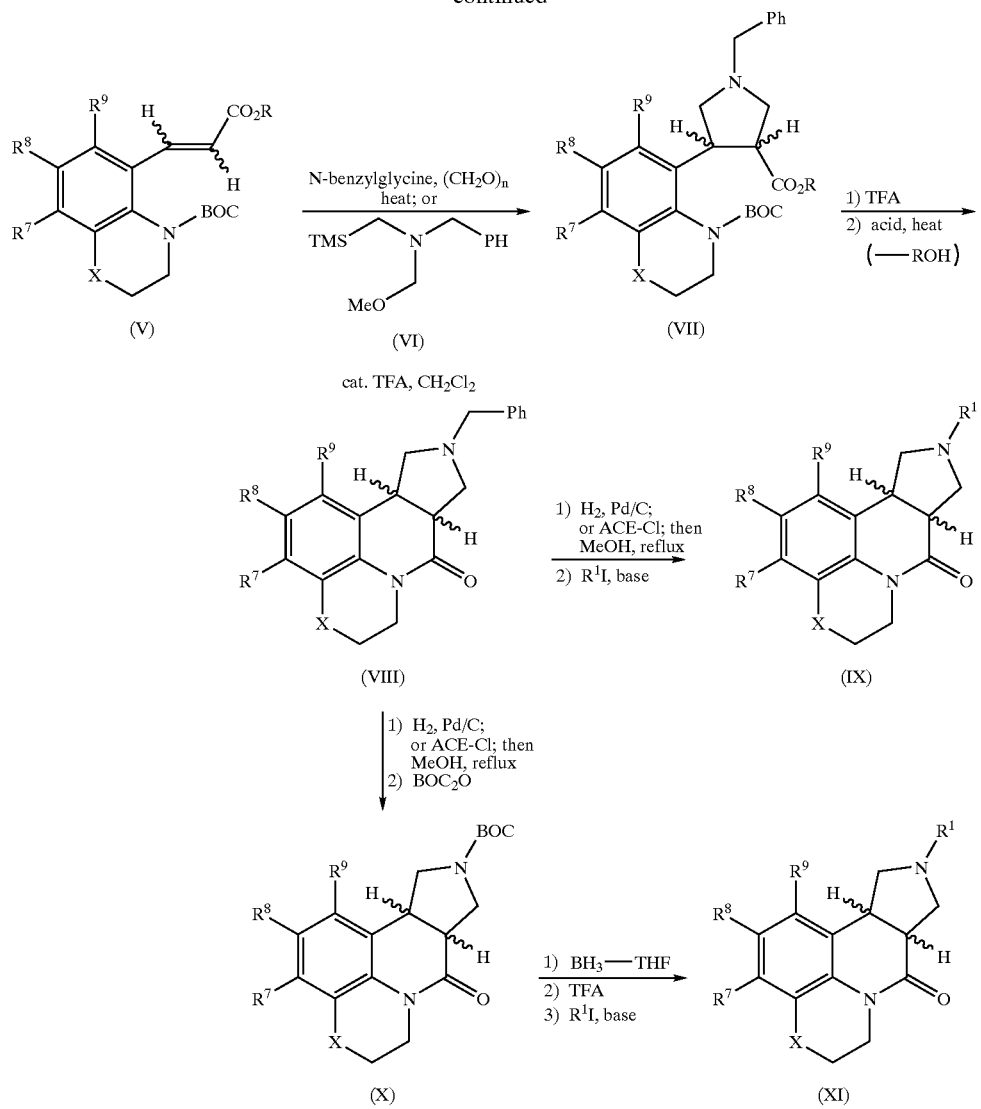

An alternative synthesis of the tricyclic esters (XII) is described in Scheme 3. Condensation of the anilines (II) with trimethyl or triethyl methanetricarboxylate at elevated temperature affords the tricyclic esters (XVIII). Conversion of the hydroxy group to chloro can be accomplished with phosphorous oxychloride and triethylamine at elevated temperature. The chloro can be reduced to afford compounds (XII) for example by treating with tributyltin hydride (see Neumann, W. P., *Synthesis*, 1987, 665). Compounds (XII) can then be carried on to the compounds of Formula (I) as described in Scheme 2.

Scheme 2.

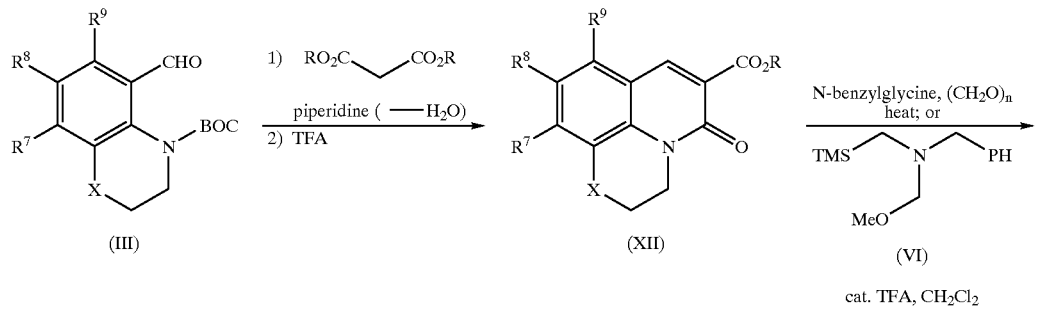

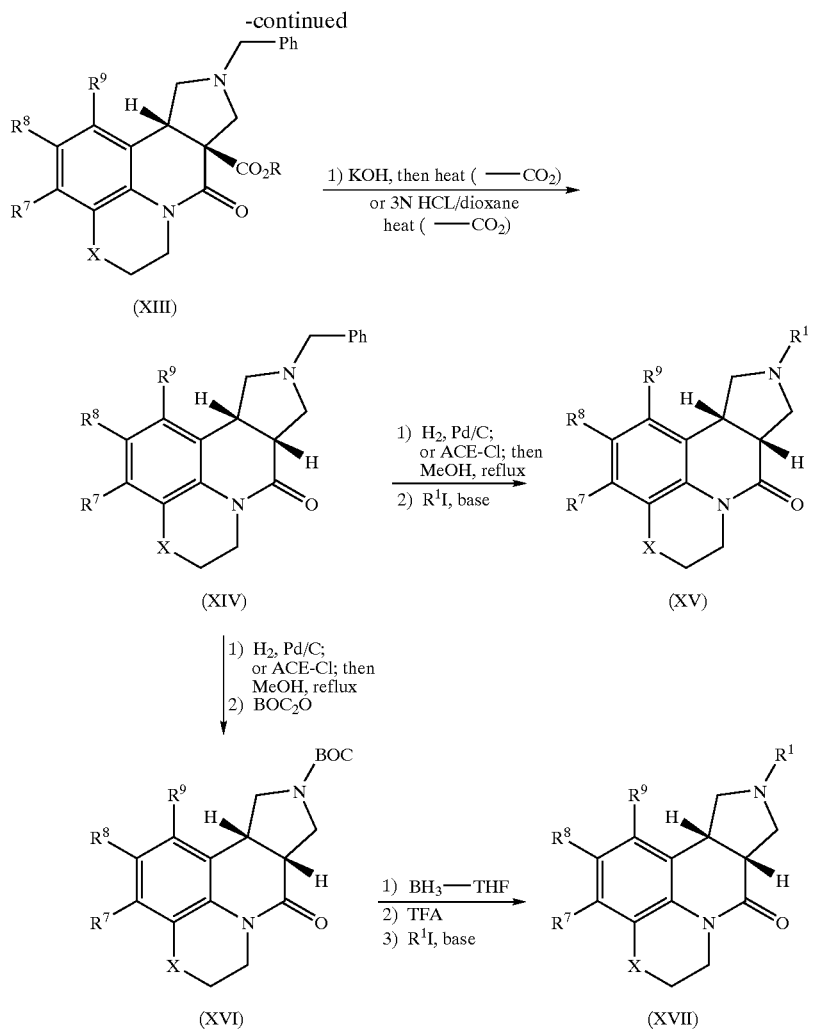

(XIII) → (XIV) → (XV)

(XVI) → (XVII)

Scheme 3.

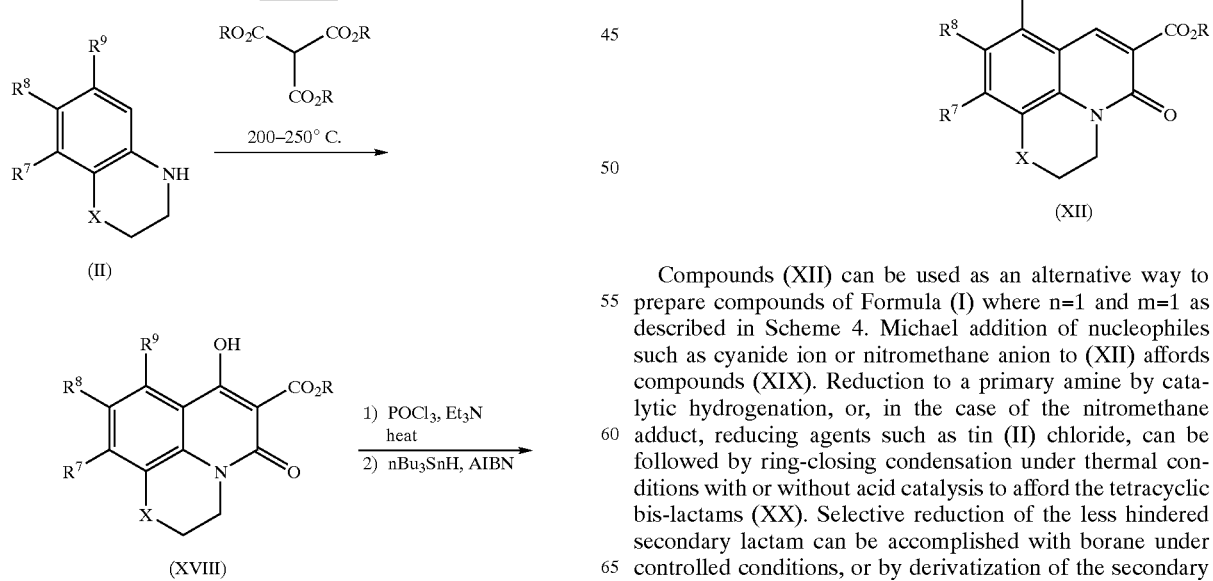

(II) → (XVIII) → (XII)

Compounds (XII) can be used as an alternative way to prepare compounds of Formula (I) where n=1 and m=1 as described in Scheme 4. Michael addition of nucleophiles such as cyanide ion or nitromethane anion to (XII) affords compounds (XIX). Reduction to a primary amine by catalytic hydrogenation, or, in the case of the nitromethane adduct, reducing agents such as tin (II) chloride, can be followed by ring-closing condensation under thermal conditions with or without acid catalysis to afford the tetracyclic bis-lactams (XX). Selective reduction of the less hindered secondary lactam can be accomplished with borane under controlled conditions, or by derivatization of the secondary lactam with phosphorous oxychloride or triethyloxonium tetrafluoroborate followed by reduction with sodium borohydride. N-alkylation of the resulting secondary amine as described in Scheme 1 affords compounds (IX). Alternately, (XX) can be exhaustively reduced using borane or LAH and subsequently N-alkylated as described to afford compounds (XI).

vides a chloro analog which can be displaced by appropriate nucleophiles such as cyanide ion and nitromethane anion to afford (XXI). Catalytic hydrogenation and subsequent ring-closing condensation affords the cis-fused tetracyclic bis-lactam (XXII), the relative stereochemistry being set by the

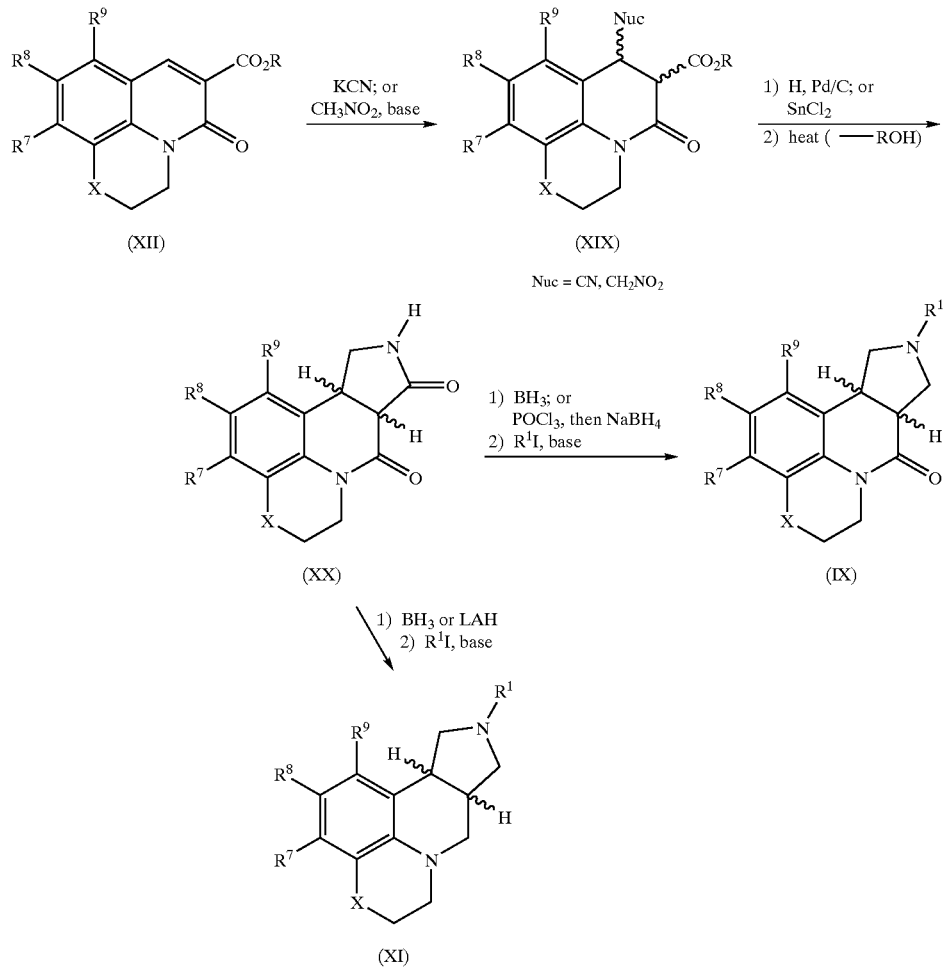

Compounds (XII) can also be used as an alternative way to prepare compounds of Formula (I) where n=1 and m=1 and the ring fusion is cis, as described in Scheme 5. Chlorination of (XVIII) with phosphorous oxychloride proaddition of hydrogen across the double bond. Following the procedures described in Scheme 4, bis-lactams (XXII) can be converted to cis-fused tetracyclic compounds (XV) and (XVII).

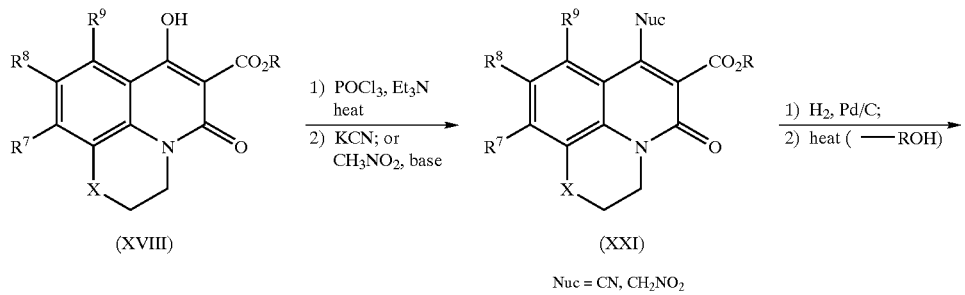

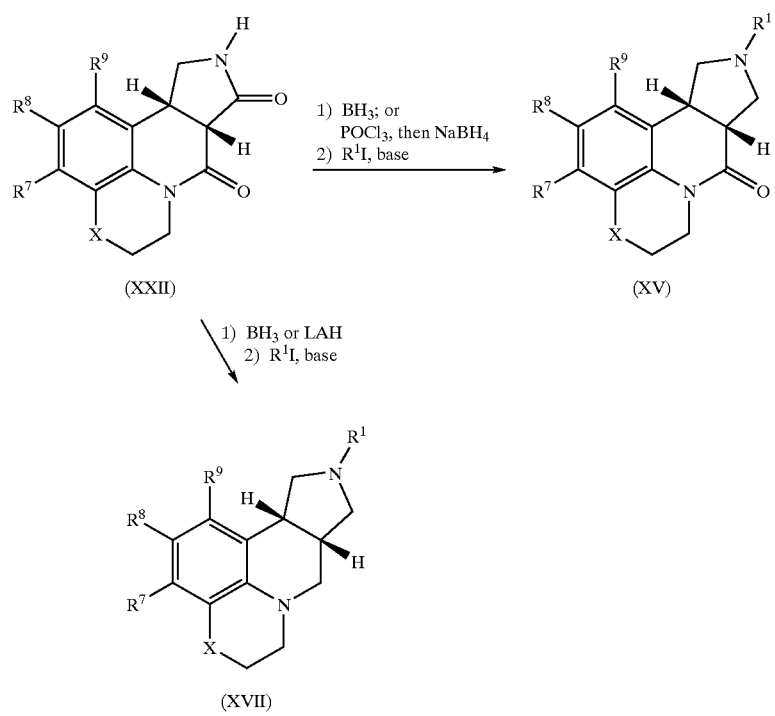

The compounds of Formula (I) where n=1 and m=2 or where n=2 and m=1, and where the ring fusion is cis can be prepared as described in the following Schemes. As described in Scheme 6, (XII) can undergo [3+2] cycloaddition with 2-[(trimethylsilyl)methyl]-2-propen-1-yl acetate (XXIII) in the presence various palladium catalysts, such as (Ph₃P)₄Pd, (Ph₃P)₄Pd/dppe, Pd(OAc)₂ and PPh₃, or Pd(OAc)₂ and P(OR)₃, to afford a cyclopentane-fused compound containing an exo-methylene group (see Trost, B. M., et. al., *J. Am. Chem. Soc.* 1983, 105, 2315). Oxidative cleavage of the exo-methylene residue, such as with ozone or osmium tetroxide and sodium periodate, affords the tetracyclic cyclopentanones (XXIV) with a cis ring fusion. Decarboxylation can be accomplished as described previously by basic hydrolysis followed by heating, such as in refluxing dioxane, to afford (XXV). Ring expansion with incorporation of the nitrogen functionality can be accomplished in several ways. For example, Schmidt rearrangement (as described by Smith, P. A. S., *J. Am. Chem. Soc.*, 1948, 320) is effected by treatment of the carbonyl derivative (XXV) with NaN₃ and methanesulfonic acid to afford a mixture of the bicyclic lactams (XXVI) and (XXVII). Alternatively, this transformation may be carried out under Hoffmann rearrangement protocol (see, for example, Dike, S. Y., et. al., *Bioorg. Med. Chem. Lett.*, 1991, 383), by initial formation of the oxime derivative of (XXV) by treatment with hydroxylamine hydrochloride. Subsequent rearrangement to the lactam is efficiently accomplished by heating in polyphosphoric acid to afford a mixture of the lactams (XXVI) and (XXVII).

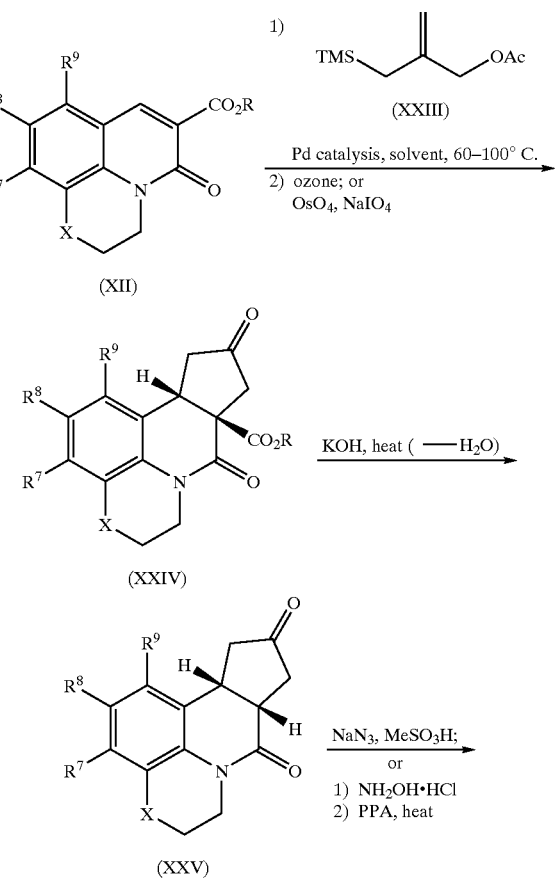

Scheme 6.

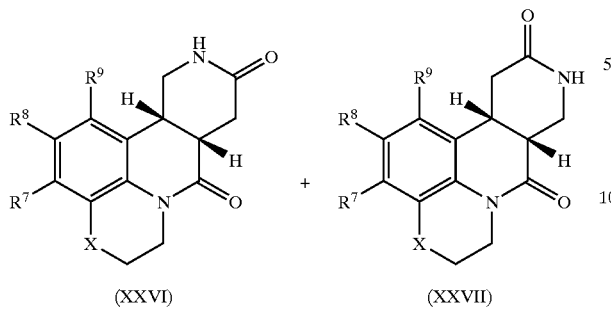

(XXVI)                (XXVII)

The conversion of lactams (XXVI) and (XXVII) to compounds of Formula (I) can be accomplished as described in Scheme 7. As described in Scheme 4, selective reduction of the secondary lactam of (XXVI) or (XXVII) followed by N-alkylation leads to tetracyclic compounds (XXVIII) or (XXX), respectively. Also as described in Scheme 4, exhaustive reduction of (XXVI) or (XXVII) and subsequent N-alkylation affords compounds (XXIX) or (XXXI), respectively.

Alternately, the compounds of Formula (I) where n=1 and m=2 or where n=2 and m=1, and where the ring fusion is trans can be prepared as described in Scheme 8. The E-olefin (XXXII), prepared as described in Scheme 1, can be subjected to the palladium catalyzed [3+2] cycloaddition with 2-[(trimethylsilyl)methyl]-2-propen-1-yl acetate (XXIII) as described in Scheme 6 and subsequently oxidatively cleaved to the ketone (XXXIII), where the E-olefin geometry is conserved in the product to give the trans cyclopentanone stereochemistry. Deprotection of the BOC carbamate under acidic conditions followed by ring-closing condensation under thermal conditions with or without acid catalysis affords the tetracyclic compounds (XXXIV). Ring expansion with incorporation of the nitrogen functionality can be accomplished in several ways as described in Scheme 6. For example, Schmidt rearrangement is effected by treatment of the carbonyl derivative (XXXIV) with $NaN_3$ and methanesulfonic acid to afford a mixture of the bicyclic lactams (XXXV) and (XXXVI). Alternatively, this transformation may be carried out under Hoffmann rearrangement protocol by initial formation of the oxime derivative of (XXXIV) by treatment with hydroxylamine hydrochloride. Subsequent rearrangement to the lactam is efficiently accomplished by heating in polyphosphoric acid to afford a mixture of the lactams (XXXV) and (XXXVI). Following procedures described in previous schemes, (XXXV) and (XXXVI) can be converted to final compounds (XXXVII) and (XXXVIII), respectively, where depending on the lactam reduction conditions, $R^{6a}$ and $R^{6b}$ can be hydrogen or taken together to be a carbonyl residue.

Scheme 7.

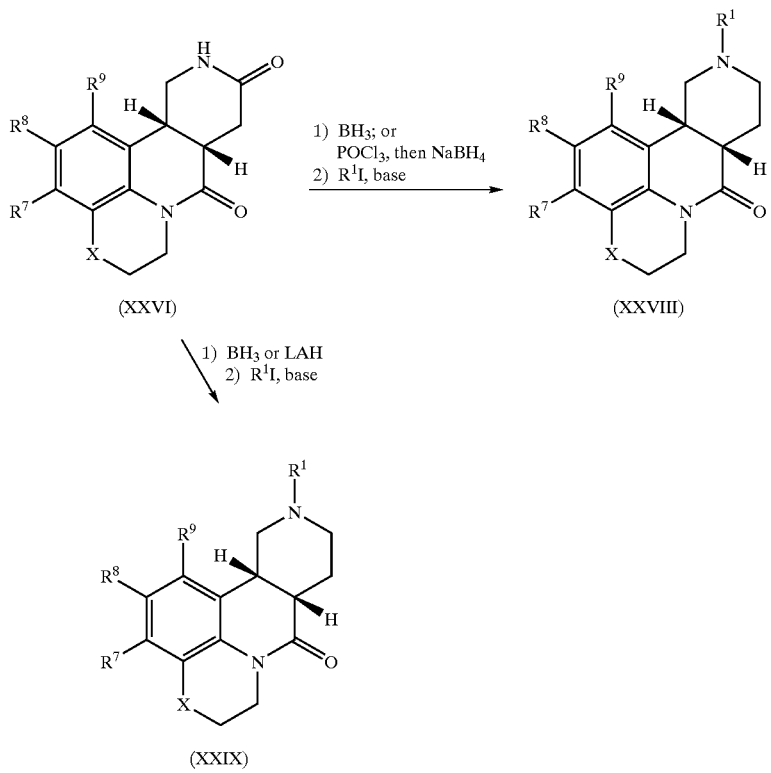

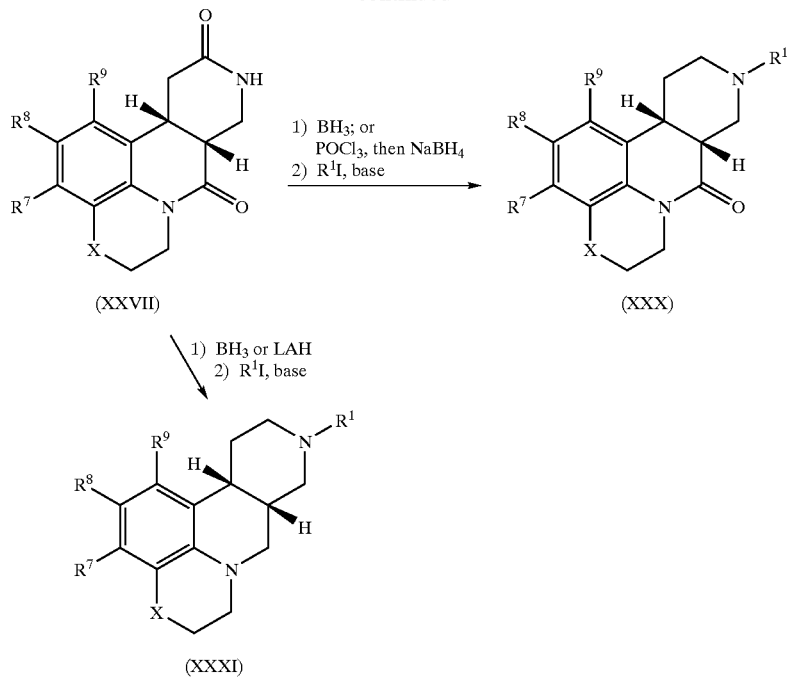

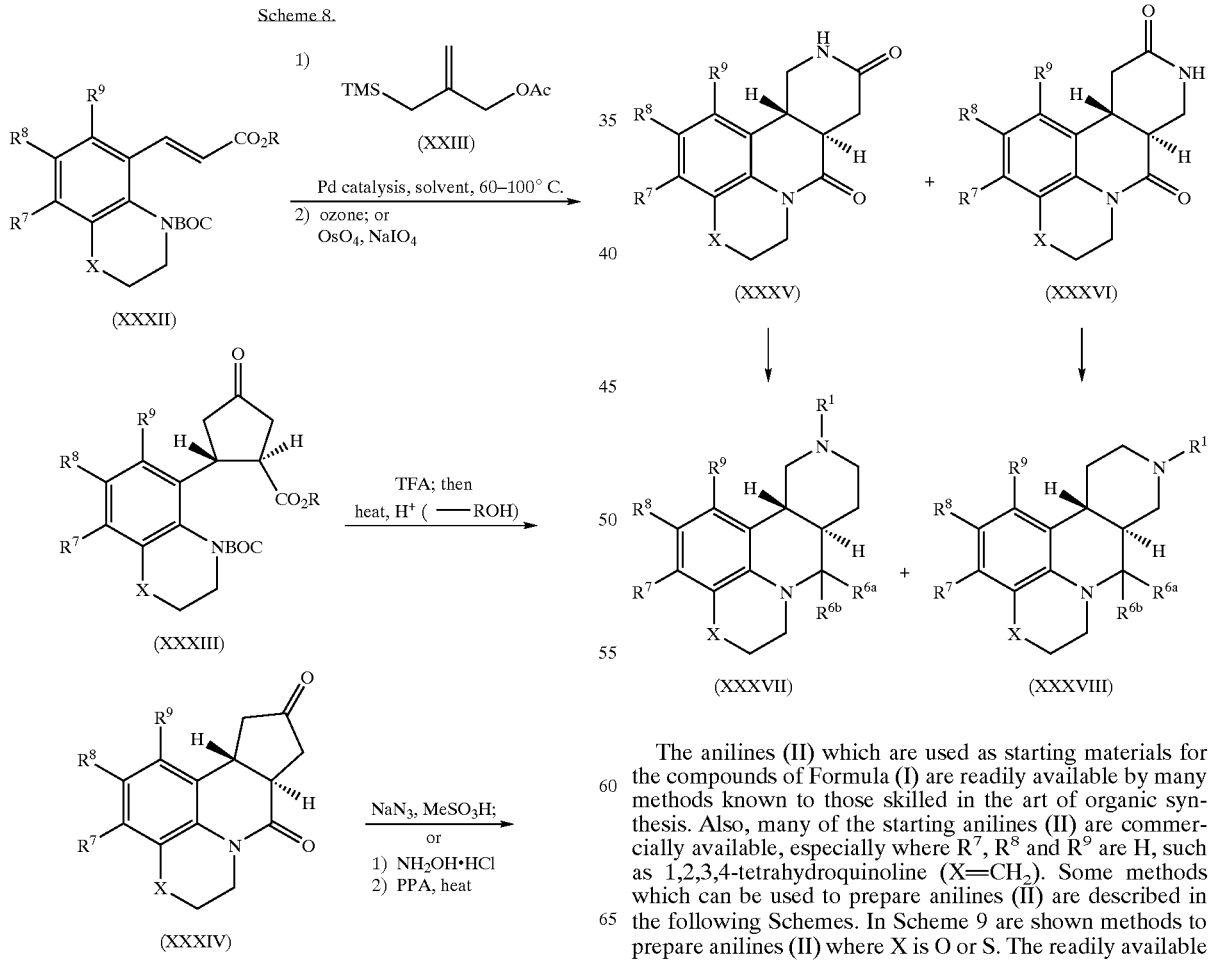

The anilines (II) which are used as starting materials for the compounds of Formula (I) are readily available by many methods known to those skilled in the art of organic synthesis. Also, many of the starting anilines (II) are commercially available, especially where $R^7$, $R^8$ and $R^9$ are H, such as 1,2,3,4-tetrahydroquinoline (X=$CH_2$). Some methods which can be used to prepare anilines (II) are described in the following Schemes. In Scheme 9 are shown methods to prepare anilines (II) where X is O or S. The readily available ortho-amino phenols or thiophenols (XXXIX) can be O- or S-alkylated with a bromoacetate in the presence of a base such as sodium hydride or potassium carbonate. Subsequent heating affords the lactams (XL). Lactams (XL) can also be prepared by a similar sequence starting with the analogous ortho-nitro phenols or thiophenols and adding an additional nitro group reduction step after the O- or S-alkylation step. The lactams (XL) can be readily reduced by a variety of reducing agents, such as borane, LAH, DIBAL, etc., to afford the anilines (II) where X is O or S. Alternately, treatment of α-halonitrobenzenes (XLI) with 2-hydroxy or 2-mercaptoacetates (XLII) in the presence of a suitable base such as triethylamine or potassium carbonate affords nitro esters (XLIII). Nitro group reduction by a variety of procedures, for example catalytic hydrogenation over palladium catalyst or treatment with tin (II) chloride, affords the aniline, which either spontaneously or upon heating provides the lactams (XL). Lactam reduction as described then affords the anilines (II) where X is O or S.

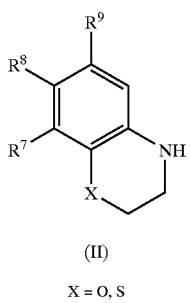

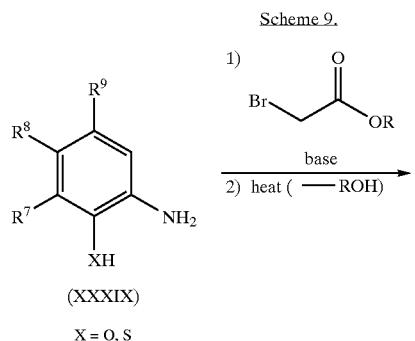

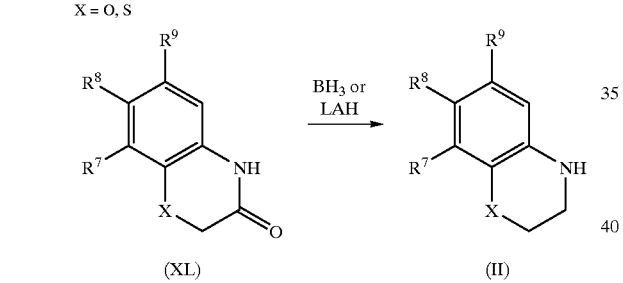

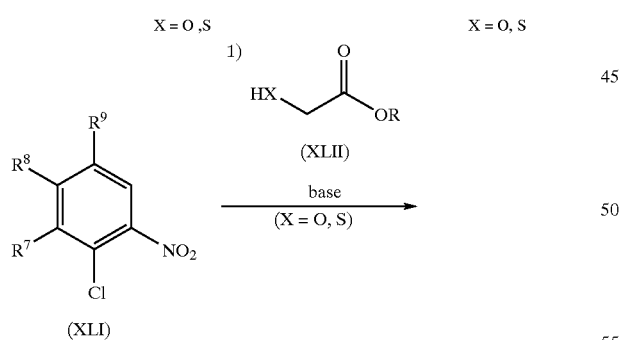

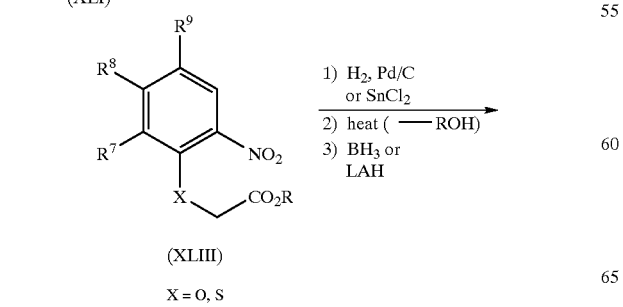

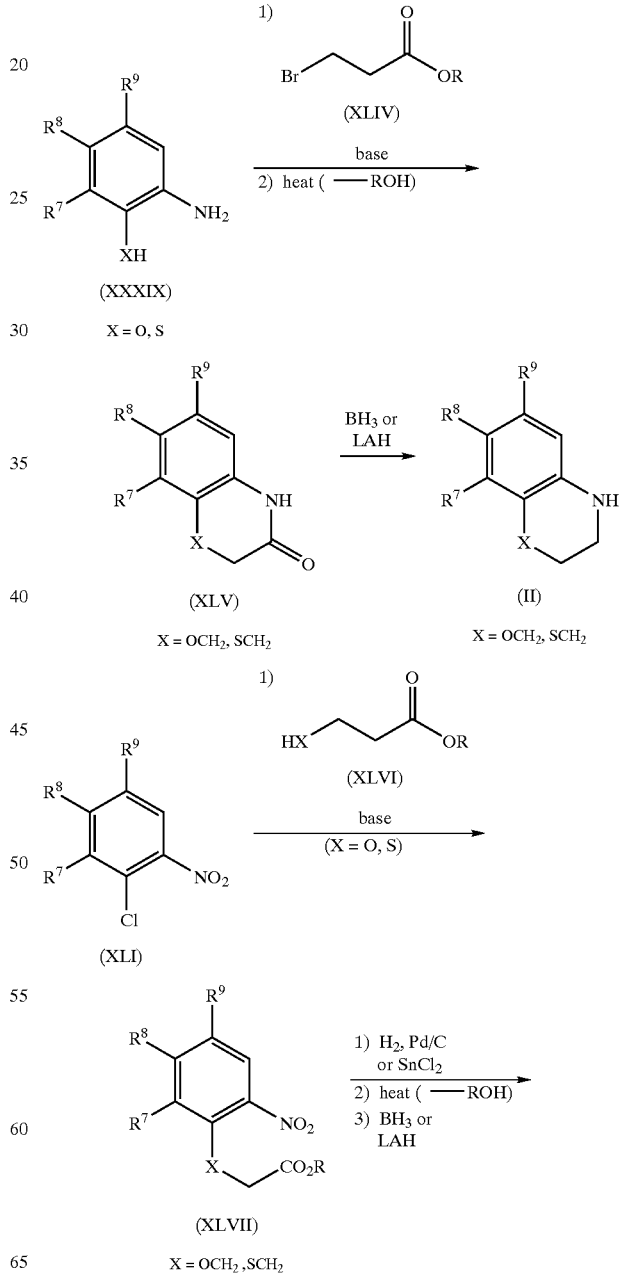

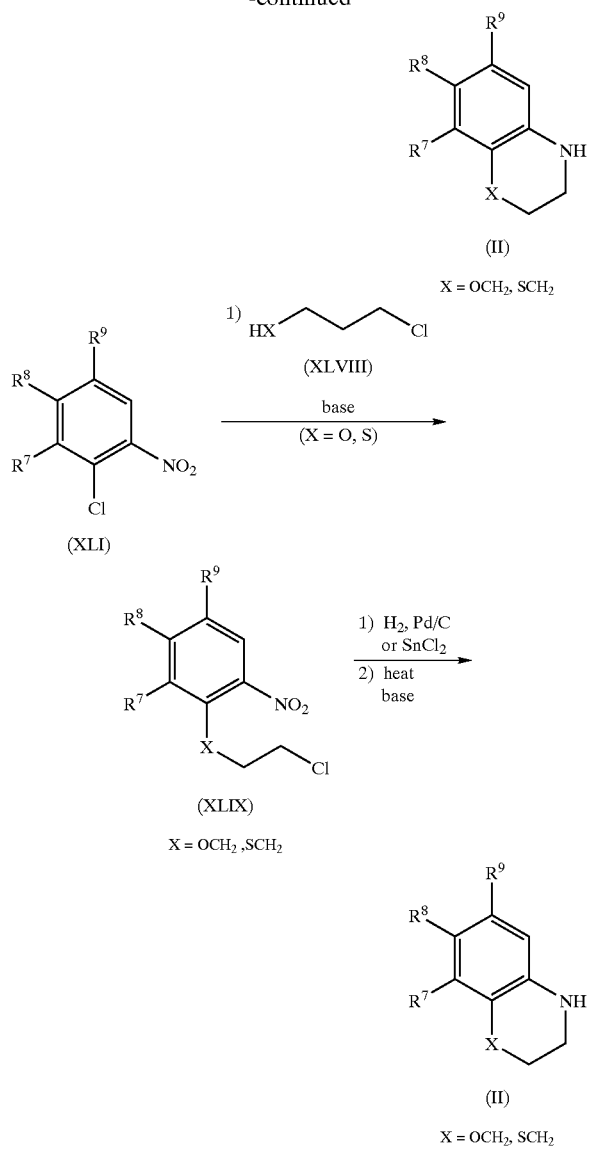

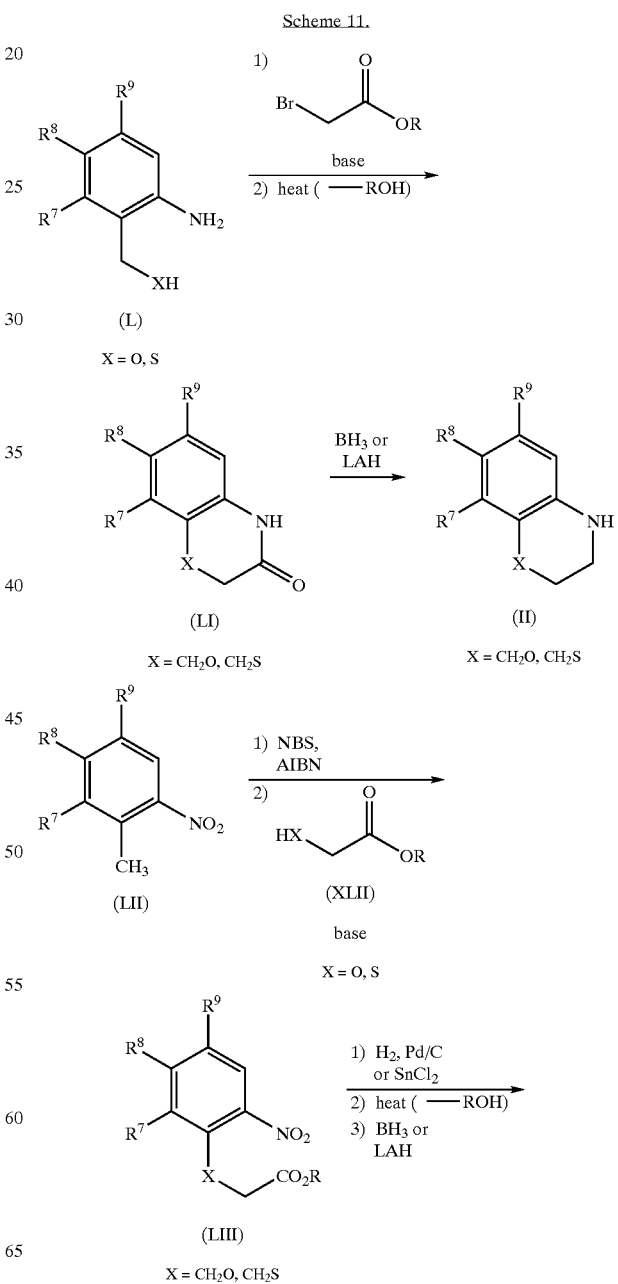

To prepare anilines (II) where X is OCH₂ or SCH₂ very similar chemistry can be used as described in Scheme 10. The ortho-amino phenols or thiophenols (XXXIX) can be O- or S-alkylated with a bromopropionate (XLIV) in the presence of a base such as sodium hydride or potassium carbonate. Subsequent heating affords the seven-membered lactams (XLV). The lactams (XLV) can be readily reduced by a variety of reducing agents, such as borane, LAH, DIBAL, etc., to afford the anilines (II) where X is OCH₂ or SCH₂. Alternately, treatment of α-halonitrobenzenes (XLI) with 3-hydroxy or 3-mercaptopropionates (XLVI) in the presence of a suitable base such as triethylamine or potassium carbonate affords nitro esters (XLVII). Nitro group reduction by a variety of procedures, for example catalytic hydrogenation over palladium catalyst or treatment with tin (II) chloride, affords the aniline, which either spontaneously or upon heating provides the lactams (XLV). Lactam reduction as described then affords the anilines (II) where X is OCH₂ or SCH₂. Alternatively, (XLI) can be displaced with alcohol or thiol (XLVIII) to afford (XLIX). Redcution of the nitro group followed by intramolecular N-alkylation, under the influence of basic and/or thermal conditions would afford anilines (II) where X is OCH₂ or SCH₂.

The anilines (II) where X is CH₂O or CH₂S can be prepared as described in Scheme 11. The ortho-amino benzyl alcohols and benzylthiols (L) are available by procedures known to those skilled in the art, for example, the benzyl alcohols are readily derived from reduction of appropriate anthranilic acid derivatives. O- or S-alkylation with bromoacetates in the presence of a base such as sodium hydride or potassium tert-butoxide affords an intermediate which when heated can undergo ring-closing condensation to afford the seven-membered lactams (LI). Reduction of the lactam as described previously affords anilines (II) where X is CH₂O or CH₂S. Alternatively, radical bromination of ortho-nitrotoluenes (LII) followed by displacement with a hydroxy- or mercaptoacetate (XLII) under basic conditions affords nitroesters (LIII). Nitro group reduction, ring-closing condensation and lactam reduction can be accomplished as described in previous Schemes to afford the anilines (II) where X is CH₂O or CH₂S.

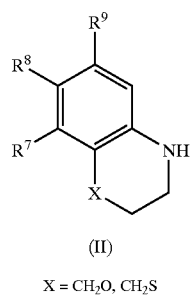

(II)

X = CH₂O, CH₂S

An alternative to the procedures described in Schemes 9–11 is described in Scheme 12. Esters (LIV) can be prepared by procedures known to those skilled in the art, including some of the procedures described in Schemes 9–11. Hydrolysis of the ester forms an acid which, when treated under Friedel-Crafts acylation conditions (see Ed. G. A. Olah, "Friedel-Crafts and Related Reactions", J. Wiley and Sons, New York, 1964, Vol 3, Pts 1 and 2 or Chem. Rev., 1955, 229, or Olah, G. A., "Friedel—Crafts Chemistry", Wiley Interscience, New York, 1973, for varying conditions and protocols), i.e. strong Lewis acids (AlCl₃, FeCl₃, etc.), affords the cyclic ketones (LV). Incorporation of the nitrogen functionality can be accomplished in several ways. For example, Schmidt rearrangement (as described by Smith, P. A. S., *J. Am. Chem. Soc.*, 1948, 320) is effected by treatment of the carbonyl derivative (LV) with NaN₃ and methanesulfonic acid to afford the bicyclic lactam (LVI). Alternatively, this transformation may be carried out under Hoffmann rearrangement protocol (see, for example, Dike, S. Y., et. al., *Bioorg. Med. Chem. Lett.*, 1991, 383), by initial formation of the oxime derivative of (LV) by treatment with hydroxylamine hydrochloride. Subsequent rearrangement to the lactam is efficiently accomplished by heating in polyphosphoric acid to afford the lactam (LVI). Reduction of the lactam (LVI) can be accomplished with a variety of reducing agents, for example, borane-THF complex, LAH and the like to afford the aniline intermediates (II).

Scheme 12.

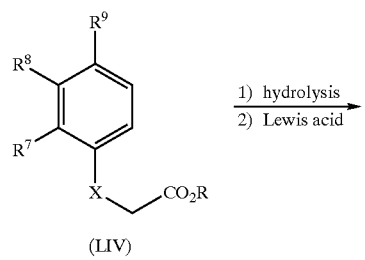

(LIV)

X = CH₂, CH₂CH₂, O, S
OCH₂, SCH₂, CH₂O, CH₂S

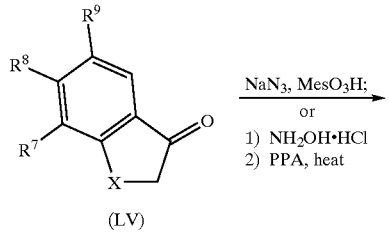

(LV)

X = CH₂, CH₂CH₂, O, S
OCH₂, SCH₂, CH₂O, CH₂S

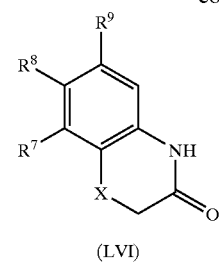

(LVI)

X = CH₂, CH₂CH₂, O, S
OCH₂, SCH₂, CH₂O, CH₂S

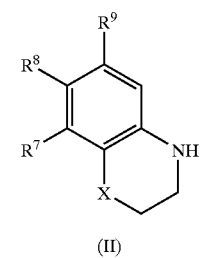

(II)

X = CH₂, CH₂CH₂, O, S
OCH₂, SCH₂, CH₂O, CH₂S

The preparation of anilines (II) where X is $NR^{10}$, $CH_2NR^{10}$, $NR^{10}CH_2$, CONH or NHCO is shown in Scheme 13. N-Acylation of readily available ortho-nitroanilines (LVII) with chloroacetyl chloride (LVIII) in the presence of a suitable base, such as triethylamine, affords an amide. Nitro group reduction and ring closure under basic or thermal conditions affords the aniline (II) where X is NHCO. The ortho-nitroanilines (LIX), which can be derived from N-alkylation of (LVII) or by displacement of an ortho-fluoro- or ortho-chloro-nitrobenzene with $R^{10}NH_2$, can be N-acylated with (LX) where n" is 1 or 2. Nitro group reduction and ring closure affords the amides (LXI). Reduction of the amide using borane or LAH then affords the anilines (II) where X is $NR^{10}CH_2$ or $NR^{10}$. N-Alkylation of amino ester (LXIII) with a benzyl bromide (LXII) affords a benzylamine intermediate. Alternatively, this benzylamine can also be derived from reductive amination of an appropriate ortho-nitrobenzaldehyde with (LXIII) in the presence of acetic acid and a hydride source such as sodium cyanoborohydride or sodium triacetoxyborohydride. N-Alkylation with $R^{10}I$ and base or by a reductive amination procedure affords (LXIV). Nitro group reduction and ring closure affords an amide, which can be reduced with borane or LAH to give aniline (II) where X is $CH_2NR^{10}$. N-Acylation of amine (LXVI) with an acid chloride (LXV) in the presence of a base such as triethylamine affords amide (LXVII). Nitro group reduction and ring closure gives aniline (II) where X is CONH.

The preparation of compounds of Formula (I) with additional diversity of functionalization of the aromatic A ring of the tetracycle is shown in the following Schemes. As shown in Scheme 14, bromination of the compounds (LXVIII, $R^8$=H) (where $R^{6a}$ and $R^{6b}$ of Formula (I) are H) when the amine is protected, for example, with the Boc or CBZ protecting groups, with, for example, NBS in DMF affords the $R^8$ brominated derivatives (LXIX). These activated aryl derivatives (LXIX) act as excellent counterparts for a number of important synthetic transformations.

Scheme 13.

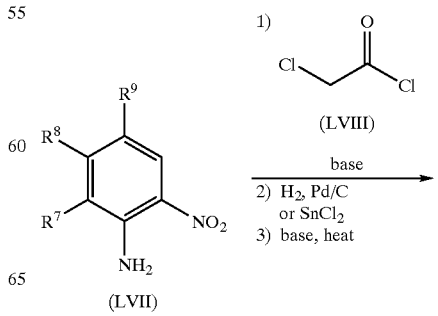

(LVII)

1)

(LVIII)

base
2) H₂, Pd/C or SnCl₂
3) base, heat

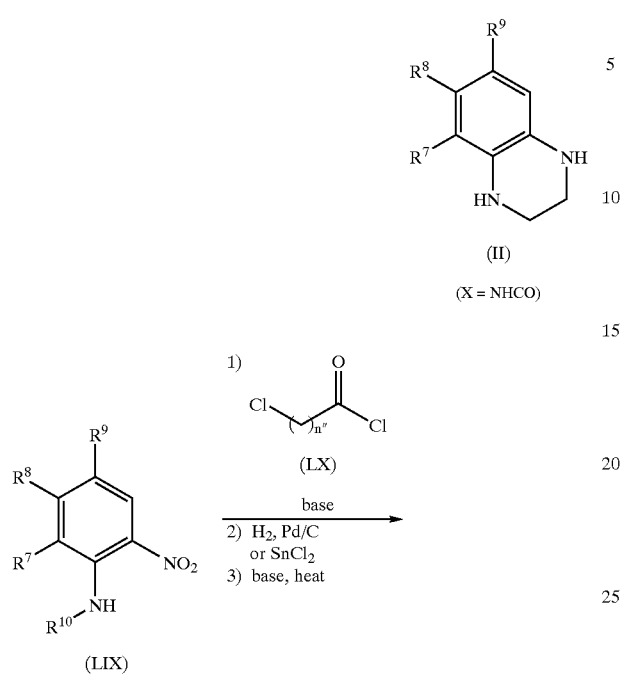

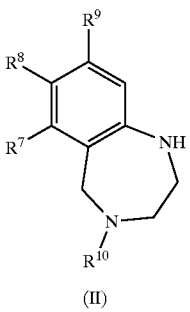

For example, biaryl coupling is accomplished under Suzuki coupling protocol. For a review and leading references of palladium catalyzed cross coupling reactions, see Miyaura, N., Suzuki, A., *Chem. Rev.*, 1995, 2457. One such procedure entails treatment of the aryl bromide (LXIX) with a functionalized aryl boronic acid (LXX) in the presence of a catalytic Pd(0) species, such as $Pd(PPh_3)_4$, $Pd(PPh_3)_2Cl_2$, $Pd(OAc)_2$, $Pd_2(dba)_3$ and a suitable ligand such as $PPh_3$, $AsPh_3$, etc., or other such Pd(0) catalyst, and a base such as $Na_2CO_3$, $Ba(OH)_2$ or $Et_3N$ in a suitable solvent such as DMF, toluene, THF, DME or the like, to afford the biaryl derivatives (LXXI).

Scheme 14.

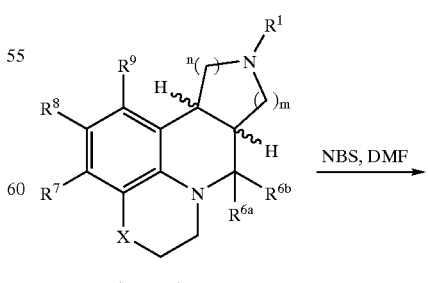

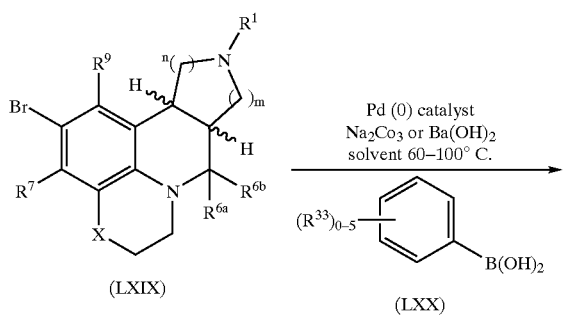

(LXIX)  (LXX)

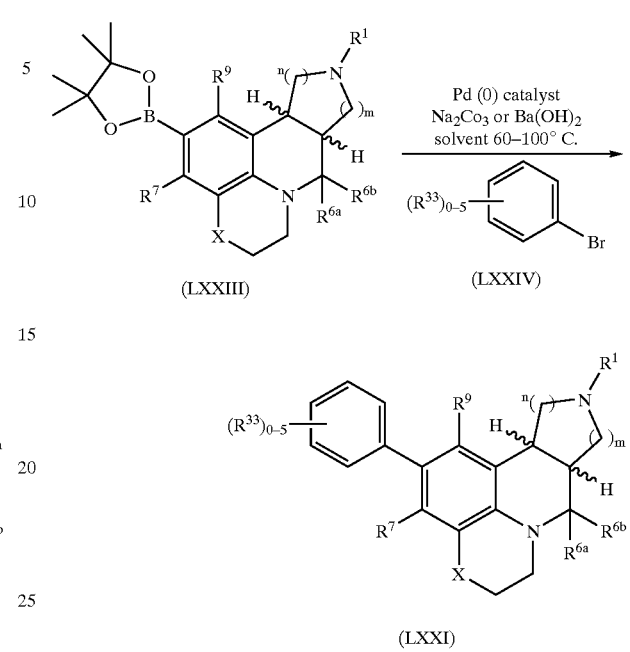

(LXXIII)  (LXXIV)

(LXXI)

(LXXI)

Alternatively formation of the boronic ester (i.e. (LXVIII, R⁸=B(OR)₂) from the bromine derivative (LXIX) would allow for greater diversity in the subsequent coupling of this boronic acid with commercially available haloaromatic derivatives in a similar Suzuki coupling strategy as described above to afford compounds (LXXI). One such procedure is shown in Scheme 15. Treatment of bromides (LXIX) with a palladium catalyst such as Pd(PPh₃)₄ or Pd(PPh₃)₂Cl₂ and a suitable base, a preferred one being potassium acetate, in the presence of diboron pinacol ester (LXXII) affords the aryl boronic ester (LXXIII). This boronic ester can undergo Suzuki coupling directly with a wide variety of commercially available aryl bromides (LXXIV) under typical Suzuki conditions as described in Scheme 13 to afford the biaryl compounds (LXXI).

Similarly, biaryl coupling of the derivatives (LXXV) is shown in Scheme 16. Protection of the amine functionality must be carried out if R¹=H (see Greene et.al for protections of amines). This is readily accomplished, for example, by treatment of the derivatives (LXXV) with (BOC)₂O in aqueous sodium hydroxide and dioxane. Subsequent Suzuki coupling with a variety of aryl boronic acids is carried out as described above in Scheme 14, to afford the biaryl adducts (LXXVI). This protocol is amenable to R⁷, R⁸, and R⁹ bromide, iodide, triflates, and/or diazo derivatives (see Miyaura, N., Suzuki, A., *Chem. Rev.*, 1995, 2457, for a review of aryl couplings).

Scheme 15.

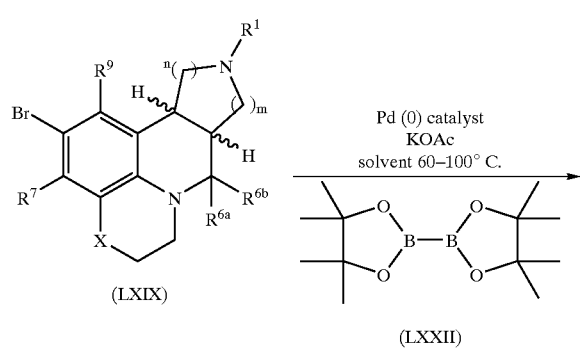

(LXIX)  (LXXII)

Scheme 16.

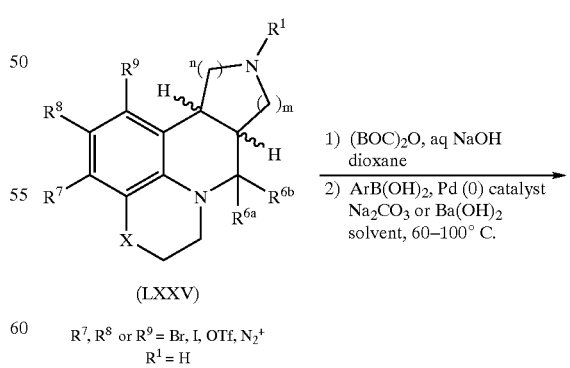

(LXXV)

R⁷, R⁸ or R⁹ = Br, I, OTf, N₂⁺
R¹ = H

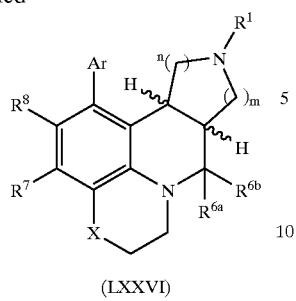

(LXXVI)

also for $R^7$, $R^8$
$R^1$ = BOC

In addition, there exists a wide range of procedures and protocols for functionalizing haloaromatics, aryldiazonium and aryltriflate compounds. These procedures are well known by those in the art and described, for example, by Stanforth, S. P., *Tetrahedron*, 1998, 263; Buchwald, S. L., et. al., *J. Am. Chem. Soc.*, 1998, 9722; Stille, J. K., et. al., *J. Am. Chem. Soc.*, 1984, 7500. Among these procedures are biaryl couplings, alkylations, acylations, aminations, and amidations. The power of palladium catalyzed functionalization of aromatic cores has been explored in depth in the last decade. An excellent review of this field can be found in J. Tsuji, "Palladium Reagents and Catalysts, Innovations in Organic Synthesis", J. Wiley and Sons, New York, 1995.

One such example is described in Scheme 17, where the aromatic A ring of Formula (I) is substituted with an arylamino group. Treatment of bromide (LXIX) with benzophenone imine in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as NaOtBu in a suitable solvent such as DMF, toluene, THF, DME or the like, affords an imine in which nitrogen is attached to the aromatic ring. Hydrolysis of this imine, for example with hydroxylamine and sodium acetate in methanol, affords the aniline (LXXVII). This aniline (LXXVII) can be treated with a wide variety of commercially available aryl bromides (LXXIV) in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as NaOtBu in a suitable solvent such as DMF, toluene, THF, DME or the like, to afford the biaryl anilines (LXXVIII). In analogy with Scheme 16, the chemistry described in Scheme 17 can also be applied to analogs of (LXIX) where the $R^7$ or $R^9$ groups are Br, I, OTf, etc., to afford analogs of (LXXVIII) where the arylamino group is on the $R^7$ or $R^9$ position.

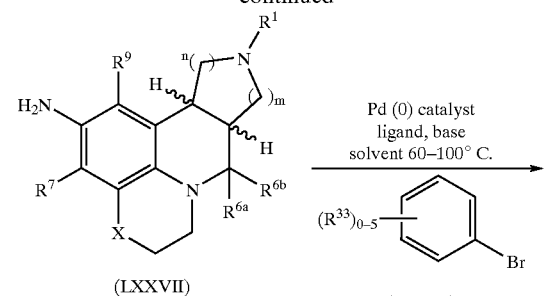

(LXXVII)  (LXXIV)

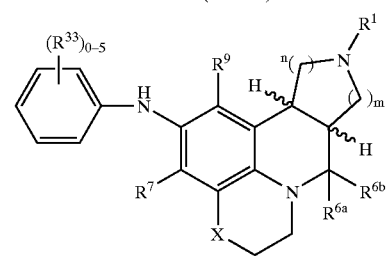

(LXXVIII)

Another Example is shown in Scheme 18. Treatment of the anilines (LXXVII) with an appropriate benzaldehyde (LXXIX) in the presence of a suitable reducing agent such as sodium triacetoxyborohydride or sodium cyanoborohydride and generally under mildly acidic conditions, such as in the presence of acetic acid, in a suitable solvent such as 1,2-dichloroethane, THF, methanol or acetonitrile, affords the benzylamine analogs (LXXX). An alternate method for preparing benzylamines (LXXX) or α-substituted benzylamines (LXXXII) proceeds from bromides (LXIX). Treatment of bromide (LXIX) with benzylamines (L), which can be chiral if $R^{10}$ is an appropriate group, such as alkyl, in the presence of a palladium (0) catalyst, such as $Pd_2(dba)_3$, $Pd(PPh_3)_4$ or $Pd(PPh_3)_2Cl_2$, and a suitable ligand such as BINAP or $PPh_3$, and a base such as NaOtBu or $Na_2CO_3$ in a suitable solvent such as DMF, toluene, THF, DME or the like, affords the benzylamines (LXXXII). In analogy with previous schemes, the chemistry described in Scheme 18 can also be applied to analogs of (LXXVII) or (LXIX) where the $R^7$ or $R^9$ groups are $NH_2$, Br, I, OTf, etc., to afford analogs of (LXXX) or (LXXXII) where the benzylamino group is on the $R^7$ or $R^9$ position.

Scheme 18.

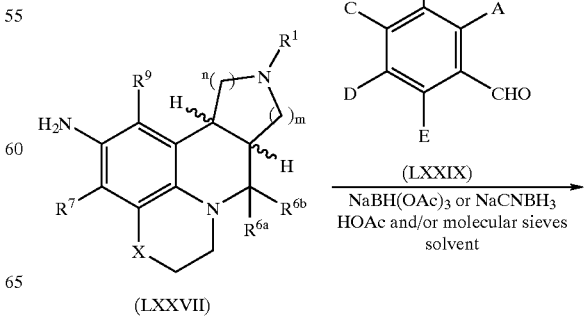

(LXXVII)  (LXXIX)

NaBH(OAc)$_3$ or NaCNBH$_3$
HOAc and/or molecular sieves
solvent

Scheme 17.

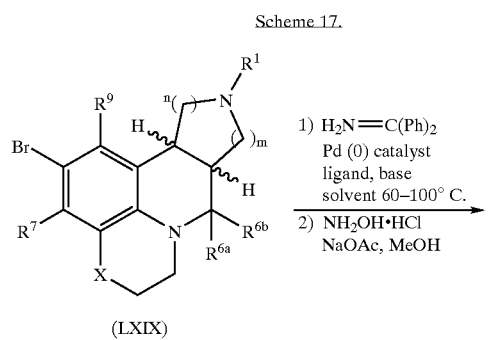

(LXIX)

1) $H_2N\!=\!\!C(Ph)_2$
Pd (0) catalyst
ligand, base
solvent 60–100° C.
2) $NH_2OH \cdot HCl$
NaOAc, MeOH

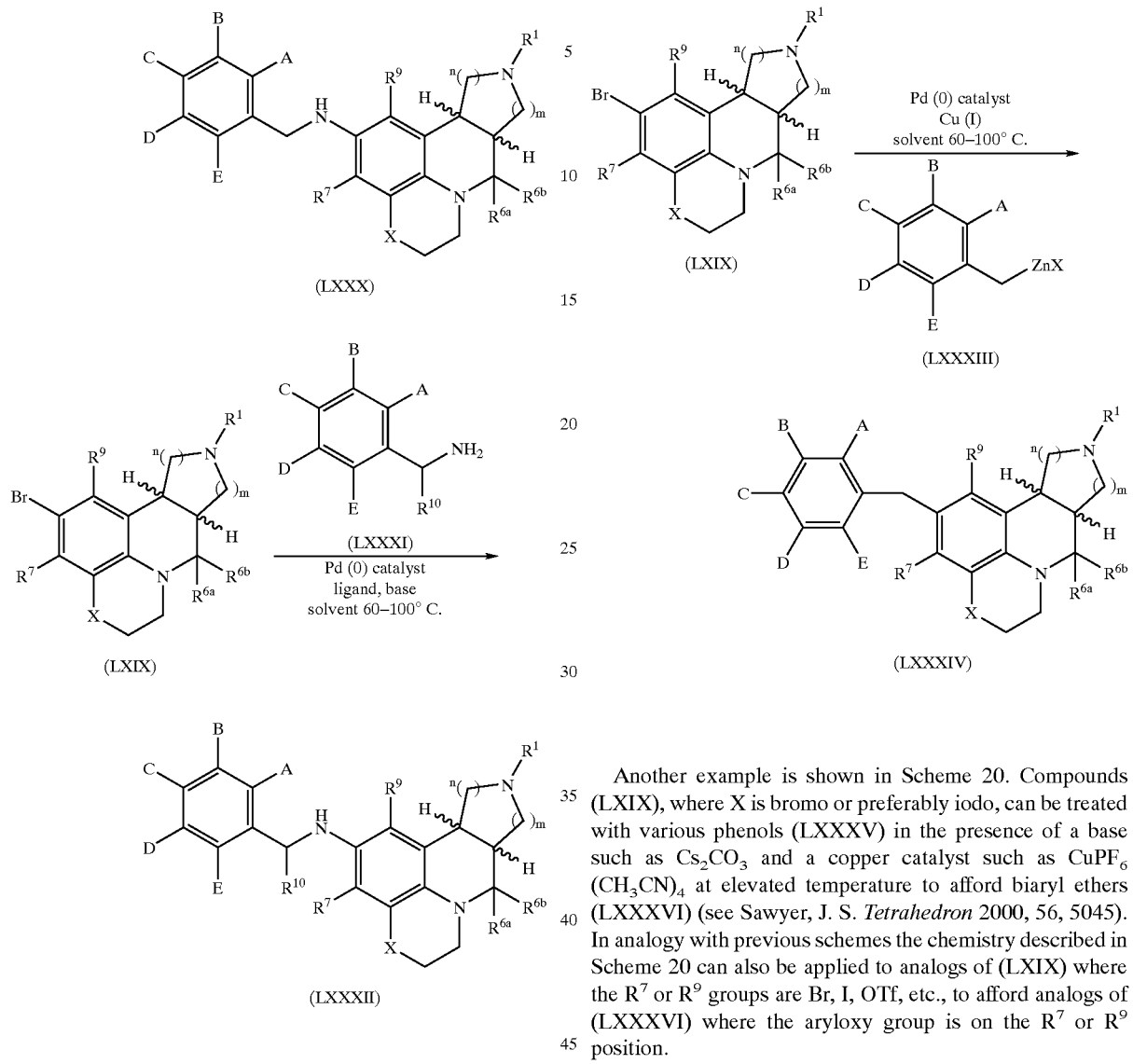

Another example is shown in Scheme 19. Treating bromides (LXIX) with an appropriate benzylic zinc reagent (LXXXIII), which can be generated from the corresponding benzyl halide, in the presence of a palladium (0) catalyst such as Pd(PPh$_3$)$_4$, Pd(PPh$_3$)$_2$Cl$_2$, or Pd$_2$(dba)$_3$, and with or without a copper (I) salt, affords the derivatives (LXXXIV) where R$^8$ is a benzyl group (see Knochel, P., et. al. *Chem. Rev.* 1993, 93, 2117; and Weichert, A., et. al. *Syn. Lett.* 1996, 473). This chemistry can also be extended to include a variety of alkylzinc and cycloalkylzinc reagents, which are available from the corresponding alkyl halides and cycloalkyl halides. In analogy with previous schemes the chemistry described in Scheme 19 can also be applied to analogs of (LXIX) where the R$^7$ or R$^9$ groups are Br, I, OTf, etc., to afford analogs of (LXXXIV) where the benzyl or alkyl or cycloalkyl group is on the R$^7$ or R$^9$ position.

Another example is shown in Scheme 20. Compounds (LXIX), where X is bromo or preferably iodo, can be treated with various phenols (LXXXV) in the presence of a base such as Cs$_2$CO$_3$ and a copper catalyst such as CuPF$_6$(CH$_3$CN)$_4$ at elevated temperature to afford biaryl ethers (LXXXVI) (see Sawyer, J. S. *Tetrahedron* 2000, 56, 5045). In analogy with previous schemes the chemistry described in Scheme 20 can also be applied to analogs of (LXIX) where the R$^7$ or R$^9$ groups are Br, I, OTf, etc., to afford analogs of (LXXXVI) where the aryloxy group is on the R$^7$ or R$^9$ position.

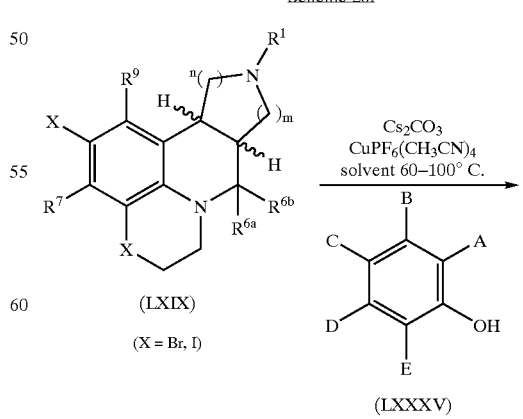

-continued

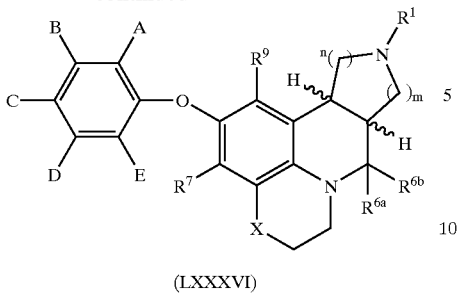

(LXXXVI)

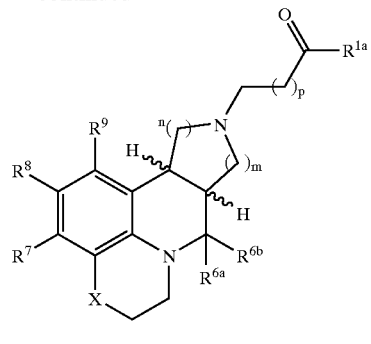

(LXXXVIII)

The compounds of Formula (I) with substituted $R^1$ sidechains can be prepared as described in Scheme 21. Alkylation of the derivatives (I, $R^1$=H) with a haloalkyl ester, such as $ClCH_2(CH_2)_pCO_2Me$, in the presence of NaI or KI and a base such as $K_2CO_3$, $Na_2CO_3$ or the like, in dioxane or THF or other such solvent while heating (see Glennon, R. A., et. al., Med. Chem. Res., 1996, 197) affords the $R^1$ alkylated esters. Subsequent formation of the activated amides (LXXXVII) is accomplished by treatment of the ester with N,O-dimethylhydroxylamine hydrochloride and a Lewis acid such as trimethylaluminum or triethylaluminum in toluene (see, for example, Golec, J. M. C., et. al., Tetrahedron, 1994, 809) at 0° C. Treatment of the amide (LXXXVII) with a variety of organometallic agents, such as Grignard reagents $R^{1a}MgBr$, alkyl and aryl lithium reagents etc. (see Sibi, M. P., et. al., Tetrahedron Lett., 1992, 1941; and more generally House, H. O., Modern Synthetic Reactions, W.A. Benjamin, Inc., Menlo Park, Calif., 1972), in a suitable solvent such as THF, ether, etc. at low temperatures affords the substituted ketones (LXXXVIII).

Compounds of Formula (I) where $R^{6a}$ and $R^{6a}$ taken together are S can be prepared as described in Scheme 22. Compounds of Formula (I) where $R^{6a}$ and $R^{6a}$ taken together are O are treated with Lawesson's reagent or $P_2S_5$ to afford the thiolactams (I), where $R^{6a}$ and $R^{6a}$ taken together are S.

Scheme 22.

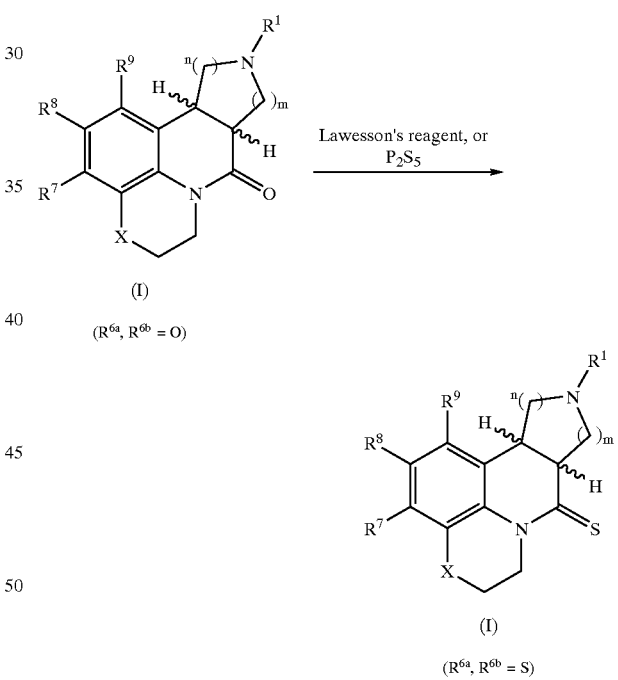

Scheme 21.

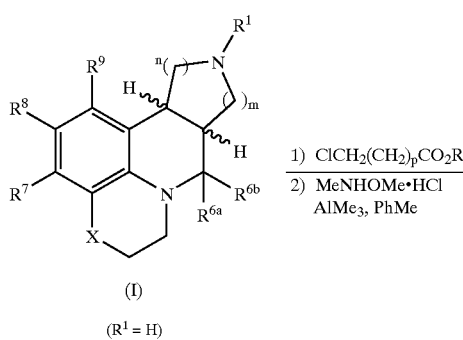

1) $ClCH_2(CH_2)_pCO_2R$
2) MeNHOMe·HCl
   AlMe$_3$, PhMe

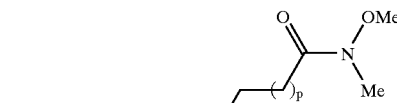

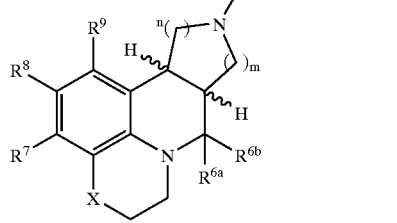

1) $R^{1a}MgBr$, THF
   0° C.
2) aq. HCl (LXXXVII)

Compounds of Formula (I) where X is $S(O)_n$, $S(O)_nCH_2$ and $CH_2S(O)_n$ are prepared as shown in Scheme 23. Compounds of Formula (I) where X=S, $SCH_2$ and $CH_2S$ can be readily oxidized by a variety of oxidizing agents, such as MCPBA, oxone or sodium periodate. Also, depending on the number of equivalents of oxidizing agent used, the reaction can be varied to provide compounds (I) where X is $S(O)_n$, $S(O)_nCH_2$ and $CH_2S(O)_n$, where n=1 (sulfoxide) or n=2 (sulfone).

Scheme 23.

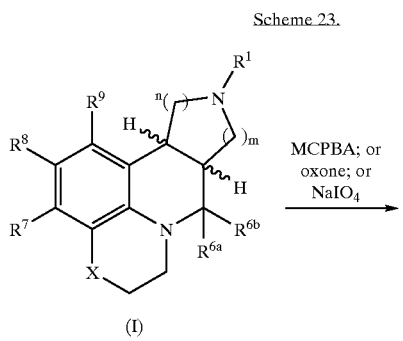

(X = S, SCH₂, CH₂S)

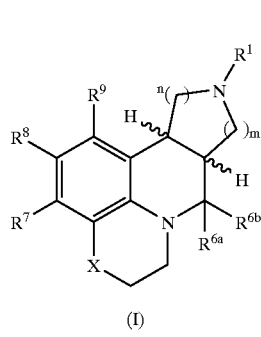

(X = S(O)$_n$, S(O)$_n$CH$_2$, CH$_2$S(O)$_n$)

The compounds of Formula (I) where $R^{6a}$ is C1–4 alkyl and $R^{6b}$ is H can be prepared as shown in Scheme 24. Treatment of (I), where $R^{6a}$ and $R^{6b}$ taken together are carbonyl, with an appropriate alkylcerium reagent, which is prepared in situ from the corresponding alkyllithium reagent, or an appropriate alkyl Grignard reagent, followed by reduction of the intermediate under acidic conditions with a borohydride reagent, such as sodium borohydride, affords the compounds (I), where $R^{6a}$ is C1–4 alkyl and $R^{6b}$ is H (see Nukui, S., et. al. *J. Org. Chem.* 1995, 60, 398; and Aube, J., et. al. *Heterocycles* 1993, 35, 1141). Alternatively, treatment of (I), where $R^{6a}$ and $R^{6b}$ taken together are carbonyl, with an appropriate dialkyl titanocene (see Petasis, N. A., et. al. *Tetrahedron Lett.* 1995, 36, 2393 and references cited therein) affords an amino olefin which can be reduced with sodium borohydride under acidic conditions to afford compounds (I), where $R^{6a}$ is C1–4 alkyl and $R^{6b}$ is H.

Scheme 24.

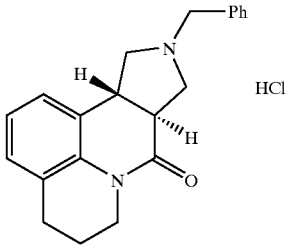

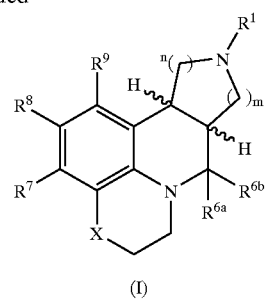

$R^{6a}$ = C1-4 alkyl, $R^{6b}$ = H

EXAMPLES

The detailed processes for preparing the compounds of Formula (I) are illustrated by the following EXAMPLES. It is, however, understood that this invention is not limited to the specific details of these EXAMPLES. The EXAMPLES as set forth below are intended to demonstrate the scope of the invention but are not intended to limit the scope of the invention.

Example 1

(±)-trans-10-benzyl-5,6,9,10,11,11a-hexahydro-4H-pyrido[3,2,1-ij]pyrrolo[3,4-c]quinolin-8(8aH)-one, hydrochloride salt

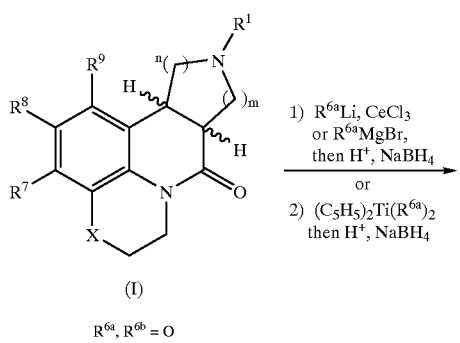

Part A. tert-butyl 3,4-dihydro-1(2H)-quinolinecarboxylate.

To a solution of 1,2,3,4-tetrahydroquinoline (20.0 g, 0.15 mol) in 300 mL of methylene chloride at ambient temperature was added di-tert-butyl dicarbonate (36.0 g, 0.165 mol) and triethylamine (23.0 mL, 0.165 mol). The resulting mixture was allowed to stir at 40° C. for 24 h. The reaction was allowed to cool to ambient temperature and the methylene chloride was removed under reduced pressure. The residue was dissolved in ethyl acetate, washed with 10% aqueous HCl, saturated aqueous sodium bicarbonate and brine, dried (MgSO$_4$) and concentrated in vacuo. The residue was purified by flash chromatography (elution with 8:1 hexane/ethyl acetate) to afford 25.4 g (72%) of the title compound as an oil. $^1$H NMR (CDCl$_3$): δ 7.66 (d, 1H, J=8.4 Hz), 7.15 (t, 1H, J=8.5 Hz), 7.09 (d, 1H, J=7.0 Hz), 7.00 (t, 1H, J=7.3 Hz), 3.75–3.71 (m, 2H), 2.78 (app t, 2H, J=6.6 Hz), 1.94 (app quintet, 2H, J=6.0 Hz), 1.54 (s, 9H).

Part B. tert-butyl 8-formyl-3,4-dihydro-1(2H)-quinolinecarboxylate.

To a solution of tert-butyl 3,4-dihydro-1(2H)-quinolinecarboxylate (10.3 g, 44.1 mmol) in 200 mL of diethyl ether at −78° C. was added N,N,N',N'-tetramethylethylenediamine (7.98 mL, 52.9 mmol) and then sec-butyllithium (40.7 mL of a 1.3 M solution in cyclohexane, 52.9 mmol) was added dropwise via addition funnel. The mixture was stirred at −78° C. for 1 h, at which time a precipitate had formed. N,N-dimethylformamide (5.1 mL, 66.1 mmol) was added dropwise in 10 mL of diethyl ether and the resulting mixture was stirred at −78° C. for 1 h, at which time the precipitate had largely disappeared. The reaction was quenched by the addition of 25 mL of saturated aqueous ammonium chloride and then was diluted with water and ethyl acetate. The organics were washed with 10% aqueous HCl, saturated aqueous sodium bicarbonate and brine, dried (MgSO$_4$) and concentrated in vacuo. The residue was purified by flash chromatography (elution with 5:1 hexane/ethyl acetate) to afford 5.7 g (50%) of the title compound a pale yellow solid. $^1$H NMR (CDCl$_3$): δ 9.98 (broad s, 1H), 7.72 (d, 1H, J=7.7 Hz), 7.34 (d, 1H, J=6.9 Hz), 7.21 (t, 1H, J=7.5 Hz), 4.50–4.30 (very broad m, 1H), 3.30–3.10 (very broad m, 1H), 2.86 (app t, 2H, J=6.7 Hz), 2.06–1.95 (broad m, 2H), 1.44 (broad s, 9H).

Part C. tert-butyl 8-[(1E)-3-ethoxy-3-oxo-1-propenyl]-3,4-dihydro-1(2H)-quinolinecarboxylate.

Sodium hydride (0.50 g of 60% dispersion in mineral oil, 12.6 mmol) was washed with 10 mL of hexane and suspended in 30 mL of tetrahydrofuran. To this suspension was added triethyl phosphonoacetate (2.52 mL, 12.6 mmol) and the resulting mixture was stirred at ambient temperature for 30 min, at which time the solution was homogeneous. To this solution was added tert-butyl 8-formyl-3,4-dihydro-1(2H)-quinolinecarboxylate (3.0 g, 11.5 mmol) in 10 mL of tetrahydrofuran and the resulting solution was stirred at ambient temperature for 1 h. The reaction was diluted with water and extracted with ethyl acetate. The organics were washed with brine, dried (MgSO$_4$), filtered through a pad of silica gel and concentrated in vacuo to afford 3.7 g (97%) of the title compound which was used without purification. $^1$H NMR (CDCl$_3$): δ 7.74 (d, 1H, J=16.1 Hz), 7.51–7.48 (m, 1H), 7.21–7.11 (m, 2H), 6.42 (d, 1H, J=16.1 Hz), 4.50–4.35 (broad m, 1H), 4.27 (dq, 2H, J=7.2, 2.4 Hz), 3.15–3.00 (broad s, 1H), 2.79–2.74 (m, 2H), 2.22–2.10 (broad m, 1H), 1.89–1.78 (broad s, 1H), 1.39 (broad s, 9H), 1.33 (t, 3H).

Part D. (±)-trans-tert-butyl 8-[1-benzyl-4-(ethoxycarbonyl)-3-pyrrolidinyl]-3,4-dihydro-1(2H)-quinolinecarboxylate.

To a solution of tert-butyl 8-[(1E)-3-ethoxy-3-oxo-1-propenyl]-3,4-dihydro-1(2H)-quinolinecarboxylate (2.55 g, 7.7 mmol) in 50 mL of methylene chloride at 0° C. was added N-(methoxymethyl)-N-(trimethylsilylmethyl)benzylamine (4.6 g, 19.3 mmol) and trifluoroacetic acid (0.24 mL, 3.1 mmol). The cooling bath was removed and the solution was allowed to stir with warming to ambient temperature for 24 h. The methylene chloride was removed under reduced pressure. The residue was dissolved in ethyl acetate, washed with saturated aqueous sodium bicarbonate and brine, dried (MgSO$_4$) and concentrated in vacuo. The residue was purified by flash chromatography (elution with 5:1 hexane/ethyl acetate) to afford 3.0 g (83%) of the title compound as an oil. LRMS (ES)$^+$: 465.3 (M+H)$^+$.

Part E. (±)-trans-10-benzyl-5,6,9,10,11,11a-hexahydro-4H-pyrido[3,2,1-ij]pyrrolo[3,4-c]quinolin-8(8aH)-one, Hydrochloride salt.

To a solution of (±)-trans-tert-butyl 8-[1-benzyl-4-(ethoxycarbonyl)-3-pyrrolidinyl]-3,4-dihydro-1(2H)-quinolinecarboxylate (0.40 g, 0.86 mmol) in 20 mL of methylene chloride was added 5 mL of trifluoroacetic acid. The mixture was allowed to stir at ambient temperature for 2 h and then was concentrated in vacuo. The residue was taken up in ethyl acetate, washed with saturated aqueous sodium bicarbonate and brine, dried (MgSO$_4$) and concentrated in vacuo to afford 0.30 g of an oil. This residue (0.30 g, 0.62 mmol) was dissolved in 20 mL of absolute ethanol and then there was added para-toluenesulfonic acid monohydrate (173 mg, 0.91 mmol) and the solution was stirred at 80° C. for 1 h. The reaction was cooled to ambient temperature, diluted with ethyl acetate, washed with saturated aqueous sodium bicarbonate and brine, dried (MgSO$_4$) and concentrated in vacuo to afford 0.22 g of an oil. A portion of this material (35 mg, 0.11 mmol) was dissolved in 5 mL of ether and then there was added 2M HCl in ether (0.055 mL, 0.11 mmol). A solid precipitated out of solution. The solvent was decanted and the solid was triturated twice with ether and dried in vacuo to afford 30 mg (77%) of the title compound of EXAMPLE 1 as an off white powder. $^1$H NMR (d6-dmso): δ 11.8–11.6 (broad m, 1H), 7.66–7.62 (m, 2H), 7.47–7.44 (m, 3H), 7.13–7.09 (m, 1H), 6.99–6.94 (m, 2H), 4.57–4.43 (m, 2H), 4.23–4.15 (m, 1H), 3.95–3.88 (m, 1H), 3.62–3.52 (m, 2H), 3.40–3.23 (m, 4H), 2.80–2.68 (m, 2H), 1.86–1.81 (m, 2H). LRMS (ES)$^+$: 319.3 (M+H)$^+$.

Example 2

(±)-trans-10-benzyl-5,6,8,8a,9,10,11,11a-octahydro-4H-pyrido[3,2,1-ij]pyrrolo[3,4-c]guinoline, bis-hydrochloride salt

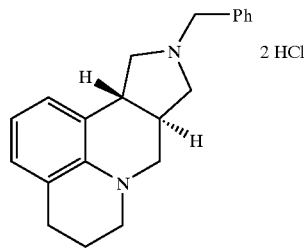

To a solution of (±)-trans-10-benzyl-5,6,9,10,11,11a-hexahydro-4H-pyrido[3,2,1-ij]pyrrolo[3,4-c]quinolin-8(8aH)-one from EXAMPLE 1, Part E (120 mg, 0.38 mmol) in 5 mL of tetrahydrofuran was added borane tetrahydrofuran complex (1.13 mL of 1.0M borane in tetrahydrofuran, 1.13 mmol) and the resulting solution was stirred at ambient temperature for 24 h. The reaction was quenched by the addition of 10 mL of methanol and was concentrated in vacuo. The residue was purified by preparative HPLC (C18 reverse phase column, elution with a H$_2$O/CH$_3$CN gradient with 0.5% TFA). Product-containing fractions were combined, concentrated and partitioned between chloroform and saturated aqueous sodium carbonate. The organics were washed with brine, dried (K$_2$CO$_3$) and concentrated in vacuo. The residue (45 mg, 0.15 mmol) was dissolved in ether and there was added 2M HCl in ether (0.15 mL, 0.30 mmol). The solvent was decanted and the remaining solid was triturated twice with ether and was dried in vacuo to afford 20 mg (36%) of the title compound of EXAMPLE 2 as an off white powder. LRMS (ES)$^+$: 305.3 (M+H)$^+$.

Example 3

(±)-trans-5,6,9,10,11,11a-hexahydro-4H-pyrido[3,2,1-ij]pyrrolo[3,4-c]quinolin-8(8aH)-one, hydrochloride salt

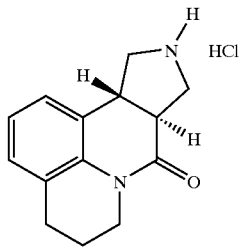

To a solution of (±)-trans-10-benzyl-5,6,9,10,11,11a-hexahydro-4H-pyrido[3,2,1-ij]pyrrolo[3,4-c]quinolin-8(8aH)-one from EXAMPLE 1, Part E (1.2 g, 3.8 mmol) in 20 mL of toluene was added 1-chloroethyl chloroformate (0.81 mL, 7.53 mmol) and the resulting solution was stirred at 110° C. for 3 h. The reaction mixture was cooled and the toluene was removed under reduced pressure. The residue was taken up in 20 mL of methanol and was stirred at 65° C. for 1 h. The reaction was cooled and the methanol was removed under reduced pressure. A portion of the residue (50 mg, 0.19 mol) was partitioned between chloroform and saturated aqueous sodium carbonate. The organics were washed with brine, dried ($K_2CO_3$) and concentrated in vacuo. The residue was dissolved in ether and there was added 2M HCl in ether (0.095 mL, 0.19 mmol). The solvent was decanted and the remaining solid was triturated twice with ether and was dried in vacuo to afford 25 mg (50%) of the title compound of EXAMPLE 3 as an off white powder. LRMS (ES)$^+$: 270.3 (M+H+$CH_3$CN)$^+$.

Example 4

(±)-trans-5,6,8,8a,9,10,11,11a-octahydro-4H-pyrido[3,2,1-ij]pyrrolo[3,4-c]quinoline, bis-hydrochloride salt

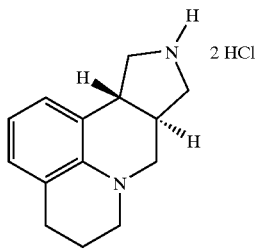

Part A. (±)-trans-tert-butyl 8-oxo-5,6,8a,9,11,11a-hexahydro-4H-pyrido[3,2,1-ij]pyrrolo[3,4-c]quinoline-10(8A)-carboxylate.

To a solution of (±)-trans-5,6,9,10,11,11a-hexahydro-4H-pyrido[3,2,1-ij]pyrrolo[3,4-c]quinolin-8(8aH)-one, hydrochloride salt (0.51 g, 1.92 mmol) in 20 mL of methylene chloride was added di-tert-butyl dicarbonate (0.50 g, 2.3 mmol) and triethylamine (0.59 mL, 4.2 mmol). The resulting mixture was allowed to stir at ambient temperature for 4 h and the methylene chloride was removed under reduced pressure. The residue was dissolved in ethyl acetate, washed with 10% aqueous HCl, saturated aqueous sodium bicarbonate and brine, dried (MgSO$_4$) and concentrated in vacuo to 0.62 g (98%) of the title compound as an oil which was used without purification. $^1$H NMR (CDCl$_3$) δ 7.07 (d, 1H), 6.97 (t, 1H), 6.88 (d, 1H), 4.42–4.36 (m, 1H), 4.15–4.05 (m, 1H), 3.90–3.80 (m, 1H), 3.57–3.39 (m, 3H), 3.25–3.15 (m, 1H), 2.84–2.70 (m, 3H), 1.95 (app quintet, 2H), 1.52 (s, 9H).

Part B. (±)-trans-tert-butyl 5,6,8a,9,11,11a-hexahydro-4H-pyrido[3,2,1-ij]pyrrolo[3,4-c]quinoline-10(8H)-carboxylate.

To a solution of (±)-trans-tert-butyl 8-oxo-5,6,8a,9,11,11a-hexahydro-4H-pyrido[3,2,1-ij]pyrrolo[3,4-c]quinoline-10(8H)-carboxylate (0.62 g, 1.89 mmol) in 20 mL of tetrahydrofuran was added borane tetrahydrofuran complex (9.4 mL of 1.0M borane in tetrahydrofuran, 9.4 mmol) and the resulting solution was stirred at ambient temperature for 24 h. The reaction was quenched by the addition of 10 mL of methanol and was concentrated in vacuo. The residue was dissolved in ethyl acetate, washed with 10% aqueous HCl, saturated aqueous sodium bicarbonate and brine, dried (MgSO$_4$), filtered through a pad of silica gel and concentrated in vacuo to afford 0.5 g (85%) of the title compound which was used without purification. LRMS (ES)$^+$: 315.3 (M+H)$^+$.

Part C. (±)-trans-5,6,8,8a,9,10,11,11a-octahydro-4H-pyrido[3,2,1-ij]pyrrolo[3,4-c]quinoline, bis-hydrochloride salt.

To a solution of (±)-trans-tert-butyl 5,6,8a,9,11,11a-hexahydro-4H-pyrido[3,2,1-ij]pyrrolo[3,4-c]quinoline-10(8H)-carboxylate (240 mg, 0.76 mmol) in 6 mL of methylene chloride was added 1 mL of trifluoroacetic acid. Stirred at ambient temperature for 2 h and then concentrated under reduced pressure. The residue was partitioned between chloroform and saturated aqueous sodium carbonate. The organics were washed with brine, dried (K$_2$CO$_3$) and concentrated in vacuo to afford 160 mg (98%) of an oil. A portion of this residue (80 mg, 0.37 mmol) was dissolved in 1 mL absolute ethanol and 5 mL ether and then 2M HCl in ether (0.37 mL, 0.75 mmol) was added and a solid fell out of solution. The solvents were decanted and the solid was triturated twice with ether and dried in vacuo to afford 50 mg (47%) of the title compound of EXAMPLE 4 as an off white powder. $^1$H NMR (d6-dmso): δ 9.4 (broad s, 2H), 6.76 (d, 1H, J=7.4 Hz), 6.63 (d, 1H, J=7.3 Hz), 6.38 (t, 1H, J=7.3 Hz), 3.55–3.45 (m, 1H), 3.38–3.10 (m, 5H), 3.02–2.92 (m, 1H), 2.90–2.75 (m, 2H), 2.66–2.60 (m, 2H), 2.08–1.98 (m, 1H), 1.92–1.83 (m, 1H), 1.81–1.72 (m, 1H). LRMS (ES)$^+$: 215.4 (M+H)$^+$.

Example 5

(±)-trans-10-methyl-5,6,9,10,11,11a-hexahydro-4H-pyrido[3,2,1-ij]pyrrolo[3,4-c]quinolin-8(8aH)-one, hydrochloride salt

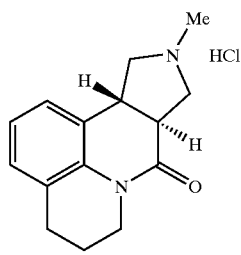

To a solution of (±)-trans-5,6,9,10,11,11a-hexahydro-4H-pyrido[3,2,1-ij]pyrrolo[3,4-c]quinolin-8(8aH)-one, hydrochloride salt from EXAMPLE 3 (200 mg, 0.76 mmol) in 5 mL of 1,2-dichloroethane was added 37% aqueous formaldehyde (0.065 mL, 0.76 mmol) and sodium triacetoxyborohydride (260 mg, 1.22 mmol). The resulting mixture was stirred at ambient temperature for 1 h and then the reaction was quenched with water. The mixture was partitioned between chloroform and saturated aqueous sodium carbonate. The organics were washed with brine, dried (K₂CO₃) and concentrated in vacuo. A portion of the residue (50 mg, 0.21 mmol) was dissolved in 1 mL ethanol and 5 mL of ether and then there was added 2M HCl in ether (0.105 mL, 0.21 mmol). A solid precipitated out of solution. The solvents were decanted and the solid was triturated twice with ether and dried in vacuo to afford 25 mg (43%) of the title compound of EXAMPLE 5 as an off white powder. ¹H NMR (d6-dmso): δ 7.12 (d, 1H, J=7.4 Hz), 6.99 (t, 1H, J=7.3 Hz), 6.97–6.90 (m, 1H), 4.25–4.12 (m, 2H), 3.75–3.65 (m, 2H), 3.40–3.20 (m, 3H), 2.97–2.90 (m, 3H), 22.81–2.70 (m, 3H), 1.88–1.80 (m, 2H). LRMS (ES)⁺: 243.4 (M+H)⁺.

Example 6

(±)-trans-10-methyl-5,6,8,8a,9,10,11,11a-octahydro-4H-pyrido[3,2,1-ij]pyrrolo[3,4-c]quinoline, bis-hydrochloride

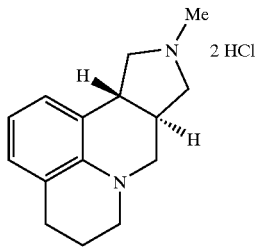

To a solution of (±)-trans-5,6,8,8a,9,10,11,11a-octahydro-4H-pyrido[3,2,1-ij]pyrrolo[3,4-c]quinoline from EXAMPLE 4 (95 mg, 0.44 mmol) in 5 mL of 1,2-dichloroethane was added 37% aqueous formaldehyde (0.043 mL, 0.53 mmol), sodium triacetoxyborohydride (168 mg, 0.79 mmol) and glacial acetic acid (0.027 mL, 0.48 mmol). The resulting mixture was stirred at ambient temperature for 1 h and then the reaction was quenched with water. The mixture was partitioned between chloroform and saturated aqueous sodium carbonate. The organics were washed with brine, dried (K₂CO₃) and concentrated in vacuo. The residue was dissolved in 1 mL ethanol and 5 mL of ether and then there was added 2M HCl in ether (0.44 mL, 0.88 mmol). A solid precipitated out of solution. The solvents were decanted and the solid was triturated twice with ether and dried in vacuo to afford 35 mg (27%) of the title compound of EXAMPLE 6 as an off white powder. ¹H NMR (d6-dmso): δ 11.22 (broad s, 1H), 6.76 (d, 1H, J=7.7 Hz), 6.57 (dd, 1H, J=7.3, 12.5 Hz), 6.38 (t, 1H, J=7.3 Hz), 4.17–4.08 (m, 1H), 3.81–3.72 (m, 1H), 3.68–3.60 (m, 1H), 3.42–3.18 (m, 5H), 2.98–2.80 (m, 4H), 2.66–2.60 (m, 2H), 2.10–1.98 (m, 1H), 1.95–1.83 (m, 1H), 1.82–1.72 (m, 1H). LRMS (ES)⁺: 229.4 (M+H)⁺.

Example 7

(±)-trans-2-[4-methoxy-2-(trifluoromethyl)phenyl]-5,6,8,8a,9,10,11,11a-octahydro-4H-pyrido[3,2,1-ij]pyrrolo[3,4-c]quinoline, bis-hydrochloride salt

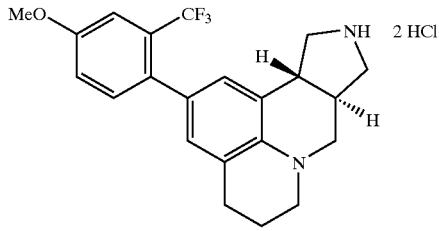

Part A. (±)-trans-tert-butyl 2-bromo-5,6,8a,9,11,11a-hexahydro-4H-pyrido[3,2,1-ij]pyrrolo[3,4-c]quinoline-10(8H)-carboxylate.

To a solution of (±)-trans-tert-butyl 5,6,8a,9,11,11a-hexahydro-4H-pyrido[3,2,1-ij]pyrrolo[3,4-c]quinoline-10(8H)-carboxylate from EXAMPLE 4, Part B (220 mg, 0.70 mmol) in 5 mL of N,N-dimethylformamide at −20° C. was added N-bromosuccinimide (137 mg, 0.77 mmol). The resulting solution was allowed to stir at −20° C. for 1 h and then was diluted with ethyl acetate. The organics were washed with saturated aqueous sodium bicarbonate and brine, dried (MgSO₄), filtered through a pad of silica gel and concentrated in vacuo to afford 150 mg (56%) of the title compound which was used without purification.

Part B. (±)-trans-tert-butyl 2-[4-methoxy-2-(trifluoromethyl)phenyl]-5,6,8a,9,11,11a-hexahydro-4H-pyrido[3,2,1-ij]pyrrolo[3,4-c]quinoline-10(8H)-carboxylate.

To a solution of (±)-trans-tert-butyl 2-bromo-5,6,8a,9,11,11a-hexahydro-4H-pyrido[3,2,1-ij]pyrrolo[3,4]quinoline-10(8H)-carboxylate (150 mg, 0.38 mmol) in 8 mL of 1,2-dimethoxyethane and 2 mL of water was added 4-methoxy-2-(trifluoromethyl)phenyl boronic acid (125 mg, 0.57 mmol) and barium hydroxide octahydrate (240 mg, 0.76 mmol). The mixture was degassed with a stream of nitrogen for 15 minutes and then there was added tetrakis(triphenylphosphine)palladium (0) (22 mg, 0.19 mmol) and the resulting mixture was stirred at 100° C. for 2 h. The reaction was allowed to cool, diluted with ethyl acetate, washed with saturated aqueous sodium bicarbonate and brine, dried (MgSO₄), filtered through a pad of silica gel and concentrated in vacuo to afford 160 mg (86%) of the title compound which was used without purification. LRMS (ES)⁺: 511.3 (M+H+Na)⁺.

Part C. (±)-trans-2-[4-methoxy-2-(trifluoromethyl)phenyl]-5,6,8,8a,9,10,11,11a-octahydro-4H-pyrido[3,2,1-ij]pyrrolo[3,4-c]quinoline, bis-hydrochloride salt.

To a solution of (±)-trans-tert-butyl 2-[4-methoxy-2-(trifluoromethyl)phenyl]-5,6,8a,9,11,11a-hexahydro-4H-pyrido[3,2,1-ij]pyrrolo[3,4-c]quinoline-10(8H)-carboxylate (160 mg, 0.33 mmol) in 5 mL of methylene chloride was added 1 mL of trifluoroacetic acid. The mixture was allowed to stir at ambient temperature for 2 h and then was concentrated in vacuo. The residue was purified by preparative HPLC (C18 reverse phase column, elution with a H₂O/CH₃CN gradient with 0.5% TFA). Product-containing fractions were combined, concentrated and partitioned between chloroform and saturated aqueous sodium carbonate. The organics were washed with brine, dried (K₂CO₃) and concentrated in vacuo. The residue (30 mg, 0.077 mmol) was dissolved in ethanol and ether and there was added 2M HCl in ether (0.077 mL, 0.15 mmol). The solvent was decanted and the remaining solid was triturated twice with ether and was dried in vacuo to afford 20 mg (57%) of the title compound of EXAMPLE 7 as an off white powder. ¹H NMR (d6-dmso): δ 9.40 (broad s, 2H), 7.29–7.18 (m, 3H), 6.71 (s, 1H), 6.58 (s, 1H), 3.82 (s, 3H), 3.57–3.49 (m, 1H), 3.40–3.18 (m, 5H), 2.93–2.80 (m, 3H), 2.70–2.62 (m, 2H), 2.16–2.06 (m, 1H), 1.95–1.88 (m, 1H), 1.85–1.78 (m, 1H). LRMS (ES)⁺: 389.2 (M+H)⁺.

Example 8

(±)-cis-10-benzyl-5,6,9,10,11,11a-hexahydro-4H-pyrido[3,2,1-ij]pyrrolo[3,4-c]quinolin-8(8aH)-one, hydrochloride salt

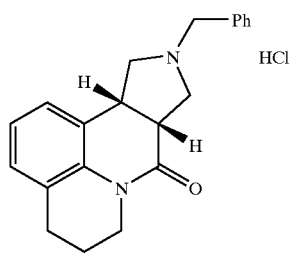

Part A. tert-butyl 8-[(1Z)-3-methoxy-3-oxo-1-propenyl]-3,4-dihydro-1(2H)-quinolinecarboxylate.

To a solution of 18-crown-6 (7.6 g, 28.7 mmol) in 100 mL of tetrahydrofuran at −78° C. was added bis(2,2,2-trifluoroethyl) (methoxycarbonylmethyl)phosphonate (2.0 g, 6.31 mmol). Potassium bis(trimethylsilyl)amide (12.6 mL of a 0.5M solution in toluene, 6.31 mmol) was added dropwise over 15 min and the mixture was stirred an additional 30 min at −78° C. Then there was added tert-butyl 8-formyl-3,4-dihydro-1(2H)-quinolinecarboxylate from EXAMPLE 1, Part B (1.5 g, 5.74 mmol) in 10 mL of tetrahydrofuran and the resulting cloudy mixture was stirred −78° C. for 1 h. The reaction was quenched with saturated aqueous ammonium chloride, diluted with ethyl acetate, washed with brine, dried (MgSO₄), filtered through a pad of silica gel and concentrated in vacuo. The residue was purified by flash chromatography (elution with 6:1 hexane/ethyl acetate) to afford 1.7 g (93%) of the title compound as a solid. ¹H NMR (CDCl₃): δ 7.42–7.36 (m, 1H), 7.12–7.08 (m, 2H), 7.02 (d, 1H, J=12.4 Hz), 5.89 (d, 1H, J=12.0 Hz), 4.37–4.22 (broad m, 1H), 4.14 (q, 2H, J=7.3 Hz), 3.10–2.98 (broad s, 1H), 2.79–2.70 (m, 2H), 2.18–2.05 (broad m, 1H), 1.95–1.88 (broad s, 1H), 1.42 (broad s, 9H), 1.28 (t, 3H, J=7.2 Hz).

Part B. (±)-cis-tert-butyl 8-[1-benzyl-4-(methoxycarbonyl)-3-pyrrolidinyl]-3,4-dihydro-1(2H)-quinolinecarboxylate.

Following the procedure described in EXAMPLE 1, Part D, tert-butyl 8-[(1Z)-3-methoxy-3-oxo-1-propenyl]-3,4-dihydro-1(2H)-quinolinecarboxylate was converted into the title compound. LRMS (ES)⁺: 451.3 (M+H)⁺.

Part C. (±)-cis-10-benzyl-5,6,9,10,11,11a-hexahydro-4H-pyrido[3,2,1-ij]pyrrolo[3,4-c]quinolin-8(8aH)-one, hydrochloride salt.

To a solution of (±)-cis-tert-butyl 8-[1-benzyl-4-(methoxycarbonyl)-3-pyrrolidinyl]-3,4-dihydro-1(2H)-quinolinecarboxylate (0.90 g, 2.00 mmol) in 30 mL of methylene chloride was added 10 mL of trifluoroacetic acid. The mixture was allowed to stir at ambient temperature for 2 h and then was concentrated in vacuo. The residue was taken up in ethyl acetate, washed with saturated aqueous sodium bicarbonate and brine, dried (MgSO₄) and concentrated in vacuo to afford 0.67 g of an oil. A portion of this material (50 mg, 0.16 mmol) was dissolved in 5 mL of ether and then there was added 2M HCl in ether (0.08 mL, 0.16 mmol). A solid precipitated out of solution. The solvent was decanted and the solid was triturated twice with ether and dried in vacuo to afford 53 mg (55%) of the title compound of EXAMPLE 8 as an off white powder. ¹H NMR (d6-dmso): δ 7.60–7.54 (m, 2H), 7.47–7.42 (m, 3H), 7.15–7.05 (m, 2H), 7.00–6.91 (m, 1H), 4.45–4.23 (m, 2H), 4.06–3.96 (m, 2H), 3.90–3.75 (m, 1H), 3.70–3.58 (m, 2H), 3.58–3.45 (m, 2H), 3.11–3.03 (m, 1H), 2.80–2.72 (m, 2H), 1.90–1.80 (m, 2H). LRMS (ES)⁺: 319.2 (M+H)⁺.

Example 9

(±)-cis-10-benzyl-5,6,8,8a,9,10,11,11a-octahydro-4H-pyrido[3,2,1-ij]pyrrolo[3,4-c]quinoline, bis-hydrochloride

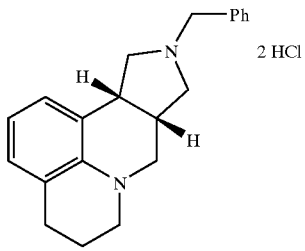

Following the procedures described in EXAMPLE 2, (±)-cis-10-benzyl-5,6,9,10,11,11a-hexahydro-4H-pyrido[3,2,1-ij]pyrrolo[3,4-c]quinolin-8(8aH)-one from EXAMPLE 8, Part C was converted into the title compound of EXAMPLE 9 as an off-white powder. ¹H NMR (d6-dmso): δ 7.43–7.38 (m, 2H), 7.34–7.28 (m, 3H), 6.85–6.73 (m, 2H), 6.65–6.57 (m, 1H), 4.07 (broad s, 2H), 3.98 (s, 2H), 3.72–3.63 (m, 1H), 3.28–3.19 (m, 2H), 3.05–2.90 (m, 3H), 2.84–2.78 (m, 1H), 2.70–2.62 (m, 2H), 2.61–2.55 (m, 1H), 1.93–1.80 (m, 2H). LRMS (ES)⁺: 305.3 (M+H)⁺.

Example 10

(±)-cis-5,6,9,10,11,11a-hexahydro-4H-pyrido[3,2,1-ij]pyrrolo[3,4-c]quinolin-8(8aH)-one, hydrochloride salt

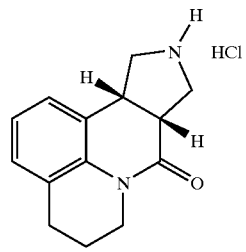

To a solution of (±)-cis-10-benzyl-5,6,9,10,11,11a-hexahydro-4H-pyrido[3,2,1-ij]pyrrolo[3,4-c]quinolin-8 (8aH)-one from EXAMPLE 8, Part C (170 mg, 0.53 mmol) in 20 5 mL of toluene was added 1-chloroethyl chloroformate (0.12 mL, 1.07 mmol) and the resulting solution was stirred at 110° C. for 3 h. The reaction mixture was cooled and the toluene was removed under reduced pressure. The residue was taken up in 20 mL of methanol and was stirred at 65° C. for 1 h. The reaction was cooled and the methanol was removed under reduced pressure. The residue was purified by preparative HPLC (C18 reverse phase column, elution with a H₂O/CH₃CN gradient with 0.5% TFA). Product-containing fractions were combined, concentrated and partitioned between chloroform and saturated aqueous sodium carbonate. The organics were washed with brine, dried (K₂CO₃) and concentrated in vacuo to afford 40 mg (32%) of the free base. The residue (40 mg, 0.17 mmol) was dissolved in ether and there was added 2M HCl in ether (0.085 mL, 0.17 mmol). The solvent was decanted and the remaining solid was triturated twice with ether and was dried in vacuo to afford 40 mg (86%) of the title compound of EXAMPLE 10 as an off white powder. ¹H NMR (d6-dmso): δ 7.16–7.10 (m, 2H), 6.97 (t, 1H, J=7.5 Hz), 4.10–4.00 (m, 2H), 3.85 (dd, 1H, J=11.5, 1.3 Hz), 3.62–3.40 (m, 4H), 2.80–2.70 (m, 3H), 1.89–1.80 (m, 2H). LRMS (ES)⁺: 229.4 (M+H)⁺.

Example 11

(±)-cis-5,6,8,8a,9,10,11,11a-octahydro-4H-pyrido[3,2,1-ij]pyrrolo[3,4-c]quinoline, bis-hydrochloride salt

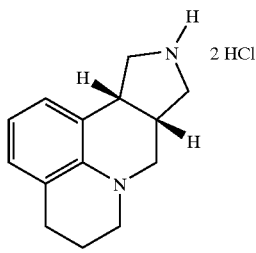

Following the procedures described in EXAMPLE 4, Parts A–C, (±)-cis-5,6,9,10,11,11a-hexahydro-4H-pyrido[3,2,1-ij]pyrrolo[3,4-c]quinolin-8(8aH)-one, hydrochloride salt, from EXAMPLE 10, was converted into the title compound of EXAMPLE 11. ¹H NMR (d6-dmso): δ 9.50–9.30 (broad m, 2H), 6.89 (d, 1H, J=7.3 Hz), 6.81 (d, 1H, J=7.5 Hz), 6.57 (t, 1H, J=7.6 Hz), 3.70–3.60 (m, 1H), 3.46–3.32 (m, 3H), 3.18–3.00 (m, 4H), 2.96–2.82 (m, 2H), 2.72–2.62 (m, 2H), 1.94–1.83 (m, 2H). LRMS (ES)⁺: 215.4 (M+H)⁺.

Example 12

(±)-cis-10-methyl-5,6,9,10,11,11a-hexahydro-4H-pyrido[3,2,1-ij]pyrrolo[3,4-c]quinolin-8(8aH)-one, hydrochloride salt

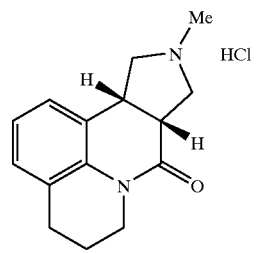

Following the procedures described in EXAMPLE 5, (±)-cis-5,6,9,10,11,11a-hexahydro-4H-pyrido[3,2,1-ij]pyrrolo[3,4-c]quiinolin-8(8aH)-one, hydrochloride salt, from EXAMPLE 10, was converted into the title compound of EXAMPLE 12. ¹H NMR (d6-dmso): δ 11.4 (broad s, 1H), 7.09–7.03 (m, 2H), 6.92 (t, 1H, J=7.5 Hz), 4.05–3.92 (m, 2H), 3.75–3.30 (m, 5H), 2.98–2.90 (m, 1H), 2.88–2.82 (m, 1H), 2.81–2.62 (m, 4H), 1.88–1.80 (m, 2H). LRMS (ES)⁺: 243.4 (M+H)⁺.

Example 13

(±)-cis-10-methyl-5,6,8,8a,9,10,11,11a-octahydro-4H-pyrido[3,2,1-ij]pyrrolo[3,4-c]quinoline, bis-hydrochloride salt

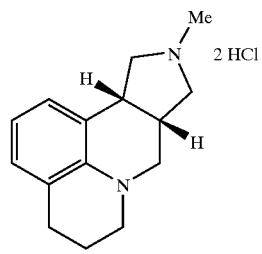

Following the procedures described in EXAMPLE 6, (±)-cis-5,6,8,8a,9,10,11,11a-octahydro-4H-pyrido[3,2,1-ij]pyrrolo[3,4-c]quinoline, bis-hydrochloride salt, from EXAMPLE 11, was converted into the title compound of EXAMPLE 13. ¹H NMR (d6-dmso): δ 6.86–6.78 (m, 2H), 6.60–6.54 (m, 1H), 3.86–3.78 (m, 1H), 3.45–3.30 (m, 2H), 3.04 (app t, 2H), 2.99–2.93 (m, 1H), 2.88–2.65 (m, 9H), 1.95–1.83 (m, 2H). LRMS (ES)⁺: 229.4 (M+H)⁺.

Example 14

(±)-cis-2-[4-methoxy-2-(trifluoromethyl)phenyl]-5,6,8,8a,9,10,11,11a-octahydro-4H-pyrido[3,2,1-ij]pyrrolo[3,4-c]quinoline, bis-hydrochloride salt

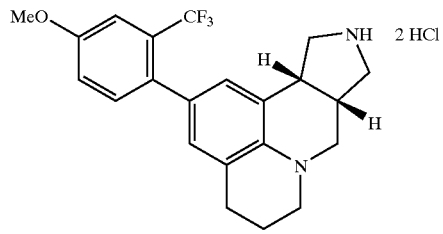

Following the procedures described in EXAMPLE 7, Parts A–C, (±)-cis-tert-butyl 5,6,8a,9,11,11a-hexahydro-4H-pyrido[3,2,1-ij]pyrrolo[3,4-c]quinoline-10(8H)-carboxylate, an intermediate from EXAMPLE 11, was converted into the title compound of EXAMPLE 14. LRMS (ES)⁺: 389.2 (M+H)⁺.

Example 15

(±)-cis-2-phenyl-5,6,8,8a,9,10,11,11a-octahydro-4H-pyrido[3,2,1-ij]pyrrolo[3,4-c]quinoline, bis-hydrochloride salt

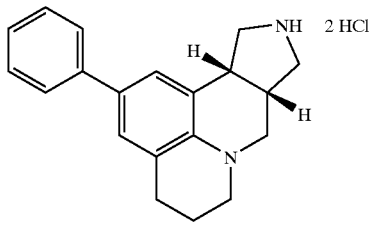

Part A. (±)-cis-tert-butyl 2-bromo-5,6,8a,9,11,11a-hexahydro-4H-pyrido[3,2,1-ij]pyrrolo[3,4-c]quinoline-10(8H)-carboxylate.

Following the procedure described in EXAMPLE 7, Part A, (±)-cis-tert-butyl 5,6,8a,9,11,11a-hexahydro-4H-pyrido[3,2,1-ij]pyrrolo[3,4-c]quinoline-10(8H)-carboxylate, an intermediate from EXAMPLE 11, was converted into the title compound as an oil. $^1$H NMR (CDCl$_3$): δ 6.90 (s, 2H), 3.90–3.77 (m, 1H), 3.61–3.52 (m, 1H), 3.35–3.25 (m, 2H), 3.20–3.12 (m, 2H), 3.08–2.95 (m, 2H), 2.85–2.68 (m, 3H), 2.57–2.47 (m, 1H), 1.98–1.88 (m, 2H), 1.42 (s, 9H).

Part B. (±)-cis-tert-butyl 2-phenyl-5,6,8a,9,11,11a-hexahydro-4H-pyrido[3,2,1-ij]pyrrolo[3,4-c]quinoline-10(8H)-carboxylate.

To a solution of (±)-cis-tert-butyl 2-bromo-5,6,8a,9,11,11a-hexahydro-4H-pyrido[3,2,1-ij]pyrrolo[3,4-c]quinoline-10(8H)-carboxylate (100 mg, 0.25 mmol) in 10 mL of toluene was added phenylboronic acid (34 mg, 0.28 mmol), tetrabutylammonium bromide (10 mg, 0.03 mmol) and 4 mL of 2M aqueous sodium carbonate. This mixture was degassed with a stream of nitrogen for 15 min and then there was added tetrakis (triphenylphosphine)palladium (0) (14 mg, 0.012 mmol) and the resulting mixture was stirred at 100° C. for 2 h. The reaction was cooled, diluted with ethyl acetate, washed with brine, dried (MgSO$_4$), filtered through a pad of silica gel and concentrated in vacuo to afford the title compound which was used without purification. LRMS (ES)$^+$: 391.3 (M+H)$^+$.

Part C. (±)-cis-2-phenyl-5,6,8,8a,9,10,11,11a-octahydro-4H-pyrido[3,2,1-ij]pyrrolo[3,4-c]quinoline, bis-hydrochloride salt.

Following the procedure described in EXAMPLE 7, Part C, (±)-cis-tert-butyl 2-phenyl-5,6,8a,9,11,11a-hexahydro-4H-pyrido[3,2,1-ij]pyrrolo[3,4-c]quinoline-10(8H)-carboxylate was converted into the title compound of EXAMPLE 15 as an off-white solid. $^1$H NMR (d6-dmso): δ 9.61 (broad s, 1H), 9.40 (broad s, 1H), 7.57–7.53 (app d, 1H, J=8.1 Hz), 7.36 (app t, 2H, J=7.5 Hz), 7.26–7.19 (m, 2H), 7.15 (s, 1H), 3.81–3.70 (m, 1H), 3.50–3.38 (m, 2H), 3.21–2.97 (m, 5H), 2.91–2.84 (m, 1H), 2.81–2.68 (m, 3H), 1.98–1.88 (m, 2H). LRMS (ES)$^+$: 291.3 (M+H)$^+$.

Example 16

(±)-cis-10-methyl-2-phenyl-5,6,8,8a,9,10,11,11a-octahydro-4H-pyrido[3,2,1-ij]pyrrolo[3,4-c]quinoline, bis-hydrochloride salt

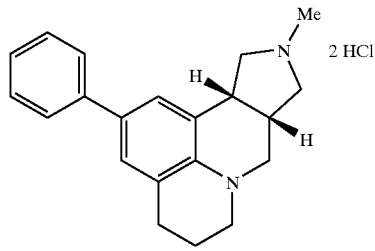

To a solution of (±)-cis-2-phenyl-5,6,8,8a,9,10,11,11a-octahydro-4H-pyrido[3,2,1-ij]pyrrolo[3,4-c]quinoline, the free base of EXAMPLE 15, (20 mg, 0.07 mmol) in 2 mL of 1,2-dichloroethane was added 37% aqueous formaldehyde (0.010 mL, 0.11 mmol), sodium triacetoxyborohydride (37 mg, 0.17 mmol) and glacial acetic acid (1 drop). The resulting mixture was stirred at ambient temperature for 1 h and then the reaction was quenched with water. The mixture was partitioned between chloroform and saturated aqueous sodium carbonate. The organics were washed with brine, dried (K$_2$CO$_3$) and concentrated in vacuo. The residue was dissolved in 1 mL ethanol and 5 mL of ether and then there was added 2M HCl in ether (0.07 mL, 0.14 mmol). A solid precipitated out of solution. The solvents were decanted and the solid was triturated twice with ether and dried in vacuo to afford 20 mg (77%) of the title compound of EXAMPLE 16 as an off white powder. $^1$H NMR (d6-dmso): δ 7.55–7.50 (m, 2H), 71.35 (app t, 2H, J=7.5 Hz), 7.24–7.17 (m, 2H), 7.14 (s, 1H), 4.07–3.98 (m, 1H), 3.82–3.73 (m, 1H), 3.44–3.32 (m, 1H), 3.10–3.03 (m, 2H), 3.02–2.97 (m, 1H), 2.94–2.70 (m, 9H), 1.97–1.85 (m, 2H). LRMS (ES)$^+$: 305.3 (M+H)$^+$.

Example 17

(±) -cis-N-phenyl-5,6,8,8a,9,10,11,11a-octahydro-4H-pyrido[3,2,1-ij]pyrrolo[3,4-c]quinolin-2-amine

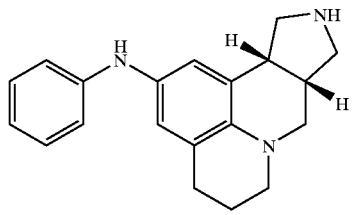

Part A. (±)-cis-tert-butyl 2-amino-5,6,8a,9,11,11a-hexahydro-4H-pyrido[3,2,1-ij]pyrrolo[3,4-c]quinoline-10(8H)-carboxylate.

A solution of (±)-cis-tert-butyl 2-bromo-5,6,8a,9,11,11a-hexahydro-4H-pyrido[3,2,1-ij] pyrrolo[3,4-c]quinoline-10(8H)-carboxylate from EXAMPLE 15, Part A (0.66 g, 1.68 mmol), benzophenone imine (0.37 g, 2.02 mmol), (S)-(−)-2,2'-bis(diphenylphosphino)-1,1'-binaphthyl (BINAP) (0.04 g, 0.07 mmol), sodium-t-butoxide (0.40 g, 4.20 mmol) and Pd$_2$DBA$_3$ (0.015 g, 0.017 mmol) in 20 ml of degassed toluene was heated for 3 hrs at 90° C. The solution was cooled and filtered through a pad of silica gel and eluted with EtOAc. The volatiles were removed under reduced pressure.

The residue was taken up in 50 mL of methanol and then there was added NaOAc (0.28 g, 3.36 mmol) and hydroxylamine hydrochloride (0.35 g, 5.04 mmol) and the mixture was stirred at ambient temperature for 30 min. The volatiles were removed under reduced pressure and the residue purified by column chromatography (eluting with a gradient of 100% diethyl ether to 100% EtOAc) to afford the title compound. LRMS (ES)$^+$: 330.4 (M+H)$^+$.

Part B. (±)-cis-tert-butyl 2-anilino-5,6,8a,9,11,11a-hexahydro-4H-pyrido[3,2,1-ij]pyrrolo[3,4-c]quinoline-10(8H)-carboxylate.

A solution of (±)-cis-tert-butyl 2-amino-5,6,8a,9,11,11a-hexahydro-4H-pyrido[3,2,1-ij]pyrrolo[3,4-c]quinoline-10(8H)-carboxylate (0.08 g, 0.25 mmol), bromobenzene (0.04 g, 0.27 mmol), BINAP (0.001 g, 0.0015 mmol), sodium-t-butoxide, (0.06 g, 0.65 mmol) and Pd$_2$DBA$_3$ (0.0005 g, 0.0005 mmol) in 10 ml of degassed toluene was heated for 16 h at 90° C. The solution was cooled and filtered through a pad of silica gel and eluted with EtOAc. The volatiles were removed under reduced pressure to afford the title compound which was used without purification. LRMS (ES)$^+$: 406.4 (M+H)$^+$.

Part C. (±)-cis-N-phenyl-5,6,8,8a,9,10,11,11a-octahydro-49-pyrido[3,2,1-ij]pyrrolo[3,4-c]quinolin-2-amine.

To a solution of (±)-cis-tert-butyl 2-anilino-5,6,8a,9,11,11a-hexahydro-4H-pyrido[3,2,1-ij]pyrrolo[3,4-c]quinoline-10(8H)-carboxylate (80 mg, 0.20 mmol) in 5 ml of CH$_2$Cl$_2$ was added 1 ml of trifluoroacetic acid and the reaction was stirred at room temperature for 3 h. The volatiles were removed under reduced pressure and the residue was purified by prep HPLC (C18 reverse phase column, elution with a H$_2$O/CH$_3$CN gradient with 0.5% TFA). Product-containing fractions were combined, concentrated and partitioned between chloroform and saturated aqueous sodium carbonate. The organics were washed with brine, dried (K$_2$CO$_3$) and concentrated in vacuo to afford 15 mg (23%) of the title compound of EXAMPLE 17. $^1$H NMR (CDCl$_3$): δ 7.18 (app t, 2H, J=7.8 Hz), 6.84 (app d, 2H, J=8.0 Hz), 6.78–6.72 (m, 1H), 6.67 (s, 1H), 6.65 (s, 1H), 5.46 (s, 1H), 3.45–3.30 (m, 2H), 3.24–3.17 (m, 1H), 3.08–3.00 (m, 2H), 2.97–2.85 (m, 1H), 2.78–2.55 (broad m, 6H), 2.05–1.93 (m, 2H). LRMS (ES)$^+$: 306.3 (M+H)$^+$.

Example 18

(4)-cis-N-(2,4-dichlorophenyl)-5,6,8,8a,9,10,11,11a-octahydro-4H-pyrido[3,2,1-ij]pyrrolo[3,4-c]quinolin-2-amine

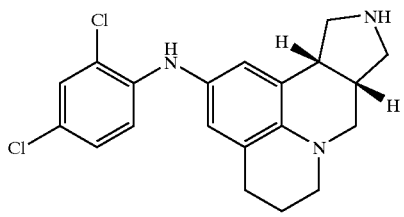

Using 2,4-dichloro-1-bromobenzene and following the procedures described in EXAMPLE 17, Parts B and C, (±)-cis-tert-butyl 2-amino-5,6,8a,9,11,11a-hexahydro-4H-pyrido[3,2,1-ij]pyrrolo[3,4-c]quinoline-10(8H)-carboxylate, from EXAMPLE 17, Part A, was converted to the title compound of EXAMPLE 18. $^1$H NMR (CDCl$_3$): δ 7.28 (d, 1H, J=2.2 Hz), 7.01 (dd, 1H, J=8.8, 2.2 Hz), 6.85 (d, 1H, J=9.2 Hz), 6.70 (8, 2H), 5.79 (S, 1H), 3.55–3.26 (m, 4H), 3.10–3.03 (m, 2H), 3.01–2.94 (m, 2H), 2.92–2.83 (m, 1H), 3.80–3.65 (m, 3H), 2.08–1.98 (m, 2H). LRMS (ES)$^+$: 374.3 (M+H)$^+$.

Example 19

(±)-cis-N-(2,5-dichlorophenyl)-5,6,8,8a,9,10,11,11a-octahydro-4H-pyrido[3,2,1-ij]pyrrolo[3,4-c]quinolin-2-amine

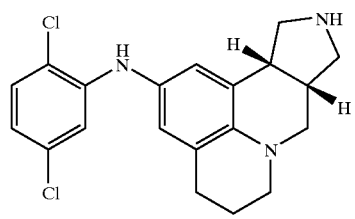

Using 2,5-dichloro-1-bromobenzene and following the procedures described in EXAMPLE 17, Parts B and C, (±)-cis-tert-butyl 2-amino-5,6,8a,9,11,11a-hexahydro-4H-pyrido[3,2,1-ij]pyrrolo[3,4-c]quinoline-10(8H)-carboxylate, from EXAMPLE 17, Part A, was converted to the title compound of EXAMPLE 19. $^1$H NMR (CDCl$_3$): δ 7.18 (d, 1H, J=8.4 Hz), 6.86 (d, 1H, J=2.2 Hz), 6.74 (s, 1H), 6.70 (s, 1H), 6.62 (dd, 1H, J=8.4, 2.6 Hz), 5.87 (s, 1H), 3.48–3.30 (m, 2H), 3.21 (q, 1H, J=7.6 Hz), 3.13–3.05 (m, 2H), 2.99 (dd, 1H, J=11.0, 4.7 Hz), 2.92–2.83 (m, 1H), 2.81–2.70 (m, 4H), 2.69–2.58 (m, 1H), 2.08–1.98 (m, 2H). LRMS (ES)$^+$: 374.3 (M+H)$^+$.

Example 20

(±)-cis-2-[4-(methylsulfanyl)phenyl]-5,6,8,8a,9,10,11,11a-octahydro-4H-pyrido[3,2,1-ij]pyrrolo[3,4-c]quinoline, trifluoroacetic acid salt

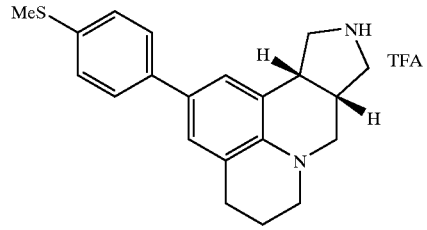

To a solution of (±)-cis-tert-butyl 2-bromo-5,6,8a,9,11,11a-hexahydro-4H-pyrido[3,2,1-ij]pyrrolo[3,4-c]quinoline-10(8H)-carboxylate from EXAMPLE 15, Part A (0.05 g, 0.13 mmol) in 4 mL of toluene and 2 mL of 2M aq sodium carbonate was added 4-(thiomethoxy)phenyl boronic acid (0.043 g, 0.26 mmol). The mixture was degassed with a stream of argon for 15 min and then there was added [1,1'-bis(diphenylphosphino)ferrocene]dichloropalladium (II) (10 mg, 0.013 mmol) and the mixture was stirred at 80° C. overnight. The reaction was cooled, diluted with ethyl acetate, washed with brine, dried (MgSO$_4$) and concentrated. The residue was purified on a prepacked silica gel tube (elution with hexanes to 1:1 hexanes/ethyl acetate) to remove catalyst and excess boronic acid. The residue was dissolved in 10 mL of methylene chloride and then there was added 2 mL of trifluoroacetic acid. The mixture was stirred for 3 h and concentrated in vacuo. The residue was purified by preparative HPLC (C18 reverse phase column, elution with a H$_2$O/CH$_3$CN gradient with 0.5% TFA) and lyophilized to afford 10 mg (23%) of the title compound of EXAMPLE 20. $^1$H NMR (d6-dmso): δ 8.80 (broad s, 2H), 7.49 (d, 2H, J=8.5 Hz), 7.24 (d, 2H, J=8.4 Hz), 7.21 (d, 1H, J=2.2 Hz), 7.12 (s, 1H), 3.78–3.66 (m, 1H), 3.50–3.40 (m, 2H), 3.13–3.00 (m, 4H), 2.82–2.65 (m, 4H), 2.55–2.46 (m, 1H), 2.45 (s, 3H), 1.95–1.84 (m, 2H). LRMS (ES)$^+$: 337.4 (M+H)$^+$.

Example 21

(±)-cis-2-(2,3-dichlorophenyl)-5,6,8,8a,9,10,11,11a-octahydro-4H-pyrido[3,2,1-ij]pyrrolo[3,4-c]quinoline, trifluoroacetic acid salt

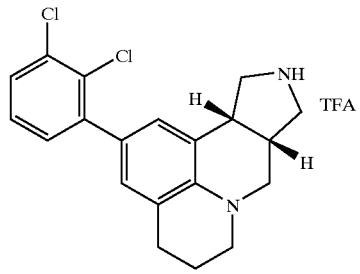

Using 2,3-dichlorophenyl boronic acid and following the procedures described in EXAMPLE 20, (±)-cis-tert-butyl 2-bromo-5,6,8a,9,11,11a-hexahydro-4H-pyrido[3,2,1-ij]pyrrolo[3,4-c]quinoline-10(8H)-carboxylate from EXAMPLE 15, Part A, was converted into the title compound of EXAMPLE 21. $^1$H NMR (d6-dmso): δ 8.95 (broad s, 2H), 7.54 (dd, 1H, J=7.9, 1.6 Hz), 7.34 (t, 1H, J=7.7 Hz), 7.27 (dd, 1H, J=7.7, 1.5 Hz), 7.00 (d, 1H, J=1.4 Hz), 6.89 (d, 1H, J=1.8 Hz), 3.80–3.65 (m, 2H), 3.50–3.38 (m, 2H), 3.18–2.98 (m, 4H), 2.87–2.80 (m, 1H), 2.78–2.62 (m, 3H), 1.98–1.83 (m, 2H). LRMS (ES)$^+$: 359.3 (M+H)$^+$.

Example 22

(±)-cis-2-(3,4-dimethoxyphenyl)-5,6,8,8a,9,10,11,11a-octahydro-4H-pyrido[3,2,1-ij]pyrrolo[3,4-c]quinoline, trifluoroacetic acid salt

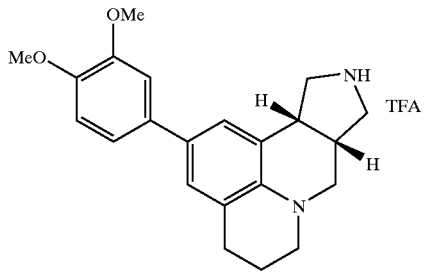

Using 3,4-dimethoxyphenyl boronic acid and following the procedures described in EXAMPLE 20, (±)-cis-tert-butyl 2-bromo-5,6,8a,9,11,11a-hexahydro-4H-pyrido[3,2,1-ij]pyrrolo[3,4-c]quinoline-10(8H)-carboxylate from EXAMPLE 15, Part A, was converted into the title compound of EXAMPLE 22. LRMS (ES)$^+$: 351.4 (M+H)$^+$.

Example 23

(±)-cis-2-(2,5-dichlorophenyl)-5,6,8,8a,9,10,11,11a-octahydro-4H-pyrido[3,2,1-ij]pyrrolo[3,4-c]quinoline, trifluoroacetic acid salt

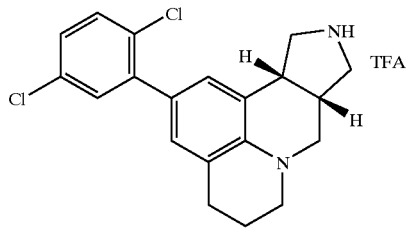

Using 2,5-dichlorophenyl boronic acid and following the procedures described in EXAMPLE 20, (±)-cis-tert-butyl 2-bromo-5,6,8a,9,11,11a-hexahydro-4H-pyrido[3,2,1-ij]pyrrolo[3,4-c]quinoline-10(8H)-carboxylate from EXAMPLE 15, Part A, was converted into the title compound of EXAMPLE 23. $^1$H NMR (d6-dmso): δ 8.95 (broad s, 2H), 7.61 (d, 1H, J=8.4 Hz), 7.48–7.41 (m, 2H), 7.12 (d, 1H, J=1.4 Hz), 7.04 (s, 1H), 3.82–3.75 (m, 1H), 3.68–3.45 (m, 3H), 3.24–3.10 (m, 4H), 2.97–2.89 (m, 1H), 2.88–2.77 (m, 3H), 2.05–1.98 (m, 2H). LRMS (ES)$^+$: 359.3 (M+H)$^+$.

Example 24

(±)-cis-2-[2-(trifluoromethyl)phenyl]-5,6,8,8a,9,10,11,11a-octahydro-4H-pyrido[3,2,1-ij]pyrrolo[3,4-c]quinoline, trifluoroacetic acid salt

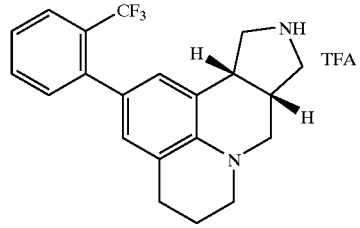

Using 2-(trifluoromethyl)phenyl boronic acid and following the procedures described in EXAMPLE 20, (±)-cis-tert-butyl 2-bromo-5,6,8a,9,11,11a-hexahydro-4H-pyrido[3,2,1-ij]pyrrolo[3,4-c]quinoline-10(8H)-carboxylate from EXAMPLE 15, Part A, was converted into the title compound of EXAMPLE 24. LRMS (ES)$^+$: 359.4 (M+H)$^+$.

Example 25

(8aR,11aR)-5,6,8,8a,9,10,11,11a-octahydro-4H-pyrido[3,2,1-ij]pyrrolo[3,4-c]quinoline, bis-hydrochloride salt

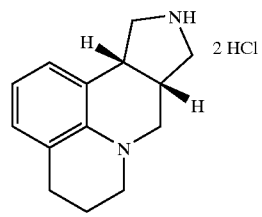

Part A. Ethyl 5-oxo-2,3-dihydro-1H,5H-pyrido[3,2,1-ij]quinoline-6-carboxylate.

To a solution of tert-butyl 8-formyl-3,4-dihydro-1(2H)-quinolinecarboxylate from EXAMPLE 1, Part B (17.0 g, 65.0 mmol) in 300 mL of benzene in a flask fitted with a Dean-Stark trap and a condenser was added diethyl malonate (10.4 g, 65 mmol), piperidine (0.61 g, 7.14 mmol) and benzoic acid (0.79 g, 6.5 mmol). The resulting solution was stirred at 80° C. for 24 h with collection of water in the Dean-Stark trap. The reaction mixture was then cooled, washed with 1N HCl, sat'd aq NaHCO$_3$ and brine, dried (MgSO$_4$), filtered through a pad of silica gel and concentrated to afford 25.1 g of a diester intermediate. This material was dissolved in 160 mL of methylene chloride and then there was added 40 mL of trifluoroacetic acid. This mixture was allowed to stir at ambient temperature for 24 h. The volatiles were then removed in vacuo and the residue was dissolved in ethyl acetate, washed with water, sat'd aq NaHCO$_3$ and brine, dried (MgSO$_4$), filtered through a pad of silica gel and concentrated to a solid. This material was triturated with hexane, filtered and dried to afford 14.4 g (86%) of the title compound of Part A as a pale yellow solid. $^1$H NMR (CDCl$_3$) δ: 8.35 (s, 1H), 7.46 (d, 1H, J=7.7 Hz), 7.36 (dd, 1H, J=7.4, 1.1 Hz), 7.13 (t, 1H, J=7.5 Hz), 4.40 (q, 2H, J 7.2 Hz), 4.19 (app t, 2H, J=5.9 Hz), 2.95 (t, 2H, J=6.2 Hz), 2.14–2.05 (m, 2H), 1.40 (t, 3H, J=7.2 Hz).

Part B. (±)-cis ethyl 10-benzyl-8-oxo-5,6,9,10,11,11a-hexahydro-4H-pyrido[3,2,1-ij]pyrrolo[3,4-c]quinoline-8a(8H)-carboxylate.

To a solution of ethyl 5-oxo-2,3-dihydro-1H,5H-pyrido[3,2,1-ij]quinoline-6-carboxylate (25.0 g, 97 mmol) in 400 mL of methylene chloride was added N-(methoxymethyl)-N-(trimethylsilylmethyl)benzylamine (46.1 g, 194 mmol) and trifluoroacetic acid (2.22 g, 19 mmol). The reaction mixture was stirred at 40° C. for 24 h. The reaction mixture was allowed to cool and was washed with sat'd aq. NaHCO$_3$ and brine, dried (K$_2$CO$_3$) and concentrated in vacuo. The residue was purified by recrystallization from 4:1 hexane/ethyl acetate to afford 36.6 g (96%) of the title compound of Part B as an off white solid. $^1$H NMR (CDCl$_3$) δ: 7.37–7.20 (m, 5H), 7.05–7.00 (m, 1H), 6.97–6.88 (m, 2H), 4.28–4.19 (m, 1H), 4.12–4.01 (m, 2H), 3.80–3.68 (m, 4H), 3.57 (ABq, 2H, J$_{AB}$=10.2 Hz), 3.17 (app t, 1H, J=8.8 Hz), 2.85–2.77 (m, 2H), 2.49 (app t, 1H, J=9.5 Hz), 2.05–1.95 (m, 2H), 1.09 (t, 3H, J=7.0 Hz).

Part C. (±)-cis 10-benzyl-5,6,9,10,11,11a-hexahydro-4H-pyrido[3,2,1-ij]pyrrolo[3,4-c]quinolin-8(8aH)-one.

To a solution of (±)-cis ethyl 10-benzyl-8-oxo-5,6,9,10,11,11a-hexahydro-4H-pyrido[3,2,1-ij]pyrrolo[3,4-c]quinoline-8a(8H)-carboxylate (36.6 g, 93.7 mmol) in 400 mL of 1,4-dioxane was added 400 mL of 3M HCl and the resulting mixture was stirred at 100° C. for 24 h. The dioxane and most of the water was removed in vacuo, and the residue was basified with 1N NaOH and extracted with ethyl acetate. The layers were separated and the organics were washed with brine, dried (MgSO$_4$) and concentrated to afford 28.0 g (94%) of the title compound of Part C, which was sufficiently pure to be used without purification. $^1$H NMR (CDCl$_3$) δ: 7.25–7.15 (m, 5H), 6.93–6.78 (m, 3H), 4.02–3.93 (m, 1H), 3.78–3.66 (m, 1H), 3.63 (8, 2H), 3.55–3.45 (m, 1H), 3.35 (dd, 1H, J=9.7, 8.3 Hz), 3.20–3.07 (m, 2H), 2.96 (dd, 1H, J=9.5, 5.1 Hz), 2.75–2.68 (m, 2H), 2.32 (app t, 1H, J=9.4 Hz), 1.92–1.82 (m, 2H).

Part D. (±)-cis tert-butyl 8-oxo-5,6,8a,9,11,11a-hexahydro-4H-pyrido[3,2,1-ij]pyrrolo[3,4-c]quinoline-10(8H)-carboxylate.

To a Parr shaker bottle which had been purged with nitrogen was added 20% palladium hydroxide on carbon catalyst (9.0 g), 250 mL of absolute ethanol, (±)-cis 10-benzyl-5,6,9,10,11,11a-hexahydro-4H-pyrido[3,2,1-ij]pyrrolo[3,4-c]quinolin-8(8aH)-one (28.0 g, 88.0 mmol) and di-tert-butyl dicarbonate (21.1 g, 96.8 mmol). This mixture was shaken on a Parr apparatus under 60 psi of hydrogen for 24 h. The reaction was filtered through Celite and was concentrated in vacuo to afford 28.8 g (99%) of the title compound of Part D, which was sufficiently pure to be used without purification. $^1$H NMR (CDCl$_3$) δ: 7.07–7.00 (m, 2H), 6.93 (t, 1H), 4.23–4.10 (m, 2H), 3.80–3.57 (m, 3H), 3.51–3.41 (m, 1H), 3.10–3.00 (m, 2H), 2.82–2.75 (m, 2H), 1.97–1.88 (m, 2H), 1.44 and 1.41 (two s, 9H).

Part E. (±)-cis tert-butyl 5,6,8a,9,11,11a-hexahydro-4H-pyrido[3,2,1-ij]pyrrolo[3,4-c]quinoline-10(8H)-carboxylate.

To a solution of (±)-cis tert-butyl 8-oxo-5,6,8a,9,11,11a-hexahydro-4H-pyrido[3,2,1-ij]pyrrolo[3,4-c]quinoline-10(8H)-carboxylate (28.8 g, 87.7 mmol) in 400 mL of tetrahydrofuran at 0° C. was added borane-THF complex (438 mL of a 1M solution in THF, 438 mmol) via an addition funnel. After the addition was complete the reaction mixture was allowed to warm to ambient temperature and was stirred for 24 h. The reaction was quenched by dropwise addition of methanol (100 mL) and then the volatiles were removed in vacuo. The residue was dissolved in ethyl acetate, washed with sat'd aq. NaHCO$_3$ and brine, dried (MgSO$_4$) filtered through a pad of silica gel and concentrated. The solid residue was triturated with hexane, filtered and dried to afford 23.5 g (85%) of the title compound of Part E as a pale yellow solid. $^1$H NMR (CDCl$_3$) δ: 6.86–6.80 (m, 2H), 6.57 (t, 1H), 3.96–3.82 (m, 1H), 3.65–3.58 (m, 2H), 3.38–3.30 (m, 1H), 3.25–2.75 (overlapping m, 7H), 2.65–2.57 (m, 1H), 2.04–1.95 (m, 2H), 1.44 (s, 9H).

Part F. tert-butyl (8aS,11aR)-5,6,8a,9,11,11a-hexahydro-4H-pyrido[3,2,1-ij]pyrrolo[3,4-c]quinoline-10(8H)-carboxylate and tert-butyl (8aR,11aS)-5,6,8a,9,11,11a-hexahydro-4H-pyrido[3,2,1-ij]pyrrolo[3,4-c]quinoline-10(8H)-carboxylate.

The racemic mixture(±)-cis tert-butyl 5,6,8a,9,11,11a-hexahydro-4H-pyrido[3,2,1-ij]pyrrolo[3,4-c]quinoline-10(8H)-carboxylate (23.5 g) from Part E was separated on a chiralcel OD HPLC column (5% acetonitrile/5% isopropanol/90% supercritical CO$_2$, ambient temperature, flow rate=2.0 mL/min, detection 250 nM) to afford 10.0 g of tert-butyl (8aS,11aR)-5,6,8a,9,11,11a-hexahydro-4H-pyrido[3,2,1-ij]pyrrolo[3,4-c]quinoline-10(8H)-carboxylate (>99% ee) as the first eluting peak (retention time 11.8 min) and 9.5 g of tert-butyl (8aR,11aS)-5,6,8a,9,11,11a-hexahydro-4H-pyrido[3,2,1-ij]pyrrolo[3,4-c]quinoline-10(8H)-carboxylate (>99% ee) as the second eluting peak (retention time 14.1 min).

Part G. (8aR,11aR)-5,6,8,8a,9,10,11,11a-octahydro-4H-pyrido[3,2,1-ij]pyrrolo[3,4-c]quinoline, bis-hydrochloride salt.

To a solution of tert-butyl (8aS,11aR)-5,6,8a,9,11,11a-hexahydro-4H-pyrido[3,2,1-ij]pyrrolo[3,4-c]quinoline-10(8H)-carboxylate (100 mg, 0.32 mmol) in 4 mL of methylene chloride was added 1 mL of trifluoroacetic acid. Stirred at ambient temperature for 2 h and then concentrated under reduced pressure. The residue was partitioned between chloroform and saturated aqueous potassium hydroxide. The organics were washed with brine, dried (K$_2$CO$_3$) and concentrated in vacuo to afford the free base as an oil. This residue (60 mg, 0.28 mmol) was dissolved in 1 mL absolute ethanol and 5 mL ether and then 2M HCl in ether (0.40 mL, 0.80 mmol) was added and a solid fell out of solution. The solvents were decanted and the solid was triturated twice with ether and dried in vacuo to afford 47 mg (51%) of the title compound of EXAMPLE 25 as an off white powder. ¹H NMR (dmso-D₆) δ: 9.70–9.35 (broad m, 2H), 6.88 (d, 1H, J=7.3 Hz), 6.80 (d, 1H, J=7.0 Hz), 6.57 (t, 1H, J=7.3 Hz), 3.70–3.59 (m, 1H), 3.65–3.53 (m, 2H), 3.18–2.97 (m, 4H), 2.92–2.77 (m, 2H), 2.75–2.60 (m, 3H), 1.97–1.83 (m, 2H). LRMS (ES)⁺: 215.3 (M+H)⁺.

Example 26

(8aS,11aS)-5,6,8,8a,9,10,11,11a-octahydro-4H-pyrido[3,2,1-ij]pyrrolo[3,4-c]quinoline, bis-hydrochloride salt

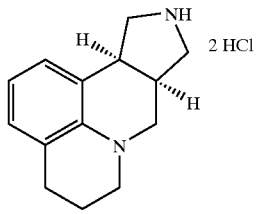

Following the procedures described in EXAMPLE 25, Part G, tert-butyl (8aR,11aS)-5,6,8a,9,11,11a-hexahydro-4H-pyrido[3,2,1-ij]pyrrolo[3,4-c]quinoline-10(8H)-carboxylate from EXAMPLE 25, Part F, was converted into the title compound of EXAMPLE 26. ¹H NMR (dmso-D₆) δ: 9.70–9.35 (broad m, 2H), 6.88 (d, 1H, J=7.3 Hz), 6.80 (d, 1H, J=7.0 Hz), 6.57 (t, 1H, J=7.3 Hz), 3.70–3.59 (m, 1H), 3.65–3.53 (m, 2H), 3.18–2.97 (m, 4H), 2.92–2.77 (m, 2H), 2.75–2.60 (m, 3H), 1.97–1.83 (m, 2H). LRMS (ES)⁺: 215.3 (M+H)⁺.

Example 27

(8aR,11aR)-2-(2,4-dichlorophenyl)-5,6,8,8a,9,10,11,11a-octahydro-4H-pyrido[3,2,1-ij]pyrrolo[3,4-c]quinoline, trifluoroacetic acid salt

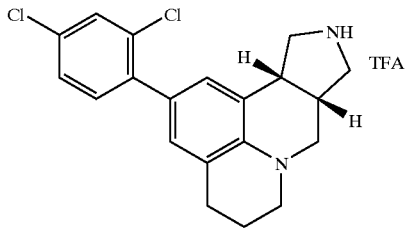

Part A. tert-butyl (8aS,11aR)-2-bromo-5,6,8a,9,11,11a-hexahydro-4H-pyrido[3,2,1-ij]pyrrolo[3,4-c]quinoline-10(8H)-carboxylate.

To a solution of tert-butyl (8aS,11aR)-5,6,8a,9,11,11a-hexahydro-4H-pyrido[3,2,1-ij]pyrrolo[3,4-c]quinoline-10(8H)-carboxylate from EXAMPLE 25, Part F (5.0 g, 15.9 mmol) in 100 mL of N,N-dimethylformamide at −20° C. was added N-bromosuccinimide (3.11 g, 17.5 mmol). The resulting solution was allowed to stir at −20° C. for 3 h and then was diluted with ethyl acetate. The organics were washed with sat'd aq. sodium bicarbonate and brine, dried (MgSO₄), filtered through a pad of silica gel and concentrated in vacuo to afford 6.0 9 (95%) of the title compound of Part A which was used without purification.

Part B. (8aR,11aR)-2-(2,4-dichlorophenyl)-5,6,8,8a,9,10,11,11a-octahydro-4H-pyrido[3,2,1-ij]pyrrolo[3,4-c]quinoline, trifluoroacetic acid salt.

Using 2,4-dichlorophenyl boronic acid and following the procedures described in EXAMPLE 20, tert-butyl (8aS,11aR)-2-bromo-5,6,8a,9,11,11a-hexahydro-4H-pyrido[3,2,1-ij]pyrrolo[3,4-c]quinoline-10(8H)-carboxylate was converted into the title compound of EXAMPLE 27. ¹H NMR (dmso-D₆) δ: 9.02 (broad s, 2H), 7.60 (d, 1H, J=2.2 Hz), 7.39 (dd, 1H, J=8.0, 2.2 Hz), 7.31 (d, 1H, J=8.4 Hz), 6.97 (d, 1H, J=1.9 Hz), 6.87 (d, 1H, J=1.8 Hz), 3.70–3.59 (m, 1H), 3.50–3.27 (m, 5H), 3.15–2.95 (m, 3H), 2.82 (app t, 1H, J=9.4 Hz), 2.73–2.60 (m, 2H), 1.93–1.80 (m, 2H). LRMS (ES)⁺: 359.2 (M+H)⁺.

Example 28

4-[(8aR,11aR)-5,6,8,8a,9,10,11,11a-octahydro-4H-pyrido[3,2,1-ij]pyrrolo[3,4-c]quinolin-2-yl]-3-methylbenzonitrile, trifluoroacetic acid salt

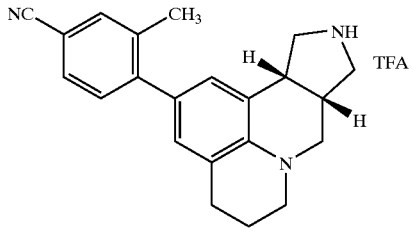

Using 2-methyl-4-cyanobenzeneboronic acid and following the procedures described in EXAMPLE 20, tert-butyl (8aS,11aR)-2-bromo-5,6,8a,9,11,11a-hexahydro-4H-pyrido[3,2,1-ij]pyrrolo[3,4-c]quinoline-10(8H)-carboxylate from EXAMPLE 27, Part A was converted into the title compound of EXAMPLE 28. ¹H NMR (dmso-D₆) δ: 8.85 (broad s, 2H), 7.74 (s, 1H), 7.65 (dd, 1H, J=8.0, 1.5 Hz), 7.34 (d, 1H, J=8.0 Hz), 7.00 (s, 1H), 6.89 (s, 1H), 3.79–3.70 (m, 1H), 3.50–3.40 (m, 2H), 3.20–3.03 (m, 5H), 2.87 (dd, 1H), 2.80–2.70 (m, 3H), 2.32 (s, 3H), 1.99–1.90 (m, 2H). LRMS (ES)⁺: 330.3 (M+H)⁺.

Example 29

(8aR,11aR)-2-(2-methylphenyl)-5,6,8,8a,9,10,11,11a-octahydro-4H-pyrido[3,2,1-ij]pyrrolo[3,4-c]quinoline, trifluoroacetic acid salt

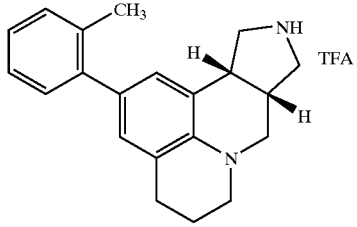

Using o-tolylboronic acid and following the procedures described in EXAMPLE 20, tert-butyl (8aS,11aR)-2-bromo-5,6,8a,9,11,11a-hexahydro-4H-pyrido[3,2,1-ij]pyrrolo[3,4-c]quinoline-10(8H)-carboxylate from EXAMPLE 27, Part A was converted into the title compound of EXAMPLE 29. ¹H NMR (dmso-D₆) δ: 9.00 (broad s, 2H), 7.20–7.03 (m, 4H), 6.86 (d, 1H, J=1.5 Hz), 6.76 (d, 1H, J=1.5 Hz), 3.71–3.62 (m, 1H), 3.50–3.36 (m, 2H), 3.12–2.95 (m, 5H), 2.79 (dd, 1H), 2.74–2.65 (m, 3H), 2.20 (s, 3H), 1.92–1.85 (m, 2H). LRMS (ES)⁺: 305.4 (M+H)⁺.

Example 30

(8aR,11aR)-2-(3-methylphenyl)-5,6,8,8a,9,10,11,11a-octahydro-4H-pyrido[3,2,1-ij]pyrrolo[3,4-c]quinoline, trifluoroacetic acid salt

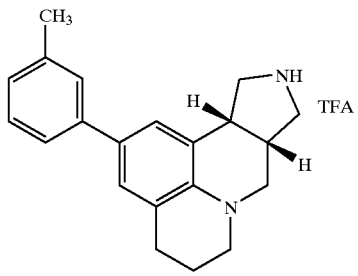

Using m-tolylboronic acid and following the procedures described in EXAMPLE 20, tert-butyl (8aS,11aR)-2-bromo-5,6,8a,9,11,11a-hexahydro-4H-pyrido[3,2,1-ij]pyrrolo[3,4-c]quinoline-10(8H)-carboxylate from EXAMPLE 27, Part A was converted into the title compound of EXAMPLE 30. $^1$H NMR (dmso-D$_6$) δ: 8.83 (broad s, 2H), 7.40–7.33 (m, 2H), 7.28 (d, 1H, J=7.3 Hz), 7.25 (s, 1H), 7.16 (s, 1H), 7.06 (d, 1H, J=7.4 Hz), 3.81–3.73 (m, 1H), 3.55–3.40 (m, 4H), 3.17–3.03 (m, 4H), 2.88–2.70 (m, 3H), 2.34 (s, 3H), 1.97–1.90 (m, 2H). LRMS (ES)$^+$: 305.4 (M+H)$^+$.

Example 31

(8aR,11aR)-2-(4-methylphenyl)-5,6,8,8a,9,10,11,11a-octahydro-4H-pyrido[3,2,1-ij]pyrrolo[3,4-c]quinoline, trifluoroacetic acid salt

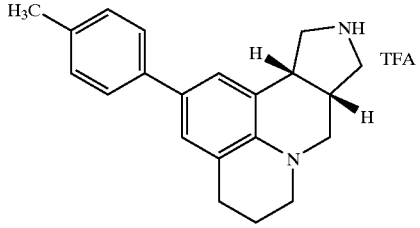

Using p-tolylboronic acid and following the procedures described in EXAMPLE 20, tert-butyl (8aS,11aR)-2-bromo-5,6,8a,9,11,11a-hexahydro-4H-pyrido[3,2,1-ij]pyrrolo[3,4-c]quinoline-10(8H)-carboxylate from EXAMPLE 27, Part A was converted into the title compound of EXAMPLE 31. $^1$H NMR (dmso-D$_6$) δ: 8.83 (broad s, 2H), 7.46 (d, 2H, J=8.0 Hz), 7.23 (d, 1H, J=1.9 Hz), 7.19 (d, 2H, J=7.7 Hz), 7.14 (s, 1H), 3.80–3.74 (m, 1H), 3.52–3.37 (m, 4H), 3.17–3.03 (m, 4H), 2.88–2.70 (m, 3H), 2.31 (s, 3H), 1.97–1.90 (m, 2H). LRMS (ES)$^+$: 305.4 (M+H)$^+$.

Example 32

2-[(8aR,11aR)-5,6,8,8a,9,10,11,11a-octahydro-4H-pyrido[3,2,1-ij]pyrrolo[3,4-c]quinolin-2-yl]-5-methylbenzaldehyde, trifluoroacetic acid salt

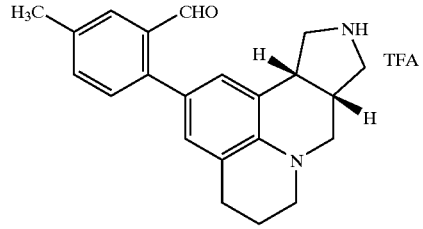

Using 2-formyl-4-methylbenzeneboronic acid and following the procedures described in EXAMPLE 20, tert-butyl (8aS,11aR)-2-bromo-5,6,8a,9,11,11a-hexahydro-4H-pyrido[3,2,1-ij]pyrrolo[3,4-c]quinoline-10(8H)-carboxylate from EXAMPLE 27, Part A was converted into the title compound of EXAMPLE 32. $^1$H NMR (dmso-D$_6$) δ: 9.91 (s, 1H), 9.18 (broad s, 1H), 9.10 (broad s, 1H), 7.67 (s, 1H), 7.52 (d, 1H, J=7.7 Hz), 7.38 (d, 1H, J=8.0 Hz), 6.99 (s, 1H), 6.91 (s, 1H), 3.51–3.42 (m, 2H), 3.20–3.00 (m, 5H), 2.91 (app t, 1H), 2.81–2.69 (m, 3H), 2.40 (s, 3H), 1.99–1.90 (m, 2H). LRMS (ES)$^+$: 333.3 (M+H)$^+$.

Example 33

{2-[(8aR,11aR)-5,6,8,8a,9,10,11,11a-octahydro-4H-pyrido[3,2,1-ij]pyrrolo[3,4-c]quinolin-2-yl]-5-methylphenyl}methanol

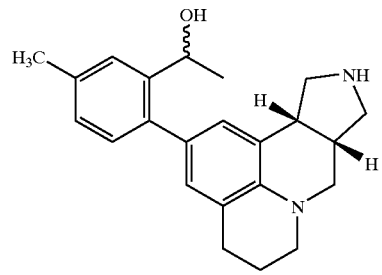

To a solution of 2-[(8aR,11aR)-5,6,8,8a,9,10,11,11a-octahydro-4H-pyrido[3,2,1-ij]pyrrolo[3,4-c]quinolin-2-yl]-5-methylbenzaldehyde, trifluoroacetic acid salt from EXAMPLE 32 (65 mg, 0.2 mmol) in 10 mL of tetrahydrofuran at 0° C. was added methyl magnesium bromide (1.3 mL of a 3M solution in THF, 3.9 mmol). The reaction was stirred at 0° C. for 30 min and then allowed to warm to room temperature. The reaction was quenched with sat'd aq ammonium chloride and the volatiles were removed in vacuo. The residue was taken up in ethyl acetate, washed with sat'd aq sodium carbonate and brine, dried (MgSO$_4$) and concentrated to afford the title compound of EXAMPLE 33 as a mixture of diastereomers at the alcohol center. LRMS (ES)$^+$: 349.3 (M+H)$^+$.

Example 34

(±)-trans 2-(2,4-dichlorophenyl)-5,6,8,8a,9,10,11,11a-octahydro-4H-pyrido[3,2,1-ij]pyrrolo[3,4-c]quinoline

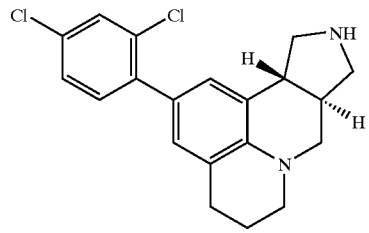

A solution of (±)-trans tert-butyl 2-bromo-5,6,8a,9,11,11a-hexahydro-4H-pyrido[3,2,1-ij]pyrrolo[3,4-c]quinoline-10(8H)-carboxylate from EXAMPLE 7, Part A (55 mg, 0.139 mmol), Ba(OH)$_2$-8 H$_2$O (70 mg, 0.222 mmol), and 2,4-dichlorophenyl boronic acid (35 mg, 0.181 mmol) in DME (3 mL) and water (2 mL) were degassed with argon at near reflux temperature. The solution was cooled to rt, and a mixture of solid PPh$_3$ (5.5 mg, 20.9 mmol) and Pd(PPh$_3$)$_2$Cl$_2$ (5 mg, 6.95 μmol) was added in a single portion. The solution was stirred at reflux under a positive pressure of argon for 4 h. After the starting bromide was consumed, the DME was removed under reduced pressure. The residue was diluted with EtOAc and washed with water followed by brine. The organic layer was dried over Na$_2$SO$_4$, and evaporated under reduced pressure to a golden oil (80 mg crude weight). The crude product was purified on a Redipak (5 g) silica column using a gradient elution of 5%–33% EtOAc in hexanes. Evaporation of the fractions containing product as identified by TLC gave N-Boc protected biaryl intermediate as a white foam (44 mg, 69%). The N-Boc protected indoline (44 mg, 95.8 μmol) was dissolved into CH$_2$Cl$_2$ (9.0 mL) and cooled to 0° C. under N$_2$. Neat trifluoroacetic acid (TFA) was added via syringe in a single portion to the stirred, cooled solution. The reaction was stirred at 0° C. for 2 h and followed by TLC analysis. When all of the N-Boc protected material had been consumed, the solution was basified to pH>10 with 3 N NaOH. The product was extracted into CH$_2$Cl$_2$, washed with brine, and dried over Na$_2$SO$_4$. The solvent was evaporated under reduced pressure to give crude free-base. The crude free-base was purified by semi-preparative HPLC (Dynamax 60 Å, C-18) using an isocratic mobile phase of 50:50:0.05 v/v/v water-:acetonitrile:TFA. The title compound of EXAMPLE 34 was obtained as a yellow semi-solid (26 mg, 76%). $^1$H NMR (500 MHz, CDCl$_3$) δ 0.88 (m, 1H), 1. 26 (broad s, 2H), 1.91–1.94 (m, 1H), 2.00–2.06 (m, 1H), 2.28 (m, 1H), 2.72 (broad s, 1H), 2.95 (m, 1H), 3.0–3.5 (m, 4H), 3.59 (m, 2H), 3.83 (broad s, 1H), 6.68 (s, 1H), 6.91 (s, 1H), 7.21 (m, 2H), 7.42 (s, 1H). LRMS (ES)$^+$: 359 (M+H)$^+$.

Example 35

(±)-trans 2-[4-isopropoxy-2-(trifluoromethyl)phenyl]-5,6,8,8a,9,10,11,11a-octahydro-4H-pyrido[3,2,1-ij]pyrrolo[3,4-c]quinoline

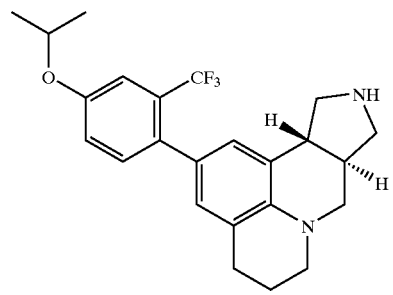

Using 2-trifluoromethyl-4-isopropoxyphenyl boronic acid and following the procedures described in EXAMPLE 34, (±)-trans tert-butyl 2-bromo-5,6,8a,9,11,11a-hexahydro-4H-pyrido[3,2,1-ij]pyrrolo[3,4-c]quinoline-10(8H)-carboxylate from EXAMPLE 7, Part A was converted into the title compound of EXAMPLE 35 as a yellow semi-solid. $^1$H NMR (500 MHz, CDCl$_3$) δ 1.26 (s, 1H), 1.30 (d, 6H, J=6.1 Hz), 1.85–2.05 (m, 2H), 2.15 (m, 1H), 2.74 (m, 4H), 2.96 (t, 1H, J=7 Hz), 3.23 (m, 1H), 3.32 (m, 4H), 3.57 (t, 1H, J=7 Hz), 4.58 (sept, 1H, J=6.1 Hz), 6.59 (s, 1H), 6.77 (s, 1H), 6.99 (dd, 1H, J=2.5, 8.4, Hz), 7.18 (s, 1H), 7.24 (m, 1H). LRMS (ES)$^+$: 417 (M+H)$^+$.

Example 36

(±)-trans 2-(4-methoxy-2-methylphenyl)-5,6,8,8a,9,10,11,11a-octahydro-4H-pyrido[3,2,1-ij]pyrrolo[3,4-c]quinoline

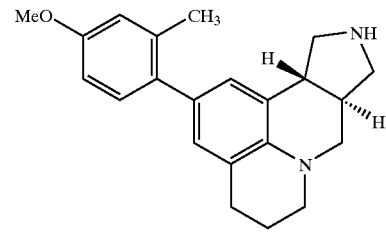

Using 2-methyl-4-methoxyphenyl boronic acid and following procedures described in EXAMPLE 34, (±)-trans tert-butyl 2-bromo-5,6,8a,9,11,11a-hexahydro-4H-pyrido[3,2,1-ij]pyrrolo[3,4-c]quinoline-10(8H)-carboxylate from EXAMPLE 7, Part A was converted into the title compound of EXAMPLE 36 as a yellow semi-solid. $^1$H NMR (500 MHz, CDCl$_3$) δ 1.26 (s, 1H), 1.95 (m, 1H), 2.01 (m, 1H), 2.16 (m, 1H), 2.28 (s, 3H), 2.70–2.90 (m, 4H), 2.98 (t, 1H, J=7 Hz), 3.22 (m, 1H), 3.30 (m, 4H), 3.38 (t, 1H, J=7 Hz), 3.60 (s, 3H), 6.58 (s, 1H), 6.74 (d, 1H, J=8.4 Hz), 6.77 (s, 2H), 7.12 (d, 1H, J=8.4 Hz). LRMS (ES)$^+$: 335 (M+H)$^+$.

Example 37

(8aR,11aR)-N-[3,5-bis(trifluoromethyl)phenyl]-5,6,8,8a,9,10,11,11a-octahydro-4H-pyrido[3,2,1-ij]pyrrolo[3,4-c]quinolin-2-amine, bis-trifluoroacetic acid salt

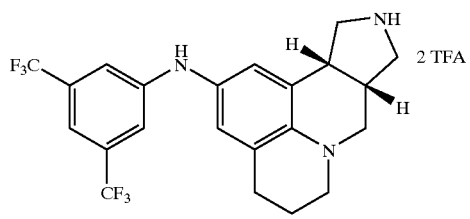

Part A. tert-butyl (8aS,11aR)-2-amino-5,6,8a,9,11,11a-hexahydro-4H-pyrido[3,2,1-ij]pyrrolo[3,4-c]quinoline-10(8H)-carboxylate Following the procedures described in EXAMPLE 17, Part A, tert-butyl (8aS,11aR)-2-bromo-5,6,8a,9,11,11a-hexahydro-4H-pyrido[3,2,1-ij]pyrrolo[3,4-c]quinoline-10(8H)-carboxylate was converted into the title compound of Part A as a tan solid. $^1$H NMR (CDCl$_3$) δ: 6.28 (broad s, 2H), 3.90–3.78 (m, 1H), 3.59 (dd, 1H, J=11.1, 6.4 Hz), 3.35–2.55 (overlapping m, 10H), 2.05–1.90 (m, 2H), 1.42 (s, 9H).

Part B. (8aR,11aR)-N-[3,5-bis(trifluoromethyl)phenyl]-5,6,8,8a,9,10,11,11a-octahydro-4H-pyrido[3,2,1-ij]pyrrolo[3,4-c]quinolin-2-amine, bis-trifluoroacetic acid salt.

Using 3,5-bis(trifluoromethyl)bromobenzene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 37. LRMS (ES)$^+$: 442.3 (M+H)$^+$.

Example 38

(8aR,11aR)-N-(4-fluoro-2-methylphenyl)-5,6,8,8a,9,10,11,11a-octahydro-4H-pyrido[3,2,1-ij]pyrrolo[3,4-c]quinolin-2-amine, bis-trifluoroacetic acid salt.

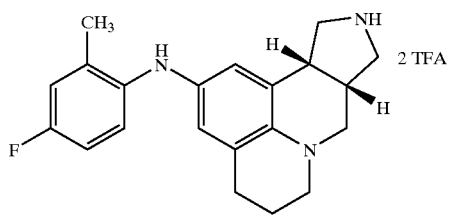

Using 2-bromo-5-fluorotoluene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H-carboxylate was converted into the title compound of EXAMPLE 38. LRMS (ES)$^+$: 338.4 (M+H)$^+$.

Example 39

(8aR,11aR)-N-[2-chloro-5-(trifluoromethyl)phenyl]-5,6,8,8a,9,10,11,11a-octahydro-4H-pyrido[3,2,1-ij]pyrrolo[3,4-c]quinolin-2-amine, bis-trifluoroacetic acid salt

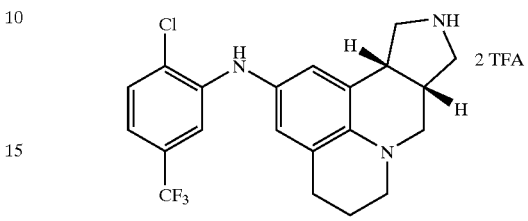

Using 3-bromo-4-chlorobenzotrifluoride and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 39. $^1$H NMR (dmso-D$_6$) δ: 8.89 (broad s, 2H), 7.57 (s, 1H), 7.51 (d, 1H, J=8.0 Hz), 7.00 (s, 1H), 6.93 (d, 1H, J=8.0 Hz), 6.82 (s, 1H), 6.70 (s, 1H), 3.70–3.60 (m, 1H), 3.58–3.32 (m, 4H), 3.10–2.85 (m, 4H), 2.80–2.60 (m, 3H), 1.96–1.83 (m, 2H). LRMS (ES)$^+$: 408.2 (M+H)$^+$.

Example 40

(8aR,11aR)-N-[2-fluoro-5-(trifluoromethyl)phenyl]-5,6,8,8a,9,10,11,11a-octahydro-4H-pyrido[3,2,1-ij]pyrrolo[3,4-c]quinolin-2-amine, bis-trifluoroacetic acid salt

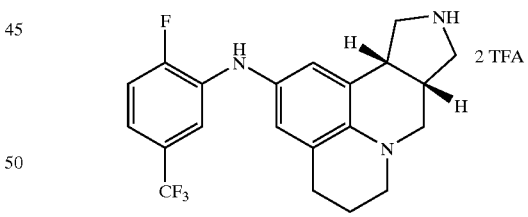

Using 3-bromo-4-fluorobenzotrifluoride and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 40. $^1$H NMR (dmso-D$_6$) (all signals very broad) δ: 8.88 (broad s, 2H), 7.90–7.79 (m, 1H), 7.35–7.22 (m, 1H), 7.17–7.07 (m, 1H), 7.02–6.90 (m, 1H), 6.77 (broad s, 1H), 6.65 (broad s, 1H), 3.85–3.57 (m, 3H), 3.50–3.30 (m, 2H), 3.10–2.85 (m, 4H), 2.80–2.60 (m, 3H), 1.95–1.80 (m, 2H). LRMS (ES)$^+$: 392.3 (M+H)$^+$.

Example 41

(8aR,11aR)-N-[3-fluoro-5-(trifluoromethyl)phenyl]-5,6,8,8a,9,10,11,11a-octahydro-4H-pyrido[3,2,1-ij]pyrrolo[3,4-c]quinolin-2-amine, bis-trifluoroacetic acid salt

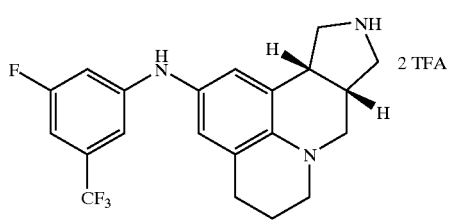

Using 3-bromo-5-fluorobenzotrifluoride and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 41. $^1$H NMR (dmso-D$_6$) (all signals broad) δ: 8.89 (broad s, 2H), 8.33 (s, 1H), 6.85–6.60 (m, 5H), 3.73–3.60 (m, 2H), 3.49–3.38 (m, 1H), 3.10–2.90 (m, 5H), 2.80–2.60 (m, 4H), 1.95–1.80 (m, 2H). LRMS (ES)$^+$: 392.3 (M+H)$^+$.

Example 42

(8aR,11aR)-N-[3-(trifluoromethyl)phenyl]-5,6,8,8a,9,10,11,11a-octahydro-4R-pyrido[3,2,1-ij]pyrrolo[3,4-c]quinolin-2-amine, bis-trifluoroacetic acid salt

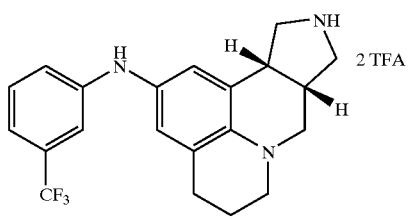

Using 3-bromobenzotrifluoride and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 42. $^1$H NMR (dmso-D$_6$) δ: 8.01 (s, 2H), 7.28 (t, 1H, J=7.7 Hz), 7.05–7.00 (m, 2H), 6.88 (d, 1H, J=7.3 Hz), 6.73 (d, 1H, J=2.2 Hz), 6.62 (d, 1H, J=1.8 Hz), 3.80–3.60 (m, 3H), 3.49–3.38 (m, 1H), 3.10–2.90 (m, 5H), 2.80–2.65 (m, 4H), 1.90–1.80 (m, 2H). LRMS (ES)$^+$: 374.3 (M+H)$^+$.

Example 43

(8aR,11aR)-N-[2-fluoro-3-(trifluoromethyl)phenyl]-5,6,8,8a,9,10,11,11a-octahydro-4H-pyrido[3,2,1-ij]pyrrolo[3,4-c]quinolin-2-amine, bis-trifluoroacetic acid

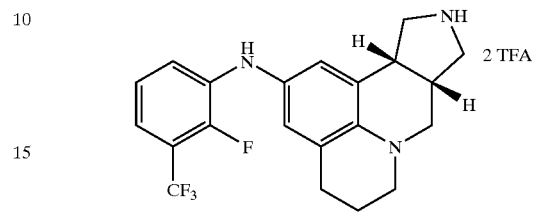

Using 3-bromo-2-fluorobenzotrifluoride and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 43. $^1$H NMR (dmso-D$_6$) δ: 7.77 (s, 2H), 7.19 (t, 1H, J=7.7 Hz), 7.08 (t, 1H, J=7.8 Hz), 6.92 (app t, 1H, J=6.4 Hz), 6.74 (d, 1H, J=2.2 Hz), 6.65 (d, 1H, J=1.8 Hz), 3.80–3.60 (m, 3H), 3.49–3.38 (m, 1H), 3.10–2.90 (m, 5H), 2.80–2.65 (m, 3H), 1.90–1.80 (m, 2H). LRMS (ES)$^+$: 392.3 (M+H)$^+$.

Example 44

(8aR,11aR)-N-[4-chloro-3-(trifluoromethyl)phenyl]-5,6,8,8a,9,10,11,11a-octahydro-4H-pyrido[3,2,1-ij]pyrrolo[3,4-c]quinolin-2-amine, bis-trifluoroacetic acid salt

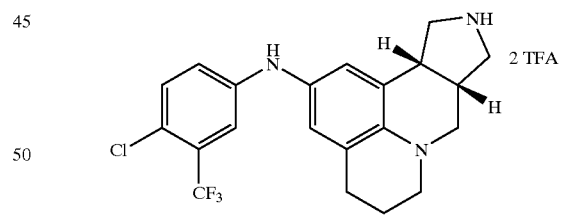

Using 5-bromo-2-chlorobenzotrifluoride and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 44. $^1$H NMR (dmso-D$_6$) δ: 9.02 (broad s, 2H), 8.17 (s, 1H), 7.34 (d, 1H, J=8.7 Hz), 7.15 (d, 1H, J=2.6 Hz), 6.99 (dd, 1H, J=8.7, 2.6 Hz), 6.74 (d, 11, J=2.2 Hz), 6.62 (d, 1H, J=2.2 Hz), 3.70–3.30 (m, 3H), 3.08–2.91 (m, 5H), 2.82–2.75 (m, 1H), 2.71–2.61 (m, 3H), 1.90–1.81 (m, 2H). LRMS (ES)$^+$: 408.3 (M+H)$^+$.

Example 45

(8aR,11aR)-N-(2,3-dichlorophenyl)-5,6,8,8a,9,10,11,11a-octahydro-4H-pyrido[3,2,1-ij]pyrrolo[3,4-c]guinolin-2-amine, bis-trifluoroacetic acid salt

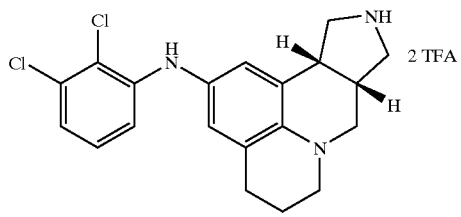

Using 1-bromo-2,3-dichlorobenzene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 45. $^1$H NMR (dmso-D$_6$) δ: 8.98 (broad s, 2H), 7.33 (s, 1H), 7.03 (t, 1H, J=8.1 Hz), 6.85 (dd, 1H, J=7.9, 1.3 Hz), 6.78–6.72 (m, 2H), 6.67 (d, 1H, J=1.9 Hz), 3.70–3.30 (m, 3H), 3.10–2.93 (m, 5H), 2.82–2.75 (m, 1H), 2.73–2.63 (m, 3H), 1.90–1.81 (m, 2H). LRMS (ES)$^+$: 374.2 (M+H)$^+$.

Example 46

(8aR,11aR)-N-(3,4-dichlorophenyl)-5,6,8,8a,9,10,11,11a-octahydro-4H-pyrido[3,2,1-ij]pyrrolo[3,4-c]quinolin-2-amine, bis-trifluoroacetic acid salt

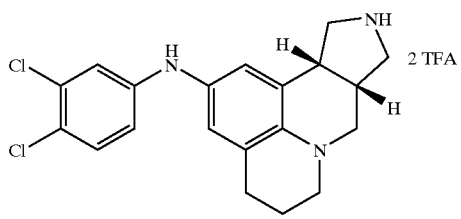

Using 1-bromo-3,4-dichlorobenzene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 46. $^1$H NMR (dmso-D$_6$) δ: 8.98 (broad s, 2H), 7.97 (s, 1H), 7.26 (d, 1H, J=9.2 Hz), 6.88 (d, 1H, J=2.6 Hz), 6.78–6.70 (m, 2H), 6.61 (s, 1H), 3.70–3.30 (m, 3H), 3.08–2.92 (m, 5H), .2.80–2.70 (m, 1H), 2.70–2.62 (m, 3H), 1.90–1.82 (m, 2H). LRMS (ES)$^+$: 374.2 (M+H)$^+$.

Example 47

(8aR,11aR)-N-(2,6-dichlorophenyl)-5,6,8,8a,9,10,11,11a-octahydro-4H-pyrido[3,2,1-ij]pyrrolo[3,4-c]quinolin-2-amine, bis-trifluoroacetic acid salt

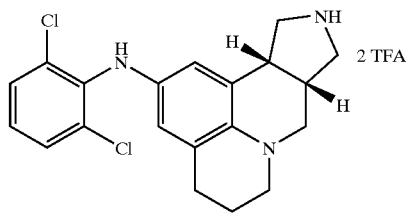

Using 1-bromo-2,6-dichlorobenzene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 47. $^1$H NMR (dmso-D$_6$) δ: 9.00 (broad s, 2H), 7.47 (d, 2H), 7.25 (s, 1H), 7.13 (t, 1H), 6.19 (d, 1H), 6.12 (d, 1H), 3.60–3.30 (m, 3H), 3.07–2.85 (m, 5H), 2.73–2.65 (m, 2H), 2.65–2.57 (m, 2H), 1.90–1.80 (m, 2H). LRMS (ES)$^+$: 374.2 (M+H)$^+$.

Example 48

(8aR,11aR)-N-(2-chloro-5-methylphenyl)-5,6,8,8a,9,10,11,11a-octahydro-4H-pyrido[3,2,1-ij]pyrrolo[3,4-c]quinolin-2-amine, bis-trifluoroacetic acid salt

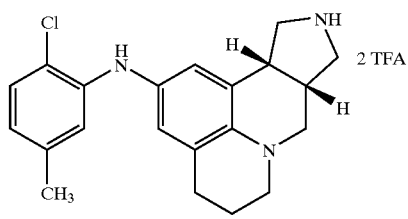

Using 3-bromo-4-chlorotoluene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H-carboxylate was converted into the title compound of EXAMPLE 48. $^1$H NMR (dmso-D$_6$) δ: 9.00 (broad s, 2H), 7.12 (d, 2H, J=8.0 Hz), 6.92 (s, 1H), 6.73–6.67 (m, 2H), 6.63 (s, 1H), 6.44 (dd, 1H, J=8.0, 1.4 Hz), 3.50–3.30 (m, 3H), 3.07–2.85 (m, 5H), 2.73–2.60 (m, 4H), 2.09 (s, 3H), 1.90–1.80 (m, 2H). LRMS (ES)$^+$: 355.4 (M+H)$^+$.

Example 49

2-[(8aR,11aR)-5,6,8,8a,9,10,11,11a-octahydro-4H-pyrido[3,2,1-ij]pyrrolo[3,4-c]quinolin-2-ylamino]benzonitrile, bis-trifluoroacetic acid salt

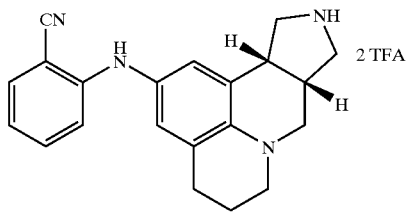

Using 2-bromobenzonitrile and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 49. LRMS (ES)$^+$: 331.4 (M+H)$^+$.

Example 50

(8aR,11aR)-N-(2-methoxy-5-methylphenyl)-5,6,8,8a,9,10,11,11a-octahydro-4H-pyrido[3,2,1-ij]pyrrolo[3,4-c]quinolin-2-amine, bis-trifluoroacetic acid salt

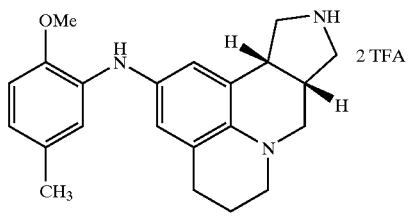

Using 3-bromo-4-methoxytoluene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 50. LRMS (ES)$^+$: 350.4 (M+H)$^+$.

Example 51

3-[(8aR,11aR)-5,6,8,8a,9,10,11,11a-octahydro-4H-pyrido[3,2,1-ij]pyrrolo[3,4-c]quinolin-2-ylamino]benzonitrile, bis-trifluoroacetic acid salt

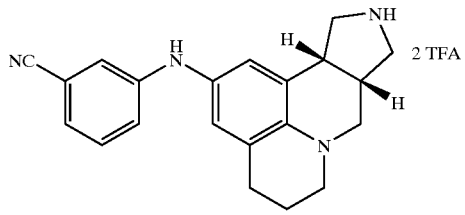

Using 3-bromobenzonitrile and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 51. LRMS (ES)$^+$: 331.4 (M+H)$^+$.

Example 52

4-[(8aR,11aR)-5,6,8,8a,9,10,11,11a-octahydro-4H-pyrido[3,2,1-ij]pyrrolo[3,4-c]quinolin-2-ylamino]benzonitrile, bis-trifluoroacetic acid salt

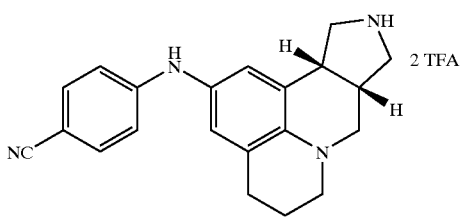

Using 4-bromobenzonitrile and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 52. $^1$H NMR (dmso-D$_6$) δ: 8.95 (broad s, 2H), 8.43 (s, 1H), 7.42 (d, 2H, J=8.7 Hz), 6.78 (d, 2H, J=8.8 Hz), 6.75 (d, 1H), 6.61 (d, 1H), 3.70–3.30 (m, 3H), 3.07–2.92 (m, 5H), 2.80–2.72 (m, 1H), 2.70–2.62 (m, 3H), 1.88–1.80 (m, 2H). LRMS:(ES)$^+$: 331.4 (M+H)$^+$.

Example 53

(8aR,11aR)-N-[2-(trifluoromethyl)phenyl]-5,6,8,8a,9,10,11,11a-octahydro-4H-pyrido[3,2,1-ij]pyrrolo[3,4-c]quinolin-2-amine, bis-trifluoroacetic acid salt

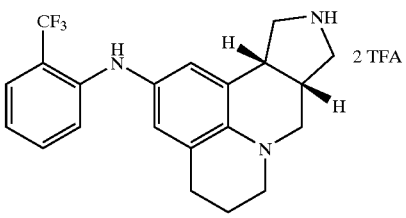

Using 2-bromobenzotrifluoride and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 53. $^1$H NMR (dmso-D$_6$) δ: 8.95 (broad s, 2H), 7.44 (d, 1H, J=8.0 Hz), 7.29 (t, 1H, J=7.9 Hz), 6.95–6.89 (m, 2H), 6.77 (t, 1H, J=7.5 Hz), 6.72 (s, 1H), 6.64 (s, 1H), 3.68–3.58 (m, 1H), 3.45–3.30 (m, 2H), 3.06–2.90 (m, 5H), 2.77–2.72 (m, 1H), 2.70–2.60 (m, 3H), 1.88–1.80 (m, 2H). LRMS (ES)$^+$: 374.3 (M+H)$^+$.

Example 54

(8aR,11aR)-N-[4-(trifluoromethyl)phenyl]-5,6,8,8a,9,10,11,11a-octahydro-4H-pyrido[3,2,1-ij]pyrrolo[3,4-c]quinolin-2-amine, bis-trifluoroacetic acid salt

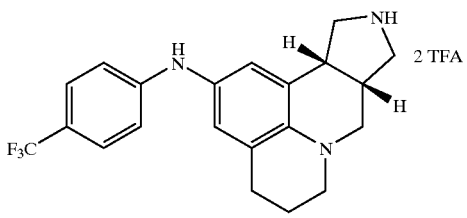

Using 4-bromobenzotrifluoride and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 54. $^1$H NMR (dmso-$D_6$) δ: 9.00(broad s, 2H), 8.17 (s, 1H), 7.35 (d, 2H, J=8.4 Hz), 6.84 (d, 2H, J=8.5 Hz), 6.72 (s, 1H), 6.63 (s, 1H), 3.68–3.58 (m, 1H), 3.45–3.30 (m, 2H), 3.05–2.90 (m, 5H), 2.75–2.60 (m, 4H), 1.90–1.80 (m, 2H). LRMS (ES)$^+$: 374.3 (M+H)$^+$.

Example 55

(8aR,11aR)-N-(2-fluoro-5-methylphenyl)-5,6,8,8a,9,10,11,11a-octahydro-4H-pyrido[3,2,1-ij]pyrrolo[3,4-c]quinolin-2-amine, bis-trifluoroacetic acid salt

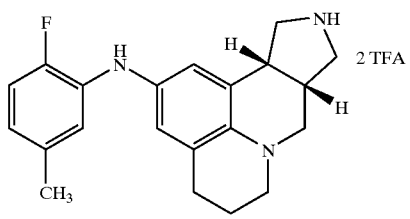

Using 3-bromo-4-fluorotoluene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 55. LRMS (ES)$^+$: 338.4 (M+H)$^+$.

Example 56

(8aR,11aR)-N-(3-quinolinyl)-5,6,8,8a,9,10,11,11a-octahydro-4H-pyrido[3,2,1-ij]pyrrolo[3,4-c]quinolin-2-amine, bis-trifluoroacetic acid salt

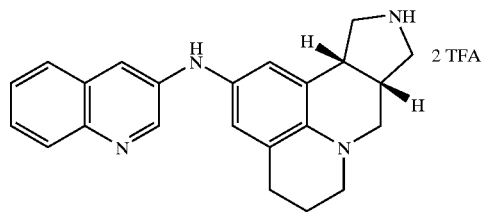

Using 3-bromoquinoline and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 56. LRMS (ES)$^+$: 357.4 (M+H)$^+$.

Example 57

(8aR,11aR)-N-(2-naphthyl)-5,6,8,8a,9,10,11,11a-octahydro-4H-pyrido[3,2,1-ij]pyrrolo[3,4-c]quinolin-2-amine, bis-trifluoroacetic acid salt

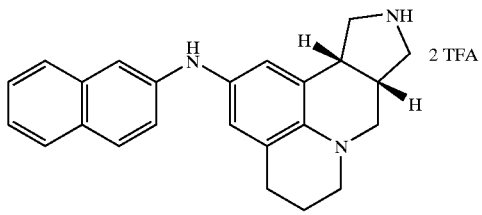

Using 2-bromonaphthalene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 57. LRMS (ES)$^+$: 356.4 (M+H)$^+$.

Example 58

(8aR,11aR)-N-(1-naphthyl)-5,6,8,8a,9,10,11,11a-octahydro-4H-pyrido[3,2,1-ij]pyrrolo[3,4-c]quinolin-2-amine, bis-trifluoroacetic acid salt

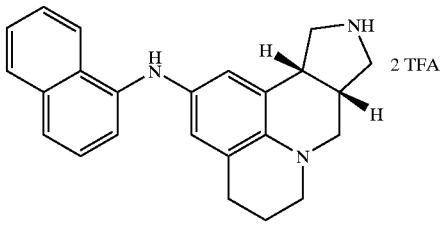

Using 1-bromonaphthalene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 58. LRMS (ES)$^+$: 356.4 (M+H)$^+$.

Example 59

(8aR,11aR)-N-(2-chloro-3-pyridinyl)-5,6,8,8a,9,10,11,11a-octahydro-4H-pyrido[3,2,1-ij]pyrrolo[3,4-c]quinolin-2-amine, bis-trifluoroacetic acid salt

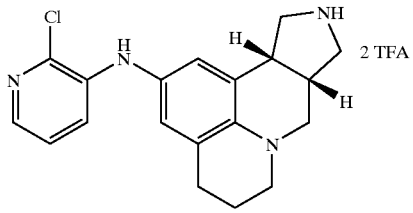

Using 3-bromo-2-chloropyridine and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 59. LRMS (ES)⁺: 341.4 (M+H)⁺.

Example 60

(8aR,11aR)-N-(4-methyl-1-naphthyl)-5,6,8,8a,9,10,11,11a-octahydro-4H-pyrido[3,2,1-ij]pyrrolo[3,4-c]quinolin-2-amine, bis-trifluoroacetic acid salt

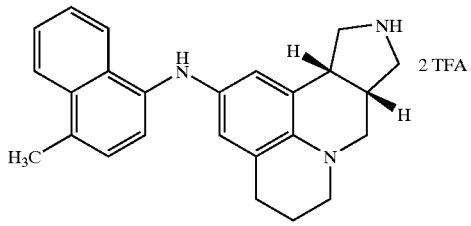

Using 1-bromo-4-methylnaphthalene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 60. LRMS (ES)⁺: 370.4 (M+H)⁺.

Example 61

(8aR,11aR)-N-(2-methyl-1-naphthyl)-5,6,8,8a,9,10,11,11a-octahydro-4H-pyrido[3,2,1-ij]pyrrolo[3,4-c]quinolin-2-amine, bis-trifluoroacetic acid salt

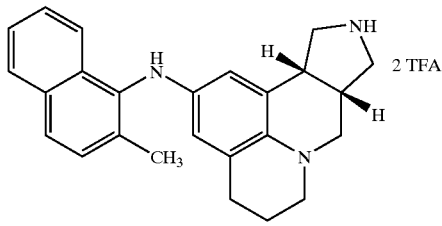

Using 1-bromo-2-methylnaphthalene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 61. LRMS (ES)⁺: 370.4 (M+H)⁺.

Example 62

(8aR,11aR)-N-(2,3-dimethylphenyl)-5,6,8,8a,9,10,11,11a-octahydro-4H-pyrido[3,2,1-ij]pyrrolo[3,4-c]quinolin-2-amine, bis-trifluoroacetic acid salt

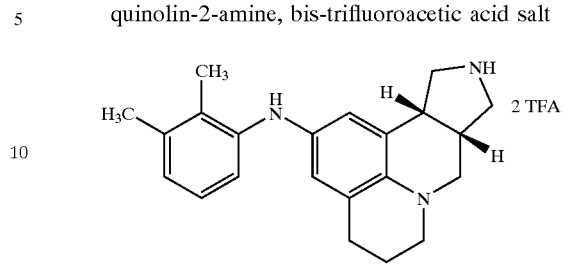

Using 3-bromo-o-xylene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 62. LRMS (ES)⁺: 334.4 (M+H)⁺.

Example 63

(8aR,11aR)-N-(3-methylphenyl)-5,6,8,8a,9,10,11,11a-octahydro-4H-pyrido[3,2,1-ij]pyrrolo[3,4-c]quinolin-2-amine, bis-trifluoroacetic acid salt

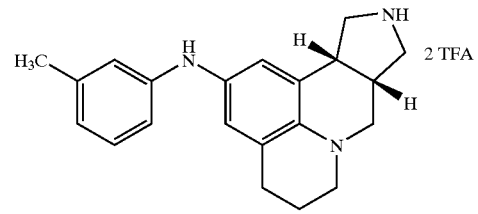

Using 3-bromotoluene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 63. LRMS (ES)⁺: 320.4 (M+H)⁺.

Example 64

(8aR,11aR)-N-(2,5-dimethylphenyl)-5,6,8,8a,9,10,11,11a-octahydro-4H-pyrido[3,2,1-ij]pyrrolo[3,4-c]quinolin-2-amine, bis-trifluoroacetic acid salt

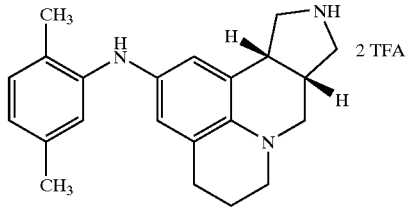

Using 2-bromo-p-xylene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 64. LRMS (ES)⁺: 334.4 (M+H)⁺.

Example 65

(8aR,11aR)-N-(3,4-dimethylphenyl)-5,6,8,8a,9,10,11,11a-octahydro-4H-pyrido[3,2,1-ij]pyrrolo[3,4-c]quinolin-2-amine, bis-trifluoroacetic acid salt

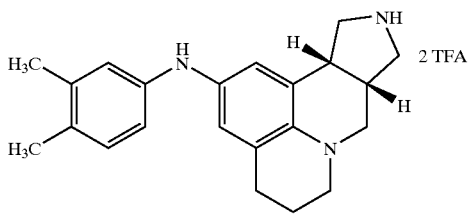

Using 4-bromo-o-xylene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 65. LRMS (ES)$^+$: 334.4 (M+H)$^+$.

Example 66

(8aR,11aR)-N-(2-methoxyphenyl)-5,6,8,8a,9,10,11,11a-octahydro-4H-pyrido[3,2,1-ij]pyrrolo[3,4-c]quinolin-2-amine, bis-trifluoroacetic acid salt

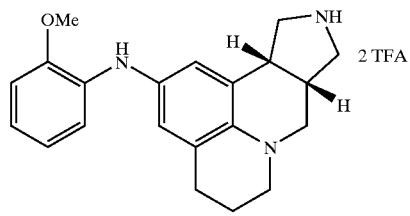

Using 2-bromoanisole and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 66. LRMS (ES)$^+$: 336.4 (M+H)$^+$.

Example 67

(8aR,11aR)-N-(2-fluoro-4-methoxyphenyl)-5,6,8,8a,9,10,11,11a-octahydro-4H-pyrido[3,2,1-ij]pyrrolo[3,4-c]quinolin-2-amine, bis-trifluoroacetic acid salt

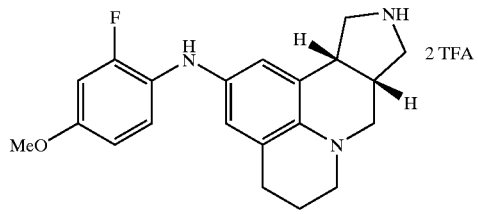

Using 4-bromo-2-fluoroanisole and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 67. $^1$H NMR (dmso-D$_6$) (all signals broad) δ: 8.85 (broad s, 2H), 7.00–6.90 (m, 2H), 6.81–6.74 (m, 1H), 6.60 (d, 1H, J=6.6 Hz), 6.43 (broad s, 1H), 6.37 (broad s, 1H), 3.65 (s, 3H), 3.65–3.30 (m, 3H), 3.05–2.85 (m, 5H), 2.70–2.55 (m, 4H), 1.87–1.77 (m, 2H). LRMS (ES)$^+$: 354.4 (M+H)$^+$.

Example 68

(8aR,11aR)-N-(3,5-dimethylphenyl)-5,6,8,8a,9,10,11,11a-octahydro-4H-pyrido[3,2,1-ij]pyrrolo[3,4-c]quinolin-2-amine, bis-trifluoroacetic acid salt

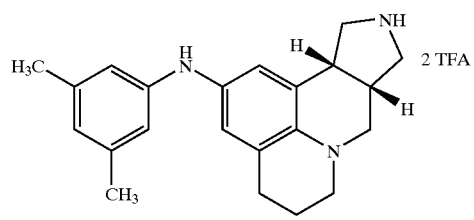

Using 5-bromo-m-xylene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 68. LRMS (ES)$^+$: 334.4 (M+H)$^+$.

Example 69

(8aR,11aR)-N-(4-fluoro-3-methylphenyl)-5,6,8,8a,9,10,11,11a-octahydro-4H-pyrido[3,2,1-ij]pyrrolo[3,4-c]quinolin-2-amine, bis-trifluoroacetic acid salt

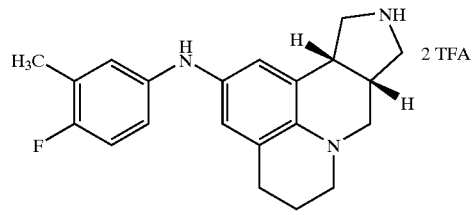

Using 5-bromo-2-fluorotoluene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 69. LRMS (ES)$^+$: 338.4 (M+H)$^+$.

Example 70

(8aR,11aR)-N-(2-fluoro-4-methylphenyl)-5,6,8,8a,9,10,11,11a-octahydro-4H-pyrido[3,2,1-ij]pyrrolo[3,4-c]quinolin-2-amine, bis-trifluoroacetic acid salt

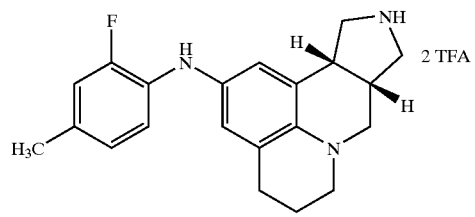

Using 4-bromo-3-fluorotoluene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 70. ¹H NMR (dmso-D6) (all signals broad) δ: 8.98 (broad s, 2H), 7.19 (s, 1H), 6.98–6.86 (m, 2H), 6.80–6.72 (m, 1H), 6.60 (broad s, 1H), 6.54 (broad s, 1H), 3.68–3.60 (m, 1H), 3.50–3.30 (m, 2H), 3.10–2.85 (m, 5H), 2.75–2.60 (m, 4H), 2.19 (s, 3H), 1.93–1.80 (m, 2H). LRMS (ES)⁺: 338.4 (M+H)⁺.

Example 71

(8aR,11aR)-N-(4-chloro-3-methylphenyl)-5,6,8,8a,9,10,11,11a-octahydro-4H-pyrido[3,2,1-ij]pyrrolo[3,4-c]quinolin-2-amine, bis-trifluoroacetic acid salt

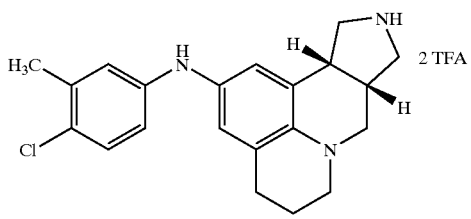

Using 5-bromo-2-chlorotoluene and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 71. LRMS (ES)⁺: 354.3 (M+H)⁺.

Example 72

(±)-trans-N-[2-chloro-5-(trifluoromethyl)phenyl]-5,6,8,8a,9,10,11,11a-octahydro-4H-pyrido[3,2,1-ij]pyrrolo[3,4-c]quinolin-2-amine

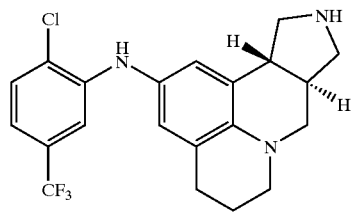

A solution of (±)-trans tert-butyl 2-amino-5,6,8a,9,11,11a-hexahydro-4H-pyrido[3,2,1-ij]pyrrolo[3,4-c]quinoline-10(8H)-carboxylate (100 mg, 0.304 mmol), sodium tert-butoxide (58 mg, 0.608 mmol), and 3-bromo-4-chlorobenzotrifluoride (95 mg, 0.365 mmol) in anhydrous toluene (6 mL) were degassed with argon at 85° C. for 15 min. The solution was cooled slightly, and a mixture of solid Pd₂(dba)₃ (5.6 mg, 6.1 μmol) and solid BINAP (11 mg, μmol) were added to the solution. The flask was capped under a positive pressure of Ar and heating was continued at 85° C. overnight. After the reaction was complete as evidenced by the lack of starting aniline by TLC analysis, the solution was cooled and diluted with ether. The red slurry was filtered through Celite 521® and concentrated under reduced pressure to give crude N-Boc protected biarylamine as a red oil (101 mg). The crude product was purified by silica gel chromatography on the Isco Combi-flash unit using a 10-g RediSep cartridge and a gradient elution of ethyl acetate in hexanes from 5% to 75%. A CH₂Cl₂ (4 mL) solution of the N-Boc protected product was cooled to 0° C. and treated with trifluoroacetic acid (TFA) (250 μL). The disappearance of N-Boc protected material was followed by TLC analysis (1:1 hexanes:EtOAc) over 8 h. The TFA solution was then basified with 3 N NaOH to pH >12 and extracted with CH₂Cl₂. Evaporations of the extracts gave 21 mg of the title compound of EXAMPLE 72 as an off-white powder. ¹H NMR (500 MHz, CDCl₃) δ 1.26 (br s, 1H), 1.95 (m, 1H), 2.0 (m, 1H), 2.15 (m, 1H), 2.74 (m, 4H), 2.90 (t, 1H, J=1.9 Hz), 3.29 (m, 1H), 3.33 (m, 4H), 3.51 (t, 1H, J=1.9 Hz), 5.96 (s, 1H), 6.52 (s, 1H), 6.69 (s, 1H), 6.86 (m, 1H), 7.07 (s, 1H), 7.34 (m, 1H). LRMS (ES)⁺: 408 (M+H)⁺.

Example 73

(±)-trans-N-(3,4-dichlorophenyl)-5,6,8,8a,9,10,11,11a-octahydro-4H-pyrido[3,2,1-ij]pyrrolo[3,4-c]quinolin-2-amine

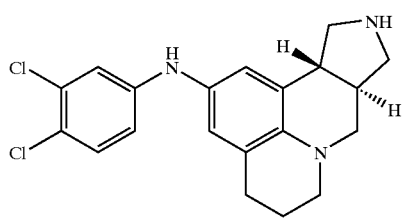

Using 3,4-dichlorobromobenzene and following the procedures described in EXAMPLE 72, (±)-trans tert-butyl 2-amino-5,6,8a,9,11,11a-hexahydro-4H-pyrido[3,2,1-ij]pyrrolo[3,4-c]quinoline-10(8H)-carboxylate was converted into the title compound of EXAMPLE 73 as a tan solid. ¹H NMR (300 MHz, CDCl₃) δ 1.25 (br s, 1H), 1.95 (m, 2H), 2.00 (m, 1H), 2.70 (m, 4H), 2.90 (t, 1H, J=9.7 Hz), 3.10–3.50 (m, 5H), 3.54 (t, 1H, J=9.7 Hz), 5.34 (br s, 1H), 6.42 (s, 1H), 6.51 (m, 1H), 6.59 (s, 1H), 6.83 (d, 1H, J=2.6 Hz), 7.16 (d, 1H, J=8.7 Hz). LRMS (ES)⁺: 374 (M+H)⁺.

Example 74

(±)-trans-N-(2,3-dichlorophenyl)-5,6,8,8a,9,10,11,11a-octahydro-4H-pyrido[3,2,1-ij]pyrrolo[3,4-c]quinolin-2-amine

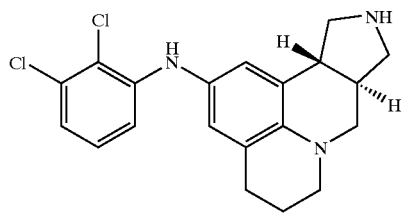

Using 2,3-dichlorobromobenzene and following the procedures described in EXAMPLE 72, (±)-trans tert-butyl 2-amino-5,6,8a,9,11,11a-hexahydro-4H-pyrido[3,2,1-ij]pyrrolo[3,4-c]quinoline-10(8H)-carboxylate was converted into the title compound of EXAMPLE 74 as an off-white powder. ¹H NMR (300 MHz, CDCl₃) δ 1.25 (br s, 1H), 1.95–2.05 (m, 2H), 2.10–2.30 (m, 1H), 2.80 (m, 4H), 2.95 (t, 1H, J=9.5 Hz), 3.30–3.55 (m, 5H), 3.54 (dd, 1H, J=9.5, 7.0 Hz), 5.93 (br s, 1H), 6.50 (s, 1H), 6.71 (s, 2H), 6.74–6.79 (m, 1H), 6.92 (t, 1H, J=8.1 Hz). LRMS (ES)⁺: 374 (M+H)⁺.

Example 75

(±)-trans-N-(2,4-dichlorophenyl)-5,6,8,8a,9,10,11,11a-octahydro-4H-pyrido[3,2,1-ij]pyrrolo[3,4-c]quinolin-2-amine

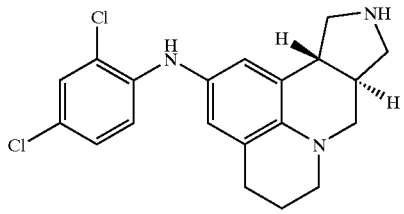

Using 2,4-dichlorobromobenzene and following the procedures described in EXAMPLE 72, (±)-trans tert-butyl 2-amino-5,6,8a,9,11,11a-hexahydro-4H-pyrido[3,2,1-ij]pyrrolo[3,4-c]quinoline-10(8H)-carboxylate was converted into the title compound of EXAMPLE 75 as an off-white powder. $^1$H NMR (300 MHz, CDCl$_3$) δ 1.25 (br s, 1H), 1.70–1.90 (br s, 1H), 1.90–2.20 (m, 2H), 2.70–2.80 (m, 4H), 2.91 (t, 1H, J=9.3 Hz), 3.30–3.60 (m, 5H), 3.54 (m, 1H), 5.78 (br s, 1H), 6.51 (s, 1H), 6.68 (s, 1H), 6.79 (d, 1H, J=8.0 Hz), 7.00 (d, 1H, J=8.0 Hz), 7.25 (s, 1H). LRMS (ES)$^+$: 374 (M+H)$^+$.

Example 76

(±)-cis-N-benzyl-5,6,8,8a,9,10,11,11a-octahydro-4H-pyrido[3,2,1-ij]pyrrolo[3,4-c]quinolin-2-amine, bis-trifluoroacetic acid salt

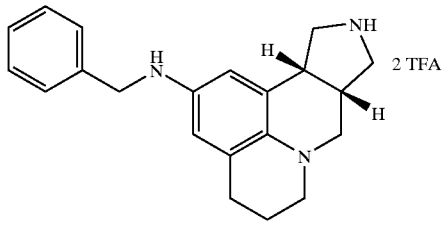

To absolution of (±)-cis-tert-butyl 2-amino-5,6,8a,9,11,11a-hexahydro-4H-pyrido[3,2,1-ij]pyrrolo[3,4-c]quinoline-10(8H)-carboxylate from EXAMPLE 17, Part B (80 mg, 0.24 mmol) in 5 mL of 1,2-dichloroethane was added benzaldehyde (28 mg, 0.26 mmol), crushed 4A molecular sieves and three drops of glacial acetic acid. The reaction was stirred at ambient temperature for 1 h and then there was added sodium triacetoxyborohydride (76 mg, 0.36 mmol). The reaction was stirred at ambient temperature for 3 h and then was quenched by the addition of aq ammonium hydroxide. The mixture was extracted with methylene chloride, washed with brine, dried (K$_2$CO$_3$) and concentrated. The residue was taken up in 10 mL of methylene chloride and then there was added 5 mL of trifluoroacetic acid. The reaction was allowed to stir at ambient temperature for 3 h and then was concentrated in vacuo. The residue was purified by preparative HPLC (C18 reverse phase column, elution with a H$_2$O/CH$_3$CN gradient with 0.5% TFA) to afford the title compound of EXAMPLE 76 as a powder. LRMS (ES)$^+$: 320.3 (M+H)$^+$.

Example 77

(±)-cis-N-(3,5-dichlorobenzyl)-5,6,8,8a,9,10,11,11a-octahydro-4H-pyrido[3,2,1-ij]pyrrolo[3,4-c]quinolin-2-amine, bis-trifluoroacetic acid salt

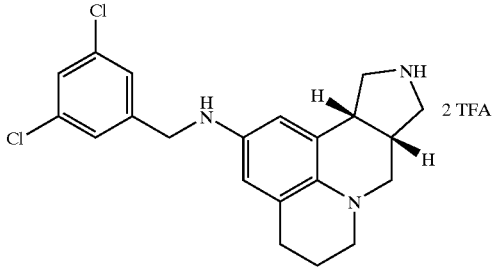

Using 3,5-dichlorobenzaldehyde and following the procedures described in EXAMPLE 76, (±)-cis tert-butyl 2-amino-5,6,8a,9,11,11a-hexahydro-4H-pyrido[3,2,1-ij]pyrrolo[3,4-c]quinoline-10(8H)-carboxylate from EXAMPLE 17, Part B was converted into the title compound of EXAMPLE 77 as a powder. $^1$H NMR (dmso-D$_6$) (all signals broad) δ: 8.85 (broad s, 2H), 7.40–7.30 (m, 3H), 6.14 (broad s, 2H), 4.15 (s, 2H), 3.70–3.55 (m, 1H), 3.48–3.35 (m, 2H), 3.30–3.18 (m, 1H), 3.05–2.75 (m, 5H), 2.70–2.50 (m, 3H), 1.87–1.77 (m, 2H). LRMS (ES)$^+$: 388.2 (M+H)$^+$.

Example 78

(±)-cis-N-(2,6-dichlorobenzyl)-5,6,8,8a,9,10,11,11a-octahydro-4H-pyrido[3,2,1-ij]pyrrolo[3,4-c]quinolin-2-amine, bis-trifluoroacetic acid salt

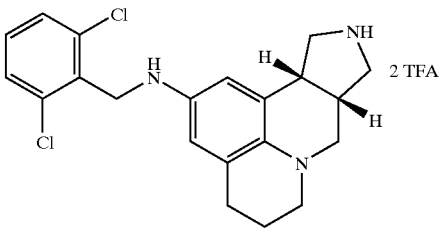

Using 2,6-dichlorobenzaldehyde and following the procedures described in EXAMPLE 76, (±)-cis-tert-butyl 2-amino-5,6,8a,9,11,11a-hexahydro-4H-pyrido[3,2,1-ij]pyrrolo[3,4-c]quinoline-10(8H)-carboxylate from EXAMPLE 17, Part B was converted into the title compound of EXAMPLE 78 as a powder. LRMS (ES)$^+$: 388.2 (M+H)$^+$.

Example 79

(8aR,11aR)-N-[2-(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid

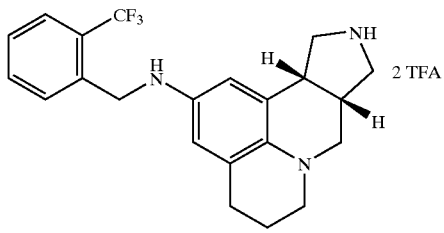

Using 2-trifluoromethylbenzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 79 as a powder. LRMS (ES)$^+$: 388.3 (M+H)$^+$.

Example 80

(8aR,11aR)-N-[2-fluoro-6-(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt

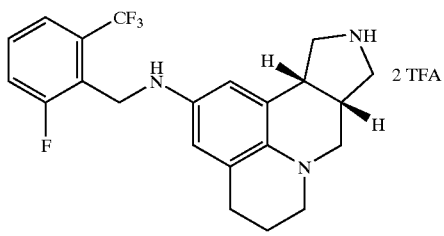

Using 2-fluoro-6-trifluoromethylbenzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 80 as a powder. LRMS (ES)$^+$: 406.3 (M+H)$^+$.

Example 81

(8aR,11aR)-N-(2,3-dichlorobenzyl)-5,6,8,8a,9,10,11,11a-octahydro-4H-pyrido[3,2,1-ij]pyrrolo[3,4-c]quinolin-2-amine, bis-trifluoroacetic acid salt

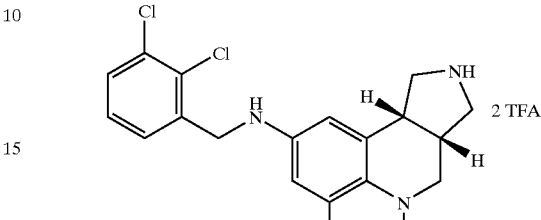

Using 2,3-dichlorobenzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 81 as a powder. LRMS (ES)$^+$: 388.4 (M+H)$^+$.

Example 82

(8aR,11aR)-N-(2,4-dichlorobenzyl)-5,6,8,8a,9,10,11,11a-octahydro-4H-pyrido[3,2,1-ij]pyrrolo[3,4-c]quinolin-2-amine, bis-trifluoroacetic acid salt

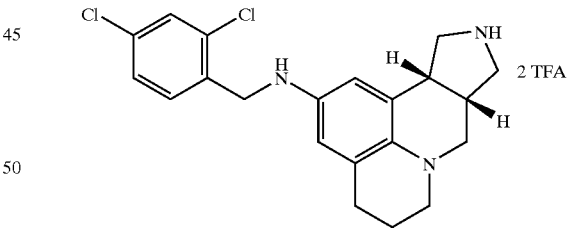

Using 2,4-dichlorobenzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 82 as a powder. LRMS (ES)$^+$: 388.2 (M+H)$^+$.

Example 83

(8aR,11aR)-N-(3,4-dichlorobenzyl)-5,6,8,8a,9,10,11,11a-octahydro-4H-pyrido[3,2,1-ij]pyrrolo[3,4-c]quinolin-2-amine, bis-trifluoroacetic acid salt

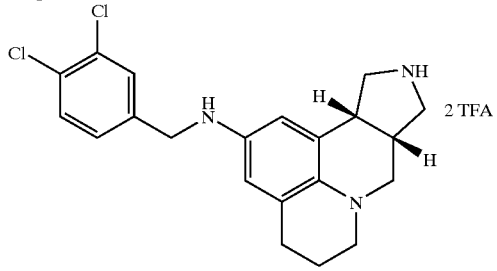

Using 3,4-dichlorobenzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 83 as a powder. $^1$H NMR (of free base) (CDCl$_3$) δ: 7.47 (d, 1H, J=1.8 Hz), 7.39 (d, 1H, J=8.4 Hz), 7.20 (dd, 1H), 6.23 (app s, 1H), 6.20 (app s, 1H), 4.21 (s, 2H), 3.41–3.28 (m, 2H), 3.17–3.10 (m, 1H), 3.00–2.92 (m, 2H), 2.90–2.81 (m, 2H), 2.80–2.64 (m, 3H), 2.63–2.56 (m, 2H), 2.02–1.95 (m, 2H). LRMS (ES)$^+$: 388.4 (M+H)$^+$.

Example 84

(8aR,11aR)-N-(2,3-dimethoxybenzyl)-5,6,8,8a,9,10,11,11a-octahydro-4H-pyrido[3,2,1-ij]pyrrolo[3,4-c]quinolin-2-amine, bis-trifluoroacetic acid salt

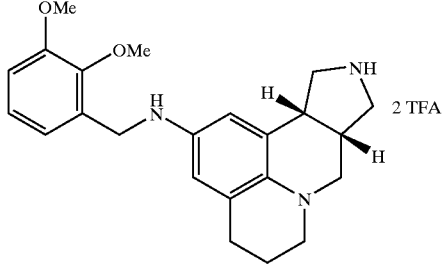

Using 2,3-dimethoxybenzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 84 as a powder. LRMS (ES)$^+$: 380.4 (M+H)$^+$.

Example 85

(8aR,11aR)-N-(3,4-dimethoxybenzyl)-5,6,8,8a,9,10,11,11a-octahydro-4H-pyrido[3,2,1-ij]pyrrolo[3,4-c]quinolin-2-amine, bis-trifluoroacetic acid salt

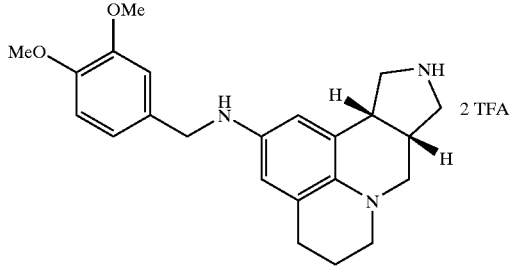

Using 3,4-dimethoxybenzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 85 as a powder. LRMS (ES)$^+$: 380.4 (M+H)$^+$.

Example 86

(8aR,11aR)-N-(2-methoxybenzyl)-5,6,8,8a,9,10,11,11a-octahydro-4H-pyrido[3,2,1-ij]pyrrolo[3,4-c]quinolin-2-amine, bis-trifluoroacetic acid salt

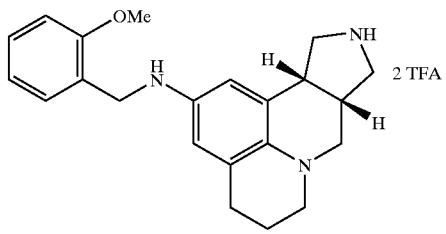

Using 2-methoxybenzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 86 as a powder. LRMS (ES)$^+$: 350.5 (M+H)$^+$.

Example 87

(8aR,11aR)-N-(2-methylbenzyl)-5,6,8,8a,9,10,11,11a-octahydro-4H-pyrido[3,2,1-ij]pyrrolo[3,4-c]quinolin-2-amine, bis-trifluoroacetic acid salt

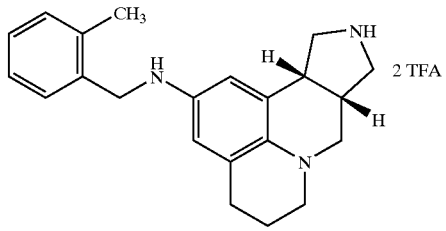

Using o-tolualdehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 87 as a powder. LRMS (ES)$^+$: 334.5 (M+H)$^+$.

Example 88

(8aR,11aR)-N-[4-fluoro-2-(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt

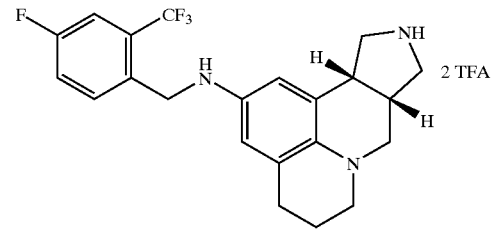

Using 4-fluoro-2-trifluoromethylbenzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 88 as a powder. LRMS (ES)$^+$: 406.5 (M+H)$^+$.

Example 89

(8aR,11aR)-N-(2,3-dimethylbenzyl)-5,6,8,8a,9,10,11,11a-octahydro-4H-pyrido[3,2,1-ij]pyrrolo[3,4-c]quinolin-2-amine, bis-trifluoroacetic acid salt

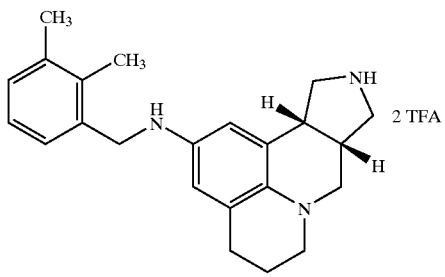

Using 2,3-dimethylbenzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 89 as a powder. LRMS (ES)$^+$: 348.5 (M+H)$^+$.

Example 90

(8aR,11aR)-N-[2,4-bis(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt

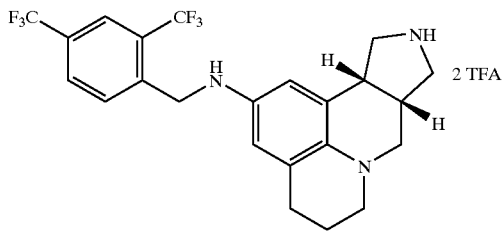

Using 2,4-bis(trifluoromethyl)benzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 90 as a powder. LRMS (ES)$^+$: 456.5 (M+H)$^+$.

Example 91

(8aR,11aR) -N-[2,5-bis(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt

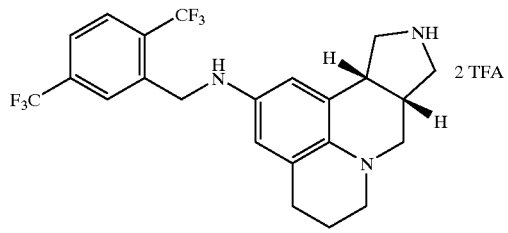

Using 2,5-bis(trifluoromethyl)benzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 91 as a powder. LRMS (ES)$^+$: 456.5 (M+H)$^+$.

Example 92

(8aR,11aR)-N-[3-(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt

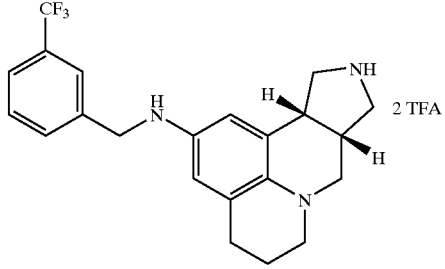

Using 3-(trifluoromethyl)benzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 92 as a powder. LRMS (ES)$^+$: 388.5 (M+H)$^+$.

Example 93

(8aR,11aR) -N-[4-(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt

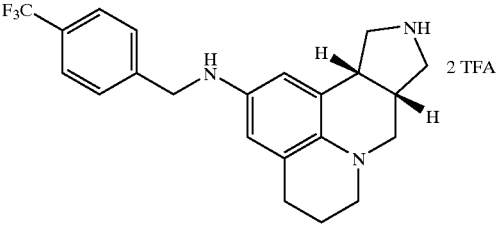

Using 4-(trifluoromethyl)benzaldehyde and following the procedures described in EXAMPLE 76, tert-butyl (8aS,11aR)-2-amino-5,6,8a,9,11,11a-hexahydro-4H-pyrido[3,2, 1-ij]pyrrolo[3,4-c]quinoline-10(8H)-carboxylate from EXAMPLE 37, Part A was converted into the title compound of EXAMPLE 93 as a powder. LRMS (ES)$^+$: 388.5 (M+H)$^+$.

Example 94

(8aR,11aR)-N-[2-(methylthio)benzyl]-5,6,8,8a,9,10,11,11a-octahydro-4H-pyrido[3,2,1-ij]pyrrolo[3,4-c]quinolin-2-amine, bis-trifluoroacetic acid salt

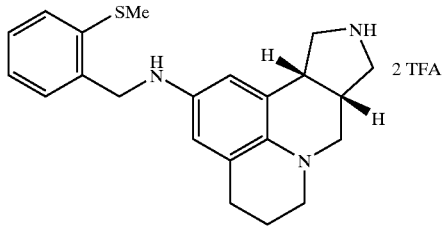

Using 2-(methylthio)benzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 94 as a powder. LRMS (ES)$^+$: 366.5 (M+H)$^+$.

Example 95

(8aR,11aR) -N-[2-(trifluoromethoxy)benzyl]-5,6,8,8a,9,10,11,11a-octahydro-4H-pyrido[3,2,1-ij]pyrrolo[3,4-c]quinolin-2-amine, bis-trifluoroacetic acid salt

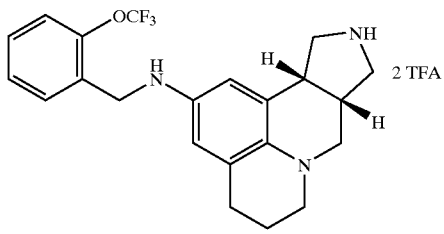

Using 2-(trifluoromethoxy)benzaldehyde and following the procedures described in EXAMPLE 76, tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A was converted into the title compound of EXAMPLE 95 as a powder. LRMS (ES)$^+$: 404.5 (M+H)$^+$.

Example 96

2-[(8aR,11aR)-5,6,8,8a,9,10,11,11a-octahydro-4H-pyrido[3,2,1-ij]pyrrolo[3,4-c]quinolin-2-yl]-1H-isoindole-1,3(2H)-dione, bis-hydrochloric acid salt

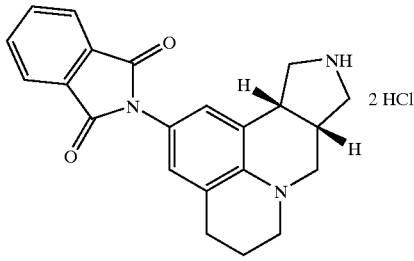

To a solution of tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A (150 mg, 0.46 mmol) in 10 mL of toluene was added phthalic anhydride (70 mg, 0.46 mmol). The mixture was stirred at 110° C. for 3 h and then was concentrated in vacuo. The residue was dissolved in ethyl acetate and filtered through a pad of silica gel and concentrated to afford an imide intermediate. LRMS (ES)$^+$: 460.4 (M+H)$^+$. A portion of this material (50 mg, 0.11 mmol) was stirred in 4 mL of 2M HCl in 1,4-dioxane at ambient temperature for 3 h. The solvent was evaporated in vacuo and the residue was triturated with ether and dried to afford the title compound of EXAMPLE 96 as a powder. $^1$H NMR (dmso-D$_6$) δ: 9.50 (broad s, 1H), 9.35 (broad s, 1H), 7.97–7.83 (m, 4H), 6.98 (s, H), 6.87 (s, 1H), 3.75–3.57 (m, 2H), 3.50–3.40 (m, 2H), 3.20–2.85 (m, 5H), 2.80–2.65 (m, 3H), 2.00–1.87 (m, 2H). LRMS (ES)$^+$: 360.4 (M+H)$^+$.

Example 97

(8aR,11aR)-2-(1,3-dihydro-2H-isoindol-2-yl)-5,6,8,8a,9,10,11,11a-octahydro-4H-pyrido[3,2,1-ij]pyrrolo[3,4-c]quinoline, bis-trifluoroacetic acid salt

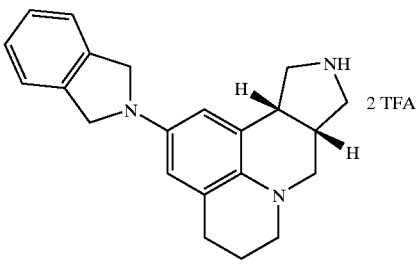

To a solution of the imide intermediate from EXAMPLE 96 (120 mg, 0.27 mmol) in 10 mL of tetrahydrofuran was added borane-THF complex (2.7 mL of 1M borane in THF, 2.7 mmol). The mixture was stirred at 70° C. for 3 h and then was cooled to 0° C. and quenched by the slow addition of methanol. The solution was concentrated and the residue was dissolved in ethyl acetate, washed with sat'd aq NaHCO$_3$ and brine, dried (MgSO$_4$), filtered through a pad of silica gel and concentrated. The residue was taken up in 10 mL of methylene chloride and then there was added 5 mL of trifluoroacetic acid. The reaction was allowed to stir at ambient temperature for 3 h and then was concentrated in vacuo. The residue was purified by preparative HPLC (C18

Example 98

2-[(8aR,11aR)-5,6,8,8a,9,10,11,11a-octahydro-4H-pyrido[3,2,1-ij]pyrrolo[3,4-c]quinolin-2-yl]-1,3(2H,4H)-isoquinolinedione, bis-hydrochloric acid salt

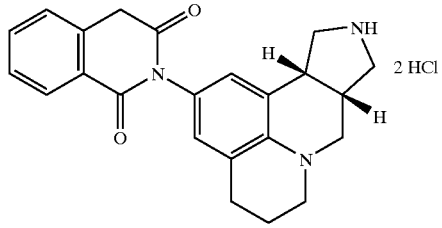

To a solution of tert-butyl (8aS,11aR)-2-amino-5,6,8a,9,11,11a-hexahydro-4H-pyrido[3,2,1-ij]pyrrolo [3,4-c]quinoline-10(8H)-carboxylate from EXAMPLE 37, Part A (150 mg, 0.46 mmol) in 10 mL of toluene was added homophthalic anhydride (75 mg, 0.46 mmol). The mixture was stirred at 110° C. for 24 h and then was concentrated in vacuo. The residue was dissolved in ethyl acetate and filtered through a pad of silica gel and concentrated to afford an imide intermediate. LRMS (ES)+: 474.5 (M+H)+. A portion of this material (50 mg, 0.11 mmol) was stirred in 4 mL of 2M HCl in 1,4-dioxane at ambient temperature for 3 h. The solvent was evaporated in vacuo and the residue was triturated with ether and dried to afford the title compound of EXAMPLE 98 as a powder. $^1$H NMR (dmso-D$_6$) δ: 9.54 (broad s, 1H), 9.43 (broad s, 1H), 8.00 (d, 1H, J=7.3 Hz), 7.67 (t, 1H, J=7.2 Hz), 7.50–7.35 (m, 2H), 6.76 (s, H), 6.66 (s, 1H), 3.70–3.50 (m, 2H), 3.50–3.30 (m, 2H), 3.20–3.00 (m, 3H), 2.950–2.82 (m, 2H), 2.77–2.60 (m, 3H), 1.98–1.85 (m, 2H). LRMS (ES)+: 374.4 (M+H)+.

Example 99

(8aR,11aR)-2-(3,4-dihydro-2(1H)-isoquinolinyl)-5,6,8,8a,9,10,11,11a-octahydro-4H-pyrido[3,2,1-ij]pyrrolo[3,4-c]quinoline, bis-trifluoroacetic acid salt

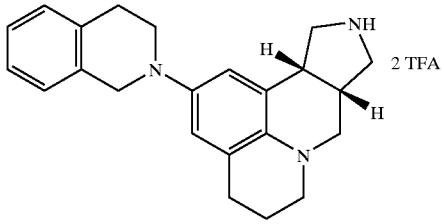

To absolution of the imide intermediate from EXAMPLE 98 (100 mg, 0.22 mmol) in 10 mL of tetrahydrofuran was added borane-THF complex (2.2 mL of 1M borane in THF, 2.2 mmol). The mixture was stirred at 70° C. for 3 h and then was cooled to 0° C. and quenched by the slow addition of methanol. The solution was concentrated and the residue was dissolved in ethyl acetate, washed with sat'd aq NaHCO$_3$ and brine, dried (MgSO$_4$), filtered through a pad of silica gel and concentrated. The residue was taken up in 10 mL of methylene chloride and then there was added 5 mL of trifluoroacetic acid. The reaction was allowed to stir at ambient temperature for 3 h and then was concentrated in vacuo. The residue was purified by preparative HPLC (C18 reverse phase column, elution with a H$_2$O/CH$_3$CN gradient with 0.5% TFA) to afford the title compound of EXAMPLE 99 as a powder. LRMS (ES)+: 346.4 (M+H)+.

Example 100

N-[(8aR,11aR)-5,6,8,8a,9,10,11,11a-octahydro-4H-pyrido[3,2,1-ij]pyrrolo[3,4-c]quinolin-2-yl] benzamide, bis-trifluoroacetic acid salt

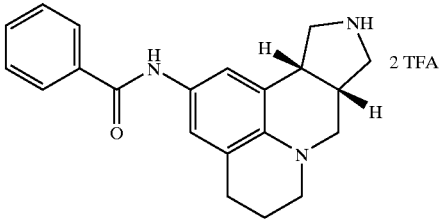

To absolution of tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A (111 mg, 0.34 mmol) in 10 mL of methylene chloride was added benzoyl chloride (52 mg, 0.37 mmol) and triethylamine (0.20 mL, 1.35 mmol). The mixture was stirred at ambient temperature for 24 h and then was concentrated in vacuo. The residue was dissolved in ethyl acetate, washed with 1N HCl, sat'd aq NaHCO$_3$ and brine, dried (MgSO$_4$), filtered through a pad of silica gel and concentrated to afford an amide intermediate. LRMS (ES)+: 434.4 (M+H)+. This intermediate was taken up in 10 mL of methylene chloride and then there was added 5 mL of trifluoroacetic acid. The reaction was allowed to stir at ambient temperature for 3 h and then was concentrated in vacuo. The residue was purified by preparative HPLC (C18 reverse phase column, elution with a H$_2$O/CH$_3$CN gradient with 0.5% TFA) to afford the title compound of EXAMPLE 100 as a powder. $^1$H NMR (dmso-D$_6$) δ: 9.88 (s, 1H), 8.89 (broad s, 2H), 7.86 (d, 2H, J=7.0 Hz), 7.55–7.40 (m, 3H), 7.28 (s, H), 7.16 (s, 1H), 3.50–3.32 (m, 4H), 3.07–2.90 (m, 5H), 2.77–2.62 (m, 3H), 1.94–1.80 (m, 2H). LRMS (ES)+: 334.4 (M+H)+.

Example 101

N-[(8aR,11aR)-5,6,8,8a,9,10,11,11a-octahydro-4H-pyrido[3,2,1-ij]pyrrolo[3,4-c]quinolin-2-yl] benzenesulfonamide, bis-trifluoroacetic acid salt

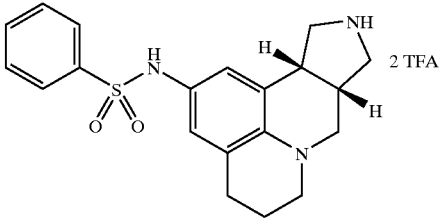

To a solution of tert-butyl (8aS,11aR)-2-amino-5,6,8a,9,11,11a-hexahydro-4H-pyrido[3,2,1-ij]pyrrolo[3,4-c]quinoline-10(8H)-carboxylate from EXAMPLE 37, Part A (111 mg, 0.34 mmol) in 10 mL of methylene chloride was added benzenesulfonyl chloride (65 mg, 0.37 mmol) and triethylamine (0.20 mL, 1.35 mmol). The mixture was stirred at ambient temperature for 24 h and then was concentrated in vacuo. The residue was dissolved in ethyl acetate, washed with 1N HCl, sat'd aq NaHCO₃ and brine, dried (MgSO₄), filtered through a pad of silica gel and concentrated to afford a sulfonamide intermediate. LRMS (ES)⁺: 470.4 (M+H)⁺. This intermediate was taken up in 10 mL of methylene chloride and then there was added 5 mL of trifluoroacetic acid. The reaction was allowed to stir at ambient temperature for 3 h and then was concentrated in vacuo. The residue was purified by preparative HPLC (C18 reverse phase column, elution with a H₂O/CH₃CN gradient with 0.5% TFA) to afford the title compound of EXAMPLE 101 as a powder. ¹H NMR (dmso-D₆) δ: 9.68 (s, 1H), 8.93 (broad s, 2H), 7.70 (d, 2H, J=6.6 Hz), 7.63–7.50 (m, 3H), 6.56 (d, H, J=1.8 Hz), 6.50 (app d, 1H), 3.50–3.38 (m, 2H), 3.35–3.22 (m, 2H), 3.07–2.93 (m, 4H), 2.82–2.58 (m, 4H), 1.88–1.78 (m, 2H). LRMS (ES)⁺: 370.4 (M+H)⁺.

Example 102

(±)-cis-10-ethyl-5,6,8,8a,9,10,11,11a-octahydro-4H-pyrido[3,2,1-ij]pyrrolo[3,4-c]quinoline, bis-hydrochloride salt

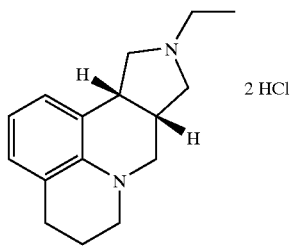

2 HCl

To a solution of (±)-cis-5,6,8,8a,9,10,11,11a-octahydro-4H-pyrido[3,2,1-ij]pyrrolo[3,4-c]quinoline free base from EXAMPLE 11 (135 mg, 0.63 mmol) in 5 mL of methylene chloride was added triethylamine (127 mg, 1.26 mmol) and acetyl chloride (52 mg, 0.66 mmol). The mixture was stirred at ambient temperature for 24 h. The reaction was then diluted with ethyl acetate, washed with brine, dried (MgSO₄) and concentrated to afford an amide intermediate. This amide was dissolved in tetrahydrofuran and then there was added borane-THF complex (3.8 mL of 1M borane in THF, 3.8 mmol). The solution was stirred at ambient temperature for 4 h and then was quenched by dropwise addition of methanol. The solution was concentrated and then dissolved in 1:1 methanol/1N HCl and stirred at reflux for 1 h. The reaction mixture was cooled and concentrated. The residue was purified by preparative HPLC (C18 reverse phase column, elution with a H₂O/CH₃CN gradient with 0.5% TFA) and the product containing fractions were concentrated, basified with sat'd aq Na₂CO₃ and extracted twice with ethyl acetate. The organics were washed with brine, dried (Na₂SO₄) and concentrated to a free base. The residue was taken up in about 4:1 ether/ethanol and then there was added 2M HCl in ether (1.0 mL, 2.0 mmol). The resulting solid was filtered, washed twice with ether and dried in vacuo to afford the title compound of EXAMPLE 102 as an off-white powder. ¹H NMR (dmso-D₆) δ: 11.33 (broad s, 1H), 6.92–6.80 (m, 2H), 6.68–6.58 (m, 1H), 3.99–3.90 (m, 1H), 3.83–3.72 (m, 1H), 3.67–3.58 (m, 1H), 3.50–3.32 (m, 2H), 3.20–2.95 (m, 4H), 2.92–2.75 (m, 3H), 2.73–2.65 (m, 2H), 1.97–1.83 (m, 2H), 1.21 (t, 3H, J=6.7 Hz). LRMS (ES)⁺: 243.1 (M+H)⁺.

Example 103

(±)-cis-10-propyl-5,6,8,8a,9,10,11,11a-octahydro-4H-pyrido[3,2,1-ij]pyrrolo[3,4-c]quinoline, bis-hydrochloride salt

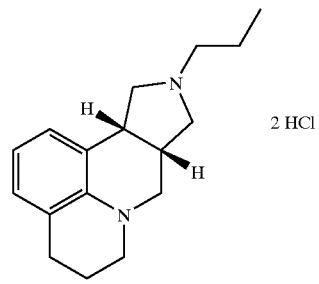

2 HCl

Using propionyl chloride and following the procedures described in EXAMPLE 102, (±)-cis-5,6,8,8a,9,10,11,11a-octahydro-4H-pyrido[3,2,1-ij]pyrrolo[3,4-c]quinoline free base from EXAMPLE 11 was converted into the title compound of EXAMPLE 103 as an off-white powder. ¹H NMR (dmso-D₆) δ: 11.10 (broad s, 1H), 6.90–6.77 (m, 2H), 6.63–6.55 (m, 1H), 3.99–3.90 (m, 1H), 3.85–3.75 (m, 1H), 3.67–3.58 (m, 1H), 3.50–3.35 (m, 2H), 3.15–2.93 (m, 4H), 2.90–2.75 (m, 3H), 2.70–2.63 (m, 2H), 1.95–1.85 (m, 2H), 1.70–1.59 (m, 2H), 0.91–0.82 (m, 3H). LRMS (ES)⁺: 257.1 (M+H)⁺.

Example 104

(±)-cis-10-butyl-5,6,8,8a,9,10,11,11a-octahydro-4H-pyrido[3,2,1-ij]pyrrolo[3,4-c]quinoline, bis-hydrochloride salt

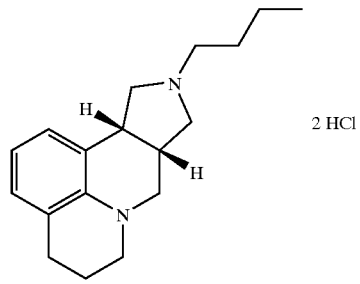

2 HCl

To a solution of (±)-cis-5,6,8,8a,9,10,11,11a-octahydro-4H-pyrido[3,2,1-ij]pyrrolo[3,4-c]quinoline free base from EXAMPLE 11 (124 mg, 0.58 mmol) in 5 mL of 1,4-dioxane was added n-butylbromide (79 mg, 0.58 mmol), potassium carbonate (160 mg, 1.16 mmol) and potassium iodide (10 mg, 0.06 mmol) The mixture was stirred at 90° C. for 24 h. The reaction was then cooled, diluted with ethyl acetate, washed with brine, dried (Na₂SO₄) and concentrated. The residue was purified by preparative HPLC (C18 reverse phase column, elution with a H₂O/CH₃CN gradient with 0.5% TFA) and the product containing fractions were concentrated, basified with sat'd aq Na₂CO₃ and extracted twice with ethyl acetate. The organics were washed with brine, dried (Na₂SO₄) and concentrated to a free base. The residue was taken up in about 4:1 ether/ethanol and then there was added 2M HCl in ether (1.0 mL, 2.0 mmol). The resulting solid was filtered, washed twice with ether and dried in vacuo to afford the title compound of EXAMPLE 104 as an off-white powder. ¹H NMR (dmso-D₆) δ:

6.90–6.78 (m, 2H), 6.62–6.55 (m, 1H), 4.00–3.93 (m, 1H), 3.85–3.77 (m, 1H), 3.65–3.59 (m, 1H), 3.50–3.35 (m, 2H), 3.15–2.95 (m, 4H), 2.92–2.75 (m, 3H), 2.73–2.63 (m, 2H), 1.95–1.85 (m, 2H), 1.65–1.55 (m, 2H), 1.33–1.22 (m, 2H), 0.91–0.83 (m, 3H). LRMS. (ES)+: 271.2 (M+H)+.

Example 105

(±)-cis-10-(cyclobutylmethyl)-5,6,8,8a,9,10,11,11a-octahydro-4H-pyrido[3,2,1-ij]pyrrolo[3,4-c]quinoline, bis-hydrochloride salt

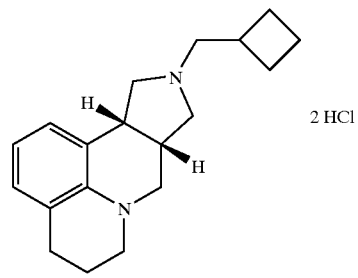

Using bromomethylcyclobutane and following the procedures described in EXAMPLE 104, (±)-cis-5,6,8,8a,9,10,11,11a-octahydro-4H-pyrido[3,2,1-ij]pyrrolo[3,4-c]quinoline free base from EXAMPLE 11 was converted into the title compound of EXAMPLE 105 as an off-white powder. $^1$H NMR (dmso-$D_6$) δ: 11.10 (broad s, 1H), 6.90–6.78 (m, 2H), 6.65–6.55 (m, 1H), 3.90–3.80 (m, 1H), 3.79–3.70 (m, 1H), 3.60–3.30 (m, 3H), 3.20–2.95 (m, 4H), 2.90–2.65 (m, 5H), 2.08–1.98 (m, 2H), 1.95–1.70 (m, 7H). LRMS (ES)+: 283.2 (M+H)+.

Example 106

(±)-cis-10-(3-methyl-2-butenyl)-5,6,8,8a,9,10,11,11a-octahydro-4H-pyrido[3,2,1-ij]pyrrolo[3,4-c]quinoline, bis-hydrochloride salt

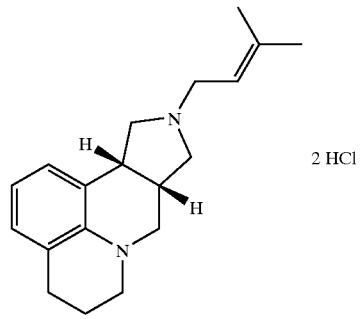

Using 4-bromo-2-methyl-2-butene and following the procedures described in EXAMPLE 104, (±)-cis-5,6,8,8a,9,10,11,11a-octahydro-4H-pyrido[3,2,1-ij]pyrrolo[3,4-c]quinoline free base from EXAMPLE 11 was converted into the title compound of EXAMPLE 106 as an off-white powder. $^1$H NMR (dmso-$D_6$) δ: 11.05 (broad s, 1H), 6.86 (t, 1H, J=6.2 Hz), 6.81 (t, 1H, J=7.0 Hz), 6.59 (q, 1H, J=7.3 Hz), 5.33–5.27 (m, 1H), 3.90–3.60 (m, 4H), 3.50–3.25 (m, 2H), 3.10–2.95 (m, 3H), 2.90–2.75 (m, 3H), 2.72–2.65 (m, 2H), 1.95–1.85 (m, 2H), 1.72 (s, 3H), 1.64 (s, 3H). LRMS (ES)+: 283.2 (M+H)+.

Example 107

(±)-cis-9-benzyl-4,5,8,9,10,10a-hexahydrodipyrrolo[3,4-c:3',2',1'-ij]quinolin-7(7aH)-one, hydrochloride salt

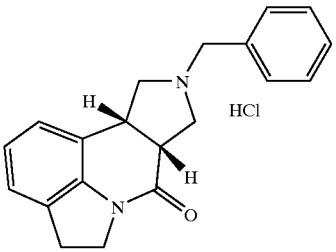

Part A. tert-butyl 1-indolinecarboxylate.

To a solution of di-tert-butyl dicarbonate (47.2 g, 21.6 mmol) in 150 mL of tetrahydrofuran at ambient temperature was added indoline (24.5 g, 20.6 mmol) dropwise via an addition funnel at a rate to maintain a steady gas evolution. The addition was complete in about 45 min and then the reaction was allowed to stir an additional 3 h. The mixture was filtered through a pad of silica gel and concentrated in vacuo. Any excess di-tert-butyl dicarbonate was removed by heating at 70° C. under high vacuum. There was obtained 44 g (97%) of the title compound of Part A which was used without purification. $^1$H NMR (CDCl$_3$) δ: 7.85 and 7.50 (very broad singlets, 1H), 7.20–7.13 (m, 2H), 6.94 (t, 1H), 3.99 (t, 2H, J=8.6 Hz), 3.11 (t, 2H, J=8.6 Hz), 1.59 (s, 9H).

Part B. tert-butyl 7-formyl-1-indolinecarboxylate.

To a solution of tert-butyl 1-indolinecarboxylate (10.0 g, 45.6 mmol) in 200 mL of diethyl ether at −78° C. was added N,N,N',N'-tetramethylethylenediamine (8.3 mL, 54.7 mmol) and then sec-butyllithium (42.0 mL of a 1.3 M solution in cyclohexane, 54.7 mmol) was added dropwise via addition funnel. The mixture was stirred at −78° C. for 1 h and then N,N-dimethylformamide (5.3 mL, 68.4 mmol) was added dropwise in 10 mL of diethyl ether and the resulting mixture was stirred at −78° C. for 1 h. The reaction was quenched by the addition of 25 mL of saturated aqueous ammonium chloride and then was diluted with water and ethyl acetate. The organics were washed with 10% aqueous HCl, sat'd aq. sodium bicarbonate and brine, dried (MgSO$_4$) and concentrated in vacuo. The residue was purified by flash chromatography (elution with 6:1 hexane/ethyl acetate) to afford 6.0 g (53%) of the title compound as an oil which solidified on standing. $^1$H NMR (CDCl$_3$) δ: 10.12 (d, 1H, J=0.7 Hz), 7.65 (d, 1H), 7.37 (dd, 1H), 7.13 (t, 1H), 4.19 (t, 2H, J=8.0 Hz), 3.09 (t, 2H, J=8.2 Hz), 1.53 (s, 9H).

Part C. ethyl 4-oxo-1,2-dihydro-4H-pyrrolo[3,2,1-ij]quinoline-5-carboxylate.

To a solution of tert-butyl 7-formyl-1-indolinecarboxylate (6.0 g, 24.3 mmol) in 150 mL of benzene in a flask fitted with a Dean-Stark trap and a condenser was added diethyl malonate (3.89 g, 24.3 mmol), piperidine (0.27 mL, 2.67 mmol) and benzoic acid (0.30 g, 2.43 mmol). The resulting solution was stirred at 80° C. for 24 h with collection of water in the Dean-Stark trap. The reaction mixture was then, cooled, washed with 1N HCl, sat'd aq NaHCO$_3$ and brine, dried (MgSO$_4$), filtered through a pad of silica gel and concentrated to afford 9.4 g of a diester intermediate. This material was dissolved in 40 ML of methylene chloride and then there was added 10 mL of trifluoroacetic acid. This mixture was allowed to stir at ambient temperature for 4 h. The volatiles were then removed in vacuo and the residue was dissolved in ethyl acetate, washed with water, sat'd aq NaHCO$_3$ and brine, dried (MgSO$_4$), filtered through a pad of silica gel and concentrated to a solid. This material was triturated with hot hexane, filtered and dried to afford 2.8 g (47%) of the title compound of Part C as a tan powder. $^1$H NMR (CDCl$_3$) δ: 8.47 (s, 1H), 7.48 (dd, 1H, J=8.0, 0.8 Hz), 7.43 (dd, 1H, J=7.1, 0.9 Hz), 7.19 (t, 1H, J=7.5 Hz), 4.53–4.38 (m, 4H), 3.45 (t, 2H, J=8.0 Hz), 1.43 (t, 3H, J=7.1 Hz).

Part D. (±)-cis ethyl 9-benzyl-7-oxo-4,5,8,9,10,10a-hexahydrodipyrrolo[3,4-c:3',2',1'-ij]quinoline-7a(7H)-carboxylate.

To a solution of ethyl 4-oxo-1,2-dihydro-4H-pyrrolo[3,2,1-ij]quinoline-5-carboxylate (2.53 g, 10.4 mmol) in 30 mL of methylene chloride was added N-(methoxymethyl)-N-(trimethylsilylmethyl)benzylamine (4.9 g, 20.8 mmol) and trifluoroacetic acid (0.16 mL, 2.1 mmol). The reaction mixture was stirred at 40° C. for 4 h. The reaction mixture was allowed to cool and was concentrated. The residue was dissolved in ethyl acetate and was washed with sat'd aq. NaHCO$_3$ and brine, dried (MgSO$_4$), filtered through a pad of silica gel and concentrated in vacuo to afford the title compound of Part D, which was used without purification. LRMS (ES)$^+$: 377.3 (M+H)$^+$.

Part E. (±)-cis-9-benzyl-4,5,8,9,10,10a-hexahydrodipyrrolo[3,4-c:3',2',1'-ij]quinolin-7(7aH)-one, hydrochloride salt.

To a solution of (±)-cis ethyl 9-benzyl-7-oxo-4,5,8,9,10,10a-hexahydrodipyrrolo[3,4-c:3',2',1'-ij]quinoline-7a(7H)-carboxylate (3.9 g, 10.4 mmol) in 50 mL of 1,4-dioxane was added 50 mL of 3N HCl and the resulting mixture was stirred at 100° C. for 24 h. The dioxane and most of the water was removed in vacuo, and the residue was basified with sat'd aq Na$_2$CO$_3$ and extracted with ethyl acetate. The layers were separated and the organics were washed with brine, dried (MgSO$_4$), filtered through a pad of silica gel and concentrated to afford 3.1 g (96%) of (±)-cis-9-benzyl-4,5,8,9,10,10a-hexahydrodipyrrolo[3,4-c:3',2',1'-ij]quinolin-7(7aH)-one free base, which was sufficiently pure to be used without purification. LRMS (ES)$^+$: 305.1 (M+H)$^+$. A portion of this material (50 mg, 0.16 mmol) was dissolved in 5 mL of ether and 1 mL of absolute ethanol. Then there was added 2M HCl in ether (0.165 mL, 0.33 mmol). The resulting solid was filtered, washed twice with ether and dried in vacuo to afford the title compound of EXAMPLE 107 as a pale yellow powder. $^1$H NMR (dmso-D6) δ: 7.60–7.50 (m, 2H), 7.48–7.38 (m, 3H), 7.19–7.15 (m, 1H), 7.12–7.07 (m, 1H), 6.98–6.90 (m, 1H), 4.45–4.37 (m, 1H), 4.30–4.18 (m, 1H), 4.02–3.90 (m, 2H), 3.87–3.77 m, 2H), 3.68–3.40 (m, 3H), 3.21–3.05 (m, 3H). LRMS (ES)$^+$: 305.1 (M+H)$^+$.

Example 108

(±)-cis-4,5,8,9,10,10a-hexahydrodipyrrolo[3,4-c:3', 2',1'-ij]quinolin-7(7aH)-one, hydrochloride salt

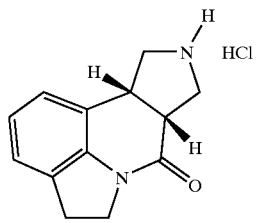

Part A. (±)-cis tert-butyl 7-oxo-4,5,7a,8,10,10a-hexahydrodipyrrolo[3,4-c:3',2',1'-ij]quinoline-9(7H)-carboxylate.

To a solution of (±)-cis-9-benzyl-4,5,8,9,10,10a-hexahydrodipyrrolo[3,4-c:3',2',1'-ij]quinolin-7(7aH)-one free base from EXAMPLE 107 (3.2 g, 10.5 mmol) in 50 mL of absolute ethanol was added di-tert-butyl dicarbonate (2.41 g, 11.0 mmol) and Pearlman's catalyst (20% Pd(OH)$_2$/C) (0.6 g). This mixture was stirred under 1 atm of hydrogen maintained by a balloon for 2 h at ambient temperature. The mixture was filtered through a pad of layered Celite/silica gel and concentrated in vacuo to afford 3.15 g (95%) of the title compound of Part A, which was used without purification.

Part B. (±)-cis-4,5,8,9,10,10a-hexahydrodipyrrolo[3,4-c:3', 2',1'-ij]quinolin-7(7aH)-one, hydrochloride salt.

To a solution of (±)-cis tert-butyl 7-oxo-4,5,7a,8,10,10a-hexahydrodipyrrolo[3,4-c:3',2',1'-ij]quinoline-9(7H)-carboxylate (100 mg, 0.32 mmol) in 5 mL of methylene chloride was added trifluoroacetic acid (1 mL). This mixture was stirred at ambient temperature for 2 h and then concentrated in vacuo. The residue was basified with sat'd aq Na$_2$CO$_3$ and extracted with chloroform. The organics were washed with brine, dried (K$_2$CO$_3$) and concentrated in vacuo to afford the free base. This residue was dissolved in 1 mL absolute ethanol and 5 mL ether and then 2M HCl in ether (0.32 mL, 0.64 mmol) was added and a solid fell out of solution. The solvents were decanted and the solid was triturated twice with ether and dried in vacuo to afford 40 mg (50%) of the title compound of EXAMPLE 108 as an off white powder. $^1$H NMR (dmso-D6) δ: 9.42 (broad s, 1H), 9.20 (broad s, 1H), 7.16 (app t, 2H, J=8.0 Hz), 6.97 (app t, 1H, J=7.5 Hz), 4.05–3.95 (m, 3H), 3.79–3.70 (m, 1H), 3.68–3.53 (m, 2H), 3.51–3.42 (m, 1H), 3.20–3.10 (m, 2H), 2.90–2.80 (m, 1H). LRMS (ES)$^+$: 214.9 (M+H)$^+$.

Example 109

(±)-cis-4,5,7,7a,8,9,10,10a-octahydrodipyrrolo[3,4-c:3',2',1'-ij]quinoline, bis-hydrochloride salt

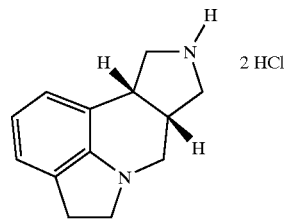

Part A. (±)-cis tert-butyl 4,5,7a,8,10,10a-hexahydrodipyrrolo[3,4-c:3',2',1'-ij]quinoline-9(7H)-carboxylate.

To a solution of (±)-cis tert-butyl 7-oxo-4,5,7a,8,10,10a-hexahydrodipyrrolo[3,4-c:3',2',1'-ij]quinoline-9(7H)-carboxylate from EXAMPLE 108, Part A (3.1 g, 9.86 mmol) in 100 mL of tetrahydrofuran at 0° C. was added borane-THF complex (59 mL of a 1M solution in THF, 59 mmol) via an addition funnel. After the addition was complete the reaction mixture was allowed to warm to ambient temperature and was stirred for 24 h. The reaction was quenched by dropwise addition of methanol (40 mL) and then the volatiles were removed in vacuo. The residue was dissolved in ethyl acetate, washed with sat'd aq. NaHCO$_3$ and brine, dried (MgSO$_4$) filtered through a pad of silica gel and concentrated to afford 2.39 g (97%) of the title compound of Part A, which was used without purification. LRMS (ES)$^+$: 301.1 (M+H)$^+$.

Part B. (±)-cis-4,5,7,7a,8,9,10,10a-octahydrodipyrrolo[3,4-c:3',2',1'-ij]quinoline, bis-hydrochloride salt.

To a solution of (±)-cis tert-butyl 4,5,7a,8,10,10a-hexahydrodipyrrolo[3,4-c:3',2',1'-ij]quinoline-9(7H)- carboxylate (400 mg, 1.33 mmol) in 10 mL of methylene chloride was added trifluoroacetic acid (3 mL). This mixture was stirred at ambient temperature for 2 h and then concentrated in vacuo. The residue was basified with sat'd aq Na$_2$CO$_3$ and extracted with chloroform. The organics were washed with brine, dried (K$_2$CO$_3$) and concentrated in vacuo to afford the free base. A portion of this residue (100 mg, 0.50 mmol) was dissolved in 1 mL absolute ethanol and 5 mL ether and then 2M HCl in ether (0.75 mL, 1.5 mmol) was added and a solid fell out of solution. The solvents were decanted and the solid was triturated twice with ether and dried in vacuo to afford 50 mg (37%) of the title compound of EXAMPLE 109 as an off white powder. $^1$H NMR (dmso-D6) δ: 9.70 (broad s, 1H), 9.40 (broad s, 1H), 6.99 (app t, 2H), 6.73 (app t, 1H, J=7.3 Hz), 3.70–3.60 (m, 1H), 3.50–3.39 (m, 2H), 3.37–3.28 (m, 1H), 3.21 (q, 1H, J=8.2 Hz), 3.10–2.99 (m, 2H), 2.95–2.79 (m, 5H). LRMS (ES)$^+$: 200.8 (M+H)$^+$.

Example 110

(±)-cis-9-methyl-4,5,7,7a,8,9,10,10a-octahydrodipyrrolo[3,4-c:3',2',1'-ij]quinoline, bis-hydrochloride salt

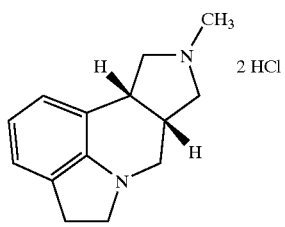

To a solution of (±)-cis-4,5,7,7a,8,9,10,10a-octahydrodipyrrolo[3,4-c:3',2',1'-ij]quinoline free base from EXAMPLE 109 (140 mg, 0.70 mmol) in 10 mL of 1,2-dichloroethane was added 37% aqueous formaldehyde (0.125 mL, 1.4 mmol) and sodium triacetoxyborohydride (0.45 g, 2.1 mmol). The resulting mixture was stirred at ambient temperature for 1 h and then the reaction was quenched with water. The mixture was partitioned between chloroform and saturated aqueous sodium carbonate. The organics were washed with brine, dried (K$_2$CO$_3$) and concentrated in vacuo. The residue was dissolved in 1 mL ethanol and 5 mL of ether and then there was added 2M HCl in ether (1.05 mL, 2.1 mmol). A solid precipitated out of solution. The solvents were decanted and the solid was triturated twice with ether and dried in vacuo to afford 100 mg (50%) of the title compound of EXAMPLE 110 as an off white powder LRMS (ES)$^+$: 214.9 (M+H)$^+$.

Example 111

(±)-cis-2-[4-methoxy-2-(trifluoromethyl)phenyl]-4,5,7,7a,8,9,10,10a-octahydrodipyrrolo[3,4-c:3',2',1'-ij]quinoline

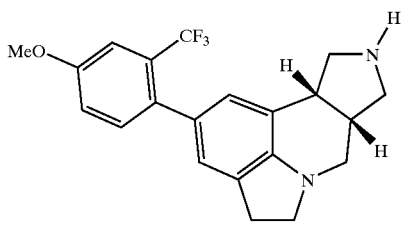

Part A. (±)-cis tert-butyl 2-bromo-4,5,7a,8,10,10a-hexahydrodipyrrolo[3,4-c:3',2',1'-ij]quinoline-9(7H)-carboxylate.

Following the procedures described in EXAMPLE 27, Part A, (±)-cis tert-butyl 4,5,7a,8,10,10a-hexahydrodipyrrolo[3,4-c:3',2',1'-ij]quinoline-9(7H)-carboxylate was converted into the title compound of Part A, which was used without purification.

Part B. (±) -cis-2-[4-methoxy-2-(trifluoromethyl)phenyl]-4, 5,7,7a,8,9,10,10a-octahydrodipyrrolo[3,4-c:3',2',1'-ij] quinoline.

Using [4-methoxy-2-(trifluoromethyl)]benzeneboronic acid and following the procedures described in EXAMPLE 20, (±)-cis tert-butyl 2-bromo-4,5,7a,8,10,10a-hexahydrodipyrrolo[3,4-c:3',2',1'-ij]quinoline-9(7H)-carboxylate was converted into (±)-cis-2-[4-methoxy-2-(trifluoromethyl)phenyl]-4,5,7,7a,8,9,10,10a-octahydrodipyrrolo[3,4-c:3',2',1'-ij]quinoline, trifluoroacetic acid salt, after HPLC purification (C18 reverse phase column, elution with a H$_2$O/CH$_3$CN gradient with 0.5% TFA). This material was free-based with aq ammonium hydroxide, extracted with chloroform, washed with brine, dried (K$_2$CO$_3$) and concentrated to the title compound of EXAMPLE 111 as the free base. $^1$H NMR (CDCl$_3$) δ: 7.24–7.20 (m, 2H), 7.05 (dd, 1H, J=8.4, 2.5 Hz), 6.93 (s, 1H), 6.80 (s, 1H), 3.88 (s, 3H), 3.60 (dd, 1H, J=11.1, 7.9 Hz), 3.50–3.25 (m, 4H), 3.15–2.95 (m, 5H), 2.94–2.85 (m, 1H), 2.80 (dd, 1H, J=10.1, 7.9 Hz). LRMS (ES)$^+$: 375.3 (M+H)$^+$.

Example 112

(±)-cis-2-(2,4-dichlorophenyl)-4,5,7,7a,8,9,10,10a-octahydrodipyrrolo[3,4-c:3',2',1'-ij]quinoline

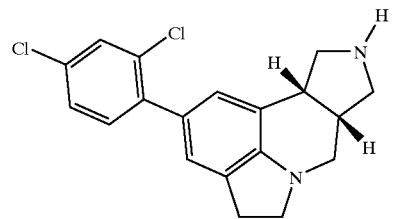

Using 2,4-dichlorobenzeneboronic acid and following the procedures described in EXAMPLE 20, (±)-cis tert-butyl 2-bromo-4,5,7a,8,10,10a-hexahydrodipyrrolo[3,4-c:3',2',1'-ij]quinoline-9(7H)-carboxylate was converted into (±)-cis-2-(2,4-dichlorophenyl)-4,5,7,7a,8,9,10,10a-octahydrodipyrrolo[3,4-c:3',2',1'-ij]quinoline, trifluoroacetic acid salt, after HPLC purification (C18 reverse phase column, elution with a H$_2$O/CH$_3$CN gradient with 0.5% TFA). This material was free-based with aq ammonium hydroxide, extracted with chloroform, washed with brine, dried (K$_2$CO$_3$) and concentrated to the title compound of EXAMPLE 112 as the free base. $^1$H NMR (CDCl$_3$) δ: 7.46 (d, 1H, J=2.2 Hz), 7.29–7.20 (m, 2H), 7.05 (d, 1H, J=1.1 Hz), 6.93 (d, 1H, J=0.8 Hz), 3.58 (dd, 1H, J=10.9, 7.7 Hz ), 3.50–3.30 (m, 4H), 3.15–2.95 (m, 5H), 2.90–2.77 (m, 2H). LRMS (ES)$^+$: 345.2 (M+H)$^+$.

Example 113

(±)-cis-N-(2,4-dichlorophenyl)-4,5,7,7a,8,9,10,10a-octahydrodipyrrolo[3,4-c:3',2',1'-ij]quinolin-2-amine

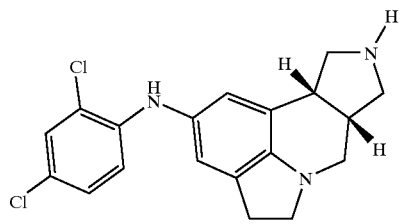

Part A. (±)-cis tert-butyl 2-amino-4,5,7a,8,10,10a-hexahydrodipyrrolo[3,4-c:3',2',1'-ij]quinoline-9(7H)-carboxylate.

Following the procedures described in EXAMPLE 17, Part A, (±)-cis tert-butyl 2-bromo-4,5,7a,8,10,10a-hexahydrodipyrrolo[3,4-c:3',2',1'-ij]quinoline-9(7H)-carboxylate was converted into the title compound of Part A as a tan solid, which was used without purification.

Part B. (±)-cis-N-(2,4-dichlorophenyl)-4,5,7,7a,8,9,10,10a-octahydrodipyrrolo[3,4-c:3',2',1'-ij]quinolin-2-amine.

Using 1-bromo-2,4-dichlorobenzene and following the procedures described in EXAMPLE 17, Parts B and C, (±)-cis tert-butyl 2-amino-4,5,7a,8,10,10a-hexahydrodipyrrolo[3,4-c:3',2',1'-ij]quinoline-9(7H)-carboxylate was converted into (±)-cis-N-(2,4-dichlorophenyl)-4,5,7,7a,8,9,10,10a-octahydrodipyrrolo[3,4-c:3',2',1'-ij]quinolin-2-amine, bis-trifluoroacetic acid salt, after HPLC purification (C18 reverse phase column, elution with a H$_2$O/CH$_3$CN gradient with 0.5% TFA). This material was free-based with aq ammonium hydroxide, extracted with chloroform, washed with brine, dried (K$_2$CO$_3$) and concentrated to the title compound of EXAMPLE 113 as the free base. $^1$H NMR (CDCl$_3$) δ: 7.30 (d, 1H, J=2.2 Hz), 7.03 (dd, 1H, J=8.8, 2.2 Hz), 6.87 (s, 1H), 6.81 (d, 1H, J=8.8 Hz), 6.71 (s, 1H), 5.85 (s, 1H), 3.75–3.65 (m, 2H), 3.57 (dd, 1H, J=11.5, 7.5 Hz), 3.49 (q, 1H, J=7.5 Hz), 3.35–3.20 (m, 3H), 3.12 (dd, 1H, J=11.6, 7.5 Hz), 3.07–2.93 (m, 3H), 2.84 (dd, 1H, J=10.3, 7.8 Hz). LRMS (ES)$^+$: 360.3 (M+H)$^+$.

Example 114

(±)-cis-N-[2-chloro-5-(trifluoromethyl)phenyl]-4,5,7,7a,8,9,10,10a-octahydrodipyrrolo[3,4-c:3',2',1'-ij]quinolin-2-amine

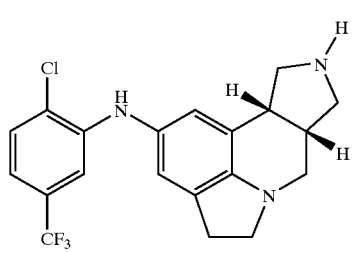

Using 3-bromo-4-chlorobenzotrifluoride and following the procedures described in EXAMPLE 17, Parts B and C, (±)-cis tert-butyl 2-amino-4,5,7a,8,10,10a-hexahydrodipyrrolo[3,4-c:3',2',1'-ij]quinoline-9(7H)-carboxylate was converted into (±) -cis-N-[2-chloro-5-(trifluoromethyl)phenyl]-4,5,7,7a,8,9,10,10a-octahydrodipyrrolo[3,4-c:3',2',1'-ij]quinolin-2-amine, bis-trifluoroacetic acid salt, after HPLC purification (c18 reverse phase column, elution with a H$_2$O/CH$_3$CN gradient with 0.5% TFA). This material was free-based with aq ammonium hydroxide, extracted with chloroform, washed with brine, dried (K$_2$CO$_3$) and concentrated to the title compound of EXAMPLE 114 as the free base. LRMS (ES)$^+$: 394.4 (M+H)$^+$.

Example 115

(±)-cis-N-[2-fluoro-5-(trifluoromethyl)phenyl]-4,5,7,7a,8,9,10,10a-octahydrodipyrrolo[3,4-c:3',2',1'-ij]quinolin-2-amine

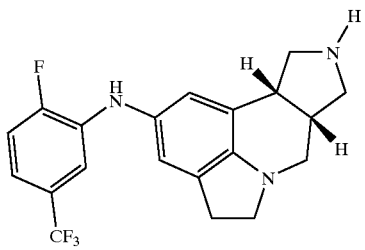

Using 3-bromo-4-fluorobenzotrifluoride and following the procedures described in EXAMPLE 17, Parts B and C, (±)-cis tert-butyl 2-amino-4,5,7a,8,10,10a-hexahydrodipyrrolo[3,4-c:3',2',1'-ij]quinoline-9(7H)-carboxylate was converted into (±) -cis-N-[2-fluoro-5-(trifluoromethyl)phenyl]-4,5,7,7a,8,9,10,10a-octahydrodipyrrolo[3,4-c:3',2',1'-ij]quinolin-2-amine, bis-trifluoroacetic acid salt, after HPLC purification (C18 reverse phase column, elution with a H$_2$O/CH$_3$CN gradient with 0.5% TFA). This material was free-based with aq ammonium hydroxide, extracted with chloroform, washed with brine, dried (K$_2$CO$_3$) and concentrated to the title compound of EXAMPLE 115 as the free base. LRMS (ES)$^+$: 378.3 (M+H)$^+$.

Example 116

(±)-cis-N-phenyl-4,5,7,7a,8,9,10,10a-octahydrodipyrrolo[3,4-c:3',2',1'-ij]quinolin-2-amine

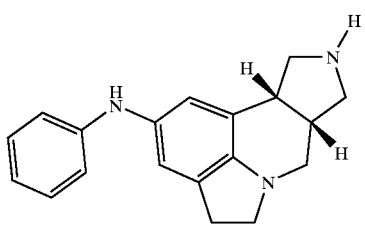

Using bromobenzene and following the procedures described in EXAMPLE 17, Parts B and C, (±)-cis tert-butyl 2-amino-4,5,7a,8,10,10a-hexahydrodipyrrolo[3,4-c:3',2',1'-ij]quinoline-9(7H)-carboxylate was converted into (±)-cis-N-phenyl-4,5,7,7a,8,9,10,10a-octahydrodipyrrolo[3,4-c:3',2',1'-ij]quinolin-2-amine, bis-trifluoroacetic acid salt, after HPLC purification (C18 reverse phase column, elution with a H$_2$O/CH$_3$CN gradient with 0.5% TFA). This material was free-based with aq ammonium hydroxide, extracted with chloroform, washed with brine, dried (K$_2$CO$_3$) and concentrated to the title compound of EXAMPLE 116 as the free base. $^1$H NMR (CDCl$_3$) δ: 7.12 (app t, 2H, J=7.9 Hz), 6.80–6.65 (m, 4H), 6.63 (s, 1H), 5.37 (broad s, 1H), 3.37 (dd, 1H, J=11.1, 7.5 Hz), 3.30–3.10 (m, 5H), 2.95–2.75 (m, 4H), 2.73–2.65 (m, 1H), 2.58 (dd, 1H). LRMS (ES)$^+$: 292.3 (M+H)$^+$.

Example 117

(±)-cis-N-(2-chloro-5-methylphenyl)-4,5,7,7a,8,9,10,10a-octahydrodipyrrolo[3,4-c:3',2',1'-ij]quinolin-2-amine

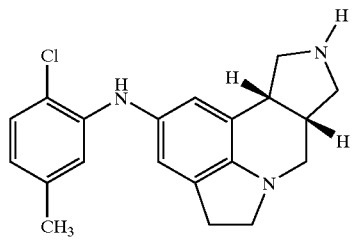

Using 3-bromo-4-chlorotoluene and following the procedures described in EXAMPLE 17, Parts B and C, (±)-cis tert-butyl 2-amino-4,5,7a,8,10,10a-hexahydrodipyrrolo[3,4-c:3',2',1'-ij]quinoline-9(7H)-carboxylate was converted into (±)-cis-N-(2-chloro-5-methylphenyl)-4,5,7,7a,8,9,10,10a-octahydrodipyrrolo[3,4-c:3',2',1'-ij]quinolin-2-amine, bis-trifluoroacetic acid salt, after HPLC purification (C18 reverse phase column, elution with a H$_2$O/CH$_3$CN gradient with 0.5% TFA). This material was free-based with aq ammonium hydroxide, extracted with chloroform, washed with brine, dried (K$_2$CO$_3$) and concentrated to the title compound of EXAMPLE 117 as the free base. $^1$H NMR (CDCl$_3$) δ: 7.18 (d, 1H, J=8.0 Hz), 6.91 (s, 1H), 6.71 (app s, 2H), 6.52 (dd, 1H, J=8.0, 1.4 Hz), 5.83 (s, 1H), 3.79 (dd, 1H, J=11.4, 8.1 Hz), 3.63 (dd, 1H, J=11.5, 7.1 Hz), 3.54 (q, 1H, J=7.5 Hz), 3.37–3.22 (m, 3H), 3.15 (dd, 1H, J=11.3, 8.4 Hz), 3.08–2.92 (m, 4H), 2.85 (dd, 1H, J=10.4, 7.5 Hz). LRMS (ES)$^+$: 340.3 (M+H)$^+$.

Example 118

(±)-cis-N-benzyl-4,5,7,7a,8,9,10,10a-octahydrodipyrrolo[3,4-c:3',2',1'-ij]quinolin-2-amine

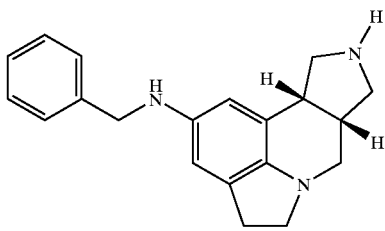

Using benzaldehyde and following the procedures described in EXAMPLE 76, (±)-cis tert-butyl 2-amino-4,5,7a,8,10,10a-hexahydrodipyrrolo[3,4-c:3',2',1'-ij]quinoline-9(7H)-carboxylate was converted into (±)-cis-N-benzyl-4,5,7,7a,8,9,10,10a-octahydrodipyrrolo[3,4-c:3',2',1'-ij]quinolin-2-amine, bis-trifluoroacetic acid salt, after HPLC purification (C18 reverse phase column, elution with a H$_2$O/CH$_3$CN gradient with 0.5% TFA). This material was free-based with aq ammonium hydroxide, extracted with chloroform, washed with brine, dried (K$_2$CO$_3$) and concentrated to the title compound of EXAMPLE 118 as the free base. LRMS (ES)$^+$: 306.3 (M+H)$^+$.

Example 119

(±)-cis-N-[2-(trifluoromethyl)benzyl]-4,5,7,7a,8,9,10,10a-octahydrodipyrrolo[3,4-c:3',2',1'-ij]quinolin-2-amine

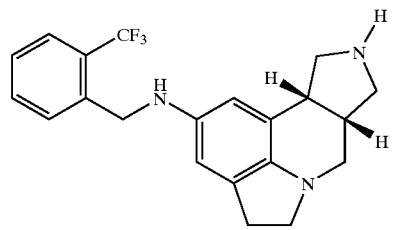

Using 2-(trifluoromethyl)benzaldehyde and following the procedures described in EXAMPLE 76, (±)-cis tert-butyl 2-amino-4,5,7a,8,10,10a-hexahydrodipyrrolo[3,4-c:3',2',1'-ij]quinoline-9(7H)-carboxylate was converted into (±)-cis-N-[2-(trifluoromethyl)benzyl]-4,5,7,7a,8,9,10,10a-octahydrodipyrrolo[3,4-c:3',2',1'-ij]quinolin-2-amine, bis-trifluoroacetic acid salt, after HPLC purification (C18 reverse phase column, elution with a H$_2$O/CH$_3$CN gradient with 0.5% TFA). This material was free-based with aq ammonium hydroxide, extracted with chloroform, washed with brine, dried (K$_2$CO$_3$) and concentrated to the compound of EXAMPLE 119 as the free base. $^1$H NMR (CDCl$_3$) δ: 7.69 (d, 1H, J=7.7 Hz), 7.65 (d, 1H, J=7.7 Hz), 7.51 (t, 1H, J=7.4 Hz), 7.37 (t, 1H, J=7.7 Hz), 6.42 (d, 1H, J=1.4 Hz), 6.14 (d, 1H, J=1.8 Hz), 4.47 (s, 2H), 3.70 (dd, 1H, J=11.4, 8.1 Hz), 3.56 (dd, 1H, J=11.9, 7.5 Hz), 3.45 (q, 1H, J=7.7 Hz), 3.28–3.10 (m, 3H), 3.05 (dd, 1H, J=11.5, 8.3 Hz), 2.97–2.85 (m, 4H), 2.72 (dd, 1H, J=11.5, 8.6 Hz). LRMS (ES)$^+$: 374.3 (M+H)$^+$.

Example 120

(±)-cis-11-benzyl-6,7,10,11,12,12a-hexahydro-5H-[1,4]oxazepino[2,3,4-ij]pyrrolo[3,4-c]quinolin-9(9aH)-one

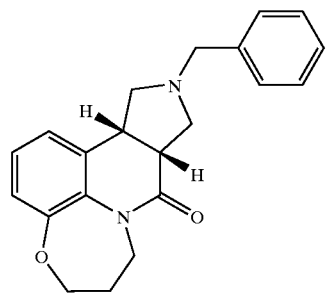

Part A. tert-butyl 3,4-dihydro-1,5-benzoxazepine-5(2H)-carboxylate.

A solution of 2,3,4,5-tetrahydro-1,5-benzoxazepine (2.6 g, 17.4 mmol) in 20 mL of methylene chloride and 20 mL of 1N NaOH was degassed with a stream of argon and then there was added di-tert-butyl dicarbonate (4.2 g, 19.2 mmol). The resulting two-phase mixture was stirred at 40° C. for 24 h with vigorous stirring. The reaction mixture was cooled, diluted with ethyl acetate, washed with H$_2$O and brine, dried (MgSO$_4$) and concentrated. The residue was purified by flash chromatography (elution with 8:1 hexane/ethyl acetate) to afford 2.3 g (53%) of the title compound of Part A. $^1$H NMR (CDCl$_3$) δ: 7.21 (broad s, 1H), 7.10 (dd, 1H, J=8.1, 1.5 Hz), 7.00 (app d, 2H, J=7.4 Hz), 4.20–4.07 (broad m, 2H), 3.77–3.65 (broad m, 2H), 2.12–2.02 (m, 2H), 1.42 (broad s, 9H).

Part B. tert-butyl 6-formyl-3,4-dihydro-1,5-benzoxazepine-5(2H)-carboxylate.

To a solution of tert-butyl 3,4-dihydro-1,5-benzoxazepine-5(2H)-carboxylate (2.15 g, 8.62 mmol) in 50 mL of diethyl ether at −78° C. was added N,N,N',N'-tetramethylethylenediamine (1.6 mL, 10.35 mmol) and then sec-butyllithium (8.0 mL of a 1.3 M solution in cyclohexane, 10.35 mmol) was added dropwise via addition funnel. The mixture was stirred at −78° C. for 1 h and then N,N-dimethylformamide (1.0 mL, 12.93 mmol) was added dropwise in 10 mL of diethyl ether and the resulting mixture was stirred at −78° C. for 1 h. The reaction was quenched by the addition of 10 mL of saturated aqueous ammonium chloride and then was diluted with water and ethyl acetate. The organics were washed with 10% aqueous HCl, sat'd aq. sodium bicarbonate and brine, dried (MgSO$_4$) and concentrated in vacuo. The residue was purified by flash chromatography (elution with 5:1 hexane/ethyl acetate) to afford 2.0 g (84%) of the title compound as an oil which was determined to be a mixture of the title compound and the 9-formyl regioisomer. The mixture of products was carried forward.

Part C. ethyl 6-oxo-3,4-dihydro-2H,6H-[1,4]oxazepino[2,3,4-ij]quinoline-7-carboxylate.

To a solution of tert-butyl 6-formyl-3,4-dihydro-1,5-benzoxazepine-5(2H)-carboxylate (1.95 g, 7.03 mmol) in 40 mL of benzene in a flask fitted with a Dean-Stark trap and a condenser was added diethyl malonate (1.07 mL, 7.03 mmol), piperidine (0.076 mL, 0.77 mmol) and benzoic acid (0.09 g, 0.70 mmol). The resulting solution was stirred at 80° C. for 24 h with collection of water in the Dean-Stark trap. The reaction mixture was then cooled, diluted with ethyl acetate, washed with 1N HCl, sat'd aq NaHCO$_3$ and brine, dried (MgSO$_4$), filtered through a pad of silica gel and concentrated to afford 2.9 g of a diester intermediate. This material was dissolved in 20 mL of methylene chloride and then there was added 5 mL of trifluoroacetic acid. This mixture was allowed to stir at ambient temperature for 4 h. The volatiles were then removed in vacuo and the residue was dissolved in ethyl acetate, washed with water, sat'd aq NaHCO$_3$ and brine, dried (MgSO$_4$), filtered through a pad of silica gel and concentrated. The residue was purified by flash chromatography (elution with 3:1 hexane/ethyl acetate) to afford 1.3 g of a non-cyclized diester resulting from the undesired 9-formyl regioisomer and 0.55 g (29%) of the title compound of Part C. $^1$H NMR (CDCl$_3$) δ: 8.31 (s, 1H), 7.32–7.27 (m, 1H), 7.25–7.20 (m, 1H), 7.12 (t, 1H, J=7.7 Hz), 4.66 (t, 2H, J=5.7 Hz), 4.42 (q, 2H, J=7.1 Hz), 4.31 (t, 2H, J=7.0 Hz), 2.38–2.30 m, 2H), 1.42 (t, 3H, J=7.1 Hz). LRMS (ES)$^+$: 274.2 (M+H)$^+$.

Part D. (±)-cis ethyl 11-benzyl-9-oxo-6,7,10,11,12,12a-hexahydro-5H-[1,4]oxazepino[2,3,4-ij]pyrrolo[3,4-c]quinoline-9a(9H)-carboxylate.

To a solution of ethyl 6-oxo-3,4-dihydro-2H,6H-[1,4]oxazepino[2,3,4-ij]quinoline-7-carboxylate (0.46 g, 1.68 mmol) in 20 mL of methylene chloride was added N-(methoxymethyl)-N-(trimethylsilylmethyl)benzylamine (0.80 g, 3.37 mmol) and trifluoroacetic acid (0.03 mL, 0.34 mmol). The reaction mixture was stirred at 40° C. for 2 h.

The reaction mixture was allowed to cool and was concentrated. The residue was dissolved in ethyl acetate and was washed with sat'd aq. NaHCO$_3$ and brine, dried (MgSO$_4$), filtered through a pad of silica gel and concentrated. The residue was recrystallized from hexane/ethyl acetate to afford the title compound of Part D. $^1$H NMR (CDCl$_3$) δ: 7.33–7.20 (m, 5H), 6.93–6.90 (m, 2H), 6.85–6.80 (m, 1H), 4.50–4.37 (m, 2H), 4.00–3.85 (m, 3H), 3.75–3.65 (m, 3H), 3.42–3.35 (m, 1H), 3.37 (ABq, 2H, J$_{AB}$=9.5 Hz), 3.33–3.28 (m, 1H), 3.11 (t, 1H, J=9.0 Hz), 2.15–2.07 ((m, 1H), 2.05–1.97 (m, 1H), 0.92 (t, 3H, J=7.0 Hz).

LRMS (ES)$^+$: 407.1 (M+H)$^+$.

Part E. (±)-cis-11-benzyl-6,7,10,11,12,12a-hexahydro-5H-[1,4]oxazepino[2,3,4-ij]pyrrolo[3,4-c]quinolin-9(9aH)-one.

To absolution of (±)-cis ethyl 11-benzyl-9-oxo-6,7,10,11,12,12a-hexahydro-5H-[1,4]oxazepino[2,3,4-ij]pyrrolo[3,4-c]quinoline-9a(9H)-carboxylate (0.45 g, 1.11 mmol) in 20 mL of 1,4-dioxane was added 20 mL of 3N HCl and the resulting mixture was stirred at 100° C. for 24 h. The dioxane and most of the water was removed in vacuo, and the residue was basified with sat'd aq Na$_2$CO$_3$ and extracted with ethyl acetate. The layers were separated and the organics were washed with brine, dried (MgSO$_4$), filtered through a pad of silica gel and concentrated to afford 0.33 g (89%) of the title compound of EXAMPLE 120 as an off-white powder. $^1$H NMR (CDCl$_3$) δ: 7.41–7.27 (m, 5H), 6.97–6.81 (m, 3H), 4.60 (dt, 1H), 4.40 (ddd, 1H), 4.13 (ddd, 1H), 3.85–3.75 (m, 1H), 3.82 (broad s, 2H), 3.68–3.57 (m, 1H), 3.52–3.40 (m, 2H), 3.28–3.20 (m, 1H), 3.20–3.10 (m, 1H), 2.56 (t, 1H, J=9.9 Hz), 2.25–2.10 (m, 2H). LRMS (ES)$^+$: 335.4 (M+H)$^+$.

Example 121

(±)-cis-6,7,9,9a,10,11,12,12a-octahydro-5H-[1,4]oxazepino[2,3,4-ij]pyrrolo[3,4-c]quinoline, bis-hydrochloride salt

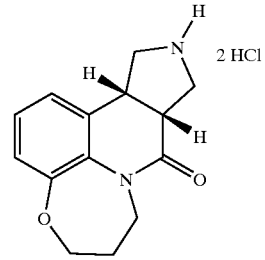

Part A. (+)-cis tert-butyl 9-oxo-6,7,9a,10,12,12a-hexahydro-5H-[1,4]oxazepino[2,3,4-ij]pyrrolo[3,4-c]quinoline-11(9H)-carboxylate.

To a solution of (±)-cis-11-benzyl-6,7,10,11,12,12a-hexahydro-5H-[1,4]oxazepino[2,3,4-ij]pyrrolo[3,4-c]quinolin-9(9aH)-one free base from EXAMPLE 120, Part E (215 mg, 0.64 mmol) in 20 mL of absolute ethanol was added di-tert-butyl dicarbonate (147 mg, 0.68 mmol) and Pearlman's catalyst (20% Pd(OH)$_2$/C) (0.05 g). This mixture was stirred under 1 atm of hydrogen maintained by a balloon for 2 h at ambient temperature. The mixture was filtered through a pad of layered Celite/silica gel and concentrated in vacuo to afford 0.21 g (95%) of the title compound of Part A, which was used without purification. $^1$H NMR (CDCl$_3$) δ: 7.01–6.88 (m, 3H), 4.58 (dt, 1H), 4.40 (ddd, 1H), 4.22–4.10 (m, 2H), 3.82–3.72 (m, 2H), 3.59 (dd, 1H), 3.50–3.42 (m, 1H), 3.18–3.07 (m, 2H), 2.22–2.12 (m, 2H), 1.48 (s, 9H).

Part B. (+)-cis tert-butyl 6,7,9a,10,12,12a-hexahydro-5H-[1,4]oxazepino[2,3,4-ij]pyrrolo[3,4-c]quinoline-11(9H)-carboxylate.

To a solution of (+)-cis tert-butyl 9-oxo-6,7,9a,10,12,12a-hexahydro-5H-[1,4]oxazepino[2,3,4-ij]pyrrolo[3,4-c]

quinoline-11(9H)-carboxylate (300 mg, 0.87 mmol) in 10 mL of tetrahydrofuran at 0° C. was added borane-THF complex (4.35 mL of a 1M solution in THF, 4.35 mmol) via an addition funnel. After the addition was complete the reaction mixture was allowed to warm to ambient temperature and was stirred for 24 h. The reaction was quenched by dropwise addition of methanol (10 mL) and then the volatiles were removed in vacuo. The residue was dissolved in ethyl acetate, washed with sat'd aq. $NaHCO_3$ and brine, dried ($MgSO_4$) filtered through a pad of silica gel and concentrated to afford 0.25 g (87%) of the title compound of Part B, which was used without purification. LRMS (ES)$^+$: 331.2 (M+H)$^+$.

Part C. (±)-cis-6,7,9,9a,10,11,12,12a-octahydro-5H-[1,4]oxazepino[2,3,4-ij]pyrrolo[3,4-c]quinoline, bis-hydrochloride salt.

To absolution of (+)-cis tert-butyl 6,7,9a,10,12,12a-hexahydro-5H-[1,4]oxazepino[2,3,4-ij]pyrrolo[3,4-c]quinoline-11(9H)-carboxylate (250 mg, 0.76 mmol) in 15 mL of methylene chloride was added trifluoroacetic acid (4 mL). This mixture was stirred at ambient temperature for 2 h and then concentrated in vacuo. The residue was basified with sat'd aq $Na_2CO_3$ and extracted with chloroform. The organics were washed with brine, dried ($K_2CO_3$) and concentrated in vacuo to afford the free base. This material was purified by preparative HPLC (C18 reverse phase column, elution with a $H_2O/CH_3CN$ gradient with 0.5% TFA) and the product containing fractions were concentrated, basified with sat'd aq $Na_2CO_3$ and extracted twice with ethyl acetate. The organics were washed with brine, dried ($Na_2SO_4$) and concentrated to a free base. A portion of the residue (30 mg, 0.13 mmol) was taken up in about 4:1 ether/ethanol and then there was added 2M HCl in ether (0.2 mL, 0.39 mmol). The resulting solid was filtered, washed twice with ether and dried in vacuo to afford the title compound of EXAMPLE 121 as an off-white powder. $^1$H NMR (dmso-D6) δ: 9.52 (broad s, 1H), 9.30 (broad s, 1H), 6.90–6.83 (m, 1H), 6.75–6.70 (m, 2H), 4.60 (dt, 1H, J=12.0, 5.1 Hz), 3.77–3.63 (m, 2H), 3.52–3.45 (m, 1H), 3.40–3.25 (m, 2H), 3.19–3.06 (m, 2H), 3.05–2.85 (m, 2H), 2.84 (t, 1H, J=12.0 Hz), 2.65–2.55 (m, 1H), 2.08–1.97 (m, 1H), 1.90–1.79 (m, 1H). LRMS (ES)$^+$: 231.0 (M+H)$^+$.

Example 122

(±)-cis-11-methyl-6,7,9,9a,10,11,12,12a-octahydro-5H-[1,4]oxazepino[2,3,4-ij]pyrrolo[3,4-c]quinoline, bis-hydrochloride salt

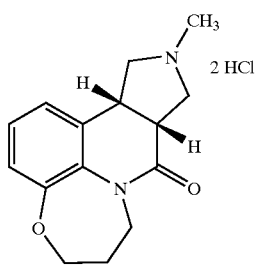

To a solution of (±)-cis-6,7,9,9a,10,11,12,12a-octahydro-5H-[1,4]oxazepino[2,3,4-ij]pyrrolo[3,4-c]quinoline trifluoroacetic acid salt from EXAMPLE 121 (100 mg, 0.29 mmol) in 10 mL of 1,2-dichloroethane was added 37% aqueous formaldehyde (0.05 mL, 0.58 mmol) and sodium triacetoxyborohydride (0.19 g, 0.87 mmol) and a couple drops of acetic acid. The resulting mixture was stirred at ambient temperature for 1 h and then the reaction was quenched with water. The mixture was partitioned between chloroform and saturated aqueous sodium carbonate. The organics were washed with brine, dried ($K_2CO_3$) and concentrated in vacuo. A portion of the residue (40 mg, 0.16 mmol) was dissolved in 1 mL ethanol and 5 mL of ether and then there was added 2M HCl in ether (0.25 mL, 0.5 mmol). A solid precipitated out of solution. The solvents were decanted and the solid was triturated twice with ether and dried in vacuo to afford the title compound of EXAMPLE 122 as an off white powder. $^1$H NMR (dmso-D6) δ: 11.20 (broad s, 1H), 6.85–6.77 (m, 1H), 6.75–6.70 (m, 2H), 4.27 (dt, 1H), 4.00–3.80 (m, 1H), 3.77–3.60 (m, 2H), 3.50–3.25 (m, 3H), 3.20–3.05 (m, 2H), 2.97–2.90 (m, 1H), 2.88–2.62 (m, 5H), 2.07–1.95 (m, 1H), 1.92–1.80 (m, 1H). LRMS (ES)$^+$: 245.0 (M+H)$^+$.

Examples 123 and 124

(±)-cis 5,6,8a,9,10,11,12,12a-octahydro-4H,8H-quino[1,8-bc]-2,6-naphthyridine, bis-hydrochloride salt (Example 123) and (±)-cis 5,6,8a,9,10,11,12,12a-octahydro-4H,8H-quino[1,8-bc]-2,7-naphthyridine, bis-hydrochloride salt (Example 124)

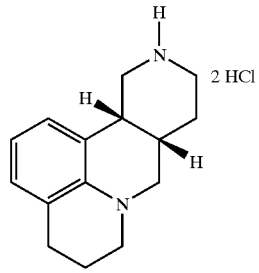

Ex 123

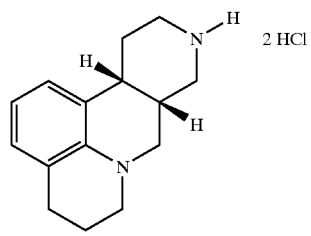

Ex 124

Part A. (±)-cis ethyl 10-methylene-8-oxo-5,6,9,10,11,11a-hexahydro-4H-cyclopenta[c]pyrido[3,2,1-ij]quinoline-8a(8H)-carboxylate.

To a solution of ethyl 5-oxo-2,3-dihydro-1H,5H-pyrido[3,2,1-ij]quinoline-6-carboxylate from EXAMPLE 25, Part A (0.92 g, 3.58 mmol) in 20 mL of tetrahydrofuran was added 2-[(trimethylsilyl)methyl]-2-propen-1-yl acetate (1.33 g, 7.15 mmol). The solution was degassed with a stream of argon for 20 min and then there was added palladium (II) acetate (0.20 g, 0.89 mmol) and triethylphosphite (0.65 g, 3.94 mmol). The resulting mixture was stirred at reflux for 4 h, at which time the reaction was about 50% complete as judged by TLC analysis. Additional portions of 2-[(trimethylsilyl)methyl]-2-propen-1-yl acetate (1.33 g, 7.15 mmol), palladium (II) acetate (0.20 g, 0.89 mmol) and triethylphosphite (0.65 g, 3.94 mmol) were added and the reaction mixture was allowed to stir at reflux for an additional 18 h. The reaction mixture was cooled and concentrated in vacuo. The residue was purified by flash chromatography (elution with solvent gradient 9:1 hexane/ethyl acetate to 6:1 hexane ethyl acetate) to afford 0.97 g (87%) of the title compound of Part A. $^1$H NMR (CDCl$_3$) δ: 7.06–7.00 (m, 2H), 6.96–6.90 (m, 1H), 4.99 (s, 1H), 4.92 (s, 1H), 4.36 (dt, 1H, J=13.2, 5.9 Hz), 4.10–3.95 (m, 2H), 3.63–3.50 (m, 3H), 3.05 (dq, 1H, J=16.6, 2.7 Hz), 2.88–2.75 (m, 3H), 2.39–2.25 (m, 1H), 2.01–1.94 (m, 2H), 1.03 (q, 3H, J=7.0 Hz).

Part B. (±)-cis ethyl 8,10-dioxo-5,6,9,10,11,11a-hexahydro-4H-cyclopenta[c]pyrido[3,2,1-ij]quinoline-8a(8H)-carboxylate.

To a solution of (±)-cis ethyl 10-methylene-8-oxo-5,6,9,10,11,11a-hexahydro-4H-cyclopenta[c]pyrido[3,2,1-ij]quinoline-8a(8H)-carboxylate (0.95 g, 3.05 mmol) in 50 mL of 9:1 acetone/water at 0° C. was added N-methylmorpholine N-oxide (0.71 g, 6.1 mmol) and osmium tetroxide (1.2 mL of a 2.5% wt solution in t-butanol, 0.09 mmol). The resulting mixture was allowed to stir with slow warming to room temperature for 4 h. The reaction was quenched with a small amount of solid sodium bisulfite and stirred for an additional 20 min. The reaction was concentrated, diluted with ethyl acetate, washed with 1N HCl, sat'd aq sodium bicarbonate and brine, dried (MgSO$_4$) and concentrated. The residue was dissolved in 20 mL of 1:1 acetone/water at 0° C. and then there was added sodium periodate (0.98 g, 4.57 mmol). The reaction was allowed to stir at 0° C. for 4 h and then was concentrated. The residue was dissolved in ethyl acetate, washed with water and brine, dried (MgSO$_4$), filtered through a pad of silica gel and concentrated to afford the title compound of Part B, which was used without purification. $^1$H NMR (CDCl$_3$) δ: 7.12–7.06 (m, 1H), 7.05–6.95 (m, 2H), 4.38 (dt, 1H), 4.18–4.00 (m, 2H), 3.61 (dd, 1H, J=12.8, 6.3 Hz), 3.65–3.58 (m, 1H), 3.22 (ABq, 2H, J$_{AB}$=18.3 Hz), 2.90–2.80 (m, 2H), 2.48 (ABx, 2H), 2.05–1.96 (m, 2H), 1.05 (q, 3H, J=7.2 Hz).

Part C. (±)-cis 5,6,8a,9,11,11a-hexahydro-4H-cyclopenta[c]pyrido[3,2,1-ij]quinoline-8,10-dione.

To a solution of (±)-cis ethyl 8,10-dioxo-5,6,9,10,11,11a-hexahydro-4H-cyclopenta[c]pyrido[3,2,1-ij]quinoline-8a(8H-carboxylate (0.76 g, 2.42 mmol) in 30 mL of 1,4-dioxane was added 20 mL of 3N HCl and the resulting solution was stirred at 100° C. for 24 h. The reaction was cooled, diluted with water and extracted with ethyl acetate. The organics were washed with sat'd sodium bicarbonate and brine, dried (MgSO$_4$), filtered through a pad of silica gel and concentrated to afford the title compound of Part C, which was used without purification.

Part D. (±)-cis 5,6,8a,9,10,11,12,12a-octahydro-4H8H-quino[1,8-bc]-2,6-naphthyridine, bis-hydrochloride salt (EXAMPLE 123) and (±)-cis 5,6,8a,9,10,11,12,12a-octahydro-4H,8H-quino[1,8-bc]-2,7-naphthyridine, bis-hydrochloride salt (EXAMPLE 124).

To a solution of (±)-cis 5,6,8a,9,11,11a-hexahydro-4H-cyclopenta[c]pyrido[3,2,1-ij]quinoline-8,10-dione (0.58 g, 2.40 mmol) in 6 mL of methanesulfonic acid at 0° C. was added sodium azide (0.24 g, 3.60 mmol). The reaction was stirred with slow warming to room temperature for 2 h, at which time gas evolution had ceased. The reaction was diluted with water, poured into sat'd aq sodium bicarbonate and extracted twice with ethyl acetate. The organics were washed with brine, dried (MgSO$_4$) and concentrated to afford 0.52 g (85%) of a bis-lactam intermediate which was used without purification. A portion (240 mg, 0.94 mmol) of this bis-lactam was dissolved in tetrahydrofuran and then there was added borane THF complex (14.0 mL of a 1M solution in THF, 14.0 mmol) and the reaction was stirred at reflux for 4 h. The reaction was allowed to cool to room temperature and was quenched by slow addition of methanol and then was concentrated. The residue was refluxed in 10 mL of 1:1 methanol/1N HCl for 1 h and then cooled to room temperature. The mixture was made basic with sat'd aq Na$_2$CO$_3$ and extracted twice with chloroform. The organics were washed with brine, dried (K$_2$CO$_3$) and concentrated. The residue was purified by prep HPLC (C18 reverse phase column, elution with a H$_2$O/CH$_3$CN gradient with 0.5% TFA) to afford two eluents (9.2 min and 9.9 min retention times). The fractions from the first eluent were concentrated, made basic with sat'd aq Na$_2$CO$_3$ and extracted twice with chloroform. The organics were washed with brine, dried (K$_2$CO$_3$) and concentrated to a free base. A portion of the free base (40 mg, 0.17 mmol) was dissolved in 1 mL ethanol and 5 mL of ether and then there was added 2M HCl in ether (0.25 mL, 0.5 mmol). A solid precipitated out of solution. The solvents were decanted and the solid was triturated twice with ether and dried in vacuo to afford the title compound of EXAMPLE 123 as an off white powder. $^1$H NMR (dmso-D6) δ: 6.82–6.75 (m, 2H), 6.50–6.41 (m, 1H), 3.39–3.30 (m, 1H), 3.18–3.02 (m, 5H), 3.00–2.83 (m, 3H), 2.70–2.60 (m, 2H), 2.36–2.25 (m, 1H), 2.07–1.96 (m, 1H), 1.90–1.80 (m, 2H), 1.78–1.70 (m, 1H). LRMS (ES)$^+$: 229.4 (M+H)$^+$. The fractions from the second eluent were concentrated, made basic with sat'd aq Na$_2$CO$_3$ and extracted twice with chloroform. The organics were washed with brine, dried (K$_2$CO$_3$) and concentrated to a free base. A portion of the free base (40 mg, 0.17 mmol) was dissolved in 1 mL ethanol and 5 mL of ether and then there was added 2M HCl in ether (0.25 mL, 0.5 mmol). A solid precipitated out of solution. The solvents were decanted and the solid was triturated twice with ether and dried in vacuo to afford the title compound of EXAMPLE 124 as an off white powder. $^1$H NMR (dmso-D6) δ: 9.00 (broad s, 1H), 8.65 (broad s, 1H), 6.84 (d, 1H, J=7.3 Hz), 6.74 (d, 1H, J=7.0 Hz), 6.48 (t, 1H, J=7.5 Hz), 3.25–3.12 (m, 2H), 3.10–3.02 (m, 3H), 3.01–2.90 (m, 3H), 2.89–2.80 (m, 1H), 2.68–2.61 (m, 2H), 2.39–2.32 (m, 1H), 2.08–1.98 (m, 1H), 1.95–1.80 (m, 3H). LRMS (ES)$^+$: 229.4 (M+H)$^+$.

Example 125

(±)-cis 11-methyl-5,6,8a,9,10,11,12,12a-octahydro-4H,8H-quino[1,8-bc]-2,6-naphthyridine, bis-hydrochloride salt

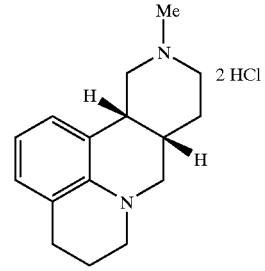

To a solution of (±)-cis 5,6,8a,9,10,11,12,12a-octahydro-4H,8H-quino[1,8-bc]-2,6-naphthyridine free base from EXAMPLE 123 (50 mg, 0.22 mmol) in 10 mL of 1,2-dichloroethane was added 37% aqueous formaldehyde (0.05 mL, 0.58 mmol) and sodium triacetoxyborohydride (0.19 g, 0.87 mmol) and a couple drops of acetic acid. The resulting mixture was stirred at ambient temperature for 1 h and then the reaction was quenched with water. The mixture was partitioned between chloroform and saturated aqueous sodium carbonate. The organics were washed with brine, dried (K₂CO₃) and concentrated in vacuo. The residue (40 mg, 0.16 mmol) was dissolved in 1 mL ethanol and 5 mL of ether and then there was added 2M HCl in ether (0.25 mL, 0.5 mmol). A solid precipitated out of solution. The solvents were decanted and the solid was triturated twice with ether and dried in vacuo to afford the title compound of EXAMPLE 125 as an off white powder. ¹H NMR (dmso-D6) δ: 10.65 (broad s, 1H), 6.77 (d, 1H, J=7.0 Hz), 6.73 (d, 1H, J=7.7 Hz), 6.47 (t, 1H, J=7.4 Hz), 3.45–3.35 (m, 1H), 3.30–2.85 (overlapping m, 8H), 2.80–2.58 (m, 8H), 2.35–2.25 (m, 1H), 2.22–2.15 (m, 1H), 1.90–1.75 (m, 3H). LRMS (ES)⁺: 243.4 (M+H)⁺.

Example 126

(±)-cis 10-methyl-5,6,8a,9,10,11,12,12a-octahydro-4H,8H-quino[1,8-bc]-2,7-naphthyridine, bis-hydrochloride salt

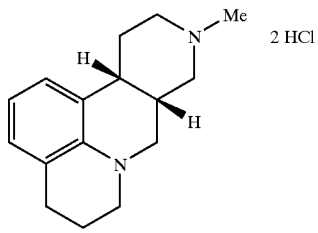

To a solution of (±)-cis 5,6,8a,9,10,11,12,12a-octahydro-4H,8H-quino[1,8-bc]-2,7-naphthyridine free base from EXAMPLE 124 (50 mg, 0.22 mmol) in 10 mL of 1,2-dichloroethane was added 37% aqueous formaldehyde (0.05 mL, 0.58 mmol) and sodium triacetoxyborohydride (0.19 g, 0.87 mmol) and a couple drops of acetic acid. The resulting mixture was stirred at ambient temperature for 1 h and then the reaction was quenched with water. The mixture was partitioned between chloroform and saturated aqueous sodium carbonate. The organics were washed with brine, dried (K₂CO₃) and concentrated in vacuo. The residue (40 mg, 0.16 mmol) was dissolved in 1 mL ethanol and 5 mL of ether and then there was added 2M HCl in ether (0.25 mL, 0.5 mmol). A solid precipitated out of solution. The solvents were decanted and the solid was triturated twice with ether and dried in vacuo to afford the title compound of EXAMPLE 126 as an off white powder. LRMS (ES)⁺: 243.4 (M+H)⁺.

Example 127

(±)-cis 2-phenyl-5,6,8a,9,10,11,12,12a-octahydro-4H,8H-quino[1,8-bc]-2,6-naphthyridine, trifluoroacetic acid salt

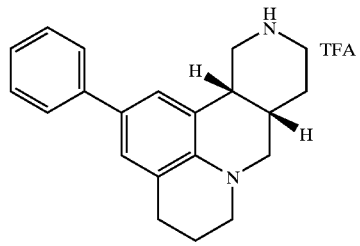

Part A. 1-isonicotinoyl-1,2,3,4-tetrahydroquinoline

To a solution of 1,2,3,4-tetrahydroquinoline (3.74 g, 28.1 mmol) in 50 mL of methylene chloride was added isonicotinoyl chloride hydrochloride (5.0 g, 28.1 mmol) and triethylamine (7.87 mL, 56.5 mmol). The resulting mixture was stirred at ambient temperature for 24 h. The reaction mixture was filtered through a pad of silica gel and concentrated. The residue was purified by flash chromatography (elution with 1:1 hexane/ethyl acetate) to afford 6.7 g (97%) of the title compound of Part A. ¹H NMR (CDCl₃) δ: 8.47 (d, 2H, J=5.5 Hz), 7.12 (d, 2H, J=5.5 Hz), 7.12–7.05 (m, 1H), 6.95 (t, 1H, J=7.5 Hz), 6.78 (t, 1H, J=7.1 Hz), 6.60 (broad s, 1H), 3.80 (t, 2H, J=6.5 Hz), 2.76 (t, 2H, J=6.5 Hz), 2.02–1.90 (m, 2H).

Part B. 1-[(1-benzyl-1,2,3,6-tetrahydro-4-pyridinyl)carbonyl]-1,2,3,4-tetrahydroquinoline.

To a solution of 1-isonicotinoyl-1,2,3,4-tetrahydroquinoline (6.50 g, 27.3 mmol) in 100 mL of acetone was added benzyl bromide (10.8 mL, 90.8 mmol) and the resulting solution was stirred at 70° C. for 4 h. The mixture was allowed to cool to room temperature and the resulting solid was filtered, washed with acetone and dried in vacuo to afford 8.8 g of an intermediate quaternary salt. This solid was suspended in 20 mL of absolute ethanol, cooled to 0° C. and then there was added, over a 20 min period, sodium borohydride (2.44 g, 64.5 mmol) as a solution in 25 mL of water and 2.5 mL of 50% NaOH. The reaction was allowed to warm to room temperature and was stirred for 3 h. The reaction was diluted with ethyl acetate, washed with water and brine, dried (MgSO₄) and concentrated. The residue was purified by flash chromatography (elution with 1:1 hexane/ethyl acetate) to afford 5.6 g (79%) of the title compound of Part B. ¹H NMR (CDCl₃) δ: 7.35–7.02 (overlapping m, 9H), 5.93 (app s, 1H), 3.81 (t, 2H, J=6.4 Hz), 3.57 (s, 2H), 3.01 (d, 2H, J=2.9 Hz), 2.75 (t, 2H, J=6.6 Hz), 2.57 (t, 2H, J=5.7 Hz), 2.27 (app d, 2H, J=1.5 Hz), 2.02–1.91 (m, 2H). LRMS (ES)⁺: 243.4 (M+H)⁺.

Part C. tert-butyl 4-(3,4-dihydro-1(2H)-quinolinylcarbonyl)-3,6-dihydro-1(2H)-pyridinecarboxylate.

To a solution of 1-[(1-benzyl-1,2,3,6-tetrahydro-4-pyridinyl)carbonyl]-1,2,3,4-tetrahydroquinoline (5.7 g, 17.1 mmol) in 1,2-dichloroethane (50 mL) was added 1-chloroethyl chloroformate (ACE-Cl) (1.84 mL, 17.1 mmol) and the mixture was stirred at reflux for 1 h. The volatiles were removed in vacuo and the residue was dissolved in methanol and stirred at reflux for 1 h. The reaction was cooled and concentrated in vacuo to afford an amine salt. This salt was taken up in methylene chloride and then there was added triethylamine (2.61 mL, 18.7 mmol) and di-tert-butyl dicarbonate (4.46 g, 20.5 mmol). The reaction was stirred at room temperature for 4 h. The reaction mixture was filtered through a pad of silica gel and concentrated to afford 4.6 g (79%) of the title compound of Part C, which was used without purification.

Part D. (±)-cis tert-butyl 8-oxo-5,6,8,8a,9,10,12,12a-octahydro-4H,11H-quino[1,8-bc]-2,6-naphthyridine-11-carboxylate.

A solution of tert-butyl 4-(3,4-dihydro-1(2H)-quinolinylcarbonyl)-3,6-dihydro-1(2H)-pyridinecarboxylate (4.5 g, 13.1 mmol) in 200 mL of toluene was cooled with a water jacket and was irradiated with a mercury vapor lamp for 3% days. The mixture was concentrated in vacuo. The residue was purified by flash chromatography (elution with 3:1 hexane/ethyl acetate) to afford a 3:1 mixture of the desired cis and undesired trans ring fusion isomers. Recrystallization of this mixture from absolute ethanol afforded 2.4 g (53%) of the desired cis isomer title compound of Part D as a white solid Part E. (±)-cis tert-butyl 5,6,8,8a,9,10,12,12a-octahydro-4H, 11H-quino[1,8-bc]-2,6-naphthyridine-11-carboxylate.

To a solution of (±)-cis tert-butyl 8-oxo-5,6,8,8a,9,10,12, 12a-octahydro-4H,11H-quino[1,8-bc]-2,6-naphthyridine-11-carboxylate (2.38 g, 6.95 mmol) in tetrahydrofuran (50 mL) was added borane THF complex (41.7 mL of a 1M solution in THF, 41.7 mmol) and the reaction was stirred at reflux for 4 h. The reaction was allowed to cool to room temperature and was quenched by slow addition of methanol and then was concentrated. The residue was diluted with ethyl acetate, washed with sat'd aq NaHCO₃ and brine, dried (MgSO₄) and concentrated to afford the title compound of Part E. ¹H NMR (CDCl₃) δ: 6.76–6.67 (m, 2H), 6.40 (t, 1H, J=7.5 Hz), 4.59 (broad s, 1H), 4.10–4.00 (m, 1H), 3.11–3.06 (m, 2H), 3.03 (dd, 1H), 2.90 (t, 1H, J=11.0 Hz), 2.78–2.55 (m, 4H), 2.29 (dt, 1H, J=11.1, 4.2 Hz), 1.87–1.77 (m, 2H), 1.73–1.60 (m, 2H), 1.41 (s, 9H), 1.20–1.05 (m, 1H). LRMS (ES)⁺: 243.4 (M+H)⁺.

Part F. (±)-cis tert-butyl 2-bromo-5,6,8,8a,9,10,12,12a-octahydro-4H,11H-quino[1,8-bc]-2,6-naphthyridine-11-carboxylate.

Following the procedures described in EXAMPLE 7, Part A, (±)-cis tert-butyl 5,6,8,8a,9,10,12,12a-octahydro-4H, 11H-quino[1,8-bc]-2,6-naphthyridine-11-carboxylate was converted into the title compound of Part F.

Part G. (±)-cis 2-phenyl-5,6,8a,9,10,11,12,12a-octahydro-4H,8H-quino[1,8-bc]-2,6-naphthyridine, trifluoroacetic acid salt.

Using phenylboronic acid and following the procedures described in EXAMPLE 20, (±)-cis tert-butyl 2-bromo-5,6, 8,8a,9,10,12,12a-octahydro-4H,11H-quino[1,8-bc]-2,6-naphthyridine-11-carboxylate was converted into the title compound of EXAMPLE 127. ¹H NMR (CDCl₃) δ: 9.78 (broad s, 1H), 9.28 (broad s, 1H), 7.41–7.32 (m, 2H), 7.28 (t, 2H, J=7.3 Hz), 7.20–7.10 (m, 1H), 7.03 (s, 1H), 6.84 (s, 1H), 4.05 (d, 1H, J=9.9 Hz), 3.60–3.40 (m, 2H), 3.20–2.70 (overlapping m, 7H), 2.00–1.80 (m, 4H), 1.72–1.60 (m, 1H), 0.82–0.70 (m, 1H). LRMS (ES)⁺: 305.3 (M+H)⁺.

EXAMPLE 128

(±)-cis 2-(2,4-dichlorophenyl)-5,6,8a,9,10,11,12, 12a-octahydro-4H,8H-quino[1,8-bc]-2,6-naphthyridine

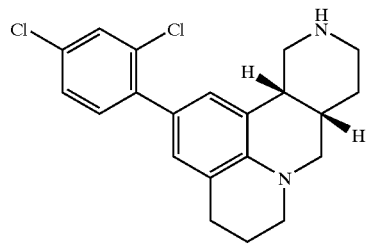

Using 2,4-dichlorophenylboronic acid and following the procedures described in EXAMPLE 20, (±)-cis tert-butyl 2-bromo-5,6,8,8a,9,10,12,12a-octahydro-4H,11H-quino[1, 8-bc]-2,6-naphthyridine-11-carboxylate from EXAMPLE 127, Part F was converted into the title compound of EXAMPLE 128. ¹H NMR (CDCl₃) δ: 7.44 (d, 1H, J=1.6 Hz), 7.27–7.18 (m, 2H), 6.94 (B, 1H), 6.81 (s, 1H), 3.96 (dd, 1H, J=11.5, 3.1 Hz), 3.51–3.43 (m, 1H), 3.30–3.20 (m, 2H), 3.13 (d, 2H, J=7.3 Hz), 2.98–2.85 (m, 2H), 2.84–2.73 (m, 2H), 2.08–1.88 (m, 4H), 1.71–1.60 (m, 1H), 0.90–0.80 (m, 1H). LRMS (ES)⁺: 373.3 (M+H)⁺.

EXAMPLE 129

(±) -cis 2-[4-methoxy-2-(trifluoromethyl)phenyl]-5, 6,8a,9,10,11,12,12a-octahydro-4H,8H-quino[1,8-bc]-2,6-naphthyridine, trifluoroacetic acid salt

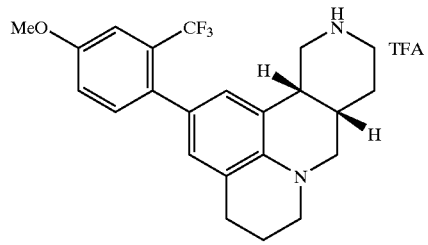

Using 4-methoxy-2-(trifluoromethyl)phenylboronic acid and following the procedures described in EXAMPLE 20, (±)-cis tert-butyl 2-bromo-5,6,8,8a,9,10,12,12a-octahydro-4H,11H-quino[1,8-bc]-2,6-naphthyridine-11-carboxylate from EXAMPLE 127, Part F was converted into the title compound of EXAMPLE 129. ¹H NMR (CDCl₃) δ: 7.25–7.17 (m, 2H), 7.04 (dd, 1H, J=8.4, 2.2 Hz), 6.82 (s, 1H), 6.64 (s, 1H), 3.93 (d, 1H, J=8.4 Hz), 3.88 (s, 3H), 3.51 (d, 1H, J=11.3 Hz), 3.28–3.17 (m, 2H), 3.13 (d, 2H, J=6.9 Hz), 3.00–2.90 (m, 2H), 2.85–2.70 (m, 2H), 2.08–1.88 (m, 4H), 1.79–1.70 (m, 1H), 0.90–0.83 (m, 1H). LRMS (ES)⁺: 403.3 (M+H)⁺.

EXAMPLE 130

(±)-cis 2-(2,6-dichlorophenyl)-5,6,8a,9,10,11,12, 12a-octahydro-4H,8H-quino [1,8-bc]-2,6-naphthyridine, trifluoroacetic acid salt

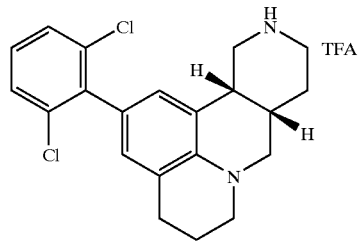

Using 2,6-dichlorophenylboronic acid and following the procedures described in EXAMPLE 20, (±)-cis tert-butyl 2-bromo-5,6,8,8a,9,10,12,12a-octahydro-4H,11H-quino[1, 8-bc]-2,6-naphthyridine-11-carboxylate from EXAMPLE 127, Part F was converted into the title compound of EXAMPLE 130. ¹H NMR (CDCl₃) δ: 7.28 (d, 2H, J=8.1 Hz), 7.05 (t, 1H, J=7.8 Hz), 6.67 (s, 1H), 6.61 (s, 1H), 3.65 (d, 1H, J=8.0 Hz), 3.25–3.08 (m, 3H), 3.05–2.9.5 (m, 2H), 2.75–2.62 (m, 2H), 2.59–2.50 (m, 2H), 2.00–1.82 (m, 2H), 1.79–1.69 (m, 2H), 138–1.23 (m, 1H), 0.83–0.75 (m, 1H). LRMS (ES)⁺: 373.3 (M+H)⁺.

EXAMPLE 131

2-[(8aR,11aR)-5,6,8,8a,9,10,11,11a-octahydro-4H-pyrido[3,2,1-ij]pyrrolo[3,4-ca]quinolin-2-ylamino]-4-chlorobenzonitrile, bis-trifluoroacetic acid salt

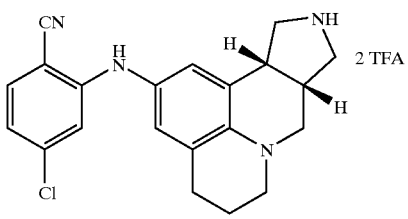

Usings 2-bromo-4-chlorobenzonitrile and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 131. $^1$H NMR (dmso-D$_6$) δ: 8.92 (broad s, 2H), 8.20 (s, 1H), 7.53 (d, 1H, J=9.2 Hz), 6.78 (s, 1H), 6.75–6.68 (m, 2H), 6.67 (s, 1H), 3.70–3.60 (m, 1H), 3.50–3.30 (m, 2H), 3.10–2.85 (m, 5H), 2.80–2.60 (m, 4H), 1.90–1.80 (m, 2H). LRMS (ES)$^+$: 1365.4 (M+H)$^+$.

EXAMPLE 132

2-[(8aR,11aR)-5,6,8,8a,9,10,11,11a-octahydro-4H-pyrido[3,2,1-ij]pyrrolo[3,4-c]quinolin-2-ylamino]-6-fluorobenzonitrile, bis-trifluoroacetic acid salt

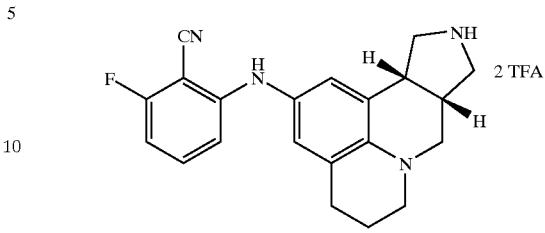

Using 2-bromo-6-fluorobenzonitrile and following the procedures described in EXAMPLE 17, Parts B and C, tert-butyl (8aS,11aR)-2-amino-5,6,8a,9,11,11a-hexahydro-4H-pyrido[3,2,1-ij]pyrrolo[3,4-c]quinoline-10(8H)-carboxylate was converted into the title compound of EXAMPLE 132. $^1$H NMR (dmso-D$_6$) δ: 8.95 (broad s, 2H), 8.26 (s, 1H), 7.31 (d, 1H, J=7.4 Hz), 6.77 (d, 1H, J=2.2 Hz), 6.67 (d, 1H, J=2.2 Hz), 6.65–6.55 (m, 2H), 3.68–3.58 (m, 1H), 3.48–3.30 (m, 2H), 3.10–2.85 (m, 5H), 2.78–2.60 (m, 4H), 1.90–1.80 (m, 2H). LRMS (ES)$^+$: 349.3 (M+H)$^+$.

The following Tables provide representative EXAMPLES, the syntheses of which are described above, of the compounds of Formula (I) of the present invention.

TABLE 1

| Ex # | X | b | R$^6$, R$^{6a}$ | n | m | R$^1$ |
|---|---|---|---|---|---|---|
| 1 | CH$_2$ | sgl-trans | =O | 1 | 1 | —CH$_2$-phenyl |
| 2 | CH$_2$ | sgl-trans | H, H | 1 | 1 | —CH$_2$-phenyl |
| 3 | CH$_2$ | sgl-trans | =O | 1 | 1 | H |
| 4 | CH$_2$ | sgl-trans | H, H | 1 | 1 | H |
| 5 | CH$_2$ | sgl-trans | =O | 1 | 1 | CH$_3$ |
| 6 | CH$_2$ | sgl-trans | H, H | 1 | 1 | CH$_3$ |
| 8 | CH$_2$ | sgl-cis | =O | 1 | 1 | —CH$_2$-phenyl |
| 9 | CH$_2$ | sgl-cis | H, H | 1 | 1 | —CH$_2$-phenyl |
| 10 | CH$_2$ | sgl-cis | =O | 1 | 1 | H |
| 11 | CH$_2$ | sgl-cis | H, H | 1 | 1 | H |
| 12 | CH$_2$ | sgl-cis | =O | 1 | 1 | CH$_3$ |
| 13 | CH$_2$ | sgl-cis | H, H | 1 | 1 | CH$_3$ |
| 25 | CH$_2$ | Sgl-cis (8aR, 11aR) | H, H | 1 | 1 | H |
| 26 | CH$_2$ | Sgl-cis (8aS, 11aS) | H, H | 1 | 1 | H |
| 102 | CH$_2$ | sgl-cis | H, H | 1 | 1 | —CH$_2$CH$_3$ |
| 103 | CH$_2$ | sgl-cis | H, H | 1 | 1 | n-propyl |
| 104 | CH$_2$ | sgl-cis | H, H | 1 | 1 | n-butyl |
| 105 | CH$_2$ | sgl-cis | H, H | 1 | 1 | —CH$_2$-cyclobutyl |
| 106 | CH$_2$ | sgl-cis | H, H | 1 | 1 | —CH$_2$C=C(CH$_3$)$_2$ |
| 107 | bond | sgl-cis | =O | 1 | 1 | —CH$_2$-phenyl |
| 108 | bond | sgl-cis | =O | 1 | 1 | H |
| 109 | bond | sgl-cis | H, H | 1 | 1 | H |
| 110 | bond | sgl-cis | H, H | 1 | 1 | CH$_3$ |
| 120 | —O—CH$_2$— | sgl-cis | =O | 1 | 1 | —CH$_2$-phenyl |
| 121 | —O—CH$_2$— | sgl-cis | H, H | 1 | 1 | H |
| 122 | —O—CH$_2$— | sgl-cis | H, H | 1 | 1 | CH$_3$ |
| 123 | CH$_2$ | sgl-cis | H, H | 1 | 2 | H |
| 124 | CH$_2$ | sgl-cis | H, H | 2 | 1 | H |

TABLE 1-continued

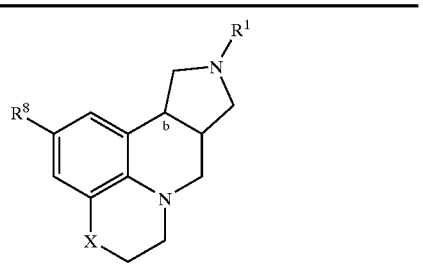

| Ex # | X | b | $R^6$, $R^{6a}$ | n | m | $R^1$ |
|---|---|---|---|---|---|---|
| 125 | CH$_2$ | sgl-cis | H, H | 1 | 2 | CH$_3$ |
| 126 | CH$_2$ | sgl-cis | H, H | 2 | 1 | CH$_3$ |

TABLE 2

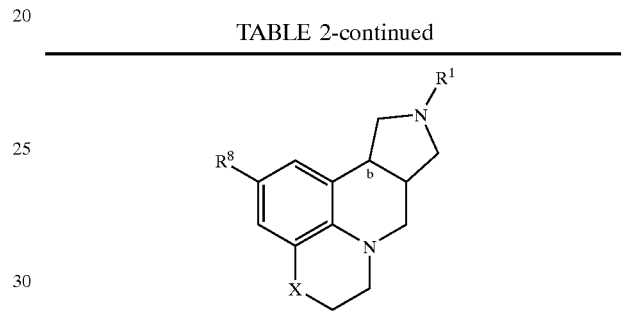

| Ex # | X | b | $R^8$ | $R^1$ |
|---|---|---|---|---|
| 7 | CH$_2$ | sgl-trans | 2-CF$_3$-4-OMe-phenyl | H |
| 14 | CH$_2$ | sgl-cis | 2-CF$_3$-4-OMe-phenyl | H |
| 15 | CH$_2$ | sgl-cis | phenyl | H |
| 16 | CH$_2$ | sgl-cis | phenyl | CH$_3$ |
| 17 | CH$_2$ | sgl-cis | phenyl-NH— | H |
| 18 | CH$_2$ | sgl-cis | (2,4-dichlorophenyl)-NH— | H |
| 19 | CH$_2$ | sgl-cis | (2,5-dichlorophenyl)-NH— | H |
| 20 | CH$_2$ | sgl-cis | 4-SMe-phenyl | H |
| 21 | CH$_2$ | sgl-cis | 2,3-dichlorophenyl | H |
| 22 | CH$_2$ | sgl-cis | 3,4-dimethoxyphenyl | H |
| 23 | CH$_2$ | sgl-cis | 2,5-dichlorophenyl | H |
| 24 | CH$_2$ | sgl-cis | 2-CF$_3$-phenyl | H |
| 27 | CH$_2$ | Sgl-cis (8aR, 11aR) | 2,4-dichlorophenyl | H |
| 28 | CH$_2$ | Sgl-cis (8aR, 11aR) | 2-CH$_3$-4-CN-phenyl | H |
| 29 | CH$_2$ | Sgl-cis (8aR, 11aR) | 2-CH$_3$-phenyl | H |
| 30 | CH$_2$ | Sgl-cis (8aR, 11aR) | 3-CH$_3$-phenyl | H |
| 31 | CH$_2$ | Sgl-cis (8aR, 11aR) | 4-CH$_3$-phenyl | H |
| 32 | CH$_2$ | Sgl-cis (8aR, 11aR) | 2-CHO-4-CH$_3$-phenyl | H |
| 33 | CH$_2$ | Sgl-cis (8aR, 11aR) | 2-CH(OH)CH$_3$-4-CH$_3$-phenyl | H |
| 34 | CH$_2$ | sgl-trans | 2,4-dichlorophenyl | H |
| 35 | CH$_2$ | sgl-trans | 2-CF$_3$-4-(O-iPr)-phenyl | H |
| 36 | CH$_2$ | sgl-trans | 2-CH$_3$-4-OMe-phenyl | H |
| 37 | CH$_2$ | Sgl-cis (8aR, 11aR) | (3,5-bis(trifluoromethyl)phenyl)-NH— | H |
| 38 | CH$_2$ | Sgl-cis (8aR, 11aR) | (4-F-2-CH$_3$-phenyl)-NH— | H |
| 39 | CH$_2$ | Sgl-cis (8aR, 11aR) | (2-Cl-5-CF$_3$-phenyl)-NH— | H |
| 40 | CH$_2$ | Sgl-cis (8aR, 11aR) | (2-F-5-CF$_3$-phenyl)-NH— | H |
| 41 | CH$_2$ | Sgl-cis (8aR, 11aR) | (3-F-5-CF$_3$-phenyl)-NH— | H |
| 42 | CH$_2$ | Sgl-cis (8aR, 11aR) | (3-CF$_3$-phenyl)-NH— | H |
| 43 | CH$_2$ | Sgl-cis (8aR, 11aR) | (2-F-3-CF$_3$-phenyl)-NH— | H |
| 44 | CH$_2$ | Sgl-cis (8aR, 11aR) | (4-Cl-3-CF$_3$-phenyl)-NH— | H |
| 45 | CH$_2$ | Sgl-cis (8aR, 11aR) | (2,3-dichlorophenyl)-NH— | H |
| 46 | CH$_2$ | Sgl-cis (8aR, 11aR) | (3,4-dichlorophenyl)-NH— | H |
| 47 | CH$_2$ | Sgl-cis (8aR, 11aR) | (2,6-dichlorophenyl)-NH— | H |
| 48 | CH$_2$ | Sgl-cis (8aR, 11aR) | (2-Cl-5-CH$_3$-phenyl)-NH— | H |
| 49 | CH$_2$ | Sgl-cis (8aR, 11aR) | (2-CN-phenyl)-NH— | H |
| 50 | CH$_2$ | Sgl-cis (8aR, 11aR) | (2-OMe-5-CH$_3$-phenyl)-NH— | H |
| 51 | CH$_2$ | Sgl-cis (8aR, 11aR) | (3-CN-phenyl)-NH— | H |
| 52 | CH$_2$ | Sgl-cis (8aR, 11aR) | (4-CN-phenyl)-NH— | H |
| 53 | CH$_2$ | Sgl-cis (8aR, 11aR) | (2-CF$_3$-phenyl)-NH— | H |
| 54 | CH$_2$ | Sgl-cis (8aR, 11aR) | (4-CF$_3$-phenyl)-NH— | H |
| 55 | CH$_2$ | Sgl-cis (8aR, 11aR) | (2-F-5-CH$_3$-phenyl)-NH— | H |
| 56 | CH$_2$ | Sgl-cis (8aR, 11aR) | (3-quinolinyl)-NH— | H |
| 57 | CH$_2$ | Sgl-cis (8aR, 11aR) | (2-naphthyl)-NH— | H |
| 58 | CH$_2$ | Sgl-cis (8aR, 11aR) | (1-naphthyl)-NH— | H |
| 59 | CH$_2$ | Sgl-cis (8aR, 11aR) | (2-Cl-pyrid-3-yl)-NH— | H |
| 60 | CH$_2$ | Sgl-cis (8aR, 11aR) | (4-CH$_3$-1-naphthyl)-NH— | H |
| 61 | CH$_2$ | Sgl-cis (8aR, 11aR) | (2-CH$_3$-1-naphthyl)-NH— | H |

TABLE 2-continued

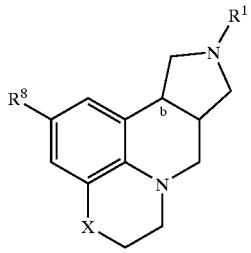

| Ex # | X | b | R8 | R1 |
|---|---|---|---|---|
| 62 | CH2 | Sgl-cis (8aR, 11aR) | (2,3-dimethylphenyl)-NH— | H |
| 63 | CH2 | Sgl-cis (8aR, 11aR) | (3-CH3-phenyl)-NH— | H |
| 64 | CH2 | Sgl-cis (8aR, 11aR) | (2,5-dimethylphenyl)-NH— | H |
| 65 | CH2 | Sgl-cis (8aR, 11aR) | (3,4-dimethylphenyl)-NH— | H |
| 66 | CH2 | Sgl-cis (8aR, 11aR) | (2-OMe-phenyl)-NH— | H |
| 67 | CH2 | Sgl-cis (8aR, 11aR) | (2-F-4-OMe-phenyl)-NH— | H |
| 68 | CH2 | Sgl-cis (8aR, 11aR) | (3,5-dimethylphenyl)-NH— | H |
| 69 | CH2 | Sgl-cis (8aR, 11aR) | (4-F-3-CH3-phenyl)-NH— | H |
| 70 | CH2 | Sgl-cis (8aR, 11aR) | (2-F-4-CH3-phenyl)-NH— | H |
| 71 | CH2 | Sgl-cis (8aR, 11aR) | (4-Cl-3-CH3-phenyl)-NH— | H |
| 72 | CH2 | sgl-trans | (2-Cl-5-CF3-phenyl)-NH— | H |
| 73 | CH2 | sgl-trans | (3,4-dichlorophenyl)-NH— | H |
| 74 | CH2 | sgl-trans | (2,3-dichlorophenyl)-NH— | H |
| 75 | CH2 | sgl-trans | (2,4-dichlorophenyl)-NH— | H |
| 76 | CH2 | sgl-cis | (Phenyl)-CH2—NH— | H |
| 77 | CH2 | sgl-cis | (3,5-dichlorophenyl)-CH2—NH— | H |
| 78 | CH2 | sgl-cis | (2,6-dichlorophenyl)-CH2—NH— | H |
| 79 | CH2 | Sgl-cis (8aR, 11aR) | (2-CF3-phenyl)-CH2—NH— | H |
| 80 | CH2 | Sgl-cis (8aR, 11aR) | (2-F-6-CF3-phenyl)-CH2—NH— | H |
| 81 | CH2 | Sgl-cis (8aR, 11aR) | (2,3-dichlorophenyl)-CH2—NH— | H |
| 82 | CH2 | Sgl-cis (8aR, 11aR) | (2,4-dichlorophenyl)-CH2—NH— | H |
| 83 | CH2 | Sgl-cis (8aR, 11aR) | (3,4-dichlorophenyl)-CH2—NH— | H |
| 84 | CH2 | Sgl-cis (8aR, 11aR) | (2,3-dimethoxyphenyl)-CH2—NH— | H |
| 85 | CH2 | Sgl-cis (8aR, 11aR) | (3,4-dimethoxyphenyl)-CH2—NH— | H |
| 86 | CH2 | Sgl-cis (8aR, 11aR) | (2-OMe-phenyl)-CH2—NH— | H |
| 87 | CH2 | Sgl-cis (8ar, 11aR) | (2-CH3-phenyl)-CH2—NH— | H |
| 88 | CH2 | Sgl-cis (8ar, 11aR) | (4-F-2-CF3-phenyl)-CH2—NH— | H |
| 89 | CH2 | Sgl-cis (8aR, 11aR) | (2,3-dimethylphenyl)-CH2—NH— | H |
| 90 | CH2 | Sgl-cis (8aR, 11aR) | (2,4-bis(trifluoromethyl)phenyl)-CH2—NH— | H |
| 91 | CH2 | Sgl-cis (8aR, 11aR) | (2,5-bis(trifluoromethyl)phenyl)-CH2—NH— | H |
| 92 | CH2 | Sgl-cis (8aR, 11aR) | (3-CF3-phenyl)-CH2—NH— | H |
| 93 | CH2 | Sgl-cis (8aR, 11aR) | (4-CF3-phenyl)-CH2—NH— | H |
| 94 | CH2 | Sgl-cis (8aR, 11aR) | (2-SMe-phenyl)-CH2—NH— | H |
| 95 | CH2 | Sgl-cis (8aR, 11aR) | (2-OCF3-phenyl)-CH2—NH— | H |

TABLE 2-continued

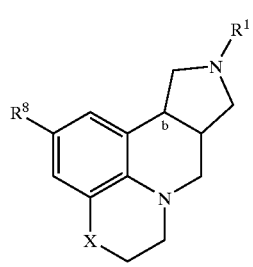

| Ex # | X | b | R8 | R1 |
|---|---|---|---|---|
| 96 | CH2 | Sgl-cis (8aR, 11aR) | (phthalimido group) | H |
| 97 | CH2 | Sgl-cis (8aR, 11aR) | (isoindoline group) | H |
| 98 | CH2 | Sgl-cis (8aR, 11aR) | (isoquinoline-1,3-dione group) | H |
| 99 | CH2 | Sgl-cis (8aR, 11aR) | (tetrahydroisoquinoline group) | H |
| 100 | CH2 | Sgl-cis (8aR, 11aR) | Phenyl-CO—NH— | H |
| 101 | CH2 | Sgl-cis (8aR, 11aR) | Phenyl-SO2—NH— | H |
| 111 | bond | sgl-cis | 2-CF3-4-OMe-phenyl | H |
| 112 | bond | sgl-cis | 2,4-dichlorophenyl | H |
| 113 | bond | sgl-cis | (2,4-dichlorophenyl)-NH— | H |
| 114 | bond | sgl-cis | (2-Cl-5-CF3-phenyl)-NH— | H |
| 115 | bond | sgl-cis | (2-F-5-CF3-phenyl)-NH— | H |
| 116 | bond | sgl-cis | Phenyl-NH— | H |
| 117 | bond | sgl-cis | (2-Cl-5-CH3-phenyl)-NH— | H |
| 118 | bond | sgl-cis | (Phenyl)-CH2—NH— | H |
| 119 | bond | sgl-cis | (2-CF3-phenyl)-CH2—NH— | H |
| 131 | CH2 | Sgl-cis (8aR, 11aR) | (5-Cl-2-CN-phenyl)-NH— | H |
| 132 | CH2 | Sgl-cis (8aR, 11aR) | (3-F-2-CN-phenyl)-NH— | H |

TABLE 3

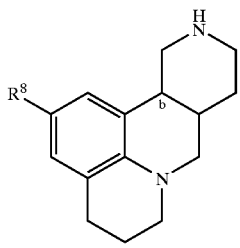

| Ex # | b | R8 |
|---|---|---|
| 127 | sgl-cis | phenyl |
| 128 | sgl-cis | 2,4-dichlorophenyl |
| 129 | sgl-cis | 2-CF$_3$-4-OMe-phenyl |
| 130 | sgl-cis | 2,6-dichlorophenyl |

UTILITY

The compounds of the present invention have therapeutic utility for illnesses or disorders involving the neurotransmitter serotonin (5-hydroxy tryptamine or 5-HT) and either agonism or antagonism of 5-HT2 receptors, as demonstrated by the assays described below. Therapeutic utility for these illnesses or disorders could involve numerous biological processes affected by serotonin including, but not limited to, appetite, mood, sleep, sexual activity, and arterial constriction. These biological processes may also be important to numerous central nervous system (CNS) disorders including those related to the affective disorders of depression, anxiety, psychosis, and schizophrenia, as well as, disorders of food intake such as anorexia, bulemia, and obesity. The compounds of the present invention potentially have therapeutic utility in other conditions in which serotonin has been implicated, such as migraine, attention deficit disorder or attention deficit hyperactivity disorder, addictive behavior, and obsessive-compulsive disorder, as well as, conditions associated with cephalic pain, social phobias, and gastrointestinal disorders such as dysfunction of the gastrointestinal tract motility. Lastly, compounds of the present invention potentially have therapeutic utility in neurodegenerative diseases and traumatic conditions represented by the examples of Alzheimer's disease and brain/spinal cord trauma.

The pharmacological analysis of each compound for either antagonism or agonism of at 5-HT2A and 5-HT2C receptors consisted of in vitro and in vivo studies. In vitro analyses included $K_i$ determinations at 5-HT2A and 5-HT2C receptors and an assessment of functional (i.e., agonism or antagonism) activity at each receptor class by IP3 hydrolysis assays. Additional receptor assays were conducted to evaluate receptor specificity of 5-HT2A and 5-HT2C receptors over monoamine and nuisance receptors (e.g. histamine, dopamine, and muscarinic). A compound is considered active as a 5-HT2A antagonist or a 5-HT2C agonist if it has an $IC_{50}$ value or a $K_i$ value of less than about 50 micromolar; preferably less than about 0.1 micromolar; more preferably less than about 0.01 micromolar. Using the assays disclosed herein, compounds of the present invention have been shown to have an $IC_{50}$ value of less than about 50 micromolar for 5-HT2A antagonism or 5-HT2C agonism.

In vivo assays assessed compound activity in a variety of behavioral paradigms including quipazine head twitch, acute and chronic feeding models, anxiety and depression models (learned-helplessness, elevated plus maze, Geller-Siefter, conditioned taste aversion, taste reactivity, satiety sequence). In aggregate, these models reflect activity as a 5-HT2A antagonist (quipazine head twitch, depression models) or 5-HT2C agonist (feeding models, anxiety models, depression models) and provide some indication as to bioavailability, metabolism and pharmacokinetics.

Radioligand binding experiments were conducted on recombinant human 5-HT2A and 5-HT2C receptors expressed in HEK293E cells. The affinities of compounds of the present invention to bind at these receptors is determined by their capacity to compete for [$^{125}$I]-1-(2,5-dimethoxy-4-iodophenyl)-2-amino-propane (DOI) binding at the 5-HT2A or 5-HT2C. General references for binding assays include 1) Lucaites V L, Nelson D L, Wainscott D B, Baez M (1996) Receptor subtype and density determine the coupling repertoire of the 5-HT2 receptor subfamily. Life Sci., 59(13):1081–95. J Med Chem 1988 Jan;31(1):5–7; 2) Glennon R A, Seggel M R, Soine W H, Herrick-Davis K, Lyon R A, Titeler M (1988) [125I]-1-(2,5-dimethoxy-4-iodophenyl)-2-amino-propane: an iodinated radioligand that specifically labels the agonist high-affinity state of 5-HT2 serotonin receptors. J. Med. Chem. 31(1):5–7 and 3) Leonhardt S, Gorospe E, Hoffman B J, Teitler M (1992) Molecular pharmacological differences in the interaction of serotonin with 5-hydroxytryptamine1C and 5-hydroxytryptamine2 receptors. Mol Pharmacol., 42(2):328–35.

The functional properties of compounds (efficacy and potency) were determined in whole cells expressing 5-HT2A or 5-HT2C receptors by assessing their ability to stimulate or inhibit receptor-mediated phosphoinositol hydrolysis. The procedures used are described below.

In Vitro Binding Assays

Stable Expression of 5-HT2A and 5-HT2C Receptors in HEK293E Cells

Stable cell lines were generated by transfecting 293EBNA cells with plasmids containing human 5-HT2A, 5-HT2B, or 5-HT2C (VNV edited isoform) cDNA using calcium phosphate. These plasmids also contained the cytomegalovirus (CMV) immediate early promoter to drive receptor expression and EBV oriP for their maintenance as an extrachromosomal element, and the hph gene from *E. Coli* to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% CO$_2$) for 10 days. The 5-HT2A cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation

On the day of assay, pellets of whole cells (containing approximately 1×108 cells) expressing the 5-HT2A or 5-HT2C receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000× g for 10 min and the resulting pellet washed twice by repeated homogenization and centrifugation steps. The final pellet was resuspended in tissue buffer and protein determinations were made by the bichichoninic acid (BCA) assay (Pierce Co., IL) using bovine serum albumin as the standard.

Radioligand Binding Assays for the 5-HT2A, and 5-HT2C Receptors.

Radioligand binding studies were conducted to determine the binding affinities (KI values) of compounds for the human recombinant 5-HT2A, 5-HT2B, and 5-HT2C receptors (Fitzgerald et al., 1999). Assays were conducted in disposable polypropylene 96-well plates (Costar Corp., Cambridge, Mass.) and were initiated by the addition of 5-HT2A, 5-HT2B, or 5-HT2C membrane homogenate in tissue buffer (10–30 (g/well) to assay buffer (50 mM Tris HCl, 0.5 mM EDTA, 10 mM pargyline, 10 mM $MgSO_4$, 0.05% ascorbic acid, pH 7.5) containing [$^{125}$I]DOI for the 5-HT2A and 5-HT2C receptors (0.3–0.5 nM, final) or [$^3$H] LSD (2–2.5 nM, final) for the 5-HT2B receptor, with or without competing drug (i.e, newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (cell harvestor; Inotech Biosystems Inc., Lansing, Mich.) over GFF glass-fiber filters that had been pre-soaked in 0.3% polyethyleneimine. Filters were washed in ice-cold 50 mM Tris HCl buffer (pH 7.5) and then counted in a gamma counter for the 5-HT2A and 5-HT2C assays, or by liquid scintillation spectroscopy for the 5-HT2B assay.

Phosphoinositide Hydrolysis Studies.

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT2A, 5-HT2B, or 5-HT2C receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 (g/ml hygromycin B, and 250 (g/ml G418. Following a 24–48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H]inositol for 16–18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AGI-X8 resin), and counted by liquid scintillation spectroscopy as described previously (Egan et al., 1998).

Data Analyses

The equilibrium apparent dissociation constants (Ki's) from the competition experiments were calculated using an iterative nonlinear regression curve-fitting program (GraphPad Prism; San Diego, Calif.). For the PI hydrolysis experiments, EC50's were calculated using a one-site 'pseudo' Hill model: y=((Rmax−Rmin)/(1+R/EC50)nH))+ Rmax where R=response (DeltaGraph, Monterey, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

In Vivo Experiments for Serotonergic Ligands.

Preclinical Efficacy, Potency, and Side Effect Liability.

a) Anti-Serotonin Efficacy.

Antagonism of Quipazine-Induced Head Twitch in Rat. Quipazine, an agonist at 5-HT receptors, produces a characteristic head twitch response in rats. 5-HT receptor antagonists effectively antagonize this 5-HT agonist-induced behavioral effect (Lucki et al., 1984). Accordingly, the quipazine-induced head twitch model in rat can function as an in vivo behavioral correlate to 5-HT receptor binding. Compounds are administered 30 minutes before behavioral testing (and 25 minutes before quipazine), and a dose-related antagonism of the quipazine response is determined.

b) Antipsychotic Efficacy.

Inhibition of the Conditioned Avoidance Response (CAR) in Rat. Rats are trained to consistently avoid (by climbing onto a pole suspended from the ceiling of the test chamber) an electric foot shock (0.75 mA) delivered to the grid floor of the testing chamber. All antipsychotic drugs effectively inhibit this conditioned avoidance response (Arnt, 1982). The ability of a compound to inhibit this response is used to determine the antipsychotic efficacy of potential drug candidates.

c) Extrapyramidal Side Effect Liability.

Induction of Catalepsy in Rat. Typical antipsychotic drugs produce extrapyramidal side effects (EPS) at clinically effective doses. The most widely accepted preclinical indicator of EPS liability in humans is a drug-induced catalepsy syndrome in rat (Costall and Naylor, 1975), a condition whereby the animal will remain immobile in an externally imposed posture (analogous to a catatonic stupor in humans). Rats are tested for induction of catalepsy in a dose-response test after oral administration of compounds.

d) CNS Penetration; In vivo Brain Receptor Occupancy.

In Vivo Binding. To determine the level of in vivo receptor occupancy, an in vivo receptor binding protocol is used. This procedure uses an appropriate radioligand to label the receptor of interest. For example, to measure both Dopamine D2 and 5-HT2A receptors in vivo, one can use $^3$H-N-methyl spiperone ($^3$H-NMSP), (Frost, et. al. 1987) The procedure uses rats (or mice) fasted overnight. To measure the effects of compounds on the receptors of interest, compounds are dosed, usually p.o. for example in 2 microliters/gram body weight in 0.25% Methocel suspension. The radiolabeled compound (in this example, 3H-NMSP) is administered by i.v. tail vein injection (10 microcuries label/200 gram rat). Time course experiments are used to determine the optimal time of binding for both the radiolabeled and unlabeled compound. These optimal time frames are used for all subsequent dose-response experiments. After the appropriate time frame of compound/ radioligand exposure, the animals are sacrificed and the relevant brain regions dissected (frontal cortex for 5-HT2A and striatum for D2 receptors) and examined for their content of radioactivity. The level of non-specific binding is determined by examining a brain region known not to contain the receptor of interest (in this case the cerebellum) or by administering an excess of compound known pharmacologically to interact with the receptor.

REFERENCES

Arnt, J. Acta Pharmacol. et Toxicol. 1982: 51, 321–329.
Berridge M. J., Downes P. C. , Hanley M. R. (1982) Lithium amplifies agonist-dependent phosphotidyinositol response in brain and salivary glands. Biochem. J., 206, 587–595.
Costall, B and Naylor, R J. Psychopharmacology. 1975: 43, 69–74.
Egan C. T., Herrick-Davis K., Miller K., Glennon R. A., and Teitlier M. (1998) Agonist activity of LSD and lisuride at cloned 5-HT2A and 5-HT2C receptors. Psychopharmacology, 136, 409–414.
Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT2A and 5-HT2C receptors: evidence favoring the ternary complex and two-state models of agonist action. J. Neurochem., 72, 2127–2134.

Frost, J. J., Smith, A. C., Kuhar, M. J., Dannals, R. F., Wagner, H. N., 1987, In Vivo Binding of 3H-N-Methylspiperone to Dopamine and Serotonin Receptors. Life Sciences, 40:987–995.

Horlick, R. A., Sperle, K., Breth, L. A., Reid, C. C., Shen, E. S., Robbinds, A. K:, Cooke, G. M., Largent, B. L. (1997) Rapid Generation of stable cell lines expressing corticotrophin-releasing hormone receptor for drug discovery. Protein Expr. Purif. 9, 301–308.

Lucki, I, Nobler, M. S., Frazer, A., 1984, Differential actions of serotonin antagonists on two behavioral models of serotonin receptor activation in the rat. J. Pharmacol. Exp. Ther. 228(1):133–139.

Dosage and Formulation

The serotonin agonist and serotonin antagonist compounds of this invention can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in *Remington's Pharmaceutical Sciences*, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly-used techniques.

What is claimed is:

1. A compound of the formula (I):

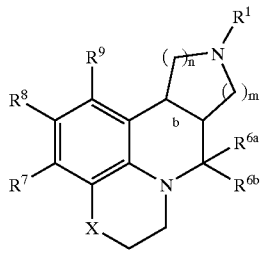

or a stereoisomer or a pharmaceutically acceptable salt form thereof, wherein:
b is a single bond wherein the bridging hydrogens are either cis or trans;
X is —CH$_2$—
R$^1$ is selected from
H,
C(=O)R$^2$,
C(=O)OR$^2$,
C$_{1-8}$ alkyl,
C$_{2-8}$ alkenyl,
C$_{2-8}$ alkynyl,
C$_{3-7}$ cycloalkyl,
C$_{1-6}$ alkyl substituted with Z,
C$_{2-6}$ alkenyl substituted with Z,
C$_{2-6}$ alkynyl substituted with Z,
C$_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
C$_{1-3}$ alkyl substituted with Y,
C$_{2-3}$ alkenyl substituted with Y,
C$_{2-3}$ alkynyl substituted with Y,
C$_{1-6}$ alkyl substituted with 0–2 R$^2$,
C$_{2-6}$ alkenyl substituted with 0–2 R$^2$,
C$_{2-6}$ alkynyl substituted with 0–2 R$^2$, aryl substituted with 0–2 R$^2$, and
5–6 membered heterocyclic ring system containing at least one heteroatom selected from the group consisting of N, O, and S, said heterocyclic ring system substituted with 0–2 R$^2$;
Y is selected from
C$_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
C$_{3-6}$ cycloalkyl substituted with —(C$_{1-3}$ alkyl)-Z,
aryl substituted with —(C$_{1-3}$ alkyl)-Z, and
5–6 membered heterocyclic ring system containing at least one heteroatom selected from the group consisting of N, O, and S, said heterocyclic ring system substituted with —(C$_{1-3}$ alkyl)-Z;
Z is selected from H,
—CH(OH)R$^2$,
—C(ethylenedioxy)R$^2$,
—SR$^2$,
—NR$^2$R$^3$,
—C(O)R$^2$,
—C(O)NR$^2$R$^3$,
—NR$^3$C(O)R$^2$,
—C(O)OR$^2$,
—OC(O)R$^2$,
—CH(=NR$^4$)NR$^2$R$^3$,
—NHC(=NR$^4$)NR$^2$R$^3$,
—S(O)R$^2$,
—S(O)$^2$R$^2$,
—S(O)$_2$NR$^2$R$^3$, and —NR$^3$S(O)$_2$R$^2$;
R$^2$, at each occurrence, is independently selected from
halo,
C$_{1-3}$ haloalkyl,
C$_{1-4}$ alkyl,
C$_{2-4}$ alkenyl,
C$_{2-4}$ alkynyl,
C$_{3-6}$ cycloalkyl,
aryl substituted with 0–5 R$^{42}$;
C$_{3-10}$ carbocyclic residue substituted with 0–3 R$^{41}$, and
5–10 membered heterocyclic ring system containing from 1–4 heteroatoms selected from the group consisting of N, O, and S substituted with 0–3 R$^{41}$;
R$^3$, at each occurrence, is independently selected from
H, C$_{1-4}$ alkyl, C$_{2-4}$ alkenyl, C$_{2-4}$ alkynyl, and
C$_{1-4}$ alkoxy;
R$^4$, at each occurrence, is independently selected from H and C$_{1-4}$ alkyl;
R$^{6a}$ is H or C$_{1-4}$ alkyl;
R$^{6b}$ is H;
alternatively, R$^{6a}$ and R$^{6b}$ are taken together to form =O or =S;
R$^7$ and R$^9$, at each occurrence, are independently selected from
H, halo, —CF$_3$, —OCF$_3$, —OH, —CN, —NO$_2$, —NR$^{46}$R$^{47}$,
C$_{1-8}$ alkyl, C$_{2-8}$ alkenyl, C$_{2-8}$ alkynyl, C$_{1-4}$ haloalkyl, C-$_{1-8}$ alkoxy, (C$_{1-4}$ haloalkyl)oxy,
C$_{3-10}$ cycloalkyl substituted with 0–2 R$^{33}$,
C$_{1-4}$ alkyl substituted with 0–2 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)$_2$R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;
R$^8$ is selected from
H, halo, —CF$_3$, —OCF$_3$, —OH, —CN, —NO$_2$,
C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
C$_{3-10}$ cycloalkyl substituted with 0–2 R$^{33}$,
C$_{1-4}$ alkyl substituted with 0–2 R$^{11}$,
C$_{2-4}$ alkenyl substituted with 0–2 R$^{11}$,
C$_{2-4}$ alkynyl substituted with 0–1 R$^{11}$,
C$_{3-10}$ carbocyclic residue substituted with 0–3 R$^{33}$,
aryl substituted with 0–5 R$^{33}$,
5–10 membered heterocyclic ring system containing from 1–4 heteroatoms selected from the group consisting of N, O, and S substituted with 0–3 R$^{31}$;
OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$ $NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{10}$ is selected from H,
$C_{1-4}$ alkyl substituted with 0–2 $R^{10A}$,
$C_{2-4}$ alkenyl substituted with 0–2 $R^{10A}$,
$C_{2-4}$ alkynyl substituted with 0–1 $R^{10A}$, and
$C_{1-4}$ alkoxy;

$R^{10A}$ is selected from
$C_{1-4}$ alkoxy,
$C_{3-6}$ carbocyclic residue substituted with 0–3 $R^{33}$,
phenyl substituted with 0–3 $R^{33}$, and
5–6 membered heterocyclic ring system containing 1, 2, or 3 heteroatoms selected from the group consisting of N, O, and S; substituted with 0–2 $R^{44}$;

$R^{11}$ is selected from
H, halo, —$CF_3$, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from
H, $C_{1-4}$ alkyl, $C_{2-4}$ alkenyl, and $C_{2-4}$ alkynyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from
H, OH, halo, CN, $NO_2$, $CF_3$, $SO_2R^{45}$, $NR^{46}R^{47}$,
—$C(=O)H$,
$C_{1-4}$ alkyl, $C_{2-4}$ alkenyl, $C_{2-4}$ alkynyl, $C_{1-4}$ haloalkyl, $C_{1-3}$ haloalkyl-oxy-, $C_{1-3}$ alkyloxy-, and =O;

$R^{31}$, at each occurrence, is independently selected from H, OH, halo, $CF_3$, $SO_2R^{45}$, $NR^{46}R^{47}$, $C_{1-4}$ alkyl, and =O;

$R^{33}$, at each occurrence, is independently selected from
H, OH, halo, CN, $NO_2$, $CF_3$, $SO_2R^{45}$, $NR^{46}R^{47}$,
—$C(=O)H$, =O, phenyl, $C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-$C(=O)$—,
$C_{1-4}$ alkyl-$C(=O)NH$—, $C_{1-4}$ alkyl-$OC(=O)$—,
$C_{1-4}$ alkyl-$C(=O)O$—, $C_{3-6}$ cycloalkyl-oxy-,
$C_{3-6}$ cycloalkylmethyloxy-;
$C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—; and
$C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—;

$R^{41}$, at each occurrence, is independently selected from
H, $CF_3$, halo, OH, $CO_2H$, $SO_2R^{45}$, $NR^{46}R^{47}$, $NO_2$, CN, =O;
$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SOR^{45}$, $SR^{45}$, $NR^{46}SO_2R^{45}$, $NR^{46}COR^{45}$, $NR^{46}R^{47}$, $NO_2$, CN, $CH(=NH)NH_2$, $NHC(=NH)NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H, $C_{1-4}$ alkyl, —$C(=O)NH(C_{1-4}$ alkyl), —$SO_2(C_{1-4}$ alkyl), —$C(=O)O(C_{1-4}$ alkyl), —$C(=O)(C_{1-4}$ alkyl), and —$C(=O)H$;

n is 1 or 2;

m is 1 or 2; and n plus m is 2, 3, or 4.

2. A compound of claim 1 wherein:

$R^1$ is selected from
H,
$C(=O)R^2$,
$C(=O)OR^2$,
$C_{1-8}$ alkyl,
$C_{2-8}$ alkenyl,
$C_{2-8}$ alkynyl,
$C_{3-7}$ cycloalkyl,
$C_{1-6}$ alkyl substituted with 0–2 $R^2$,
$C_{2-6}$ alkenyl substituted with 0–2 $R^2$,
$C_{2-6}$ alkynyl substituted with 0–2 $R^2$,
aryl substituted with 0–2 $R^2$, and 5–6 membered heterocyclic ring system containing at least one heteroatom selected from the group consisting of N, O, and S, said heterocyclic ring system substituted with 0–2 $R^2$;

$R^2$, at each occurrence, is independently selected from
F, Cl, $CH_2F$, $CHF_2$, $CF_3$,
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^{6a}$ is H or $C_{1-4}$ alkyl;

$R^{6b}$ is H;

alternatively, $R^{6a}$ and $R^{6b}$ are taken together to form =O or =S;

$R^7$ and $R^9$, at each occurrence, are independently selected from
H, halo, —$CF_3$, —$OCF_3$, —OH, —CN, —$NO_2$, —$NR^{46}R^{47}$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^8$ is selected from
H, halo, —$CF_3$, —$OCF_3$, —OH, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{10}$ is selected from H, $C_{1-4}$ alkyl, $C_{2-4}$ alkenyl, $C_{2-4}$ alkynyl, and $C_{1-4}$ alkoxy;

$R^{11}$ is selected from
H, halo, —$CF_3$, —CN, —$NO_2$,
$C_{1-8}$ alkyl, $C_{2-8}$ alkenyl, $C_{2-8}$ alkynyl, $C_{1-4}$ haloalkyl, $C_{1-8}$ alkoxy, $C_{3-10}$ cycloalkyl
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, $C(O)H$, $C(O)R^{12}$, $C(O)NR^{12}R^{13}$, $NR^{14}C(O)R^{12}$, $C(O)OR^{12}$, $OC(O)R^{12}$, $OC(O)OR^{12}$, $CH(=NR^{14})NR^{12}R^{13}$, $NHC(=NR^{14})NR^{12}R^{13}$, $S(O)R^{12}$, $S(O)_2R^{12}$, $S(O)NR^{12}R^{13}$, $S(O)_2NR^{12}R^{13}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{12}$, at each occurrence, is independently selected from
$C_{1-4}$ alkyl substituted with 0–1 $R^{12a}$;
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$, $R^{14}$, at each occurrence, is independently selected from H and $C_{1-4}$ alkyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, halo, CN, $NO_2$, $CF_3$, $SO_2R^{45}$, $NR^{46}R^{47}$, —$C(=O)H$,
$C_{1-4}$ alkyl, $C_{2-4}$ alkenyl, $C_{2-4}$ alkynyl, $C_{1-4}$ haloalkyl, $C_{1-3}$ haloalkyl-oxy-, $C_{1-3}$ alkyloxy-, and =O;

$R^{31}$, at each occurrence, is independently selected from H, OH, halo, $CF_3$, $SO_2R^{45}$, $NR^{46}R^{47}$, $C_{1-4}$ alkyl, and =O;

$R^{33}$, at each occurrence, is independently selected from H, OH, halo, CN, $NO_2$, $CF_3$, $SO_2R^{45}$, $NR^{46}R^{47}$, —$C(=O)H$, =O, phenyl, $C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—,
$C_{1-4}$ alkyl-C(=O)NH—, $C_{1-4}$ alkyl-OC(=O)—,
$C_{1-4}$ alkyl-C(=O)O—, $C_{3-6}$ cycloalkyl-oxy-,
$C_{3-6}$ cycloalkylmethyl-oxy-;
$C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—; and
$C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or ($C_{1-4}$ alkyl)$CO_2$—;

$R^{41}$, at each occurrence, is independently selected from H, $CF_3$, halo, OH, $CO_2H$, $SO_2R^{45}$, $NR^{46}R^{47}$, $NO_2$, CN;

$C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$; halo, OH, $CO_2H$, $SO_2R^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

n is 1 or 2;

m is 1 or 2; and n plus m is 2, 3, or 4.

3. A compound of claim 2 wherein:

$R^1$ is selected from
H,
C(=O) $R^2$,
C(O)$OR^2$,
$C_{1-6}$ alkyl,
$C_{2-6}$ alkenyl,
$C_{2-6}$ alkynyl,
$C_{3-6}$ cycloalkyl,
$C_{1-4}$ alkyl substituted with 0–2 $R^2$,
$C_{2-4}$ alkenyl substituted with 0–2 $R^2$, and
$C_{2-4}$ alkynyl substituted with 0–2 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^{6a}$ is H or $C_{1-4}$ alkyl;

$R^{6b}$ is H;

alternatively, $R^{6a}$ and $R^{6b}$ are taken together to form =O or =S;

$R^7$ and $R^9$, at each occurrence, are independently selected from
H, halo, —$CF_3$, —$OCF_3$, —OH, —CN, —$NO_2$, —$NR^{46}R^{47}$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, and $NR^{14}$S(O)$_2R^{12}$;

$R^8$ is selected from
H, halo, —$CF_3$, —$OCF_3$, —OH, —CN, —$NO_2$,
$C_{1-6}$ alkyl, $C_{2-6}$ alkenyl, $C_{2-6}$ alkynyl, $C_{1-6}$ haloalkyl, $C_{1-6}$ alkoxy, ($C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}$C(O)$R^{12}$, C(O)$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$S(O)$_2R^{12}$, S(O)$NR^{12}R^{13}$, S(O)$_2NR^{12}R^{13}$, $NR^{14}$S(O)$R^{12}$, $NR^{14}$, $NR^{12}$C(O)$R^{15}$, $NR^{12}$C(O)$OR^{15}$, $NR^{12}$S(O)$_2R^{15}$, and $NR^{12}$C(O)$NHR^{15}$;

$R^{11}$ is selected from
H, halo, —$CF_3$, —CN, —$NO_2$, $C_{1-6}$ alkyl,
$C_{2-6}$ alkenyl, $C_{2-6}$ alkynyl, $C_{1-4}$ haloalkyl, $C_{1-6}$ alkoxy, $C_{3-10}$ cycloalkyl,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O) C(O)$R^{12}$, C(O)$NR^{12}R^{13}$, $NR^{14}$C(O)$R^{12}$, C())$OR^{12}$, OC(O)$R^{12}$, OC(O)$OR^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$NR^{12}R^{13}$, S(O)$_2NR^{12}R^{13}$, $NR^{14}$S(O)$R^{12}$, and $NR^{14}$S(O)$_2R^{12}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S, wherein said bicyclic heterocyclic ring system is unsaturated or partially saturated, wherein said bicyclic heterocyclic ring system is substituted with 0–3 $R^{16}$;

$R^{14}$, at each occurrence, is independently selected from H, methyl, ethyl, propyl, and butyl;

$R^{15}$, at each occurrence, is independently selected from H, $C_{1-4}$ alkyl, $C_{2-4}$ alkenyl, and $C_{2-4}$ alkynyl;

$R^{16}$, at each occurrence, is independently selected from H, OH, F, Cl, CN, $NO_2$, $CF_3$, $SO_2R^{45}$, $NR^{46}R^{47}$, —C(=O)H,
methyl, ethyl, methoxy, ethoxy, trifluoromethyl, trifluoromethoxy, and =O;

$R^{31}$, at each occurrence, is independently selected from H, OH, halo, $CF_3$, $SO_2R^{45}$, $NR^{46}R^{47}$, $C_{1-4}$ alkyl, and =O;

$R^{33}$, at each occurrence, is independently selected from H, OH, halo, CN, $NO_2$, $CF_3$, $SO_2R^{45}$, $NR^{46}R^{47}$, —C(=O)H, =O, phenyl, $C_{1-6}$ alkyl, $C_{2-6}$ alkenyl, $C_{2-6}$ alkynyl,
$C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{2-6}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;
$C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or $(C_{1-4}$ alkyl$)CO_2$—; and
$C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or $(C_{1-4}$ alkyl$)CO_2$—;

$R^{41}$, at each occurrence, is independently selected from H, $CF_3$, halo, OH, $CO_2H$, $SO_2R^{45}$, $NR^{46}R^{47}$, $NO_2$, CN, $C_{2-8}$ alkenyl, $C_{2-8}$ alkynyl, $C_{1-4}$ alkoxy, $C_{1-4}$ haloalkyl
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl, $C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-4}$ alkyl;

$R^{47}$, at each occurrence, is independently selected from H and $C_{1-4}$ alkyl;

n is 1 or 2;

m is 1 or 2; and n plus m is 2, 3, or 4.

4. A compound of claim 2 wherein:

$R^1$ is selected from
H,
$C_{1-4}$ alkyl,
$C_{2-4}$ alkenyl,
$C_{2-4}$ alkynyl,
$C_{3-4}$ cycloalkyl,
$C_{1-3}$ alkyl substituted with 0–1 $R^2$,
$C_{2-3}$ alkenyl substituted with 0–1 $R^2$, and
$C_{2-3}$ alkynyl substituted with 0–1 $R^2$;

$R^2$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{42}$;
$C_{3-6}$ carbocyclic residue substituted with 0–3 $R^{41}$, and
5–6 membered heterocyclic ring system containing 1, 2, or 3 heteroatoms selected from the group consisting of N, O, and S substituted with 0–3 $R^{41}$;

$R^{6a}$ is H, methyl, ethyl, propyl, or butyl;

$R^{6b}$ is H;

alternatively, $R^{6a}$ and $R^{6b}$ are taken together to form =O or =S;

$R^7$ and $R^9$, at each occurrence, are independently selected from
H, halo, —$CF_3$, —$OCF_3$, —OH, —CN, —$NO_2$, —$NR^{46}R^{47}$,
$C_{1-4}$ alkyl, $C_{2-4}$ alkenyl, $C_{2-4}$ alkynyl, $C_{1-4}$ haloalkyl, $C_{1-4}$ alkoxy, $(C_{1-4}$ haloalkyl)oxy,
$C_{3-10}$ cycloalkyl substituted with 0–2 $R^{33}$,
$C_{1-4}$ alkyl substituted with 0–2 $R^{11}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^8$ is selected from
H, halo, —$CF_3$, —$OCF_3$, —OH, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, $(C_{1-4}$ haloalkyl)oxy,
$C_{3-16}$ cycloalkyl substituted with 0–2 $R^{33}$,
$C_{1-4}$ alkyl substituted with 0–2 $R^{11}$,
$C_{2-4}$ alkenyl substituted with 0–2 $R^{11}$,
$C_{2-4}$ alkynyl substituted with 0–1 $R^{11}$,
$C_{3-10}$ carbocyclic residue substituted with 0–3 $R^{33}$,
aryl substituted with 0–5 $R^{33}$,
5–6 membered heterocyclic ring system containing 1, 2, or 3 heteroatoms selected from the group consisting of N, O, and S substituted with 0–3 $R^{31}$;
$OR^{12}$, $SR^{12}$, $NR^{12}R^{13}$, $NR^{12}C(O)R^{15}$, $NR^{12}C(O)OR^{15}$, $NR^{12}S(O)_2R^{15}$, $NR^{12}C(O)NHR^{15}$, $NR^{14}C(O)R^{12}$, $NR^{14}C(O)OR^{12}$, and $NR^{14}S(O)_2R^{12}$;

$R^{11}$ is selected from
H, halo, —$CF_3$, —CN, —$NO_2$,
$C_{1-4}$ alkyl, $C_{2-4}$ alkenyl, $C_{2-4}$ alkynyl, $C_{1-4}$ haloalkyl, $C_{1-4}$ alkoxy, $(C_{1-4}$ haloalkyl)oxy,
$C_{3-10}$ cycloalkyl substituted with 0–2 $R^{33}$,
$C_{3-10}$ carbocyclic residue substituted with 0–3 $R^{33}$,
aryl substituted with 0–5 $R^{33}$, and
5–6 membered heterocyclic ring system containing 1, 2, or 3 heteroatoms selected from the group consisting of N, O, and S substituted with 0–3 $R^{31}$;

$R^{12}$, at each occurrence, is independently selected from
$C_{1-4}$ alkyl substituted with 0–1 $R^{12a}$,
$C_{2-4}$ alkenyl substituted with 0–1 $R^{12a}$,
$C_{2-4}$ alkynyl substituted with 0–1 $R^{12a}$,
$C_{3-6}$ cycloalkyl substituted with 0–3 $R^{33}$,
aryl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{12a}$, at each occurrence, is independently selected from
  phenyl substituted with 0–5 $R^{33}$;
  $C_{3-10}$ carbocyclic residue substituted with 0–3 $R^{33}$, and
  5–10 membered heterocyclic ring system containing
    from 1–4 heteroatoms selected from the group consisting of N, O, and S substituted with 0–3 $R^{31}$;
$R^{13}$, at each occurrence, is independently selected from
  H, $C_{1-4}$ alkyl, $C_{2-4}$ alkenyl, and $C_{2-4}$ alkynyl;
alternatively, $R^{12}$ and $R^{13}$ when attached to N may be combined to form a 9- or 10-membered bicyclic heterocyclic ring system containing from 1–3 heteroatoms selected from the group consisting of one N, two N, three N, one N one O, and one N one S; wherein said bicyclic heterocyclic ring system is unsaturated or partially saturated, wherein said bicyclic heterocyclic ring system is substituted with 0–2 $R^{16}$;
$R^{14}$, at each occurrence, is independently selected from H, methyl, ethyl, propyl, and butyl;
$R^{15}$, at each occurrence, is independently selected from H, methyl, ethyl, propyl, and butyl;
$R^{16}$, at each occurrence, is independently selected from H, OH, F, Cl, CN, $NO_2$, methyl, ethyl, methoxy, ethoxy, trifluoromethyl, and trifluoromethoxy;
$R^{31}$, at each occurrence, is independently selected from H, OH, halo, $CF_3$, methyl, ethyl, and propyl;
$R^{33}$, at each occurrence, is independently selected from
  H, OH, halo, CN, $NO_2$, $CF_3$, $SO_2R^{45}$, $NR^{46}R^{47}$,
  —C(=O)H, phenyl, $C_{1-6}$ alkyl, $C_{2-6}$ alkenyl, $C_{2-6}$ alkynyl,
  $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;
  $C_{1-6}$ alkyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—; and
  $C_{2-6}$ alkenyl substituted with OH, methoxy, ethoxy, propoxy, butoxy, —$SO_2R^{45}$, —$NR^{46}R^{47}$, $NR^{46}R^{47}$C(=O)—, or ($C_{1-4}$ alkyl)$CO_2$—;
$R^{41}$, at each occurrence, is independently selected from
  H, $CF_3$, halo, OH, $CO_2H$, $SO_2R^{45}$, $NR^{46}R^{47}$, $NO_2$, CN,
  $C_{2-4}$ alkenyl, $C_{2-4}$ alkynyl, $C_{1-3}$ alkoxy, $C_{1-3}$ haloalkyl, and $C_{1-3}$ alkyl;
$R^{42}$, at each occurrence, is independently selected from
  H, $CF_3$, halo, OH, $CO_2H$, $SO_2R^{45}$, $NR^{46}R^{47}$, $NO_2$, CN,
  CH(=NH)$NH_2$, NHC(=NH)$NH_2$,
  $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;
$R^{43}$ is cyclopropyl, cyclobutyl, cyclopentyl, cyclohexyl, phenyl, or pyridyl, each substituted with 0–3 $R^{44}$;
$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;
$R^{45}$ is methyl, ethyl, propyl, or butyl;
$R^{46}$, at each occurrence, is independently selected from H, methyl, ethyl, propyl, and butyl;
$R^{47}$, at each occurrence, is independently selected from from H, methyl, ethyl, propyl, and butyl;
n is 1 or 2;
m is 1 or 2; and
n plus m is 2 or 3.
5. A compound of claim 2 wherein:

$R^1$ is selected from
  H,
  $C_{1-4}$ alkyl,
  $C_{2-4}$ alkenyl,
  $C_{2-4}$ alkynyl,
  $C_{3-4}$ cycloalkyl,
  $C_{1-3}$ alkyl substituted with 0–1 $R^2$,
  $C_{2-3}$ alkenyl substituted with 0–1 $R^2$, and
  $C_{2-3}$ alkynyl substituted with 0–1 $R^2$;
$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  phenyl substituted with 0–5 $R^{42}$;
  $C_{3-6}$ carbocyclic residue substituted with 0–3 $R^{41}$, and
  5–6 membered heterocyclic ring system containing 1, 2, or 3 heteroatoms selected from the group consisting of N, O, and S substituted with 0–3 $R^{41}$;
$R^{6a}$ is H;
$R^{6b}$ is H;
alternatively, $R^{6a}$ and $R^{6b}$ are taken together to form =O;
$R^7$ and $R^9$, at each occurrence, are independently selected from
  H, F, Cl, —$CH_3$, —$OCH_3$, —$CF_3$, —$OCF_3$, —CN, and —$NO_2$,
$R^8$ is selected from
  H, F, Cl, Br, —$CF_3$, —$OCF_3$, —OH, —CN, —$NO_2$,
  $C_{1-4}$ alkyl, $C_{2-4}$ alkenyl, $C_{2-4}$ alkynyl, $C_{1-4}$ haloalkyl,
  $C_{1-4}$ alkoxy, ($C_{1-4}$ haloalkyl)oxy,
  $C_{3-10}$ cycloalkyl substituted with 0–2 $R^{33}$,
  $C_{1-4}$ alkyl substituted with 0–2 $R^{11}$,
  $C_{2-4}$ alkenyl substituted with 0–2 $R^{11}$,
  $C_{2-4}$ alkynyl substituted with 0–1 $R^{11}$,
  $C_{3-10}$ carbocyclic residue substituted with 0–3 $R^{33}$,
  aryl substituted with 0–5 $R^{33}$,
  5–6 membered heterocyclic ring system containing 1, 2, or 3 heteroatoms selected from the group consisting of N, O, and S substituted with 0–3 $R^{31}$;
  $OR^{12}$, $SR^{12}$, $NR^{12}R^{13}$, $NR^{12}C(O)R^{15}$, $NR^{12}C(O)OR^{15}$, $NR^{12}S(O)_2R^{15}$, $NR^{12}C(O)NHR^{15}$, $NR^{14}C(O)R^{12}$, $NR^{14}C(O)OR^{12}$, and $NR^{14}S(O)_2R^{12}$;
$R^{11}$ is selected from
  H, halo, —$CF_3$, —CN, —$NO_2$,
  $C_{1-4}$ alkyl, $C_{2-4}$ alkenyl, $C_{2-4}$ alkynyl, $C_{1-4}$ haloalkyl,
  $C_{1-4}$ alkoxy, ($C_{1-4}$ haloalkyl)oxy,
  $C_{3-10}$ cycloalkyl substituted with 0–2 $R^{33}$,
  $C_{3-10}$ carbocyclic residue substituted with 0–3 $R^{33}$,
  aryl substituted with 0–5 $R^{33}$, and
  5–6 membered heterocyclic ring system containing 1, 2, or 3 heteroatoms selected from the group consisting of N, O, and S substituted with 0–3 $R^{31}$;
$R^{12}$, at each occurrence, is independently selected from
  $C_{1-4}$ alkyl substituted with 0–1 $R^{12a}$,
  $C_{2-4}$ alkenyl substituted with 0–1 $R^{12a}$,
  $C_{2-4}$ alkynyl substituted with 0–1 $R^{12a}$,
  $C_{3-6}$ cycloalkyl substituted with 0–3 $R^{33}$,
  aryl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O, and S substituted with 0–3 $R^{31}$;
$R^{12a}$, at each occurrence, is independently selected from
  phenyl substituted with 0–5 $R^{33}$;
  $C_{3-10}$ carbocyclic residue substituted with 0–3 $R^{33}$, and
  5–10 membered heterocyclic ring system containing from 1–4 heteroatoms selected from the group consisting of N, O and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, quinolinyl, tetrahydroquinolinyl, isoquinolinyl, and tetrahydroisoquinolinyl; wherein said bicyclic heterocyclic ring system is substituted with 0–1 $R^{16}$;

$R^{14}$, at each occurrence, is independently selected from H, methyl, ethyl, propyl, and butyl;

$R^{15}$, at each occurrence, is independently selected from H, methyl, ethyl, propyl, and butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{31}$, at each occurrence, is independently selected from H, OH, halo, $CF_3$, methyl, ethyl, and propyl;

$R^{33}$, at each occurrence, is independently selected from H, OH, halo, CN, $NO_2$, $CF_3$, $SO_2R^{45}$, $NR^{46}R^{47}$, —C(=O)H, phenyl, $C_{1-6}$ alkyl, $C_{2-6}$ alkenyl, $C_{2-6}$ alkynyl,
  $C_{3-6}$ cycloalkyl, $C_{1-4}$ haloalkyl, $C_{1-4}$ haloalkyl-oxy-, $C_{1-4}$ alkyloxy-, $C_{1-4}$ alkylthio-, $C_{1-4}$ alkyl-C(=O)—, $C_{1-4}$ alkyl-C(=O)NH—, $C_{1-4}$ alkyl-OC(=O)—, $C_{1-4}$ alkyl-C(=O)O—, $C_{3-6}$ cycloalkyl-oxy-, $C_{3-6}$ cycloalkylmethyl-oxy-;
  $C_{1-6}$ alkyl substituted with OH, methoxy, ethoxy, propoxy, butoxy, —$SO_2R^{45}$, —$NR^{46}R^{47}$, $NR^{46}R^{47}C(=O)$—, or $(C_{1-4}$ alkyl$)CO_2$—; and
  $C_{2-6}$ alkenyl substituted with OH, methoxy, ethoxy, propoxy, butoxy, —$SO_2R^{45}$, —$NR^{46}R^{47}$, $NR^{46}R^{47}C(=O)$—, or $(C_{1-4}$ alkyl$)CO_2$—;

$R^{41}$, at each occurrence, is independently selected from H, $CF_3$, halo, OH, $CO_2H$, $SO_2R^{45}$, $NR^{46}R^{47}$, $NO_2$, CN, $C_{2-4}$ alkenyl, $C_{2-4}$ alkynyl, $C_{1-3}$ alkoxy, $C_{1-3}$ haloalkyl, and $C_{1-3}$ alkyl;

$R^{42}$, at each occurrence, is independently selected from H, $CF_3$, halo, OH, $CO_2H$, $SO_2R^{45}$, $NR^{46}R^{47}$, $NO_2$, CN, CH(=NH)$NH_2$, NHC(=NH)$NH_2$,
  $C_{2-4}$ alkenyl, $C_{2-4}$ alkynyl, $C_{1-3}$ alkoxy, $C_{1-3}$ haloalkyl, $C_{3-6}$ cycloalkyl, and $C_{1-3}$ alkyl;

$R^{43}$ is cyclopropyl, cyclobutyl, cyclopentyl, cyclohexyl, phenyl, or pyridyl, each substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, methyl, ethyl, propyl, butyl, methoxy, ethoxy, propoxy, and butoxy;

$R^{45}$ is methyl, ethyl, propyl, or butyl;

$R^{46}$, at each occurrence, is independently selected from H, methyl, ethyl, propyl, and butyl;

$R^{47}$, at each occurrence, is independently selected from from H, methyl, ethyl, propyl, and butyl;

n is 1; and m is 1.

6. A compound of claim 2 wherein:

$R^1$ is selected from H,
  $C_{1-5}$ alkyl substituted with 0–1 $R^2$,
  $C_{2-5}$ alkenyl substituted with 0–1 $R^2$, and
  $C_{2-3}$ alkynyl substituted with 0–1 $R^2$;

$R^2$ is cyclopropyl, cyclobutyl, cyclopentyl, cyclohexyl, or phenyl;

$R^{6a}$ is H;

$R^{6b}$ is H;

$R^7$ and $R^9$, at each occurrence, are independently selected from H, F, Cl, —$CH_3$, —$OCH_3$, —$CF_3$, —$OCF_3$, —CN, and —$NO_2$;

$R^8$ is selected from $R^{11}$;
  methyl substituted with $R^{11}$;
  phenyl substituted with 0–3 $R^{33}$;
  pyridyl substituted with 0–2 $R^{33}$;
  $OR^{12}$, $SR^{12}$, $NR^{12}R^{13}$, $NR^{12}C(O)R^{15}$, $NR^{12}C(O)OR^{15}$, $NR^{12}S(O)_2R^{15}$, $NR^{12}C(O)NHR^{15}$, $NR^{14}C(O)R^{12}$, $NR^{14}C(O)OR^{12}$, and $NR^{14}S(O)_2R^{12}$;

$R^{11}$ is selected from
  phenyl-substituted with 0–5 fluoro;
  pyridyl substituted with 0–2 $R^{33}$;
  naphthyl-substituted with 0–2 $R^{33}$;
  2-($H_3CCH_2C(=O)$)-phenyl-substituted with $R^{33}$;
  2-($H_3CC(=O)$)-phenyl-substituted with $R^{33}$;
  2-(HC(=O))-phenyl-substituted with $R^{33}$;
  2-($H_3COCH(OH)$)-phenyl-substituted with $R^{33}$;
  2-($H_3CCH_2CH(OH)$)-phenyl-substituted with $R^{33}$;
  2-($HOCH_2$)-phenyl-substituted with $R^{33}$;
  2-($HOCH_2CH_2$)-phenyl-substituted with $R^{33}$;
  2-($H_3COCH_2$)-phenyl-substituted with $R^{33}$;
  2-($H_3COCH_2CH_2$)-phenyl-substituted with $R^{33}$;
  2-($H_3CCH(OMe)$)-phenyl-substituted with $R^{33}$;
  2-($H_3COC(=O)$)-phenyl-substituted with $R^{33}$;
  2-($HOCH_2CH=CH$)-phenyl-substituted with $R^{33}$;
  2-((MeOC=O)CH=CH)-phenyl-substituted with $R^{33}$;
  2-(methyl)-phenyl-substituted with $R^{33}$;
  2-(ethyl)-phenyl-substituted with $R^{33}$;
  2-(i-propyl)-phenyl-substituted with $R^{33}$;
  2-($F_3C$)-phenyl-substituted with $R^{33}$;
  2-(NC)-phenyl-substituted with $R^{33}$;
  2-($H_3CO$)-phenyl-substituted with $R^{33}$;
  2-(fluoro)-phenyl-substituted with $R^{33}$;
  2-(chloro)-phenyl-substituted with $R^{33}$;
  3-(NC)-phenyl-substituted with $R^{33}$;
  3-($H_3CO$)-phenyl-substituted with $R^{33}$;
  3-(fluoro)-phenyl-substituted with $R^{33}$;
  3-(chloro)-phenyl-substituted with $R^{33}$;
  3-($H_3C$)-phenyl-substituted with $R^{33}$;
  3-($F_3C$)-phenyl-substituted with $R^{33}$;
  3-($H_3CS$)-phenyl-substituted with $R^{33}$;
  4-(NC)-phenyl-substituted with $R^{33}$;
  4-(fluoro)-phenyl-substituted with $R^{33}$;
  4-(chloro)-phenyl-substituted with $R^{33}$;
  4-($H_3CS$)-phenyl-substituted with $R^{33}$;
  4-($H_3CO$)-phenyl-substituted with $R^{33}$;
  4-(ethoxy)-phenyl-substituted with $R^{33}$;
  4-(i-propoxy)-phenyl-substituted with $R^{33}$;
  4-(i-butoxy)-phenyl-substituted with $R^{33}$;
  4-($H_3CCH_2CH_2C(=O)$)-phenyl-substituted with $R^{33}$;
  4-(($H_3C)_2CHC(=O)$)-phenyl-substituted with $R^{33}$;
  4-($H_3CCH_2C(=O)$)-phenyl-substituted with $R^{33}$;
  4-($H_3CC(=O)$)-phenyl-substituted with $R^{33}$;
  4-($H_3CCH_2CH_2CH(OH)$)-phenyl-substituted with $R^{33}$;
  4-(($H_3C)_2CHCH(OH)$)-phenyl-substituted with $R^{33}$;
  4-($H_3CCH_2CH(OH)$)-phenyl-substituted with $R^{33}$;
  4-($H_3CCH(OH)$)-phenyl-substituted with $R^{33}$;
  4-(cyclopropyloxy)-phenyl-substituted with $R^{33}$;
  4-(cyclobutyloxy)-phenyl-substituted with $R^{33}$; and
  4-(cyclopentyloxy)-phenyl-substituted with $R^{33}$;

$R^{12}$ is selected from
  methyl substituted with $R^{11}$;

phenyl substituted with 0–5 fluoro;
pyridyl, substituted with 0–2 $R^{33}$;
naphthyl substituted with 0–2 $R^{33}$;
2-($H_3CCH_2C(=O)$)-phenyl-substituted with $R^{33}$;
2-($H_3CC(=O)$)-phenyl-substituted with $R^{33}$;
2-($HC(=O)$)-phenyl-substituted with $R^{33}$;
2-($H_3CCH(OH)$)-phenyl-substituted with $R^{33}$;
2-($H_3CCH_2CH(OH)$)-phenyl-substituted with $R^{33}$;
2-($HOCH_2$)-phenyl-substituted with $R^{33}$;
2-($HOCH_2CH_2$)-phenyl-substituted with $R^{33}$;
2-($H_3COCH_2$)-phenyl-substituted with $R^{33}$;
2-($H_3COCH_2CH_2$)-phenyl-substituted with $R^{33}$;
2-($H_3CCH(OMe)$)-phenyl-substituted with $R^{33}$;
2-($H_3COC(=O)$)-phenyl-substituted with $R^{33}$;
2-($HOCH_2CH=CH$)-phenyl-substituted with $R^{33}$;
2-(($MeOC=O)CH=CH$)-phenyl-substituted with $R^{33}$;
2-(methyl)-phenyl-substituted with $R^{33}$;
2-(ethyl)-phenyl-substituted with $R^{33}$;
2-(i-propyl)-phenyl-substituted with $R^{33}$;
2-($F_3C$)-phenyl-substituted with $R^{33}$;
2-(NC)-phenyl-substituted with $R^{33}$;
2-($H_3CO$)-phenyl-substituted with $R^{33}$;
2-(fluoro)-phenyl-substituted with $R^{33}$;
2-(chloro)-phenyl-substituted with $R^{33}$;
3-(NC)-phenyl-substituted with $R^{33}$;
3-($H_3CO$)-phenyl-substituted with $R^{33}$;
3-(fluoro)-phenyl-substituted with $R^{33}$;
3-(chloro)-phenyl-substituted with $R^{33}$;
3-($H_3C$)-phenyl-substituted with $R^{33}$;
3-($F_3C$)-phenyl-substituted with $R^{33}$;
3-($H_3CS$)-phenyl-substituted with $R^{33}$;
4-(fluoro)-phenyl-substituted with $R^{33}$;
4-(chloro)-phenyl-substituted with $R^{33}$;
4-($H_3CS$)-phenyl-substituted with $R^{33}$;
4-($H_3CO$)-phenyl-substituted with $R^{33}$;
4-(ethoxy)-phenyl-substituted with $R^{33}$;
4-(i-propoxy)-phenyl-substituted with $R^{33}$;
4-(i-butoxy)-phenyl-substituted with $R^{33}$;
4-($H_3CCH_2CH_2C(=O)$)-phenyl-substituted with $R^{33}$;
4-(($H_3C)_2CHC(=O)$)-phenyl-substituted with $R^{33}$;
4-($H_3CCH_2C(=O)$)-phenyl-substituted with $R^{33}$;
4-($H_3CC(=O)$)-phenyl-substituted with $R^{33}$;
4-($H_3CCH_2CH_2CH(OH)$)-phenyl-substituted with $R^{33}$;
4-(($H_3C)_2CHCH(OH)$)-phenyl-substituted with $R^{33}$;
4-($H_3CCH_2CH(OH)$)-phenyl-substituted with $R^{33}$;
4-($H_3CCH(OH)$)-phenyl-substituted with $R^{33}$;
4-(cyclopropyloxy)-phenyl-substituted with $R^{33}$;
4-(cyclobutyloxy)-phenyl-substituted with $R^{33}$; and
4-(cyclopentyloxy)-phenyl-substituted with $R^{33}$;

$R^{13}$ is H, methyl, or ethyl;

alternatively, $R^{12}$ and $R^{13}$ when attached to N may be combined to form a 9- or 10-membered bicyclic heterocyclic ring system containing from 1–3 heteroatoms selected from the group consisting of N, O, and S; wherein said bicyclic heterocyclic ring system is selected from indolyl, indolinyl, indazolyl, benzimidazolyl, benzimidazolinyl, benztriazolyl, quinolinyl, tetrahydroquinolinyl, isoquinolinyl, and tetrahydroisoquinolinyl; wherein said bicyclic heterocyclic ring system is substituted with 0–1 $R^{16}$;

$R^{15}$ is H, methyl, ethyl, propyl, or butyl;

$R^{16}$, at each occurrence, is independently selected from H, OH, F, Cl, CN, $NO_2$, methyl, ethyl, methoxy, ethoxy, trifluoromethyl, and trifluoromethoxy;

$R^{33}$, at each occurrence, is independently selected from H, F, Cl, $-CH_3$, $-OCH_3$, $-SCH_3$, $-CF_3$, $-OCF_3$, $-CN$, and $-NO_2$;

n is 1; and m is 1.

7. A compound of claim 2 of Formula (I-a)

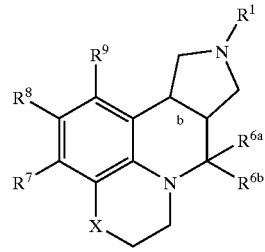

(I-a)

wherein:

b is a single bond wherein the bridging hydrogens are either cis or trans;

$R^1$ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl,
2-propenyl, 2-methyl-2-propenyl, trans-2-butenyl, 3-methyl-2-butenyl, 3-butenyl, trans-2-pentenyl, cis-2-pentenyl, 4-pentenyl, 4-methyl-3-pentenyl, 3,3-dichloro-2-propenyl, trans-3-phanyl-2-propenyl,
cyclopropyl, cyclobutyl, cyclopentyl, cyclohexyl, cyclopropylmethyl, cyclobutylmethyl, cyclopentylmethyl, cyclohexylmethyl,
benzyl, 2-methylbenzyl, 3-methylbenzyl, 4-methylbenzyl, 2,5-dimethylbenzyl, 2,4-dimethylbenzyl, 3,5-dimethylbenzyl, 2,4,6-trimethyl-benzyl, 3-methoxy-benzyl, 3,5-dimethoxy-benzyl, pentafluorobenzyl, 2-phenylethyl, 1-phenyl-2-propyl, 4-phenylbutyl, 4-phenylbenzyl, 2-phenylbenzyl,
(2,3-dimethoxy-phenyl)C(=O)—, (2,5-dimethoxy-phenyl)C(=O)—, (3,4-dimethoxy-phenyl)C(=O)—, (3,5-dimethoxy-phenyl)C(=O)—, cyclopropyl-C(=O)—, isopropyl-C(=O)—, ethyl-$CO_2$—, propyl-$CO_2$—, t-butyl-$CO_2$—, 2,6-dimethoxy-benzyl, 2,4-dimethoxy-benzyl, 2,4,6-trimethoxy-benzyl, 2,3-dimethoxy-benzyl, 2,4,5-trimethoxy-benzyl, 2,3,4-trimethoxy-benzyl, 3,4-dimethoxy-benzyl, 3,4,5-trimethoxy-benzyl, (4-fluoro-phenyl)ethyl,
$-CH=CH_2$, $-CH_2-CH=CH_2$, $-CH=CH-CH_3$, $-C\equiv CH$, $-C\equiv C-CH_3$, and $-CH_2-C\equiv CH$; and $R^{6a}$ is H;

$R^{6b}$ is H;

attentively, $R^{6a}$ and $R^{6b}$ are taken together to form =O;

$R^7$, $R^8$, and $R^9$, at each occurrence, are independently selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl;
2-Cl-phenyl; 2-F-phenyl; 2-Br-phenyl; 2-CN-phenyl; 2-Me-phenyl; 2-$CF_3$-phenyl; 2-MeO-phenyl;

2-CF₃O-phenyl; 2-NO₂-phenyl; 2-MeS-phenyl; 2-CHO-phenyl; 2-HOCH₂-phenyl;

3-Cl-phenyl; 3-F-phenyl; 3-Br-phenyl; 3-CN-phenyl; 3-Me-phenyl; 3-Et-phenyl; 3-n-Pr-phenyl; 3-isoPr-phenyl; 3-n-Bu-phenyl; 3-CF₃-phenyl; 3-MeO-phenyl; 3-MeS-phenyl; 3-isopropoxyphenyl; 3-CF₃O-phenyl; 3-NO₂-phenyl; 3-CHO-phenyl; 3-HOCH₂-phenyl; 3-MeOCH₂-phenyl; 3-Me₂NCH₂-phenyl;

4-Cl-phenyl; 4-F-phenyl; 4-Br-phenyl; 4-CN-phenyl; 4-Me-phenyl; 4-Et-phenyl; 4-n-Pr-phenyl; 4-iso-Pr-phenyl; 4-n-Bu-phenyl; 4-CF₃-phenyl; 4-MeO-phenyl; 4-isopropoxyphenyl; 4-CF₃O-phenyl; 4-MeS-phenyl;

4-acetylphenyl; 3-acetamidophenyl; 4-pyridyl; 2-furanyl; 2-thiophenyl; 2-naphthyl; 1-pyrrolidinyl;

2,3-diCl-phenyl; 2,3-diF-phenyl; 2,3-diMe-phenyl; 2,3-diCF₃-phenyl; 2,3-diMeO-phenyl; 2,3-diCF₃O-phenyl;

2,4-diCl-phenyl; 2,4-diF-phenyl; 2,4-diMe-phenyl; 2,4-diCF₃-phenyl; 2,4-diMeO-phenyl; 2,4-diCF₃O-phenyl;

2,5-diCl-phenyl; 2,5-diF-phenyl; 2,5-diMe-phenyl; 2,5-diCF₃-phenyl; 2,5-diMeO-phenyl; 2,5-diCF₃O-phenyl;

2,6-diCl-phenyl; 2,6-diF-phenyl; 2,6-diMe-phenyl; 2,6-diCF₃-phenyl; 2,6-diMeO-phenyl; 2,6-diCF₃O-phenyl;

3,4-diCl-phenyl; 3,4-diF-phenyl; 3,4-diMe-phenyl; 3,4-diCF₃-phenyl; 3,4-diMeO-phenyl; 3,4-diCF₃O-phenyl;

2,4,6-triCl-phenyl; 2,4,6-triF-phenyl; 2,4,6-triMe-phenyl; 2,4,6-triCF₃-phenyl; 2,4,6-triMeO-phenyl; 2,4,6-triCF₃O-phenyl; 2,4,5-triMe-phenyl; 2,3,4-triF-phenyl; 2-Me-4-MeO-5-F-phenyl; 2,6-diCl-4-MeO-phenyl; 2,4-diMeO-6-F-phenyl; 2,6-diF-4-Cl-phenyl; 2,3,4,6-tetraF-phenyl; 2,3,4,5,6-pentaF-phenyl;

2-Cl-4-F-phenyl; 2-Cl-6-F-phenyl; 2-Cl-3-Me-phenyl; 2-Cl-4-MeO-phenyl; 2-Cl-4-EtO-phenyl; 2-Cl-4-iPrO-phenyl; 2-Cl-4-CF₃-phenyl; 2-Cl-4-CF₃O-phenyl; 2-Cl-4-(CHF₂)O-phenyl; 2-F-3-Cl-phenyl; 2-F-4-MeO-phenyl; 2-F-5-Me-phenyl;

2-Me-3-Cl-phenyl; 2-Me-3-CN-phenyl; 2-Me-4-Cl-phenyl; 2-Me-4-F-phenyl; 2-Me-4-CN-phenyl; 2-Me-4-MeO-phenyl; 2-Me-4-EtO-phenyl; 2-Me-4-MeS-phenyl; 2-Me-4-H₂NCO-phenyl; 2-Me-4-MeOC(=O)-phenyl; 2-Me-4-CH₃C(=O)-phenyl; 2-Me-5-F-phenyl; 2-Et-4-MeO-phenyl; 2-MeO-5-F-phenyl; 2-MeO-4-isopropyl-phenyl; 2-CF₃-4-Cl-phenyl; 2-CF₃-4-F-phenyl; 2-CF₃-4-MeO-phenyl; 2-CF₃-4-EtO-phenyl; 2-CF₃-4-iPrO-phenyl; 2-CF₃-4-CN-phenyl; 2-CF₃-6-F-phenyl; 2-CHO-4-MeO-phenyl; 2-MeOC(=O)-3-MeO-phenyl; 2-CH₃CH(OH)-4-MeO-phenyl; 2-CH₃CH(OH)-4-F-phenyl; 2-CH₃CH(OH)-4-Cl-phenyl; 2-CH₃CH(OH)-4-Me-phenyl; 2-CH₃CH(OMe)-4-MeO-phenyl; 2-CH₃C(=O)-4-MeO-phenyl; 2-CH₃C(=O)-4-F-phenyl; 2-CH₃C(=O)-4-Cl-phenyl; 2-CH₃C(=O)-4-Me-phenyl; 2-H₂C(OH)-4-MeO-phenyl; 2-H₂C(OMe)-4-MeO-phenyl; 2-H₃CCH₂CH(OH)-4-MeO-phenyl; 2-H₃CCH₂C(=O)-4-MeO-phenyl; 2-CH₃CO₂CH₂CH₂-4-MeO-phenyl; (Z)-2-HOCH₂CH=CH-4-MeO-phenyl; (E)-2-HOCH₂CH=CH-4-MeO-phenyl; (Z)-2-CH₃CO₂CH=CH-4-MeO-phenyl; (E)-2-CH₃CO₂CH=CH-4-MeO-phenyl; 2-CH₃OCH₂CH₂-4-MeO-phenyl;

3-CN-4-F-phenyl; 3-H₂NCO-4-F-phenyl; (2-Cl-phenyl)-CH=CH—; (3-Cl-phenyl)-CH=CH—; (2,6-diF-phenyl)-CH=CH—; phenyl-CH=CH—; (2-Me-4-MeO-phenyl)-CH=CH—;

cyclohexyl; cyclopentyl; cyclohexylmethyl; benzyl; 2-F-benzyl; 3-F-benzyl; 4-F-benzyl; 3-MeO-benzyl; 3-OH-benzyl; 2-MeO-benzyl; 2-OH-benzyl; tetrahydroquinolin-1-yl; tetrahydroindolin-1-yl; tetrahydroisoindolin-1-yl;

phenyl-S—; phenyl-NH—; pyrid-3-yl-NH—; (4-Me-pyrid-3-yl)-NH—; (4-Cl-pyrid-3-yl)-NH—; (1-naphthyl)-NH—; (2-naphthyl)-NH—; (2-Me-naphth-1-yl)-NH—; (4-Me-naphth-1-yl)-NH—; (3-quinolinyl)-NH—;

(2-[1,1'-biphenyl])-NH—; (3-[1,1'-biphenyl])-NH—; (4-[1,1'-biphenyl])-NH—; (2-F-phenyl)-NH—; (2-Cl-phenyl)-NH—; (2-CF₃-phenyl)-NH—; (2-CH₃-phenyl)-NH—; (2-OMe-phenyl)-NH—; (2-CN-phenyl)-NH—; (2-OCF₃-phenyl)-NH—; (2-SMe-phenyl)-NH—; (3-F-phenyl)-NH—; (3-Cl-phenyl)-NH—; (3-CF₃-phenyl)-NH—; (3-CH₃-phenyl)-NH—; (3-OMe-phenyl)-NH—; (3-CN-phenyl)-NH—; (3-OCF₃-phenyl)-NH—; (3-SMe-phenyl)-NH—; (4-F-phenyl)-NH—; (4-Cl-phenyl)-NH—; (4-CF₃-phenyl)-NH—; (4-CH₃-phenyl)-NH—; (4-OMe-phenyl)-NH—; (4-CN-phenyl)-NH—; (4-OCF₃-phenyl)-NH—; (4-SMe-phenyl)-NH—; (2,3-diCl-phenyl)-NH—; (2,4-diCl-phenyl)-NH—; (2,5-diCl-phenyl)-NH—; (2,6-diCl-phenyl)-NH—; (3,4-diCl-phenyl)-NH—; (3,5-diCl-phenyl)-NH—; (2,3-diF-phenyl)-NH—; (2,4-diF-phenyl)-NH—; (2,5-diF-phenyl)-NH—; (2,6-diF-phenyl)-NH—; (3,4-diF-phenyl)-NH—; (3,5-diF-phenyl)-NH—; (2,3-diCH₃-phenyl)-NH—; (2,4-diCH₃-phenyl)-NH—; (2,5-diCH₃-phenyl)-NH—; (2,6-diCH₃-phenyl)-NH—; (3,4-diCH₃-phenyl)-NH—; (3,5-diCH₃-phenyl)-NH—; (2,3-diCF₃-phenyl)-NH—; (2,4-diCF₃-phenyl)-NH—; (2,5-diCF₃-phenyl)-NH—; (2,6-diCF₃-phenyl)-NH—; (3,4-diCF₃-phenyl)-NH—; (3,5-diCF₃-phenyl)-NH—; (2,3-diOMe-phenyl)-NH—; (2,4-diOMe-phenyl)-NH—; (2,5-diOMe-phenyl)-NH—; (2,6-diOMe-phenyl)-NH—; (3,4-diOMe-phenyl)-NH—; (3,5-diOMe-phenyl)-NH—; (2-F-3-Cl-phenyl)-NH—; (2-F-4-Cl-phenyl)-NH—; (2-F-5-Cl-phenyl)-NH—; (2-F-6-Cl-phenyl)-NH—; (2-F-3-CH₃-phenyl)-NH—; (2-F-4-CH₃-phenyl)-NH—; (2-F-5-CH₃-phenyl)-NH—; (2-F-6-CH₃-phenyl)-NH—; (2-F-3-CF₃-phenyl)-NH—; (2-F-4-CF₃-phenyl)-NH—; (2-F-5-CF₃-phenyl)-NH—; (2-F-6-CF₃-phenyl)-NH—; (2-F-3-OMe-phenyl)-NH—; (2-F-4-OMe-phenyl)-NH—; (2-F-5-OMe-phenyl)-NH—; (2-F-6-OMe-phenyl)-NH—; (2-Cl-3-F-phenyl)-NH—; (2-Cl-4-F-phenyl)-NH—; (2-Cl-5-F-phenyl)-NH—; (2-Cl-6-F-phenyl)-NH—; (2-Cl-3-CH₃-phenyl)-NH—; (2-Cl-4-CH₃-phenyl)-NH—; (2-Cl-5-CH₃-phenyl)-NH—; (2-Cl-6-CH₃-phenyl)-NH—; (2-Cl-3-CF₃-phenyl)-NH—; (2-Cl-4-CF₃-phenyl)-NH—; (2-Cl-5-CF₃-phenyl)-NH—; (2-Cl-6-CF₃-phenyl)-NH—; (2-Cl-3-OMe-phenyl)-NH—; (2-Cl-4-OMe-phenyl)-NH—; (2-Cl-5-OMe-phenyl)-NH—; (2-Cl-6-OMe-phenyl)-NH—; (2-CH₃-3F-phenyl)-NH—; (2-CH₃-4-F-phenyl)-NH—; (2-CH₃-5-F-phenyl)-NH—; (2-CH₃-6-F-phenyl)-NH—; (2-CH₃-3-Cl-phenyl)-NH—; (2-CH₃-4-Cl-phenyl)-NH—; (2-CH₃-5-Cl-phenyl)-NH—; (2-CH₃-6-Cl-phenyl)-NH—; (2-CH₃-3-CF₃-phenyl)-NH—; (2-CH₃-4-

CF₃-phenyl)-NH—; (2-CH₃-5-CF₃-phenyl)-NH—; (2-CH₃-6-CF₃-phenyl)-NH—; (2-CH₃-3-OMe-phenyl)-NH—; (2-CH₃-4-OMe-phenyl)-NH—; (2-CH₃-5-OMe-phenyl)-NH—; (2-CH₃-6-OMe-phenyl)-NH—; (2-CF₃-3-F-phenyl)-NH—; (2-CF₃-4-F-phenyl)-NH—; (2-CF₃-5-F-phenyl)-NH—; (2-CF₃-6-F-phenyl)-NH—; (2-CF₃-3-Cl-phenyl)-NH—; (2-CF₃-4-Cl-phenyl)-NH—; (2-CF₃-5-Cl-phenyl)-NH—; (2-CF₃-6-Cl-phenyl)-NH—; (2-CF₃-3-CH₃-phenyl)-NH—; (2-CF₃-4-CH₃-phenyl)-NH—; (2-CH₃-5-CF₃-phenyl)-NH—; (2-CF₃-6-CH₃-phenyl)-NH—; (2-CF₃-3-OMe-phenyl)-NH—; (2-CF₃-4-OMe-phenyl)-NH—; (2-CF₃-5-OMe-phenyl)-NH—; (2-CF₃-6-OMe-phenyl)-NH—; (2-OMe-3-F-phenyl)-NH—; (2-OMe-4-F-phenyl)-NH—; (2-OMe-5-F-phenyl)-NH—; (2-OMe-6-F-phenyl)-NH—; (2-OMe-3-Cl-phenyl)-NH—; (2-OMe-4-Cl-phenyl)-NH—; (2-OMe-5-Cl-phenyl)-NH—; (2-OMe-6-Cl-phenyl)-NH—; (2-OMe-4-CN-phenyl)-NH—; (2-OMe-4-CHO-phenyl)-NH—; (2-OMe-3-CH₃-phenyl)-NH—; (2-OMe-4-CH₃-phenyl)-NH—; (2-OMe-5-CH₃-phenyl)-NH—; (2-OMe-6-CH₃-phenyl)-NH—; (2-OMe-3-CF₃-phenyl)-NH—; (2-OMe-4-CF₃-phenyl)-NH—; (2-OMe-5-CF₃-phenyl)-NH—; (2-OMe-6-CF₃-phenyl)-NH—; (2-acetyl-4-Cl-phenyl)-NH—; (2-acetyl-4-Me-phenyl)-NH—; (2-acetyl-4-MeO-phenyl)-NH—; (2-CH₃CH(OH)-4-Cl-phenyl)-NH—; (2-CH₃CH(OH)-4-Me-phenyl)-NH—; (2-CH₃CH(OH)-4-MeO-phenyl)-NH—;

(3-CF₃-4-Cl-phenyl)-NH—; (3-F-4-CHO-phenyl)-NH—; (3-CH₃-4-CN-phenyl)-NH—; (3-CH₃-4-MeO-phenyl)-NH—; (3-CH₃-4-Cl-phenyl)-NH—; (3-CH₃-4-F-phenyl)-NH—; (3-F-5-CF₃-phenyl)-NH—;

(3-CH₃-4-CO₂Me-phenyl)NH—; (3-CF₃-4-C(O)CH₃-phenyl)NH—; (3-CHO-4-OMe-phenyl)-NH—; (4-F-3-CF₃-phenyl)-NH—;

(2,3,5-triCl-phenyl)-NH—; (2,4,5-triF-phenyl)-NH—; (2,6-diCl-3-Me-phenyl)-NH—; (3,5-diMe-4-MeO-phenyl)-NH—; (2-F-3-Cl-6-CF₃-phenyl)-NH—;

benzyl-NH—; (3-quinolinyl)CH₂NH—; (2-F-phenyl)CH₂NH—; (2-Cl-phenyl)CH₂NH—; (2-CF₃-phenyl)CH₂NH—; (2-CH₃-phenyl)CH₂NH—; (2-OMe-phenyl)CH₂NH—; (2-CN-phenyl)CH₂NH—; (2-OCF₃-phenyl)CH₂NH—; (2-SMe-phenyl)CH₂NH—; (3-F-phenyl)CH₂NH—; (3-Cl-phenyl)CH₂NH—; (3-CF₃-phenyl)CH₂NH—; (3-CH₃-phenyl)CH₂NH—; (3-OMe-phenyl)CH₂NH—; (3-CN-phenyl)CH₂NH—; (3-OCF₃-phenyl)CH₂NH—; (3-SMe-phenyl)CH₂NH—; (4-F-phenyl)CH₂NH—; (4-Cl-phenyl)CH₂NH—; (4-CF₃-phenyl)CH₂NH—; (4-CH₃-phenyl)CH₂NH—; (4-OMe-phenyl)CH₂NH—; (4-CN-phenyl)CH₂NH—; (4-OCF₃-phenyl)CH₂NH—; (4-SMe-phenyl)CH₂NH—; (2,3-diCl-phenyl)CH₂NH—; (2,4-diCl-phenyl)CH₂NH—; (2,5-diCl-phenyl)CH₂NH—; (2,6-diCl-phenyl)CH₂NH—; (3,4-diCl-phenyl)CH₂NH—; (3,5-diCl-phenyl)CH₂NH—; (2,3-diF-phenyl)CH₂NH—; (2,4-diF-phenyl)CH₂NH—; (2,5-diF-phenyl)CH₂NH—; (2,6-diF-phenyl)CH₂NH—; (3,4-diF-phenyl)CH₂NH—; (3,5-diF-phenyl)CH₂NH—; (2,3-diCH₃-phenyl)CH₂NH—; (2,4-diCH₃-phenyl)CH₂NH—; (2,5-diCH₃-phenyl)CH₂NH—; (2,6-diCH₃-phenyl)CH₂NH—; (3,4-diCH₃-phenyl)CH₂NH—; (3,5-diCH₃-phenyl)CH₂NH—; (2,3-diCF₃-phenyl)CH₂NH—; (2,4-diCF₃-phenyl)CH₂NH—; (2,5-diCF₃-phenyl)CH₂NH—; (2,6-diCF₃-phenyl)CH₂NH—; (3,4-diCF₃-phenyl)CH₂NH—; (3,5-diCF₃-phenyl)CH₂NH—; (2,3-diOMe-phenyl)CH₂NH—; (2,4-diOMe-phenyl)CH₂NH—; (2,5-diOMe-phenyl)CH₂NH—; (2,6-diOMe-phenyl)CH₂NH—; (3,4-diOMe-phenyl)CH₂NH—; (3,5-diOMe-phenyl)CH₂NH—; (2-F-3-Cl-phenyl)CH₂NH—; (2-F-4-Cl-phenyl)CH₂NH—; (2-F-5-Cl-phenyl)CH₂NH—; (2-F-6-Cl-phenyl)CH₂NH—; (2-F-3-CH₃-phenyl)CH₂NH—; (2-F-4-CH₃-phenyl)CH₂NH—; (2-F-5-CH₃-phenyl)CH₂NH—; (2-F-6-CH₃-phenyl)CH₂NH—; (2-F-3-CF₃-phenyl)CH₂NH—; (2-F-4-CF₃-phenyl)CH₂NH—; (2-F-5-CF₃-phenyl)CH₂NH—; (2-F-6-CF₃-phenyl)CH₂NH—; (2-F-3-OMe-phenyl)CH₂NH—; (2-F-4-OMe-phenyl)CH₂NH—; (2-F-5-OMe-phenyl)CH₂NH—; (2-F-6-OMe-phenyl)CH₂NH—; (2-Cl-3-F-phenyl)CH₂NH—; (2-Cl-4-F-phenyl)CH₂NH—; (2-Cl-5-F-phenyl)CH₂NH—; (2-Cl-6-F-phenyl)CH₂NH—; (2-Cl-3-CH₃-phenyl)CH₂NH—; (2-Cl-4-CH₃-phenyl)CH₂NH—; (2-Cl-5-CH₃-phenyl)CH₂NH—; (2-Cl-6-CH₃-phenyl)CH₂NH—; (2-Cl-3-CF₃-phenyl)CH₂NH—; (2-Cl-4-CF₃-phenyl)CH₂NH—; (2-Cl-5-CF₃-phenyl)CH₂NH—; (2-Cl-6-CF₃-phenyl)CH₂NH—; (2-Cl-3-OMe-phenyl)CH₂NH—; (2-Cl-4-OMe-phenyl)CH₂NH—; (2-Cl-5-OMe-phenyl)CH₂NH—; (2-Cl-6-OMe-phenyl)CH₂NH—; (2-CH₃-3-F-phenyl)CH₂NH—; (2-CH₃-4-F-phenyl)CH₂NH—; (2-CH₃-5-F-phenyl)CH₂NH—; (2-CH₃-6-F-phenyl)CH₂NH—; (2-CH₃-3-Cl-phenyl)CH₂NH—; (2-CH₃-4-Cl-phenyl)CH₂NH—; (2-CH₃-5-Cl-phenyl)CH₂NH—; (2-CH₃-6-Cl-phenyl)CH₂NH—; (2-CH₃-3-CF₃-phenyl)CH₂NH—; (2-CH₃-4-CF₃-phenyl)CH₂NH—; (2-CH₃-5-CF₃-phenyl)CH₂NH—; (2-CH₃-6-CF₃-phenyl)CH₂NH—; (2-CH₃-3-OMe-phenyl)CH₂NH—; (2-CH₃-4-OMe-phenyl)CH₂NH—; (2-CH₃-5-OMe-phenyl)CH₂NH—; (2-CH₃-6-OMe-phenyl)CH₂NH—; (2-CF₃-3-F-phenyl)CH₂NH—; (2-CF₃-4-F-phenyl)CH₂NH—; (2-CF₃-5-F-phenyl)CH₂NH—; (2-CF₃-6-F-phenyl)CH₂NH—; (2-CF₃-3-Cl-phenyl)CH₂NH—; (2-CF₃-4-Cl-phenyl)CH₂NH—; (2-CF₃-5-Cl-phenyl)CH₂NH—; (2-CF₃-6-Cl-phenyl)CH₂NH—; (2-CF₃-3-CH₃-phenyl)CH₂NH—; (2-CF₃-4-CH₃-phenyl)CH₂NH—; (2-CF₃-5-CH₃-phenyl)CH₂NH—; (2-CF₃-6-CH₃-phenyl)CH₂NH—; (2-CF₃-3-OMe-phenyl)CH₂NH—; (2-CF₃-4-OMe-phenyl)CH₂NH—; (2-CF₃-5-OMe-phenyl)CH₂NH—; (2-CF₃-6-OMe-phenyl)CH₂NH—; (2-OMe-3-F-phenyl)CH₂NH—; (2-OMe-4-F-phenyl)CH₂NH—; (2-OMe-5-F-phenyl)CH₂NH—; (2-OMe-6-F-phenyl)CH₂NH—; (2-OMe-3-Cl-phenyl)CH₂NH—; (2-OMe-4-Cl-phenyl)CH₂NH—; (2-OMe-5-Cl-phenyl)CH₂NH—; (2-OMe-6-Cl-phenyl)CH₂NH—; (2-OMe-4-CN-phenyl)CH₂NH—; (2-OMe-4-CHO-phenyl)CH₂NH—; (2-OMe-3-CH₃-phenyl)CH₂NH—; (2-OMe-4-CH₃-phenyl)CH₂NH—; (2-OMe-5-CH₃-phenyl)CH₂NH—; (2-OMe-6-CH₃-phenyl)CH₂NH—; (2-OMe-3-CF₃-phenyl)CH₂NH—; (2-OMe-4-CF₃-phenyl)CH₂NH—; (2-OMe-S-CF₃-phenyl)CH₂NH—; (2-OMe-6-CF₃-phenyl)CH₂NH—; (2-acetyl-4-Cl-phenyl)CH₂NH—; (2-acetyl-4-Me-phenyl)CH₂NH—; (2-acetyl-4-MeO-phenyl)CH₂NH—; (2-CH₃CH (OH)-4-Cl-phenyl)CH₂NH—; (2-CH₃CH(OH)-4-Me-phenyl)CH₂NH—; (2-CH₃CH(OH)-4-MeO-phenyl)CH₂NH—;
(3-CF₃-4-Cl-phenyl)CH₂NH—; (3-F-4-CHO-phenyl)CH₂NH—; (3-CH₃-4-CN-phenyl)CH₂NH—; (3-CH₃-4-MeO-phenyl)CH₂NH—; (3-CH₃-4-Cl-phenyl)CH₂NH—; (3-CH₃-4-F-phenyl)CH₂NH—; (4-F-3-CF₃-phenyl)CH₂NH—; (3-CH₃-4-CO₂Me-phenyl)CH₂NH—; (3-CF₃-4-C(O)CH₃-phenyl)CH₂NH—; (3-CHO-4-OMe-phenyl)CH₂NH—;
(2,3,5-triCl-phenyl)CH₂NH—; (2,4,5-triF-phenyl)CH₂NH—; (2,6-diCl-3-Me-phenyl)CH₂NH—; (3,5-diMe-4-MeO-phenyl)CH₂NH—; and (2-F-3-Cl-6-CF₃-phenyl)CH₂NH—;

provided that two of $R^7$, $R^8$, and $R^9$, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy.

8. A compound of claim 7 of Formula (II)

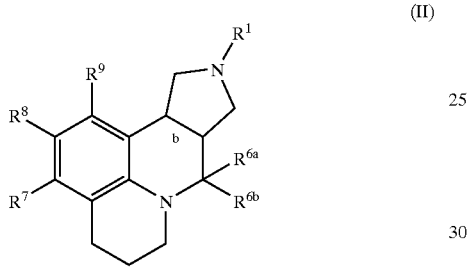

(II)

wherein:

b is a single bond, wherein the bridge hydrogens are in a cis or trans position;

$R^1$ is selected from
hydrogen, methyl, ethyl, n-propyl, n-butyl, s-butyl, t-butyl, n-pentyl, n-hexyl, 2-propyl, 2-butyl, 2-pentyl, 2-hexyl, 2-methylpropyl, 2-methylbutyl, 2-methylpentyl, 2-ethylbutyl, 3-methylpentyl, 3-methylbutyl, 4-methylpentyl, 2-fluoroethyl, 2,2-difluoroethyl, 2,2,2-trifluoroethyl, 2-propenyl, 2-methyl-2-propenyl, trans-2-butenyl, 3-methyl-2-butenyl, 3-butenyl, trans-2-pentenyl, cis-2-pentenyl, 4-pentenyl, 4-methyl-3-pentenyl, 3,3-dichloro-2-propenyl, trans-3-phenyl-2-propenyl, cyclopropyl, cyclobutyl, cyclopentyl, cyclohexyl, cyclopropylmethyl, cyclobutylmethyl, cyclopentylmethyl, cyclohexylmethyl, —CH=CH₂, —CH₂—CH=CH₂, —CH=CH—CH₃, —C≡CH, —C≡C—CH₃, and —CH₂—C≡CH;

$R^{6a}$ is H;

$R^{6b}$ is H;

alternatively, $R^{6a}$ and $R^{6b}$ are taken together to form =O;

$R^7$ and $R^9$, at each occurrence, are independently selected from hydrogen, fluoro, methyl, trifluoromethyl, and methoxy;

$R^8$ is selected from
hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl;

2-Cl-phenyl; 2-F-phenyl; 2-Br-phenyl; 2-CN-phenyl; 2-Me-phenyl; 2-CF₃-phenyl; 2-MeO-phenyl; 2-CF₃O-phenyl; 2-NO₂-phenyl; 2-MeS-phenyl; 2-CHO-phenyl; 2-HOCH₂-phenyl;

3-Cl-phenyl; 3-F-phenyl; 3-Br-phenyl; 3-CN-phenyl; 3-Me-phenyl; 3-Et-phenyl; 3-n-Pr-phenyl; 3-isoPr-phenyl; 3-n-Bu-phenyl; 3-CF₃-phenyl; 3-MeO-phenyl; 3-MeS-phenyl; 3-isopropoxyphenyl; 3-CF₃O-phenyl; 3-NO₂-phenyl; 3-CHO-phenyl; 3-HOCH₂-phenyl; 3-MeOCH₂-phenyl; 3-Me₂NCH₂-phenyl;

4-Cl-phenyl; 4-F-phenyl; 4-Br-phenyl; 4-CN-phenyl; 4-Me-phenyl; 4-Et-phenyl; 4-n-Pr-phenyl; 4-iso-Pr-phenyl; 4-n-Bu-phenyl; 4-CF₃-phenyl; 4-MeO-phenyl; 4-isopropoxyphenyl; 4-CF₃O-phenyl; 4-MeS-phenyl;

4-acetylphenyl; 3-acetamidophenyl; 4-pyridyl; 2-furanyl; 2-thiophenyl; 2-naphthyl; 1-pyrrolidinyl, 2,3-diCl-phenyl; 2,3-diF-phenyl; 2,3-diMe-phenyl; 2,3-diCF₃-phenyl; 2,3-diMeO-phenyl; 2,3-diCF₃O-phenyl;

2,4-diCl-phenyl; 2,4-diF-phenyl; 2,4-diMe-phenyl; 2,4-diCF₃-phenyl; 2,4-diMeO-phenyl; 2,4-diCF₃O-phenyl;

2,5-diCl-phenyl; 2,5-diF-phenyl; 2,5-diMe-phenyl; 2,5-diCF₃-phenyl; 2,5-diMeO-phenyl; 2,5-diCF₃O-phenyl;

2,6-diCl-phenyl; 2,6-diF-phenyl; 2,6-diMe-phenyl; 2,6-diCF₃-phenyl; 2,6-diMeO-phenyl; 2,6-diCF₃O-phenyl;

3,4-diCl-phenyl; 3,4-diF-phenyl; 3,4-diMe-phenyl; 3,4-diCF₃-phenyl; 3,4-diMeO-phenyl; 3,4-diCF₃O-phenyl;

2,4,6-triCl-phenyl; 2,4,6-triF-phenyl; 2,4,6-triMe-phenyl; 2,4,6-triCF₃-phenyl; 2,4,6-triMeO-phenyl; 2,4,6-triCF₃O-phenyl; 2,4,5-triMe-phenyl; 2,3,4-triF-phenyl; 2-Me₄-MeO-5-F-phenyl; 2,6-diCl-4-MeO-phenyl; 2,4-diMeO-6-F-phenyl; 2,6-diF-4-Cl-phenyl; 2,3,4,6-tetraF-phenyl; 2,3,4,5,6-pentaF-phenyl;

2-Cl-4-F-phenyl; 2-Cl-6-F-phenyl; 2-Cl-3-Me-phenyl; 2-Cl-4-MeO-phenyl; 2-Cl-4-EtO-phenyl; 2-Cl-4-iPrO-phenyl; 2-Cl-4-CF₃-phenyl; 2-Cl-4-CF₃O-phenyl; 2-Cl-4-(CH F₂)O-phenyl; 2-F-3-Cl-phenyl; 2-F-4-MeO-phenyl; 2-F-5-Me-phenyl;

2-Me-3-Cl-phenyl; 2-Me-3-CN-phenyl; 2-Me-4-Cl-phenyl;

2-Me-4-F-phenyl; 2-Me-4-CN-phenyl; 2-Me-4-MeO-phenyl; 2-Me-4-EtO-phenyl; 2-Me-4-MeS-phenyl; 2-Me-4-H₂NCO-phenyl; 2-Me-4-MeOC(=O)-phenyl; 2-Me-4-CH₃C(=O)-phenyl; 2-Me-5-F-phenyl; 2-Et-4-MeO-phenyl; 2-MeO-5-F-phenyl; 2-MeO-4-isopropyl-phenyl; 2-CF₃-4-Cl-phenyl; 2-CF₃-4-F-phenyl; 2-CF₃-4-MeO-phenyl; 2-CF₃-4-EtO-phenyl; 2-CF₃-4-iPrO-phenyl; 2-CF₃-4-CN-phenyl; 2-CF₃-6-F-phenyl; 2-CHO-4-MeO-phenyl; 2-MeOC(=O)-3-MeO-phenyl; 2-CH₃CH(OH)-4-MeO-phenyl; 2-CH₃CH(OH)-4-F-phenyl; 2-CH₃CH(OH)-4-Cl-phenyl; 2-CH₃CH(OH)-4-Me-phenyl; 2-CH₃CH(OMe)-4-MeO-phenyl; 2-CH₃C(=O)-4-MeO-phenyl; 2-CH₃C(=O)-4-F-phenyl; 2-CH₃C(=O)-4-Cl-phenyl; 2-CH₃C(=O)-4-Me-phenyl; 2-H₂C(OH)-4-MeO-phenyl; 2-H₂C(OMe)-4-MeO-phenyl: 2-H₃CCH₂CH(OH)-4-MeO-phenyl; 2-H₃CCH₂C(=O)-4-MeO-phenyl; 2-CH₃CO₂CH₂CH₂-4-MeO-phenyl; (Z)-2-HOCH₂CH=CH-4-MeO-phenyl; (E)-2-HOCH₂CH=CH-4-MeO-phenyl; (Z)-2-CH₃CO₂CH=CH-4-MeO-phenyl; (E)-2-CH₃CO₂CH=CH₄-MeO-phenyl; 2-CH₃OCH₂CH₂-4-MeO-phenyl;

3-CN-4-F-phenyl; 3-H₂NCO-4-F-phenyl; (2-Cl-phenyl)-CH=CH—; (3Cl-phenyl)-CH=CH—; (2,6diF-phenyl)-CH=CH—; phenyl-CH=CH—; (2-Me-4-MeO-phenyl)-CH=CH—;

cyclohexyl; cyclopentyl; cyclohexylmethyl; benzyl; 2-F-benzyl; 3-F-benzyl; 4-F-benzyl; 3-MeO-benzyl; 3-OH-benzyl; 2-MeO-benzyl; 2-OH-benzyl; tetrahydroquinolin-1-yl; tetrahydroindolin-1-yl; tetrahydroisoindolin-1-yl;

phenyl-S—; phenyl-NH—; pyrid-3-yl-NH—; (4-Me-pyrid-3-yl)-NH—; (4-Cl-pyrid-3-yl)-NH—; (1-naphthyl)-NH—; (2-naphthyl)-NH—; (2-Me-naphth-1-yl)-NH—; (4-Me-naphth-1-yl)-NH—; (3quinolinyl)-NH—;

(2-[1,1'-biphenyl])-NH—; (3-[1,1'-biphenyl])-NH—; (4-[1,1'-biphenyl])-NH—; (2-F-phenyl)-NH—; (2-Cl-phenyl)-NH—; (2-CF₃-phenyl)-NH—; (2-CH₃-phenyl)-NH—; (2-OMe-phenyl)-NH—; (2-CN-phenyl)-NH—; (2-OCF₃-phenyl)-NH—; (2-SMe-phenyl)-NH—; (3-F-phenyl)-NH—; (3-Cl-phenyl)-NH—; (3-CF₃-phenyl)-NH—; (3-CH₃-phenyl)-NH—; (3-OMe-phenyl)-NH—; (3-CN-phenyl)-NH—; (3-OCF₃-phenyl)-NH—; (3-SMe-phenyl)-NH—; (4-F-phenyl)-NH—; (4-Cl-phenyl)-NH—; (4-CF₃-phenyl)-NH—; (4-CH₃-phenyl)-NH—; (4-OMe-phenyl)-NH—; (4-CN-phenyl)-NH—; (4-OCF₃-phenyl)-NH—; (4-SMe-phenyl)-NH—; (2,3-diCl-phenyl)-NH—; (2,4diCl-phenyl)-NH—; (2,5-diCl-phenyl)-NH—; (2,6-diCl-phenyl)-NH—; (3,4-diCl-phenyl)-NH—; (3,5-diCl-phenyl)-NH—; (2,3-diF-phenyl)-NH—; (2,4-diF-phenyl)-NH—; (2,5-diF-phenyl)-NH—; (2,6-diF-phenyl)-NH—; (3,4-diF-phenyl)-NH—; (3,5-diF-phenyl)-NH—; (2,3-diCH₃-phenyl)-NH—; (2,4-diCH₃-phenyl)-NH—; (2,5-diCH₃-phenyl)-NH—; (2,6-diCH₃-phenyl)-NH—; (3,4-diCH₃-phenyl)-NH—; (3,5-diCH₃-phenyl)-NH—; (2,3-diCF₃-phenyl)-NH—; (2,4-diCF₃-phenyl)-NH—; (2,5-diCF₃-phenyl)-NH—; (2,6-diCF₃-phenyl)-NH—; (3,4-diCF₃-phenyl)-NH—; (3,5-diCF₃-phenyl)-NH—; (2,3-diOMe-phenyl)-NH—; (2,4-diOMe-phenyl)-NH—; (2,5-diOMe-phenyl)-NH—; (2,6-diOMe-phenyl)-NH—; (3,4-diOMe-phenyl)-NH—; (3,5-diOMe-phenyl)-NH—; (2-F-3-Cl-phenyl)-NH—; (2-F-4-Cl-phenyl)-NH—; (2-F-5-Cl-phenyl)-NH—; (2-F-6-Cl-phenyl)-NH—; (2-F-3-CH₃-phenyl)-NH—; (2-F-4-CH₃-phenyl)-NH—; (2-F-5-CH₃-phenyl)-NH—; (2-F-6-CH₃-phenyl)-NH—; (2-F-3-CF₃-phenyl)-NH—; (2-F-4-CF₃-phenyl)-NH—; (2-F-5-CF₃-phenyl)-NH—; (2-F-6-CF₃-phenyl)-NH—; (2-F-3-OMe-phenyl)-NH—; (2-F-4-OMe-phenyl)-NH—; (2-F-5-OMe-phenyl)-NH—; (2-F-6-OMe-phenyl)-NH—; (2-Cl-3-F-phenyl)-NH—; (2-Cl-4-F-phenyl)-NH—; (2-Cl-5-F-phenyl)-NH—; (2-Cl-6-F-phenyl)-NH—; (2-Cl-3-CH₃-phenyl)-NH—; (2-Cl-4-CH₃-phenyl)-NH—; (2-Cl-5-CH₃-phenyl)-NH—; (2-Cl-6-CH₃-phenyl)-NH—; (2-Cl-3-CF₃-phenyl)-NH—; (2-Cl-4-CF₃-phenyl)-NH—; (2-Cl-5-CF₃-phenyl)-NH—; (2-Cl-6-CF₃-phenyl)-NH—; (2-Cl-3-OMe-phenyl)-NH—; (2-Cl-4-OMe-phenyl)-NH—; (2-Cl-5-OMe-phenyl)-NH—; (2-Cl-6-OMe-phenyl)-NH—; (2-CH₃-3-F-phenyl)-NH—; (2-CH₃-4-F-phenyl)-NH—; (2-CH₃-5-F-phenyl)-NH—; (2-CH₃-6-F-phenyl)-NH—; (2-CH₃-3-Cl-phenyl)-NH—; (2-CH₃-4-Cl-phenyl)-NH—; (2-CH₃-5-Cl-phenyl)-NH—; (2-CH₃-6-Cl-phenyl)-NH—; (2-CH₃-3-CF₃-phenyl)-NH—; (2-CH₃-4-CF₃-phenyl)-NH—; (2-CH₃-5-CF₃-phenyl)-NH—; (2-CH₃-6-CF₃-phenyl)-NH—; (2-CH₃-3-OMe-phenyl)-NH—; (2-CH₃-4-OMe-phenyl)-NH—; (2-CH₃-5-OMe-phenyl)-NH—; (2-CH₃-6-OMe-phenyl)-NH—; (2-CF₃-3-F-phenyl)-NH—; (2-CF₃-4-F-phenyl)-NH—; (2-CF₃-5-F-phenyl)-NH—; (2-CF₃-6-F-phenyl)-NH—; (2-CF₃-3-Cl-phenyl)-NH—; (2-CF₃-4-Cl-phenyl)-NH—; (2-CF₃-5-Cl-phenyl)-NH—; (2-CF₃-6-Cl-phenyl)-NH—; (2-CF₃-3-CH₃-phenyl)-NH—; (2-CF₃-4-CH₃-phenyl)-NH—; (2-CH₃-5-CF₃-phenyl)-NH—; (2-CF₃-6-CH₃-phenyl)-NH—; (2-CF₃-3-OMe-phenyl)-NH—; (2-CF₃-4-OMe-phenyl)-NH—; (2-CF₃-5-OMe-phenyl)-NH—; (2-CF₃-6-OMe-phenyl)-NH—; (2-OMe-3-F-phenyl)-NH—; (2-OMe-4-F-phenyl)-NH—; (2-OMe-5-F-phenyl)-NH—; (2-OMe-6-F-phenyl)-NH—; (2-OMe-3-Cl-phenyl)-NH—; (2-OMe-4-Cl-phenyl)-NH—; (2-OMe-5-Cl-phenyl)-NH—; (2-OMe-6-Cl-phenyl)-NH—; (2-OMe-4-CN-phenyl)-NH—; (2-OMe-4-CHO-phenyl)-NH—; (2-OMe-3-CH₃-phenyl)-NH—; (2-OMe-4-CH₃-phenyl)-NH—; (2-OMe-5-CH₃-phenyl)-NH—; (2-OMe-6-CH₃-phenyl)-NH—; (2-OMe-3-CF₃-phenyl)-NH—; (2-OMe-4-CF₃-phenyl)-NH—; (2-OMe-5-CF₃-phenyl)-NH—; (2-OMe-6-CF₃-phenyl)-NH—; (2-acetyl-4-Cl-phenyl)-NH—; (2-acetyl-4-Me-phenyl)-NH—; (2-acetyl-4-MeO-phenyl)-NH—; (2-CH₃CH(OH)-4-Cl-phenyl)-NH—; (2-CH₃CH(OH)-4-Me-phenyl)-NH—; (2-CH₃CH(OH)-4-MeO-phenyl)-NH—;

(3-CF₃-4-Cl-phenyl)-NH—; (3-F-4-CHO-phenyl)-NH—; (3-CH₃-4-CN-phenyl)-NH—; (3-CH₃-4-MeO-phenyl)-NH—; (3-CH₃-4-Cl-phenyl)-NH—; (3-CH₃-4-F-phenyl)-NH—; (3-F-5-CF₃-phenyl)-NH—;

(3-CH₃-4-CO₂Me-phenyl)NH—; (3-CF₃-4-C(O)CH₃-phenyl)NH—; (3-CHO-4-OMe-phenyl)-NH—; (4-F-3-CF₃-phenyl)-NH—;

(2,3,5-triCl-phenyl)-NH—; (2,4,5-triF-phenyl)-NH—; (2,6-diCl-3-Me-phenyl)-NH—; (3,5-diMe-4-MeO-phenyl)-NH—; (2-F-3-Cl-6-CF₃-phenyl)-NH—;

benzyl-NH—; (3-quinolinyl)CH₂NH—; (2-F-phenyl)CH₂NH—; (2-Cl-phenyl)CH₂NH—; (2-CF₃-phenyl)CH₂NH—; (2-CH₃-phenyl)CH₂NH—; (2-OMe-phenyl)CH₂NH—; (2-CN-phenyl)CH₂NH—; (2-OCF₃-phenyl)CH₂NH—; (2-SMe-phenyl)CH₂NH—; (3-F-phenyl)CH₂NH—; (3-Cl-phenyl)CH₂NH—; (3-CF₃-phenyl)CH₂NH—; (3-CH₃-phenyl)CH₂NH—; (3-OMe-phenyl)CH₂NH—; (3-CN-phenyl)CH₂NH—; (3-OCF₃-phenyl)CH₂NH—; (3-SMe-phenyl)CH₂NH—; (4-F-phenyl)CH₂NH—; (4-Cl-phenyl)CH₂NH—; (4-CF₃-phenyl)CH₂NH—; (4-CH₃-phenyl)CH₂NH—; (4-OMe-phenyl)CH₂NH—; (4-CN-phenyl)CH₂NH—; (4-OCF₃-phenyl)CH₂NH—; (4-SMe-phenyl)CH₂NH—; (2,3-diCl-phenyl)CH₂NH—; (2,4-diCl-phenyl)CH₂NH—; (2,5-diCl-phenyl)CH₂NH—; (2,6-diCl-phenyl)CH₂NH—; (3,4-diCi-phenyl)CH₂NH—; (3,5-diCl-phenyl)CH₂NH—; (2,3-diF-phenyl)CH₂NH—; (2,4-diF-phenyl)CH₂NH—; (2,5-diF-phenyl)CH₂NH—; (2,6-diF-phenyl)CH₂NH—; (3,4-diF-phenyl)CH₂NH—; (3,5-diF-phenyl)CH₂NH—; (2,3-diCH₃-phenyl)CH₂NH—; (2,4-diCH₃-phenyl)CH₂NH—; (2,5-diCH₃-phenyl)CH₂NH—; (2,6-diCH₃-phenyl)CH₂NH—; (3,4-diCH₃-phenyl)CH₂NH—; (3,5- diCH₃-phenyl)CH₂NH—; (2,3-diCF₃-phenyl)CH₂NH—; (2,4-diCF₃-phenyl)CH₂NH—; (2,5-diCF₃-phenyl)CH₂NH—; (2,6-diCF₃-phenyl)CH₂NH—; (3,4-diCF₃-phenyl)CH₂NH—; (3,5-diCF₃-phenyl)CH₂NH—; (2,3-diOMe-phenyl)CH₂NH—; (2,4-diOMe-phenyl)CH₂NH—; (2,5-diOMe-phenyl)CH₂NH—; (2,6-diOMe-phenyl)CH₂NH—; (3,4-diOMe-phenyl)CH₂NH—; (3,5-diOMe-phenyl)CH₂NH—; (2-F-3-Cl-phenyl)CH₂NH—; (2-F-4-Cl-phenyl)CH₂NH—; (2-F-5-Cl-phenyl)CH₂NH—; (2-F-6-Cl-phenyl)CH₂NH—; (2-F-3-CH₃-phenyl)CH₂NH—; (2-F-4-CH₃-phenyl)CH₂NH—; (2-F-5-CH₃-phenyl)CH₂NH—; (2-F-6-CH₃-phenyl)CH₂NH—; (2-F-3-CF₃-phenyl)CH₂NH—; (2-F-4-CF₃-phenyl)CH₂NH—; (2-F-5-CF₃-phenyl)CH₂NH—; (2-F-6-CF₃-phenyl)CH₂NH—; (2-F-3-OMe-phenyl)CH₂NH—; (2-F-4-OMe-phenyl)CH₂NH—; (2-F-5-OMe-phenyl)CH₂NH—; (2-F-6-OMe-phenyl)CH₂NH—; (2-Cl-3-F-phenyl)CH₂NH—; (2-Cl-4-F-phenyl)CH₂NH—; (2-Cl-5-F-phenyl)CH₂NH—; (2-Cl-6-F-phenyl)CH₂NH—; (2-Cl-3-CH₃-phenyl)CH₂NH—; (2-Cl-4-CH₃-phenyl)CH₂NH—; (2-Cl-5-CH₃-phenyl)CH₂NH—; (2-Cl-6-CH₃-phenyl)CH₂NH—; (2-Cl-3-CF₃-phenyl)CH₂NH—; (2-Cl-4-CF₃-phenyl)CH₂NH—; (2-Cl-5-CF₃-phenyl)CH₂NH—; (2-Cl-6-CF₃-phenyl)CH₂NH—; (2-Cl-3-OMe-phenyl)CH₂NH—; (2-Cl-4-OMe-phenyl)CH₂NH—; (2-Cl-5-OMe-phenyl)CH₂NH—; (2-Cl-6-OMe-phenyl)CH₂NH—; (2-CH₃-3-F-phenyl)CH₂NH—; (2-CH₃-4-F-phenyl)CH₂NH—; (2-CH₃-5-F-phenyl)CH₂NH—; (2-CH₃-6-F-phenyl)CH₂NH—; (2-CH₃-3-Cl-phenyl)CH₂NH—; (2-CH₃-4-Cl-phenyl)CH₂NH—; (2-CH₃-5-Cl-phenyl)CH₂NH—; (2-CH₃-6-Cl-phenyl)CH₂NH—; (2-CH₃-3-CF₃-phenyl)CH₂NH—; (2-CH₃-4-CF₃-phenyl)CH₂NH—; (2-CH₃-5-CF₃-phenyl)CH₂NH—; (2-CH₃-6-CF₃-phenyl)CH₂NH—; (2-CH₃-3-OMe-phenyl)CH₂NH—; (2-CH₃-4-OMe-phenyl)CH₂NH—; (2-CH₃-5-OMe-phenyl)CH₂NH—; (2-CH₃-6-OMe-phenyl)CH₂NH—; (2-CF₃-3-F-phenyl)CH₂NH—; (2-CF₃-4-F-phenyl)CH₂NH—; (2-CF₃-5-F-phenyl)CH₂NH—; (2-CF₃-6-F-phenyl)CH₂NH—; (2-CF₃-3-Cl-phenyl)CH₂NH—; (2-CF₃-4-Cl-phenyl)CH₂NH—; (2-CF₃-5-Cl-phenyl)CH₂NH—; (2-CF₃-6-Cl-phenyl)CH₂NH—; (2-CF₃-3-CH₃-phenyl)CH₂NH—; (2-CF₃-4-CH₃-phenyl)CH₂NH—; (2-CH₃-5-CF₃-phenyl)CH₂NH—; (2-CF₃-6-CH₃-phenyl)CH₂NH—; (2-CF₃-3-OMe-phenyl)CH₂NH—; (2-CF₃-4-OMe-phenyl)CH₂NH—; (2-CF₃-5-OMe-phenyl)CH₂NH—; (2-CF₃-6-OMe-phenyl)CH₂NH—; (2-OMe-3-F-phenyl)CH₂NH—; (2-OMe-4-F-phenyl)CH₂NH—; (2-OMe-5-F-phenyl)CH₂NH—; (2-OMe-6-F-phenyl)CH₂NH—; (2-OMe-3-Cl-phenyl)CH₂NH—; (2-OMe-4-Cl-phenyl)CH₂NH—; (2-OMe-5-Cl-phenyl)CH₂NH—; (2-OMe-6-Cl-phenyl)CH₂NH—; (2-OMe-4-CN-phenyl)CH₂NH—; (2-OMe-4-CHO-phenyl)CH₂NH—; (2-OMe-3-CH₃-phenyl)CH₂NH—; (2-OMe-4-CH₃-phenyl)CH₂NH—; (2-OMe-5-CH₃-phenyl)CH₂NH—; (2-OMe-6-CH₃-phenyl)CH₂NH—; (2-OMe-3-CF₃-phenyl)CH₂NH—; (2-OMe-4-CF₃-phenyl)CH₂NH—; (2-OMe-5-CF₃-phenyl)CH₂NH—; (2-OMe-6-CF₃-phenyl)CH₂NH—; (2-acetyl-4-Cl-phenyl)CH₂NH—; (2-acetyl-4-Me-phenyl)CH₂NH—; (2-acetyl-4-MeO-phenyl)CH₂NH—; (2-CH₃CH(OH)-4-Cl-phenyl)CH₂NH—; (2-CH₃CH(OH)-4-Me-phenyl)CH₂NH—; (2-CH₃CH(OH)-4-MeO-phenyl)CH₂NH—; (3-CF₃-4-Cl-phenyl)CH₂NH—; (3-F-4-CHO-phenyl)CH₂NH—; (3-CH₃-4-CN-phenyl)CH₂NH—; (3-CH₃-4-MeO-phenyl)CH₂NH—; (3-CH₃-4-Cl-phenyl)CH₂NH—; (3-CH₃-4-F-phenyl)CH₂NH—; (4-F-3-CF₃-phenyl)CH₂NH—; (3-CH₃-4-CO₂Me-phenyl)CH₂NH—; (3-CF₃-4-C(O)CH₃-phenyl)CH₂NH—; (3-CHO-4-OMe-phenyl)CH₂NH—; (2,3,5-triCl-phenyl)CH₂NH—; (2,4,5-triF-phenyl)CH₂NH—; (2,6-diCl-3-Me-phenyl)CH₂NH—; (3,5-diMe-4-MeO-phenyl)CH₂NH—; and (2-F-3-Cl-6-CF₃-phenyl)CH₂NH—.

9. A compound of claim 1 wherein:

$R^1$ is selected from
  $C_{1-6}$ alkyl substituted with Z,
  $C_{2-6}$ alkenyl substituted with Z,
  $C_{2-6}$ alkynyl substituted with Z,
  $C_{3-6}$ cycloalkyl substituted with Z,
  aryl substituted with Z,
  5–6 membered heterocyclic ring system containing at least one heteroatom selected from the group consisting of N, O, and S, said heterocyclic ring system substituted with Z;
  $C_{1-6}$ alkyl substituted with 0–2 $R^2$,
  $C_{2-6}$ alkenyl substituted with 0–2 $R^2$,
  $C_{2-6}$ alkynyl substituted with 0–2 $R^2$,
  aryl substituted with 0–2 $R^2$, and
  5–6 membered heterocyclic ring system containing at least one heteroatom selected from the group consisting of N, O, and S, said heterocyclic ring system substituted with 0–2 $R^2$;

Z is selected from H,
  —CH(OH) $R^2$,
  —C(ethylenedioxy)$R^2$,
  —OR$^2$,
  —SR$^2$,
  —NR$^2$R$^3$,
  —C(O)R$^2$,
  —C(O)NR$^2$R$^3$,
  —NR$^3$C(O)R$^2$,
  —C(O)OR$^2$,
  —OC(O) R$^2$,
  —CH(=NR$^4$)NR$^2$R$^3$,
  —NHC(=NR$^4$)NR$^2$R$^3$,
  —S(O)R$^2$,
  —S(O)$_2$R$^2$,
  —S(O)$_2$NR$^2$R$^3$, and —NR$^3$S(O)$_2$R$^2$;

$R^2$, at each occurrence, is independently selected from
  $C_{1-4}$ alkyl,
  $C_{2-4}$ alkenyl,
  $C_{2-4}$ alkynyl,
  $C_{3-6}$ cycloalkyl,
  aryl substituted with 0–5 $R^{42}$;
  $C_{3-10}$ carbocyclic residue substituted with 0–3 $R^{41}$, and
  5–10 membered heterocyclic ring system containing from 1–4 heteroatoms selected from the group consisting of N, O, and S substituted with 0–3 $R^{41}$;

$R^3$, at each occurrence, is independently selected from H, $C_{1-4}$ alkyl, $C_{2-4}$ alkenyl, $C_{2-4}$ alkynyl, and $C_{1-4}$ alkoxy;

$R^4$, at each occurrence, is independently selected from H, methyl, ethyl, propyl, and butyl;

$R^{6a}$ is H or $C_{1-4}$ alkyl;

$R^{6b}$ is H;

alternatively, $R^{6a}$ and $R^{6b}$ are taken together to form =O or =S;

$R^7$, $R^8$, and $R^9$, at each occurrence, are independently selected from
- H, halo, —CF$_3$, —OCF$_3$, —OH, —CN, —NO$_2$, —NR$^{46}$R$^{47}$,
- C$_{1-8}$ alkyl, C$_{2-8}$ alkenyl, C$_{2-8}$ alkynyl, C$_{1-4}$ haloalkyl, C$_{1-8}$ alkoxy, (C$_{1-4}$ haloalkyl)oxy,
- C$_{1-4}$ alkyl substituted with 0–2 R$^{11}$,
- C$_{3-10}$ carbocyclic residue substituted with 0–3 R$^{33}$,
- aryl substituted with 0–5 R$^{33}$,
- 5–10 membered heterocyclic ring system containing from 1–4 heteroatoms selected from the group consisting of N, O, and S substituted with 0–3 R$^{31}$;
- OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, NR$^{14}$S(O)$_2$R$^{12}$, NR$^{12}$C(O)R$^{15}$, NR$^{12}$C(O)OR$^{15}$, NR$^{12}$S(O)$_2$R$^{15}$, and NR$^{12}$C(O)NHR$^{15}$;

$R^{10}$ is selected from H, C$_{1-4}$ alkyl, C$_{2-4}$ alkenyl, C$_{2-4}$ alkynyl, and C$_{1-4}$ alkoxy;

$R^{11}$ is selected from
- H, halo, —CF$_3$, —CN, —NO$_2$,
- C$_{1-8}$ alkyl, C$_{2-8}$ alkenyl, C$_{2-8}$ alkynyl, C$_{1-4}$ haloalkyl, C$_{1-8}$ alkoxy, C$_{3-10}$ cycloalkyl,
- C$_{3-10}$ carbocyclic residue substituted with 0–3 R$^{33}$,
- aryl substituted with 0–5 R$^{33}$,
- 5–10 membered heterocyclic ring system containing from 1–4 heteroatoms selected from the group consisting of N, O, and S substituted with 0–3 R$^{31}$;
- OR$^{12}$, SR$^{12}$, NR$^{12}$R$^{13}$, C(O)H, C(O)R$^{12}$, C(O)NR$^{12}$R$^{13}$, NR$^{14}$C(O)R$^{12}$, C(O)OR$^{12}$, OC(O)R$^{12}$, OC(O)OR$^{12}$, CH(=NR$^{14}$)NR$^{12}$R$^{13}$, NHC(=NR$^{14}$)NR$^{12}$R$^{13}$, S(O)R$^{12}$, S(O)$_2$R$^{12}$, S(O)NR$^{12}$R$^{13}$, S(O)$_2$NR$^{12}$R$^{13}$, NR$^{14}$S(O)R$^{12}$, and NR$^{14}$S(O)$_2$R$^{12}$;

$R^{12}$, at each occurrence, is independently selected from
- C$_{1-4}$ alkyl,
- C$_{2-4}$ alkenyl,
- C$_{2-4}$ alkynyl,
- C$_{3-6}$ cycloalkyl,
- phenyl substituted with 0–5 R$^{33}$;
- C$_{3-10}$ carbocyclic residue substituted with 0–3 R$^{33}$, and
- 5–10 membered heterocyclic ring system containing from 1–4 heteroatoms selected from the group consisting of N, O, and S substituted with 0–3 R$^{31}$;

$R^{13}$, at each occurrence, is independently selected from H, C$_{1-4}$ alkyl, C$_{2-4}$ alkenyl, and C$_{2-4}$ alkynyl;

$R^{14}$, at each occurrence, is independently selected from H and C$_{1-4}$ alkyl;

$R^{31}$, at each occurrence, is independently selected from H, OH, halo, CF$_3$, SO$_2$R$^{45}$, NR$^{46}$R$^{47}$, methyl, ethyl, and propyl;

$R^{33}$, at each occurrence, is independently selected from
- H, OH, halo, CN, NO$_2$, CF$_3$, SO$_2$R$^{45}$, NR$^{46}$R$^{47}$,
- C$_{1-3}$ alkyl, C$_{2-3}$ alkenyl, C$_{2-3}$ alkynyl, C$_{3-5}$ cycloalkyl, C$_{1-3}$ haloalkyl, C$_{1-3}$ haloalkyl-oxy-, C$_{1-3}$ alkyloxy-, C$_{1-3}$ alkylthio-, C$_{1-3}$ alkyl-C(=O)—, and C$_{1-3}$ alkyl-C(=O)NH—;

$R^{41}$, at each occurrence, is independently selected from
- H, CF$_3$, halo, OH, CO$_2$H, SO$_2$R$^{45}$, NR$^{46}$R$^{47}$, NO$_2$, CN, =O,
- C$_{2-8}$ alkenyl, C$_{2-8}$ alkynyl, C$_{1-4}$ alkoxy, C$_{1-4}$ haloalkyl
- C$_{1-4}$ alkyl substituted with 0–1 R$^{43}$,
- aryl substituted with 0–3 R$^{42}$, and
- 5–10 membered heterocyclic ring system containing from 1–4 heteroatoms selected from the group consisting of N, O, and S substituted with 0–3 R$^{44}$;

$R^{42}$, at each occurrence, is independently selected from
- H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$,
- C$_{2-6}$ alkenyl, C$_{2-6}$ alkynyl, C$_{1-4}$ alkoxy, C$_{1-4}$ haloalkyl, C$_{3-6}$ cycloalkyl,
- C$_{1-4}$ alkyl substituted with 0–1 R$^{43}$,
- aryl substituted with 0–3 R$^{44}$, and
- 5–10 membered heterocyclic ring system containing from 1–4 heteroatoms selected from the group consisting of N, O, and S substituted with 0–3 R$^{44}$;

$R^{43}$ is C$_{3-6}$ cycloalkyl or aryl substituted with 0–3 R$^{44}$;

$R^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, C$_{1-4}$ alkyl, and C$_{1-4}$ alkoxy;

$R^{45}$ is C$_{1-4}$ alkyl;

$R^{46}$, at each occurrence, is independently selected from H and C$_{1-4}$ alkyl;

$R^{47}$, at each occurrence, is independently selected from H, C$_{1-4}$ alkyl, —C(=O)NH(C$_{1-4}$ alkyl), —SO$_2$(C$_{1-4}$ alkyl), —SO$_2$(phenyl), —C(=O)O(C$_{1-4}$ alkyl), —C(=O)(C$_{1-4}$ alkyl), and —C(=O)H;

$R^{48}$, at each occurrence, is independently selected from H, C$_{1-4}$ alkyl, —C(=O)NH(C$_{1-4}$ alkyl), —C(=O)O(C$_{1-4}$ alkyl), —C(=O)(C$_{1-4}$ alkyl), and —C(=O)H;

n is 1 or 2;

m is 1 or 2; and n plus m is 2, 3, or 4.

10. A compound of claim 1 wherein:

$R^1$ is selected from
- C$_{2-5}$ alkyl substituted with Z,
- C$_{2-5}$ alkenyl substituted with Z,
- C$_{2-5}$ alkynyl substituted with Z,
- C$_{3-6}$ cycloalkyl substituted with Z,
- aryl substituted with Z,
- 5–6 membered heterocyclic ring system containing at least one heteroatom selected from the group consisting of N, O, and S, said heterocyclic ring system substituted with Z;
- C$_{1-5}$ alkyl substituted with 0–2 R$^2$,
- C$_{2-5}$ alkenyl substituted with 0–2 R$^2$, and
- C$_{2-5}$ alkynyl substituted with 0–2 R$^2$;

Z is selected from H,
- —CH(OH)R$^2$,
- —C(ethylenedioxy)R$^2$,
- —OR$^2$,
- —SR$^2$,
- —NR$^2$R$^3$,
- —C(O)R$^2$,
- —C(O)NR$^2$R$^3$,
- —NR$^3$C(O)R$^2$,
- —C(O)OR$^2$,
- —OC(O)R$^2$,
- —CH(=NR$^4$)NR$^2$R$^3$,
- —NHC(=NR$^4$)NR$^2$R$^3$,
- —S(O)R$^2$,
- —S(O)$_2$R$^2$,
- —S(O)$_2$NR$^2$R$^3$, and —NR$^3$S(O)$_2$R$^2$;

$R^2$, at each occurrence, is independently selected from
- C$_{1-4}$ alkyl,
- C$_{2-4}$ alkenyl, $C_{2-4}$ alkynyl,
$C_{3-6}$ cycloalkyl,
aryl substituted with 0–5 $R^{42}$;
$C_{3-10}$ carbocyclic residue substituted with 0–3 $R^{41}$, and
5–10 membered heterocyclic ring system containing from 1–4 heteroatoms selected from the group consisting of N, O, and S substituted with 0–3 $R^{41}$;

$R^3$, at each occurrence, is independently selected from
H, $C_{1-4}$ alkyl, $C_{2-4}$ alkenyl, $C_{2-4}$ alkynyl, and $C_{1-4}$ alkoxy;

$R^4$, at each occurrence, is independently selected from H, methyl, ethyl, propyl, and butyl;

$R^{6a}$ is H or $C_{1-4}$ alkyl;

$R^{6b}$ is H;

alternatively, $R^{6a}$ and $R^{6b}$ are taken together to form =O or =S;

$R^7$, $R^8$, and $R^9$, at each occurrence, are independently selected from
H, halo, —$CF_3$, —$OCF_3$, —OH, —$OCH_3$, —CN, —$NO_2$, —$NR^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{1-4}$ alkyl substituted with 0–2 $R^{11}$,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$R^{12}$, C(O)$NR^{12}R^{13}$, $NR^{14}C(O)R^{12}$, C(O)$OR^{12}$, OC(O)$R^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$_2NR^{12}R^{13}$, $NR^{14}S(O)_2R^{12}$, $NR^{14}S(O)R^{12}$, $NR^{14}S(O)_2R^{12}$, $NR^{12}C(O)R^{15}$, $NR^{12}C(O)OR^{15}$, $NR^{12}S(O)_2R^{15}$, and $NR^{12}C(O)NHR^{15}$;

$R^{11}$ is selected from
H, halo, —$CF_3$, —$OCF_3$, —OH, —$OCH_3$, —CN, —$NO_2$, —$NR^{46}R^{47}$,
$C_{1-6}$ alkyl, $C_{2-6}$ alkenyl, $C_{2-6}$ alkynyl, $C_{1-4}$ haloalkyl, $C_{1-6}$ alkoxy, ($C_{1-4}$ haloalkyl)oxy,
$C_{3-10}$ carbocyclic residue substituted with 0–3 $R^{33}$,
aryl substituted with 0–5 $R^{33}$,
5–10 membered heterocyclic ring system containing from 1–4 heteroatoms selected from the group consisting of N, O, and S substituted with 0–3 $R^{31}$;
$OR^{12}$, $SR^{12}$, $NR^{12}R^{13}$, C(O)H, C(O)$NR^{12}$, C(O)$NR^{12}R^{13}$, $NR^{14}C(O)R^{12}$, C(O)$OR^{12}$, OC(O)$R^{12}$, CH(=$NR^{14}$)$NR^{12}R^{13}$, NHC(=$NR^{14}$)$NR^{12}R^{13}$, S(O)$R^{12}$, S(O)$_2R^{12}$, S(O)$_2NR^{12}R^{13}$, and $NR^{14}S(O)_2R^{12}$;

$R^{12}$, at each occurrence, is independently selected from
$C_{1-4}$ alkyl,
$C_{2-4}$ alkenyl,
$C_{2-4}$ alkynyl,
$C_{3-6}$ cycloalkyl,
phenyl substituted with 0–5 $R^{33}$;
$C_{3-10}$ carbocyclic residue substituted with 0–3 $R^{33}$, and
5–10 membered heterocyclic ring system containing from 1–4 heteroatoms selected from the group consisting of N, O, and S substituted with 0–3 $R^{31}$;

$R^{13}$, at each occurrence, is independently selected from H, $C_{1-4}$ alkyl, $C_{2-4}$ alkenyl, and $C_{2-4}$ alkynyl;

$R^{14}$, at each occurrence, is independently selected from H and $C_{1-4}$ alkyl;

$R^{31}$, at each occurrence, is independently selected from
H, OH, halo, $CF_3$, methyl, and ethyl;

$R^{33}$, at each occurrence, is independently selected from
H, OH, halo, CN, $NO_2$, $CF_3$, methyl, and ethyl;

$R^{41}$, at each occurrence, is independently selected from
H, $CF_3$, halo, OH, $CO_2H$, $SO_2R^{45}$, $NR^{46}R^{47}$, $NO_2$, CN, =O,
$C_{2-8}$ alkenyl, $C_{2-8}$ alkynyl, $C_{1-4}$ alkoxy, $C_{1-4}$ haloalkyl,
$C_{1-4}$ alkyl substituted with 0–1 $R^{43}$,
aryl substituted with 0–3 $R^{42}$, and
5–10 membered heterocyclic ring system containing from 1–4 heteroatoms selected from the group consisting of N, O, and S substituted with 0–3 $R^{44}$;

$R^{42}$, at each occurrence, is independently selected from
H, $CF_3$, halo, OH, $CO_2H$, $SO_2R^{45}$, $SR^{45}$, $NR^{46}R^{47}$, $OR^{48}$, $NO_2$, CN, CH(=NH)$NH_2$, NHC(=NH)$NH_2$,
$C_{2-6}$ alkenyl, $C_{2-6}$ alkynyl, $C_{1-4}$ alkoxy, $C_{1-4}$ haloalkyl,
$C_{3-6}$ cycloalkyl,
$C_{1-4}$ alkyl substituted with 0–1 $R^{43}$,
aryl substituted with 0–3 $R^{44}$, and
5–10 membered heterocyclic ring system containing from 1–4 heteroatoms selected from the group consisting of N, O, and S substituted with 0–3 $R^{44}$;

$R^{43}$ is $C_{3-6}$ cycloalkyl or aryl substituted with 0–3 $R^{44}$;

$R^{44}$, at each occurrence, is independently selected from H, halo, —OH, $NR^{46}R^{47}$, $CO_2H$, $SO_2R^{45}$, —$CF_3$, —$OCF_3$, —CN, —$NO_2$, $C_{1-4}$ alkyl, and $C_{1-4}$ alkoxy;

$R^{45}$ is $C_{1-4}$ alkyl;

$R^{46}$, at each occurrence, is independently selected from H and $C_{1-3}$ alkyl;

$R^{47}$, at each occurrence, is independently selected from H, $C_{1-4}$ alkyl, —C(=O)NH($C_{1-4}$ alkyl), —$SO_2$($C_{1-4}$ alkyl),
—$SO_2$(phenyl), —C(=O)O($C_{1-4}$ alkyl), —C(=O)($C_{1-4}$ alkyl), and —C(=O)H;

$R^{48}$, at each occurrence, is independently selected from H, $C_{1-4}$ alkyl, —C(=O)NH($C_{1-4}$ alkyl), —C(=O)O($C_{1-4}$ alkyl),
—C(=O)($C_{1-4}$ alkyl), and —C(=O)H;

n is 1 or 2;

m is 1 or 2; and n plus m is 2, 3, or 4.

11. A compound of claim 9 wherein:

$R^1$ is selected from
$C_{2-4}$ alkyl substituted with Z,
$C_{2-4}$ alkenyl substituted with Z,
$C_{2-4}$ alkynyl substituted with Z,
$C_{3-6}$ cycloalkyl substituted with Z,
aryl substituted with Z,
5–6 membered heterocyclic ring system containing at least one heteroatom selected from the group consisting of N, O, and S, said heterocyclic ring system substituted with Z;
$C_{2-4}$ alkyl substituted with 0–2 $R^2$, and
$C_{2-4}$ alkenyl substituted with 0–2 $R^2$;

Z is selected from H,
—CH(OH)$R^2$,
—C(ethylenedioxy)$R^2$,
—$OR^2$,
—$SR^2$,
—$NR^2R^3$,
—C(O)$R^2$,
—C(O)$NR^2R^3$,
—$NR^3$C(O)$R^2$,
—C(O)$OR^2$,
—S(O)$R^2$, —S(O)$_2$R$^2$,
—S(O)$_2$NR$^2$R$^3$, and —NR$^3$S(O)$_2$R$^2$;

R$^2$ at each occurrence, is independently selected from
  phenyl substituted with 0–5 R$^{42}$;
  C$_{3-10}$ carbocyclic residue substituted with 0–3 R$^{41}$, and
  5–10 membered heterocyclic ring system containing from 1–4 heteroatoms selected from the group consisting of N, O, and S substituted with 0–3 R$^{41}$;

R$^3$, at each occurrence, is independently selected from
  H, C$_{1-4}$ alkyl, C$_{2-4}$ alkenyl, C$_{2-4}$ alkynyl, and
  C$_{1-4}$ alkoxy;

R$^4$, at each occurrence, is independently selected from H, methyl, ethyl, propyl, and butyl;

R$^{6a}$ is H or C$_{1-4}$ alkyl;

R$^{6b}$ is H;

alternatively, R$^{6a}$ and R$^{6b}$ are taken together to form =O or =S;

R$^7$, R$^8$, and R$^9$, at each occurrence, are independently selected from
  H, halo, —CF$_3$, —OCF$_3$, —OH, —OCH$_3$, —CN, —NO$_2$,
  C$_{1-4}$ alkyl, C$_{1-4}$ haloalkyl, C$_{1-4}$ alkoxy, (C$_{1-3}$ haloalkyl)oxy, and
  C$_{1-4}$ alkyl substituted with 0–2 R$^{11}$;

R$^{11}$ is selected from
  H, halo, —CF$_3$, —OCF$_3$, —OH, —OCH$_3$, —CN, —NO$_2$,
  C$_{1-4}$ alkyl, C$_{1-4}$ haloalkyl, C$_{1-4}$ alkoxy, and (C$_{1-3}$ haloalkyl)oxy;

R$^{33}$, at each occurrence, is independently selected from H, OH, halo, CF$_3$, and methyl;

R$^{41}$, at each occurrence, is independently selected from
  H, CF$_3$, halo, OH, CO$_2$H, SO$_2$R$^{45}$, NR$^{46}$R$^{47}$, NO$_2$, CN, =O,
  C$_{2-8}$ alkenyl, C$_{2-8}$ alkynyl, C$_{1-4}$ alkoxy, C$_{1-4}$ haloalkyl,
  C$_{1-4}$ alkyl substituted with 0–1 R$^{43}$,
  aryl substituted with 0–3 R$^{42}$, and
  5–10 membered heterocyclic ring system containing from 1–4 heteroatoms selected from the group consisting of N, O, and S substituted with 0–3 R$^{44}$;

R$^{42}$, at each occurrence, is independently selected from
  H, CF$_3$, halo, OH, CO$_2$H, SO$_2$R$^{45}$, SR$^{45}$, NR$^{46}$R$^{47}$, OR$^{48}$, NO$_2$, CN, CH(=NH)NH$_2$, NHC(=NH)NH$_2$,
  C$_{2-6}$ alkenyl, C$_{2-6}$ alkynyl, C$_{1-4}$ alkoxy, C$_{1-4}$ haloalkyl,
  C$_{3-6}$ cycloalkyl,
  C$_{1-4}$ alkyl substituted with 0–1 R$^{43}$,
  aryl substituted with 0–3 R$^{44}$, and
  5–10 membered heterocyclic ring system containing from 1–4 heteroatoms selected from the group consisting of N, O, and S substituted with 0–3 R$^{44}$; p1 R$^{43}$ is cyclopropyl, cyclobutyl, cyclopentyl, cyclohexyl, phenyl, or pyridyl, each substituted with 0–3 R$^{44}$.

R$^{44}$, at each occurrence, is independently selected from H, halo, —OH, NR$^{46}$R$^{47}$, CO$_2$H, SO$_2$R$^{45}$, —CF$_3$, —OCF$_3$, —CN, —NO$_2$, methyl, ethyl, propyl, butyl, methoxy, ethoxy, propoxy, and butoxy;

R$^{45}$ is methyl, ethyl, propyl, or butyl;

R$^{46}$, at each occurrence, is independently selected from H, methyl, ethyl, propyl, and butyl;

R$^{47}$, at each occurrence, is independently selected from
  H, methyl, ethyl, n-propyl, i-propyl, n-butyl, i-butyl, —C(=O)NH(methyl), —C(=O)NH(ethyl), —SO$_2$(methyl), —SO$_2$(ethyl), —SO$_2$(phenyl), —C(=O)O(m ethyl), —C(=O)O(ethyl), —C(=O)(methyl), —C(=O)(ethyl), and —C(=O)H;

R$^{48}$, at each occurrence, is independently selected from
  H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

n is 1 or 2;
m is 1 or 2; and
n plus m is 2 or 3.

12. A compound of claim 9 wherein:

R$^1$ is selected from
  ethyl substituted with Z,
  propyl substituted with Z,
  butyl substituted with Z,
  propenyl substituted with Z,
  butenyl substituted with Z,
  ethyl substituted with R$^2$,
  propyl substituted with R$^2$,
  butyl substituted with R$^2$,
  propenyl substituted with R$^2$, and
  butenyl substituted with R$^2$;

Z is selected from H,
  —CH(OH)R$^2$,
  —SR$^2$,
  —OR$^2$,
  —NR$^2$R$^3$,
  —C(O)R$^2$,
  —C(O)NR$^2$R$^3$,
  —NR$^3$C(O)R$^2$,
  —C(O)OR$^2$,
  —S(O)R$^2$,
  —S(O)$_2$R$^2$,
  —S(O)$_2$NR$^2$R$^3$, and —NR$^3$S(O)$_2$R$^2$;

R$^2$, at each occurrence, is independently selected from
  phenyl substituted with 0–3 R$^{42}$;
  naphthyl substituted with 0–3 R$^{42}$;
  cyclopropyl substituted with 0–3 R$^{41}$;
  cyclobutyl substituted with 0–3 R$^{41}$;
  cyclopetyl substituted with 0–3 R$^{41}$;
  cyclohexyl substituted with 0–3 R$^{41}$;
  pyridyl substituted with 0–3 R$^{41}$;
  indolyl substituted with 0–3 R$^{41}$;
  indolinyl substituted with 0–3 R$^{41}$;
  benzimidazolyl substituted with 0–3 R$^{41}$;
  benzotriazolyl substituted with 0–3 R$^{41}$;
  benzothienyl substituted with 0–3 R$^{41}$;
  benzofuranyl substituted with 0–3 R$^{41}$;
  phthalimid-1-yl substituted with 0–3 R$^{41}$;
  inden-2-yl substituted with 0–3 R$^{41}$;
  2,3-dihydro-1H-inden-2-yl substituted with 0–3 R$^{41}$;
  indazolyl substituted with 0–3 R$^{41}$;
  tetrahydroquinolinyl substituted with 0–3 R$^{41}$; and
  tetrahydro-isoquinolinyl substituted with 0–3 R$^{41}$;

R$^3$, at each occurrence, is independently selected from H, methyl, and ethyl;

R$^{6a}$ is H or C$_{1-4}$ alkyl;

R$^{6b}$ is H;

alternatively, R$^{6a}$ and R$^{6b}$ are taken together to form =O or =S;

R$^7$, R$^8$, and R$^9$, at each occurrence, are independently selected from H, F, Cl, methyl, ethyl, methoxy, —CF$_3$, and —OCF$_3$;

R$^{41}$, at each occurrence, is independently selected from H, F, Cl, Br, OH, CF$_3$, NO$_2$, CN, =O, methyl, ethyl, propyl, butyl, methoxy, and ethoxy;

R$^{42}$, at each occurrence, is independently selected from H, F, Cl, Br, OH, CF$_3$, SO$_2$R$^{45}$, SR$^{45}$, NR$^{46}$R$^{47}$, OR$^{48}$, NO$_2$, CN, =O, methyl, ethyl, propyl, butyl, methoxy, and ethoxy;

R$^{45}$ is methyl, ethyl, propyl, or butyl;

R$^{46}$, at each occurrence, is independently selected from H, methyl, ethyl, propyl, and butyl;

R$^{47}$, at each occurrence, is independently selected from H, methyl, ethyl, n-propyl, i-propyl, n-butyl, i-butyl, —C(=O)NH(methyl), —C(=O)NH(ethyl), —SO$_2$(methyl), —SO$_2$(ethyl), —SO$_2$(phenyl), —C(=O)O(methyl), —C(=O)O(ethyl), —C(=O)(methyl), —C(=O)(ethyl), and —C(=O)H;

R$^{48}$, at each occurrence, is independently selected from H, methyl, ethyl, n-propyl, i-propyl, —C(=O)NH(methyl), —C(=O)NH(ethyl), —C(=O)O(methyl), —C(=O)O(ethyl), —C(=O)(methyl), —C(=O)(ethyl), and —C(=O)H;

n is 1; and m is 1.

13. A compound of claim 9 of Formula (II)

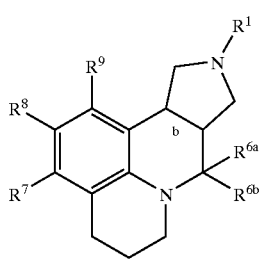

(II)

wherein:
b is a single bond wherein the bridging hydrogens are either cis or trans;

R$^1$ is selected from
—(CH$_2$)$_3$C(=O)(4-fluoro-phenyl),
—(CH$_2$)$_3$C(=O)(4-bromo-phenyl),
—(CH$_2$)$_3$C(=O)(4-methyl-phenyl),
—(CH$_2$)$_3$C(=O)(4-methoxy-phenyl),
—(CH$_2$)$_3$C(=O)(4-(3,4-dichloro-phenyl)phenyl),
—(CH$_2$)$_3$C(=O)(3-methyl-4-fluoro-phenyl),
—(CH$_2$)$_3$C(=O)(2,3-dimethoxy-phenyl),
—(CH$_2$)$_3$C(=O)(phenyl),
—(CH$_2$)$_3$C(=O)(4-chloro-phenyl),
—(CH$_2$)$_3$C(=O)(3-methyl-phenyl),
—(CH$_2$)$_3$C(=O)(4-t-butyl-phenyl),
—(CH$_2$)$_3$C(=O)(3,4-difluoro-phenyl),
—(CH$_2$)$_3$C(=O)(2-methoxy-5-fluoro-phenyl),
—(CH$_2$)$_3$C(=O)(4-fluoro-1-naphthyl),
—(CH$_2$)$_3$C(=O)(benzyl),
—(CH$_2$)$_3$C(=O)(4-pyridyl),
—(CH$_2$)$_3$C(=O)(3-pyridyl),
—(CH$_2$)$_3$CH(OH)(4-fluoro-phenyl),
—(CH$_2$)$_3$CH(OH)(4-pyridyl),
—(CH$_2$)$_3$CH(OH)(2,3-dimethoxy-phenyl),
—(CH$_2$)$_3$S(3-fluoro-phenyl),
—(CH$_2$)$_3$S(4-fluoro-phenyl),
—(CH$_2$)$_3$S(=O)(4-fluoro-phenyl),
—(CH$_2$)$_3$SO$_2$(3-fluoro-phenyl),
—(CH$_2$)$_3$SO$_2$(4-fluoro-phenyl),
—(CH$_2$)$_3$O(4-fluoro-phenyl),
—(CH$_2$)$_3$O(phenyl),
—(CH$_2$)$_3$O(3-pyridyl),
—(CH$_2$)$_3$O(4-pyridyl),
—(CH$_2$)$_3$O(2-NH$_2$-phenyl),
—(CH$_2$)$_3$O(2-NH$_2$-5-F-phenyl),
—(CH$_2$)$_3$O(2-NH$_2$-4-F-phenyl),
—(CH$_2$)$_3$O(2-NH$_2$-3-F-phenyl),
—(CH$_2$)$_3$O(2-NH$_2$-4-Cl-phenyl),
—(CH$_2$)$_3$O(2-NH$_2$-4-OH-phenyl),
—(CH$_2$)$_3$O(2-NH$_2$-4-Br-phenyl),
—(CH$_2$)$_3$O(2-NHC(=O)Me-4-F-phenyl),
—(CH$_2$)$_3$O(2-NHC(=O)Me-phenyl),
—(CH$_2$)$_3$NH(4-fluoro-phenyl),
—(CH$_2$)$_3$N(methyl)(4-fluoro-phenyl),
—(CH$_2$)$_3$CO$_2$(ethyl),
—(CH$_2$)$_3$C(=O)N(methyl)(methoxy),
—(CH$_2$)$_3$C(=O)NH(4-fluoro-phenyl),
—(CH$_2$)$_2$NHC(=O)(phenyl),
—(CH$_2$)$_2$NMeC(=O)(phenyl),
—(CH$_2$)$_2$NHC(=O)(2-fluoro-phenyl),
—(CH$_2$)$_2$NMeC(=O)(2-fluoro-phenyl),
—(CH$_2$)$_2$NHC(=O)(4-fluoro-phenyl),
—(CH$_2$)$_2$NMeC(=O)(4-fluoro-phenyl),
—(CH$_2$)$_2$NHC(=O)(2,4-difluoro-phenyl),
—(CH$_2$)$_2$NMeC(=O)(2,4-difluoro-phenyl),
—(CH$_2$)$_3$(3-indolyl),
—(CH$_2$)$_3$(1-methyl-3-indolyl),
—(CH$_2$)$_3$(1-indolyl),
—(CH$_2$)$_3$(1-indolinyl),
—(CH$_2$)$_3$(1-benzimidazolyl),
—(CH$_2$)$_3$(1H-1,2,3-benzotriazol-1-yl),
—(CH$_2$)$_3$(1H-1,2,3-benzotriazol-2-yl),
—(CH$_2$)$_2$(1H-1,2,3-benzotriazol-1-yl),
—(CH$_2$)$_2$(1H-1,2,3-benzotriazol-2-yl),
—(CH$_2$)$_3$(3,4 dihydro-1(2H)-quinolinyl),
—(CH$_2$)$_2$C(=O)(4-fluoro-phenyl),
—(CH$_2$)$_2$C(=O)NH(4-fluoro-phenyl),
—CH$_2$CH$_2$(3-indolyl),
—CH$_2$CH$_2$(1-phthalimidyl),
—(CH$_2$)$_4$C(=O)N(methyl)(methoxy),
—(CH$_2$)$_4$CO$_2$(ethyl),
—(CH$_2$)$_4$C(=O)(phenyl),
—(CH$_2$)$_4$(cyclohexyl),
—(CH$_2$)$_3$CH(phenyl)$_2$,
—CH$_2$CH$_2$CH=C(phenyl)$_2$,
—CH$_2$CH$_2$CH=CMe(4-F-phenyl),
—(CH$_2$)$_3$CH(4-fluoro-phenyl)$_2$,
—CH$_2$CH$_2$CH=C(4-fluorophenyl)$_2$,
—(CH$_2$)$_2$(2,3-dihydro-1H-inden-2-yl),
—(CH$_2$)$_3$C(=O)(2-NH$_2$-phenyl),
—(CH$_2$)$_3$C(=O)(2-NH$_2$-5-F-phenyl),
—(CH$_2$)$_3$C(=O)(2-NH$_2$-4-F-phenyl),
—(CH$_2$)$_3$C(=O)(2-NH$_2$-3-F-phenyl),
—(CH$_2$)$_3$C(=O)(2-NH$_2$-4-Cl-phenyl),
—(CH$_2$)$_3$C(=O)(2-NH$_2$-4-OH-phenyl),
—(CH$_2$)$_3$C(=O)(2-NH$_2$-4-Br-phenyl),
—(CH$_2$)$_3$(1H-indazol-3-yl),
—(CH$_2$)$_3$(5-F-1H-indazol-3-yl),
—(CH$_2$)$_3$(7-F-1H-indazol-3-yl),
—(CH$_2$)$_3$(6-Cl-1H-indazol-3-yl),
—(CH$_2$)$_3$(6-Br-1H-indazol-3-yl),
—(CH$_2$)$_3$C(=O)(2-NHMe-phenyl),
—(CH$_2$)$_3$(1-benzothien-3-yl),
—(CH$_2$)$_3$(6-F-1H-indol-1-yl),
—(CH$_2$)$_3$(5-F-1H-indol-1-yl),
—(CH$_2$)$_3$(6-F-2,3-dihydro-1H-indol-1-yl),
—(CH$_2$)$_3$(5-F-2,3-dihydro-1H-indol-1-yl),
—(CH$_2$)$_3$(6-F-1H-indol-3-yl),
—(CH$_2$)$_3$(5-F-1H-indol-3-yl), —(CH₂)₃(5-F-1H-indol-3-yl),
—(CH₂)₃(9H-purin-9-yl),
—(CH₂)₃(7H-purin-7-yl),
—(CH₂)₃(6-F-1H-indazol-3-yl),
—(CH₂)₃C(=O)(2-NHSO₂Me-4-F-phenyl),
—(CH₂)₃C(=O)(2-NHC(=O)Me-4-F-phenyl),
—(CH₂)₃C(=O)(2-NHC(=O)Me-phenyl),
—(CH₂)₃C(=O)(2-NHCO₂Et-4-F-phenyl),
—(CH₂)₃C(=O)(2-NHC(=O)NHEt-4-F-phenyl),
—(CH₂)₃C(=O)(2-NHCHO-4-F-phenyl),
—(CH₂)₃C(=O)(2-OH-4-F-phenyl),
—(CH₂)₃C(=O)(2-MeS-4-F-phenyl),
—(CH₂)₃C(=O)(2-NHSO₂Me-4-F-phenyl),
—(CH₂)₂C(Me)CO₂Me,
—(CH₂)₂C(Me)CH(OH)(4-F-phenyl)₂,
—(CH₂)₂C(Me)CH(OH)(4-Cl-phenyl)₂,
—(CH₂)₂C(Me)C(=O)(4-F-phenyl),
—(CH₂)₂C(Me)C(=O)(2-MeO-4-F-phenyl),
—(CH₂)₂C(Me)C(=O)(3-Me-4-F-phenyl),
—(CH₂)₂C(Me)C(=O)(2-Me-phenyl),
—(CH₂)₂C(Me)C(=O)phenyl,

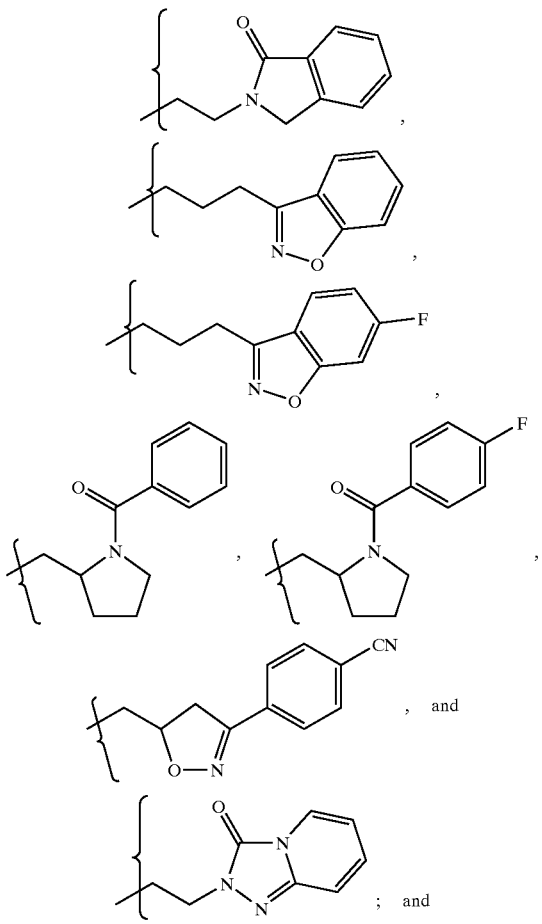

R⁷, R⁸, and R⁹, at each occurrence, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, trifluoromethoxy, phenyl, benzyl,
HC(=O)—, methylC(=O)—, ethylC(=O)—, propylC(=O)—, isopropylC(=O)—, n-butylC(=O)—, isobutylC(=O)—, secbutylC(=O)—, tertbutylC(=O)—, phenylC(=O)—,
methylC(=O)NH—, ethylC(=O)NH—, propylC(=O)NH—, isopropylC(=O)NH—, n-butylC(=O)NH—, isobutylC(=O)NH—, secbutylC(=O)NH—, tertbutylC(=O)NH—, phenylC(=O)NH—,
methylamino-, ethylamino-, propylamino-, isopropylamino-, n-butylamino-, isobutylamino-, secbutylamino-, tertbutylamino-, phenylamino-,
provided that two of substituents R⁷, R⁸, and R⁹, are independently selected from hydrogen, fluoro, chloro, bromo, cyano, methyl, ethyl, propyl, isopropyl, butyl, t-butyl, nitro, trifluoromethyl, methoxy, ethoxy, isopropoxy, and trifluoromethoxy.

14. A pharmaceutical composition comprising a pharmaceutically acceptable carrier and a therapeutically effective amount of a compound of claim 1, or a pharmaceutically acceptable salt thereof.

15. A method for treating obesity comprising administering to a patient in need thereof a therapeutically effective amount of a compound of claim 1, or a pharmaceutically acceptable salt thereof.

16. A method for treating schizophrenia comprising administering to a patient in need thereof a therapeutically effective amount of a compound of claim 1, or a pharmaceutically acceptable salt thereof.

17. A method for treating depression comprising administering to a patient in need thereof a therapeutically effective amount of a compound of claim 1, or a pharmaceutically acceptable salt thereof.

18. The compound according to claim 1, wherein the compound is selected from the group consisting of
(±)-trans-10-benzyl-5,6,9,10,11,11a-hexahydro-4H-pyrido[3,2,1-ij]pyrrolo[3,4-c]quinolin-8(8aH)-one, hydrochloride salt,
(±)-trans-10-benzyl-5,6,8,8a,9,10,11,11a-octahydro-4H-pyrido[3,2,1-ij]pyrrolo[3,4-c]quinoline bis-hydrochloride salt,
(±)-trans-5,6,9,10,11,11a-hexahydro-4H-pyrido[3,2,1-ij]pyrrolo[3,4-c]quinolin-8(8aH)-one, hydrochloride salt,
(±)-trans-5,6,8,8a,9,10,11,11a-octahydro-4H-pyrido[3,2,1-ij]pyrrolo[3,4-c]quinoline, bis-hydrochloride salt,
(±)-trans-10-methyl-5,6,9,10,11,11a-hexahydro-4H-pyrido[3,2,1-ij]pyrrolo[3,4-c]quinolin-8(8aH)-one, hydrochloride salt,
(±)-trans-10-methyl-5,6,8,8a,9,10,11,11a-octahydro-4H-pyrido[3,2,1-ij]pyrrolo[3,4-c]quinoline, bis-hydrochloride salt,
(±)-trans-2-[4-methoxy-2-(trifluoromethyl)phenyl]-5,6,8,8a,9,10,11,11a-octahydro-4H-pyrido[3,21-ij]pyrrolo[3,4-c]quinoline, bis-hydrochloride salt,
(±)-cis-10-benzyl-5,6,9,10,11,11a-hexahydro-4H-pyrido[3,2,1-ij]pyrrolo[3,4-c]quinolin-8(8aH)-one, hydrochloride salt,
(±)-cis-10-benzyl-5,6,8,8a,9,10,11,11a-octahydro-4H-pyrido[3,2,1-ij]pyrrolo[3,4-c]quinoline, bis-hydrochloride salt,
(±)-cis-5,6,9,10,11,11a-hexahydro-4H-pyrido[3,2,1-ij]pyrrolo[3,4-c]quinolin-8(8aH)-one, hydrochloride salt,
(±)-cis-5,6,8,8a,9,10,11,11a-octahydro-4H-pyrido[3,2,1-ij]pyrrolo[3,4-c]quinoline, bis-hydrochloride salt,
(±)-cis-10-methyl-5,6,9,10,11,11a-hexahydro-4H-pyrido[3,2,1-ij]pyrrolo[3,4-c]quinolin-8(8aH)-one, hydrochloride salt,
(±)-cis-10-methyl-5,6,8,8a,9,10,11,11a-octahydro-4H-pyrido[3,2,1-ij]pyrrolo[3,4-c]quinoline, bis-hydrochloride salt, (±)-cis-2-[4-methoxy-2-(trifluoromethyl)phenyl]-5,6,8,
8a,9,10,11,11a-octahydro-4H-pyrido[3,2,1-ij]pyrrolo
[3,4-c]quinoline, bis-hydrochloride salt, (±)-cis-2-phenyl-5,6,8,8a,9,10,11,11a-octahydro-4H-
pyrido[3,2,1-ij]pyrrolo[3,4-c]quinoline, bis-
hydrochloride salt, (±)-cis-10-methyl-2-phenyl-5,6,8,8a,9,10,11,11a-
octahydro-4H-pyrido[3,2,1-ij]pyrrolo[3,4-c]quinoline,
bis-hydrochloride salt, (±)-cis-N-phenyl-5,6,8,8a,9,10,11,11a-octahydro-4H-
pyrido[3,2,1-ij]pyrrolo[3,4-c]quinolin-2-amine, (±)-cis-N-(2,4-dichlorophenyl)-5,6,8,8a,9,10,11,11a-
octahydro-4H-pyrido[3,2,1-ij]pyrrolo[3,4-c]quinolin-
2-amine, (±)-cis-N-(2,5-dichlorophenyl)-5,6,8,8a,9,10,11,11a-
octahydro-4H-pyrido[3,2,1-ij]pyrrolo[3,4-c]quinolin-
2-amine, (±)-cis-2-[4-(methylsulfanyl)phenyl]-5,6,8,8a,9,10,11,
11a-octahydro-4H-pyrido[3,2,1-ij]pyrrolo[3,4-c]
quinoline, trifluoroacetic acid salt, (±)-cis-2-(2,3-dichlorophenyl)-5,6,8,8a,9,10,11,11a-
octahydro-4H-pyrido[3,2,1-ij]pyrrolo[3,4-c]quinoline,
trifluoroacetic acid salt, (±)-cis-2-(3,4-dimethoxyphenyl)-5,6,8,8a,9,10,11,11a-
octahydro-4H-pyrido[3,2,1-ij]pyrrolo[3,4-c]quinoline,
trifluoroacetic acid salt, (±)-cis-2-(2,5-dichlorophenyl)-5,6,8,8a,9,10,11,11a-
octahydro-4H-pyrido[3,2,1-ij]pyrrolo[3,4-c]quinoline,
trifluoroacetic acid salt, (±)-cis-2-[2-(trifluoromethyl)phenyl]-5,6,8,8a,9,10,11,
11a-octahydro-4H-pyrido[3,2,1-ij]pyrrolo[3,4-c]
quinoline, trifluoroacetic acid salt, (8aR,11aR)-5,6,8,8a,9,10,11,11a-octahydro-4H-pyrido[3,
2,1-ij]pyrrolo[3,4-c]quinoline, bis-hydrochloride salt, (8aS,11aS)-5,6,8,8a,9,10,11,11a-octahydro-4H-pyrido[3,
2,1-ij]pyrrolo[3,4-c]quinoline, bis-hydrochloride salt, (8aR,11aR)-2-(2,4-dichlorophenyl)-5,6,8,8a,9,10,11,11a-
octahydro-4H-pyrido[3,2,1-ij]pyrrolo[3,4-c]quinoline,
trifluoroacetic acid salt, 4-[(8aR,11aR)-5,6,8,8a,9,10,11,11a-octahydro-4H-pyrido
[3,2,1-ij]pyrrolo[3,4-c]quinolin-2-yl]-3-
methylbenzonitrile, trifluoroacetic acid salt, (8aR,11aR)-2-(2-methylphenyl)-5,6,8,8a,9,10,11,11a-
octahydro-4H-pyrido[3,2,1-ij]pyrrolo[3,4-c]quinoline,
trifluoroacetic acid salt, (8aR,11aR)-2-(3-methylphenyl)-5,6,8,8a,9,10,11,11a-
octahydro-4H-pyrido[3,2,1-ij]pyrrolo[3,4-c]quinoline,
trifluoroacetic acid salt, (8aR,11aR)-2-(4-methylphenyl)-5,6,8,8a,9,10,11,11a-
octahydro-4H-pyrido[3,2,1-ij]pyrrolo[3,4-c]quinoline,
trifluoroacetic acid salt, 2-[(8aR,11aR)-5,6,8,8a,9,10,11,11a-octahydro-4H-pyrido
[3,2,1-ij]pyrrolo[3,4-c]quinolin-2-yl]-5-
methylbenzaldehyde, trifluoroacetic acid salt, {2-[(8aR,11aR)-5,6,8,8a,9,10,11,11a-octahydro-4H-
pyrido[3,2,1-ij]pyrrolo[3,4-c]quinolin-2-yl]-5-
methylphenyl}methanol, (±)-trans 2-(2,4-dichlorophenyl)-5,6,8,8a,9,10,11,11a-
octahydro-4H-pyrido[3,2,1-ij]pyrrolo[3,4-c]quinoline, (±)-trans 2-[4-isopropoxy-2-(trifluoromethyl)phenyl]-5,
6,8,8a,9,10,11,11a-octahydro-4H-pyrido[3,2,1-ij]
pyrrolo[3,4-c]quinoline, (±)-trans 2-(4-methoxy-2-methylphenyl)-5,6,8,8a,9,10,
11,11a-octahydro-4H-pyrido[3,2,1-ij]pyrrolo[3,4-c]
quinoline, (8aR,11aR)-N-[3,5-bis(trifluoromethyl)phenyl]-5,6,8,8a,
9,10,11,11a-octahydro-4H-pyrido[3,2,1-ij]pyrrolo[3,4-
c]quinolin-2-amine, bis-trifluoroacetic acid salt, (8aR,11aR)-N-(4-fluoro-2-methylphenyl)-5,6,8,8a,9,10,
11,11a-octahydro-4H-pyrido[3,2,1-ij]pyrrolo[3,4-c]
quinolin-2-amine, bis-trifluoroacetic acid salt, (8aR,11aR)-N-[2-chloro-5-(trifluoromethyl)phenyl]-5,6,
8,8a,9,10,11,11a-octahydro-4H-pyrido[3,2,1-ij]pyrrolo
[3,4-c]quinolin-2-amine, bis-trifluoroacetic acid salt, (8aR,11aR)-N-[2-fluoro-5-(trifluoromethyl)phenyl]-5,6,
8,8a,9,10,11,11a-octahydro-4H-pyrido[3,2,1-ij]pyrrolo
[3,4-c]quinolin-2-amine, bis-trifluoroacetic acid salt, (8aR,11aR)-N-[3-fluoro-5-(trifluoromethyl)phenyl]-5,6,
8,8a,9,10,11,11a-octahydro-4H-pyrido[3,2,1-ij]pyrrolo
[3,4-c]quinolin-2-amine, bis-trifluoroacetic acid salt, (8aR,11aR)-N-[3-(trifluoromethyl)phenyl]-5,6,8,8a,9,10,
11,11a-octahydro-4H-pyrido[3,2,1-ij]pyrrolo[3,4-c]
quinolin-2-amine, bis-trifluoroacetic acid salt, (8aR,11aR)-N-[2-fluoro-3-(trifluoromethyl)phenyl]-5,6,
8,8a,9,10,11,11a-octahydro-4H-pyrido[3,2,1-ij]pyrrolo
[3,4-c]quinolin-2-amine, bis-trifluoroacetic acid salt, (8aR,11aR)-N-[4-chloro-3-(trifluoromethyl)phenyl]-5,6,
8,8a,9,10,11,11a-octahydro-4H-pyrido[3,2,1-ij]pyrrolo
[3,4-c]quinolin-2-amine, bis-trifluoroacetic acid salt, (8aR,11aR)-N-(2,3-dichlorophenyl)-5,6,8,8a,9,10,11,
11a-octahydro-4H-pyrido[3,2,1-ij]pyrrolo[3,4-c]
quinolin-2-amine, bis-trifluoroacetic acid salt, (8aR,11aR)-N-(3,4-dichlorophenyl)-5,6,8,8a,9,10,11,
11a-octahydro-4H-pyrido[3,2,1-ij]pyrrolo[3,4-c]
quinolin-2-amine, bis-trifluoroacetic acid salt, (8aR,11aR)-N-(2,6-dichlorophenyl)-5,6,8,8a,9,10,11,
11a-octahydro-4H-pyrido[3,2,1-ij]pyrrolo[3,4-c]
quinolin-2-amine, bis-trifluoroacetic acid salt, (8aR,11aR)-N-(2-chloro-5-methylphenyl)-5,6,8,8a,9,10,
11,11a-octahydro-4H-pyrido[3,2,1-ij]pyrrolo[3,4-c]
quinolin-2-amine, bis-trifluoroacetic acid salt, 2-[(8aR,11aR)-5,6,8,8a,9,10,11,11a-octahydro-4H-pyrido
[3,2,1-ij]pyrrolo[3,4-c]quinolin-2-ylamino]
benzonitrile, bis-trifluoroacetic acid salt, (8aR,11aR)-N-(2-methoxy-5-methylphenyl)-5,6,8,8a,9,
10,11,11a-octahydro-4H-pyrido[3,2,1-ij]pyrrolo[3,4-c]
quinolin-2-amine, bis-trifluoroacetic acid salt, 3-[(8aR,11aR)-5,6,8,8a,9,10,11,11a-octahydro-4H-pyrido
[3,2,1-ij]pyrrolo[3,4-c]quinolin-2-ylamino]
benzonitrile, bis-trifluoroacetic acid salt, 4-[(8aR,11aR)-5,6,8,8a,9,10,11,11a-octahydro-4H-pyrido
[3,2,1-ij]pyrrolo[3,4-c]quinolin-2-ylamino]
benzonitrile, bis-trifluoroacetic acid salt, (8aR,11aR)-N-[2-(trifluoromethyl)phenyl]-5,6,8,8a,9,10,
11,11a-octahydro-4H-pyrido[3,2,1-ij]pyrrolo[3,4-c]
quinolin-2-amine, bis-trifluoroacetic acid salt, (8aR,11aR)-N-[4-(trifluoromethyl)phenyl]-5,6,8,8a,9,10,
11,11a-octahydro-4H-pyrido[3,2,1-ij]pyrrolo[3,4-c]
quinolin-2-amine, bis-trifluoroacetic acid salt, (8aR,11aR)-N-(2-fluoro-5-methylphenyl)-5,6,8,8a,9,10,
11,11a-octahydro-4H-pyrido[3,2,1-ij]pyrrolo[3,4-c]
quinolin-2-amine, bis-trifluoroacetic acid salt, (8aR,11aR)-N-(3-quinolinyl)-5,6,8,8a,9,10,11,11a-
octahydro-4H-pyrido[3,2,1-ij]pyrrolo[3,4-c]quinolin-
2-amine, bis-trifluoroacetic acid salt, (8aR,11aR)-N-(2-naphthyl)-5,6,8,8a,9,10,11,11a-
octahydro-4H-pyrido[3,2,1-ij]pyrrolo[3,4-c]quinolin-
2-amine, bis-trifluoroacetic acid salt, (8aR,11aR)-N-(1-naphthyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2-chloro-3-pyridinyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(4-methyl-1-naphthyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2-methyl-1-naphthyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2,3-dimethylphenyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(3-methylphenyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2,5-dimethylphenyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(3,4-dimethylphenyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2-methoxyphenyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2-fluoro-4-methoxyphenyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(3,5-dimethylphenyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(4-fluoro-3-methylphenyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2-fluoro-4-methylphenyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(4-chloro-3-methylphenyl)-5,6,8,8a,9,10,11,11a-octahydro-4H-pyrido[3,2,1-ij]pyrrolo[3,4-c]quinolin-2-amine, bis-trifluoroacetic acid salt, (±)-trans-N-[2-chloro-5-(trifluoromethyl)phenyl]-5,6,8,8a,9,10,11,11a-octahydro-4H-pyrido[3,2,1-ij]pyrrolo[3,4-c]quinolin-2-amine, (±)-trans-N-(3,4-dichlorophenyl)-5,6,8,8a,9,10,11,11a-octahydro-4H-pyrido[3,2,1-ij]pyrrolo[3,4-c]quinotin-2-amine, (±)-trans-N-(2,3-dichlorophenyl)-5,6,8,8a,9,10,11,11a-octahydro-4H-pyrido[3,2,1-ij]pyrrolo[3,4-c]quinolin-2-amine, (±)-trans-N-(2,4-dichlorophenyl)-5,6,8,8a,9,10,11,11a-octahydro-4H-pyrido[3,2,1-ij]pyrrolo[3,4-c]quinolin-2-amine, (±)-cis-N-benzyl-5,6,8,8a,9,10,11,11a-octahydro-4H-pyrido[3,2,1-ij]pyrrolo[3,4-c]quinolin-2-amine, bis-trifluoroacetic acid salt, (±)-cis-N-(3,5-dichlorobenzyl)-5,6,8,8a,9,10,11,11a-octahydro-4H-pyrido[3,2,1-ij]pyrrolo[3,4-c]quinolin-2-amine, bis-trifluoroacetic acid salt, (±)-cis-N-(2,6-dichlorobenzyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-[2-(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-[2-fluoro-6-(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2,3-dichlorobenzyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2,4-dichlorobenzyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(3,4-dichlorobenzyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2,3-dimethoxybenzyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(3,4-dimethoxybenzyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2-methoxybenzyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2-methylbenzyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-[4-fluoro-2-(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-(2,3-dimethylbenzyl)-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-[2,4-bis(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-[2,5-bis(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-[3-(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-[4-(trifluoromethyl)benzyl]-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-[2-(methylthio)benzyl]-5,6,8,8a,9,10,11,11a-octahydro-4H-pyrido[3,2,1-ij]pyrrolo[3,4-c]quinolin-2-amine, bis-trifluoroacetic acid salt, (8aR,11aR)-N-[2-(trifluoromethoxy)benzyl]-5,6,8,8a,9,10,11,11a-octahydro-4H-pyrido[3,2,1-ij]pyrrolo[3,4-c]quinolin-2-amine, bis-trifluoroacetic acid salt, 2-[(8aR,11aR)-5,6,8,8a,9,10,11,11a-octahydro-4H-pyrido[3,2,1-ij]pyrrolo[3,4-c]quinolin-2-yl]-1H-isoindole-1,3(2H)-dione, bis-hydrochloric acid salt, (8aR,11aR)-2-(1,3-dihydro-2H-isoindol-2-yl)-5,6,8,8a,9,10,11,11a-octahydro-4H-pyrido[3,2,1-ij]pyrrolo[3,4-c]quinoline, bis-trifluoroacetic acid salt, 2-[(8aR,11aR)-5,6,8,8a,9,10,11,11a-octahydro-4H-pyrido[3,2,1-ij]pyrrolo[3,4-c]quinolin-2-yl]-1,3(2H,4H)-isoquinolinedione, bis-hydrochloric acid salt, (8aR,11aR)-2-(3,4-dihydro-2(1H)-isoquinolinyl)-5,6,8,8a,9,10,11,11a-octahydro-4H-pyrido[3,2,2-ij]pyrrolo[3,4-c]quinoline, bis-trifluoroacetic acid salt, N-[(8aR,11aR)-5,6,8,8a,9,10,11,11a-octahydro-4H-pyrido[3,2,1-ij]pyrrolo[3,4-c]quinolin-2-yl]benzamide, bis-trifluoroacetic acid salt, N-[(8aR,11aR)-5,6,8,8a,9,10,11,11a-octahydro-4H-pyrido[3,2,1-ij]pyrrolo[3,4-c]quinolin-2-yl]benzenesulfonamide, bis-trifluoroacetic acid salt, (±)-cis-10-ethyl-5,6,8,8a,9,10,11,11a-octahydro-4H-pyrido[3,2,1-ij]pyrrolo[3,4-c]quinoline, bis-hydrochloride salt, (±)-cis-10-propyl-5,6,8,8a,9,10,11,11a-octahydro-4H-pyrido[3,2,1-ij]pyrrolo[3,4-c]quinoline, bis-hydrochloride salt, (±)-cis-10-butyl-5,6,8,8a,9,10,11,11a-octahydro-4H-pyrido[3,2,1-ij]pyrrolo[3,4-c]quinoline, bis-hydrochloride salt, (±)-cis-10-(cyclobutylmethyl)-5,6,8,8a,9,10,11,11a-octahydro-4H-pyrido[3,2,1-ij]pyrrolo[3,4-c]quinoline, bis-hydrochloride salt, (±)-cis 5,6,8a,9,10,11,12,12a-octahydro-4H,8H-quino[1,8-bc]-2,6-naphthyridine, bis-hydrochloride salt, (±)-cis 5,6,8a,9,10,11,12,12a-octahydro-4H,8H-quino[1,8-bc]-2,7-naphthyridine, bis-hydrochloride salt, (±)-cis 11-methyl-5,6,8a,9,10,11,12,12a-octahydro-4H,8H-quino[1,8-bc]-2,6-naphthyridine, bis-hydrochloride salt, (±)-cis 10-methyl-5,6,8a,9,10,11,12,12a-octahydro-4H,8H-quino[1,8-bc]-2,7-naphthyridine, bis-hydrochloride salt, (±)-cis 2-phenyl-5,6,8a,9,10,11,12,12a-octahydro-4H,8H-quino[1,8-bc]-2,6-naphthyridine, trifluoroacetic acid salt, (±)-cis 2-(2,4-dichlorophenyl)-5,6,8a,9,10,11,12,12a-octahydro-4H,8H-quino[1,8-bc]-2,6-naphthyridine, (±)-cis 2-[4-methoxy-2-(trifluoromethyl)phenyl]-5,6,8a,9,10,11,12,12a-octahydro-4H,8H-quino[1,8-bc]-2,6-naphthyridine, trifluoroacetic acid salt, (±)-cis 2-(2,6dichlorophenyl)-5,6,8a,9,10,11,12,12a-octahydro-4H,8H-quino[1,8-bc]-2,6-naphthyridine, trifluoroacetic acid salt, 2-[(8aR,11aR)-5,6,8,8a,9,10,11,11a-octahydro-4H-pyrido[3,2,1-ij]pyrrolo[3,4-c]quinolin-2-ylamino]-4-chlorobenzonitrile, bis-trifluoroacetic acid salt and 2-[(8aR,11aR)-5,6,8,8a,9,10,11,11a-octahydro-4H-pyrido[3,2,1-ij]pyrrolo[3,4-c]quinolin-2-ylamino]-6-fluorobenzonitrile, bis-trifluoroacetic acid salt.

* * * * *

UNITED STATES PATENT AND TRADEMARK OFFICE
CERTIFICATE OF CORRECTION

PATENT NO.    : 6,777,406 B2
DATED         : August 17, 2004
INVENTOR(S)   : Fevig et al.

It is certified that error appears in the above-identified patent and that said Letters Patent is hereby corrected as shown below:

Title page,
Item [54], Title, should read -- SUBSTITUTED PYRROLOQUINOLINES AND PYRIDOQUINOLINES AS SEROTONIN AGONISTS AND ANTAGONISTS --

Signed and Sealed this

Twenty-second Day of February, 2005

JON W. DUDAS
*Director of the United States Patent and Trademark Office*